US008765389B2

(12) United States Patent
Tüereci et al.

(10) Patent No.: US 8,765,389 B2
(45) Date of Patent: Jul. 1, 2014

(54) GENETIC PRODUCTS WHICH ARE DIFFERENTIALLY EXPRESSED IN TUMORS AND USE THEREOF

(75) Inventors: Öezlem Tüereci, Mainz (DE); Ugur Sahin, Mainz (DE); Michael Koslowski, Mainz (DE)

(73) Assignee: Ganymed Pharmaceuticals AG, Mainz (DE)

(*) Notice: Subject to any disclaimer, the term of this patent is extended or adjusted under 35 U.S.C. 154(b) by 2075 days.

(21) Appl. No.: 10/570,957

(22) PCT Filed: Sep. 10, 2004

(86) PCT No.: PCT/EP2004/010164

§ 371 (c)(1),
(2), (4) Date: Mar. 10, 2006

(87) PCT Pub. No.: WO2005/026205

PCT Pub. Date: Mar. 24, 2005

(65) Prior Publication Data

US 2010/0203040 A1 Aug. 12, 2010

(30) Foreign Application Priority Data

Sep. 10, 2003 (DE) .................................. 103 41 812

(51) Int. Cl.

| | |
|---|---|
| ***G01N 33/574*** | (2006.01) |
| ***G01N 33/53*** | (2006.01) |
| ***C12Q 1/68*** | (2006.01) |
| ***C07K 14/00*** | (2006.01) |
| ***C07H 21/02*** | (2006.01) |
| ***C07H 21/04*** | (2006.01) |

(52) U.S. Cl.
USPC .......... 435/7.23; 435/7.1; 435/6.14; 530/350; 536/23.1; 536/23.5

(58) Field of Classification Search
USPC ........... 435/7.23, 7.8, 6.11, 6.14, 6.16, 4, 6.1, 435/7-1, 7.1; 530/350, 300; 424/133, 138, 424/155.1, 193.1, 139.1, 278.1; 536/23.1, 536/23.5
See application file for complete search history.

(56) References Cited

U.S. PATENT DOCUMENTS

| | | | | |
|---|---|---|---|---|
| 7,429,461 B2 * | 9/2008 | Sahin et al. | .................. | 435/7.23 |
| 2002/0160382 A1 | 10/2002 | Lasek et al. | | |
| 2006/0013817 A1 | 1/2006 | Sahin et al. | | |

FOREIGN PATENT DOCUMENTS

| | | | |
|---|---|---|---|
| AU | 2003219045 | B2 | 1/2009 |
| CA | 2383230 | A1 | 2/2001 |
| EP | 1 222 928 | A2 | 7/2002 |
| JP | 2003506085 | A | 2/2003 |
| JP | 2005519608 | A | 7/2005 |
| WO | WO 92/04381 | | 3/1992 |
| WO | WO 96/33739 | | 10/1996 |
| WO | WO-A-9633265 | | 10/1996 |
| WO | 99/41375 | A2 | 8/1999 |
| WO | 01/11040 | A1 | 2/2001 |
| WO | 02/10363 | A2 | 2/2002 |
| WO | 02/062946 | A2 | 8/2002 |
| WO | WO 03/076631 | | 9/2003 |
| WO | 03/076631 | A3 | 12/2003 |
| WO | 2005/052182 | A2 | 6/2005 |
| WO | 01/75067 | A2 | 10/2011 |

OTHER PUBLICATIONS

Jiang et al (J. Biol. Chem., 2003, 278(7) 4763-4769).*
Matsushita et al (FEBS Letters, 1999, vol. 443, pp. 348-352).*
Singh et al. (Glycobiology, 2001, vol. 11, pp. 587-592).*
Roitt et al (Immunology, Fourth Edition, 1996, Mosby, p. 7.9-7.11).*
Dong X-Y et al., "Identification of two novel CT antigens and their capacity to elicit antibody response in hepatocellular carcinoma patients" British Journal of Cancer, 89(2):291-297 (2003).
Chen, H. et al, "A testis-specific gene, TPTE, encodes a putative transmembrane tyrosine phosphatase and maps to the pericentromeric region of human chromosomes 21 and 12, and to chromosomes 15, 22, and Y", Human Genetics, Berlin, DE, 105(5):399-409 (1999).
Brun M-E et al., "Juxtracentromeric region of human chromosome 21:a boundary between centromeric heterochromatin and euchromatic chromosome arms", GENE: An international Journal of Genes and Genomes, Elsevier Science Publishers, Barking, GB, 312(17):41-50 (2003).
Tapparel, C. et at., "The TPTE gene family: cellular expression, subcellular localization and alternative splicing" Gene: An International Journal on Genes and Genomes, 323(24):189-199 (2003).
Walker, Steven M. et al., "TPIP: A novel phosphoinositide 3-phosphatase", Biochemical Journal, 360(2):277-283 (2001).
Pardoll, Drew M., Cancer Vaccines, Nat. Med. Vaccine Supp. 4(5):525-531 (1998).
Van der Bruggen et al., "A Gene Encoding an Antigen Recognized by Cytolytic T Lymphocytes on a Human Melanoma", Science 254:1643-1647 (1991).
Tureci et al., "Serological Analysis of Human Tumor Antigens: Molecular Definition and Implications", Mol. Med. Today 3:342-349 (1997).
Chen et al., "Cancer-Testis Antigens: Targets for Cancer Immunotherapy", Cancer J. Sci. Am. 5:16-17 (1999).
Marchand et al., "Tumor Regressions Observed in Patients with Metastatic Melanoma Treated with an Antigenic Peptide Encoded by Gene MAGE-3 and Presented by HLA-A1", Int. J. Cancer 80:219-230 (1999).
Knuth et al., "Cancer Immunotherapy in Clinical Oncology", Cancer Chem. Pharm. 46(Supp):S46-S51 (2000).
Schmitt et al., "Exhaustive Mining of EST Libraries for Genes Differentially Expressed in Normal and Tumour Tissues", Nucleic Acids Res. 27(21):4251-4260(1999).

(Continued)

*Primary Examiner* — Mark Halvorson
*Assistant Examiner* — Yan Xiao
(74) *Attorney, Agent, or Firm* — McAndrews Held & Malloy, Ltd.

(57) ABSTRACT

The invention relates to the identification of genetic products expressed in association with tumors and to coding nucleic acids for said products. The invention also relates to the therapy and diagnosis of diseases in which the genetic products are aberrantly expressed in association with tumors, proteins, polypeptides and peptides which are expressed in association with tumors and to the coding nucleic acids for said proteins, polypeptides and peptides.

24 Claims, 39 Drawing Sheets

(56) References Cited

OTHER PUBLICATIONS

Figure 1:
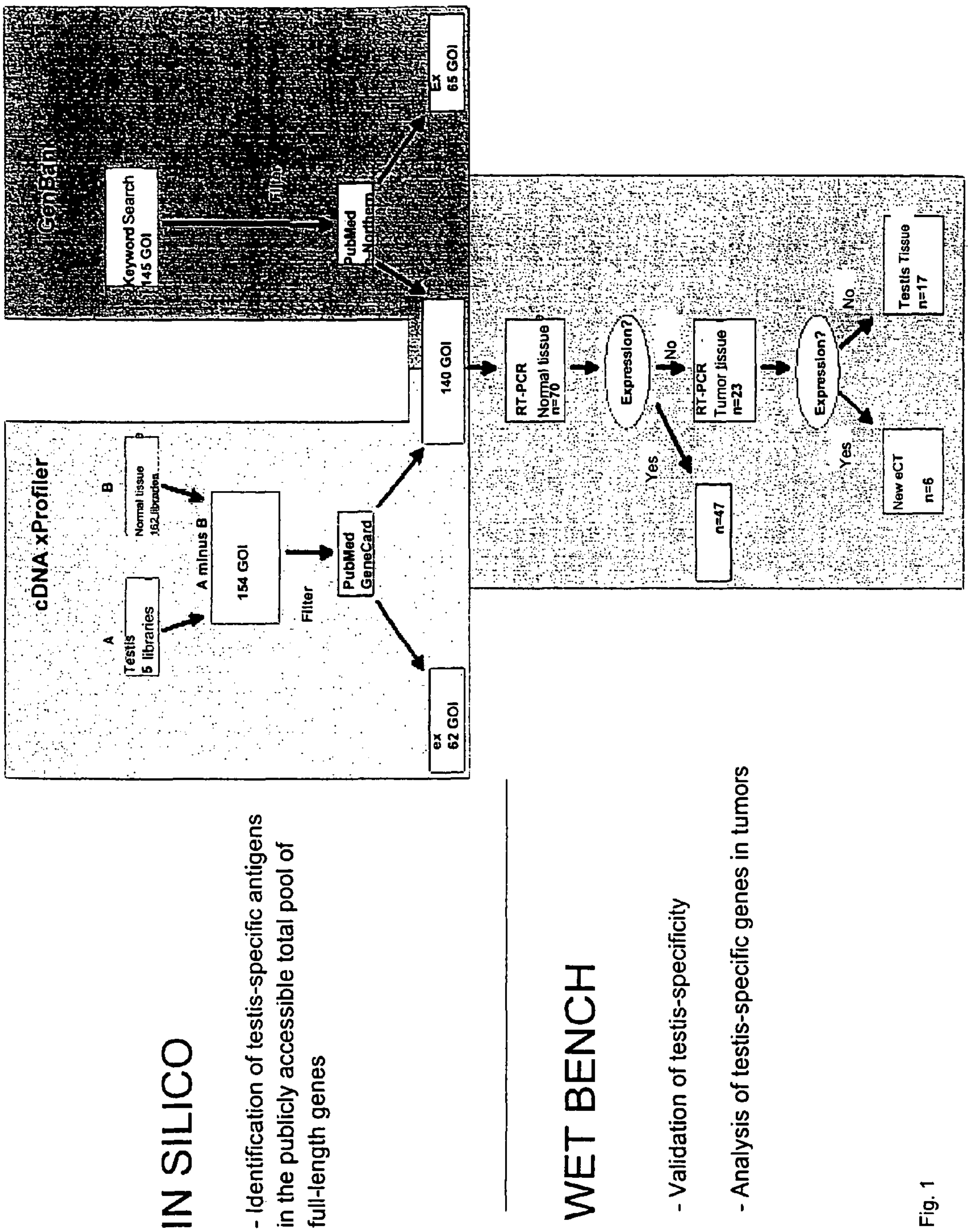

Vasmatzis et al., "Discovery of Three Genes Specifically Expressed in Human Prostate by Expressed Sequence Tag Database Analysis", Proc. Natl. Acad. Sci. USA 95(1):300-304 (1998).
Jager et al., "Identification of a Tissue-Specific Putative Transcription Factor in Breast Tissue by Serological Screening of a Breast Cancer Library", Cancer Res. 61(5):2055-2061 (2001).
Ausebel et al., Editors, John Wiley & Sons, Inc., New York, 1995.
Roitt et al., The Experimental Foundations of Modem Immunology, Wiley & Sons, Inc. New York, (1991).
Essential Immunology, $7^{th}$ Ed. Blackwell Scientific Publications, Oxford, 1991.
Goodman et al., "The Pharmacological Basis of Therapeutics", $8^{th}$ Edition (1990).
Altman et al. "Phenotypic Analysis of Antigen-specific T Lymphocytes", Science 274:94-96 (1996).
Dunbar et al., "Direct Isolation, Phenotyping and Cloning of Low-Frequency Antigen-Specific Cytotoxic T Lymphocytes from Peripheral Blood", Curr. Biol. 8:413-416 (1998).
Greenberg, Philip D., "Therapy of Murine Leukemia with Cyclophosphamide and Immune Lyt-2+ Cells: Cytolytic T Cells Can Mediate Eradication of Disseminated Leukemia", J. Immunol. 136(5):1917-1922 (1986).
Riddel et al., "Restoration of Viral Immunity in Immunodeficient Humans by the Adoptive Transfer of T Cell Clones", Science 257:238-241 (1992).
Liang et al., "Identification of a CD20-, FcεRIβ-, and HTm4-Related Gene Family: Sixteen New MS4A Family Members Expressed in Human Mouse", Genomics 71:119-127 (2001).
Stanislawski et al., "Circumventing Tolerance to a Human MDM2-Derived Tumor Antigen by TCR Gene Transfer", Nat. Immunol. 2(10):962-970 (2001).
Kessels et al., "Immunotherapy Through TCR Gene Transfer", Nat. Immunol. 2(10):957-961 (2001).
Ossendorp et al., "Importance of CD4+ T Helper Cell Responses in Tumor Immunity", Immunol. Lett. 74:75-79 (2000).
Ossendorp et al., "Specific T Helper Cell Requirement for Optimal Induction of Cytotoxic T Lymphocytes Against Major Histocompatability Complex Class II Negative Tumors", J. Exp. Med. 187(5):693-702 (1998).
Maloy et al., "Intralymphatic Immunization Enhances DNA Vaccination", Proc. Natl. Acad. Sci. USA 98(6):3299-3303 (2001).
Appella et al., "Synthetic Antigenic Peptides as a New Strategy for Immunotherapy of Cancer", Biomed. Petp. Prot. Nuc. Acids 1:177-184 (1995).
Wentworth et al., "In Vitro Induction of Primary, Antigen-Specific CTL From Human Peripheral Blood Mononuclear Cells Stimulated With Synthetic Peptides", Mol. Immunol. 32(9):603-612 (1995).
So et al., "Effect of a Novel Saponin Adjuvant Derived from Quillaja Saponaria on the Immune Response to Recombinant Hepatitis B Surface Antigen", Mol. Cells 7(2):178-186 (1997).
Kreig et al., "CpG Motifs in Bacterial DNA Trigger Direct B-Cell Activation", Nature 374:546-549 (1995).
Hellemans, "Helium-3 Crystals Captured on Video", Science 268:1434 (1995).
Zheng et al., "B7-CTLA4 Interaction Enhances Both Production of Antitumor Cytotoxic T Lymphocytes and Resistance to Tumor Challenge", Proc. Natl. Acad. Sci. USA 95(11):6284-6289 (1998).
Gajewski et al., "Costimulation With B7-1, IL-6, and IL-12 is Sufficient for Primary Generation of Murine Antitumor Cytolytic T Lymphocytes in Vitro", J. Immunol. 154:5637-5648 (1995).
Goldberg et al., "Immune Response of Male Baboons to Testis-Specific LDH-C4", Contraception 64(2):93-98 (2001).
Gupta, "LDH-C4: A Unique Target of Mammalian Spermatozoa", Crit. Rev. Biochem. Mol. Biol. 34(6):361-385 (1999).
Goldberg, Erwin, "Reproductive Implications of LDH-$C_4$ and Other Testis-specific Isozymes", E., Exp. Clin. Immunogenet. 2:120-124 (1985).
Mita et al., "Metabolism of Round Spermatids from Rats: Lactate as the Preferred Substrate", M., Biol. Reprod. 26:445-455 (1982).
Feder et al, "Testosterone and "5α-Dihydrotestosterone" Levels in Peripheral Plasma of Male and Female Ring Doves (*Streptopelia risoria*) During the Reproductive Cycle", Biol. Reprod. 16:666-677(1977).
Ridge et al., "A Conditioned Dendritic Cell can be a Temporal Bridge Between a CD4+ T-Helper and a T-Killer Cell", Nature 393:474-477 (1998).
Bennett et al., "Help for Cytotoxic-T-Cell Responses is Mediated by CD40 Signaling", Nature 393:478-479 (1998).
Schoenberger et al., "T-Cell Help for Cytotoxic T Lymphocytes is Mediated by CD40-CD40L Interactions", Nature 393:480 (1998).
Wheeler et al., "Database Resources of the National Center for Biotechnology Information", Nucleic Acids Res. 28(1):10-14 (2000).
Inoue et al., "New Gene Family Defined by MORC, a Nuclear Protein Required for Mouse Spermatogenesis", Hum. Mol. Genet. 8(7):1201-1207 (1999).
Pennisi et al., "A Catalog of Cancer Genes at the Click of a Mouse" Science 276:1023-1024 (1997).
Chomczynski et al., "Single-Step Method of RNA Isolation by Acid Gaunidinium Thiocyanate-Phenol-Chloroform Extraction", Anal. Biocehm. 162:156-159 (1987).
Lemoine et al., "Transfection and Transformation of Human Thyroid Epithelial Cells", Methods Mol. Biol. 75:441-447 (1997).
Dabbs, D. J., Diagnostic Immunohistochemistry, ISBN: 0443065667, Jan. 15, 2002.
Shi et al., "Antigen Retrieval in Formalin-Fixed, Paraffin-Embedded Tissues: An Enhancement Method for Immunohistochemical Staining Based on Microwave Oven Heating of Tissue Sections", J. Histochem. Cytochem. 39(6):741-748 (1991).
Shin et al., "Methods in Laboratory Investigation", Lab Invest. 64(5):693-702 (1991).
Dean et al., "Preparation of Rodent Monoclonal Antibodies: by in Vitro Somatic Hybridization", Immunology, pp. 1-23. (2000).
Harlow et al., Antibodies: A Laboratory Manual: ISBN: 0879693142., 1988.
Harlow et al., "Using Antibodies: A Laboratory Manual: Portable Protocol", ISBN: 0879695447., 1999.
Jung et al., "DNA-Mediated Immunization of Glycoprotein 350 of Epstein-Barr Virus Induces the Effective Humoral and Cellular Immune Responses Against the Antigen", Mol. Cells, 12(1):41-49 (2001).
Kasinrerk et al., "Production of Antibodies by Single DNA Immunization: Comparison of Various Immunization Routes", Hybridoma and Hybridomics, 21(4):287-293 (2002).
Elbashir et al., "Duplexes of 21-Nucleotide RNAs Mediate RNA Interference in Cultured Mammalian Cells", Nature 411:494-498 (2001).
Guipponi et al., "Genomic Structure of a Copy of the Human TPTE Gene Which Encompasses 87 kb on the Short Arm of Chromosome 21", Hum. Genet. 107:127-131 (2000).
Stammers et al., "BTL-II: A Polymorphic Locus with Homology to the Butyrophilin Gene Family, Located at the Border of the Major Histocompatability Complex Class II and Class III Regions in Human and Mouse", Immunogenetics 51:373-382 (2000).
Weinmaster, G., "Notch Signal Transduction: a Real Rip and More", Curr. Opin. Genet. Dev. 10:363-369 (2000).
Hoppe et al., "Membrane-Bound Transcription Factors: Regulated Release by RIP or RUP", Curr. Opin. Cell. Biol. 13:344-348 (2001).
Liang et al.,."Structural Organization of the Human MS4A Gene Cluster on Chromosome 11q12", Immunogenetics 53:357-368 (2001).
Erbsen M et al: "New Methods, Abstract 253-261, Posters", Pathology Research and Practice, Gustav Fischer, Stuttgart, DE, vol. 199, No. 4, Jan. 1, 2003, p. 244-247.
Database GenBank [online], Accession No. NM_013315, URL, http://www.ncbi.nlm.nih.gov/sviewer/viewer.fcgi?val=7019558 &sat=OLD03&satkey=4515133, Sep. 24, 2005.
Helftenbein, G. et al., In silico stratey for detection of target candidates for antibody therapy of solid tumors, Gene, vol. 414, p. 76-84 (2008).

* cited by examiner

| | | |
|---|---|---|
| SEQ_ID_6 | MSTVKEQLIEKLIEDDENSQCKITIVGTGAVGMACAISILLKDLADELALVDVALDKLKGEMMDLQHGSLFFSTSKITSGKDYSVSANSRIVIVTAGARQ | 100 |
| SEQ_ID_13 | MSTVKEQLIEKLIEDDENSQCKITIVGTGAVGMACAISILLKDLADELALVDVALDKLKGEMMDLQHGSLFFSTSKITSGKDYSVSANSRIVIVTAGARQ | 100 |
| SEQ_ID_7 | MSTVKEQLIEKLIEDDENSQCKITIVGTGAVGMACAISILLK**ITVYLQTPK**---------------------------------------------------------- | 51 |
| SEQ_ID_9 | MSTVKEQLIEKLIEDDENSQCKITIVGTGAVGMACAISILLK**WIF**------------------------------------------------------- | 45 |
| SEQ_ID_8 | ---------------------------------------------------------------------------------------------------- | |
| SEQ_ID_11 | ---------------------------------------------------------------------------------------------------- | |
| SEQ_ID_10 | ---------------------------------------------------------------------------------------------------- | |
| SEQ_ID_12 | ---------------------------------------------------------------------------------------------------- | |
| | | |
| SEQ_ID_6 | QEGETRLALVQRNVAIMKSIIPAIVHYSPDCKILVVSNPVDILTYIVWKISGLPVTRVIGSGCNLDSARFRYLIGEKLGVHPTSCHGWII[GEHGDS]SVPL | 200 |
| SEQ_ID_13 | QEGETRLALVQRNVAIMKSIIPAIVHYSPDCKILVVSNPVDILTYIVWKISGLPVTRVIGSGCNLDSARFRYLIGEKLGVHPTSCHGWII[GEHGDS]SVPL | 200 |
| SEQ_ID_7 | ---------------------------------------------------------------------------------------------------- | |
| SEQ_ID_9 | ---------------------------------------------------------------------------------------------------- | |
| SEQ_ID_8 | ----------------MKSIIPAIVHYSPDCKILVVSNPVDILTYIVWKISGLPVTRVIGSGCNLDSARFRYLIGEKLGVHPTSCHGWII[GEHGDS]SVPL | 84 |
| SEQ_ID_11 | ----------------MKSIIPAIVHYSPDCKILVVSNPVDILTYIVWKISGLPVTRVIGSGCNLDSARFRYLIGEKLGVHPTSCHGWII[GEHGDS]SGII | 84 |
| SEQ_ID_10 | ---------------------------------------------------------------------------------------------------- | |
| SEQ_ID_12 | ---------------------------------------------------------------------------------------------------- | |
| | | |
| SEQ_ID_6 | WSGVNVAGVALKTLDPKLGTDSDKEHWKNIHKQVIQSAYEIIKLKGYTSWAIGLSVMDLVGSILKNLRRVHPVSTMVKGLYGIKEELFLSIPCVLGRNGV | 300 |
| SEQ_ID_13 | WSGVNVAGVALKTLDPKLGTDSDKEHWKNIHKQVIQRDYME----------------------------------------------------------- | 241 |
| SEQ_ID_7 | ---------------------------------------------------------------------------------------------------- | |
| SEQ_ID_9 | ---------------------------------------------------------------------------------------------------- | |
| SEQ_ID_8 | WSGVNVAGVALKTLDPKLGTDSDKEHWKNIHKQVIQSAYEIIKLKGYTSWAIGLSVMDLVGSILKNLRRVHPVSTMVKGLYGIKEELFLSIPCVLGRNGV | 184 |
| SEQ_ID_11 | **WNKRRTLSQYPLCLGAEWCLRCCEN**--------------------------------------------------------------------------- | 109 |
| SEQ_ID_10 | --------------------------------------------------------MDLVGSILKNLRRVHPVSTMVKGLYGIKEELFLSIPCVLGRNGV | 44 |
| SEQ_ID_12 | ------------------------------------------------------------------**MVGLLENMVILV**GLYGIKEELFLSIPCVLGRNGV | 34 |
| | | |
| SEQ_ID_6 | SDVVKINLNSEEEALFKKSAETLWNIQKDLIF | 332 |
| SEQ_ID_13 | -------------------------------- | |
| SEQ_ID_7 | -------------------------------- | |
| SEQ_ID_9 | -------------------------------- | |
| SEQ_ID_8 | SDVVKINLNSEEEALFKKSAETLWNIQKDLIF | 216 |
| SEQ_ID_11 | -------------------------------- | |
| SEQ_ID_10 | SDVVKINLNSEEEALFKKSAETLWNIQKDLIF | 76 |
| SEQ_ID_12 | SDVVKINLNSEEEALFKKSAETLWNIQKDLIF | 66 |

Lactate dehydrogenase, active site (framed)
Tumor-specific epitopes (bold type)

Figure 3

| | | |
|---|---|---|
| SEQ_ID_19 | MNESPDPTDLAGVIIELGPNDSPQTSEFKGATEEAPAKESPHTSEFKGAARVSPISESVL | 60 |
| SEQ_ID_20 | MNESPDPTDLAGVIIELGPNDSPQTSEFKGATEEAPAKES------------------VL | 42 |
| SEQ_ID_21 | MNESPDPTDLAGVIIELGPNDSPQTSEFKGATEEAPAKESPHTSEFKGAARVSPISESVL | 60 |
| SEQ_ID_58 | MNESPDPTDLAGVIIELGPNDSPQTSEFKGATEEAPAKESPHTSEFKGAARVSPISESVL | 60 |
| SEQ_ID_59 | MNESPDPTDLAGVIIELGPNDSPQTSEFKGATEEAPAKESPHTSEFKGAARVSPISESVL | 60 |
| SEQ_ID_60 | MNESPDPTDLAGVIIELGPNDSPQTSEFKGATEEAPAKES------------------VL | 42 |
| SEQ_ID_61 | MNESPDPTDLAGVIIELGPNDSPQTSEFKGATEEAPAKES------------------VL | 42 |
| | | |
| SEQ_ID_19 | ARLSKFEVEDAENVASYDSKIKKIVHSIVSSFAFGLFGVFLVLLDVTLILADLIFTDSKL | 120 |
| SEQ_ID_20 | ARLSKFEVEDAENVASYDSKIKKIVHSIVSSFAFGLFGVFLVLLDVTLILADLIFTDSKL | 102 |
| SEQ_ID_21 | ARLSKFEVEDAENVASYDSKIKKIVHSIVSSFAFGLFGVFLVLLDVTLILADLIFTDSKL | 120 |
| SEQ_ID_58 | ARLSKFEVEDAENVASYDSKIKKIVHSIVSSFAFGLFGVFLVLLDVTLILADLIFTDSKL | 120 |
| SEQ_ID_59 | ARLSKFEVEDAENVASYDSKIKKIVHSIVSSFAFGLFGVFLVLLDVTLILADLIFTDSKL | 120 |
| SEQ_ID_60 | ARLSKFEVEDAENVASYDSKIKKIVHSIVSSFAFGLFGVFLVLLDVTLILADLIFTDSKL | 102 |
| SEQ_ID_61 | ARLSKFEVEDAENVASYDSKIKKIVHSIVSSFAFGLFGVFLVLLDVTLILADLIFTDSKL | 102 |
| | | |
| SEQ_ID_19 | YIPLEYRSISLAIALFFLMDVLLRVFVERRQQYFSDLFNILDTAIIVILLLVDVVYIFFD | 180 |
| SEQ_ID_20 | YIPLEYRSISLAIALFFLMDVLLRVFVERRQQYFSDLFNILDTAIIVILLLVDVVYIFFD | 162 |
| SEQ_ID_21 | YIPLEYRSISLAIALFFLMDVLLRVFVERRQQYFSDLFNILDTAIIVILLLVDVVYIFFD | 180 |
| SEQ_ID_58 | YIPLEYRSISLAIALFFLMDVLLRVFVERRQQYFSDLFNILDTAIIVILLLVDVVYIFFD | 180 |
| SEQ_ID_59 | YIPLEYRSISLAIALFFLMDVLLRVFVERRQQYFSDLFNILDTAIIVILLLVDVVYIFFD | 180 |
| SEQ_ID_60 | YIPLEYRSISLAIALFFLMDVLLRVFVERRQQYFSDLFNILDTAIIVILLLVDVVYIFFD | 162 |
| SEQ_ID_61 | YIPLEYRSISLAIALFFLMDVLLRVFVERRQQYFSDLFNILDTAIIVILLLVDVVYIFFD | 162 |
| | | |
| SEQ_ID_19 | IKLLRNIPRWTHLLRLLRLIILLRIFHLFHQKRQLEKLIRRRVSENKRRYTRDGFDLDLT | 240 |
| SEQ_ID_20 | IKLLRNIPRWTHLLRLLRLIILLRIFHLFHQKRQLEKLIRRRVSENKRRYTRDGFDLDLT | 222 |
| SEQ_ID_21 | IKLLRNIPRWTHLLRLLRLIILLRIFHLFHQKRQLEKLIRRRVSENKRRYTRDGFDLDLT | 240 |
| SEQ_ID_58 | IKLLRNIPRWTHLLRLLRLIILLRIFHLFHQKRQLEKLIRRRVSENKRRYTRDGFDLDLT | 240 |
| SEQ_ID_59 | IKLLRNIPRWTHLLRLLRLIILLRIFHLFHQKRQLEKLIRRRVSENKRRYTRDGFDLDLT | 240 |
| SEQ_ID_60 | IKLLRNIPRWTHLLRLLRLIILLRIFHLFHQKRQLEKLIRRRVSENKRRYTRDGFDLDLT | 222 |
| SEQ_ID_61 | IKLLRNIPRWTHLLRLLRLIILLRIFHLFHQKRQLEKLIRRRVSENKRRYTRDGFDLDLT | 222 |
| | | |
| SEQ_ID_19 | YVTERIIAMSFPSSGRQSFYRNPIKEVVRFLDKKHRNHYRVYNLCS-------------- | 286 |
| SEQ_ID_20 | YVTERIIAMSFPSSGRQSFYRNPIKEVVRFLDKKHRNHYRVYNLCS-------------- | 268 |
| SEQ_ID_21 | YVTERIIAMSFPSSGRQSFYRNPIKEVVRFLDKKHRNHYRVYNLCSMYIFLYCATVDRRQ | 300 |
| SEQ_ID_58 | YVTERIIAMSFPSSGRQSFYRNPIKEVVRFLDKKHRNHYRVYNLCS-------------- | 286 |
| SEQ_ID_59 | YVTERIIAMSFPSSGRQSFYRNPIKEVVRFLDKKHRNHYRVYNLCS-------------- | 286 |
| SEQ_ID_60 | YVTERIIAMSFPSSGRQSFYRNPIKEVVRFLDKKHRNHYRVYNLCS-------------- | 268 |
| SEQ_ID_61 | YVTERIIAMSFPSSGRQSFYRNPIKEVVRFLDKKHRNHYRVYNLCS-------------- | 268 |
| | | |
| SEQ_ID_19 | ----ERAYDPKHFHNRVVRIMIDDHNVPTLHQMVVFTKEVNEWMAQDLENIVAIHCKGGT | 342 |
| SEQ_ID_20 | ----ERAYDPKHFHNRVVRIMIDDHNVPTLHQMVVFTKEVNEWMAQDLENIVAIHCKGGT | 324 |
| SEQ_ID_21 | TTARERAYDPKHFHNRVVRIMIDDHNVPTLHQMVVFTKEVNEWMAQDLENIVAIHCKGGT | 360 |
| SEQ_ID_58 | ----ERAYDPKHFHNRVVRIMIDDHNVPTLHQMVVFTKEVNEWMAQDLENIVAIHCKGGT | 342 |
| SEQ_ID_59 | ----ERAYDPKHFHNRVVRIMIDDHNVPTLHQMVVFTKEVNEWMAQDLENIVAIHCKGGT | 342 |
| SEQ_ID_60 | ----ERAYDPKHFHNRVVRIMIDDHNVPTLHQMVVFTKEVNEWMAQDLENIVAIHCKGGT | 324 |
| SEQ_ID_61 | ----ERAYDPKHFHNRVVRIMIDDHNVPTLHQMVVFTKEVNEWMAQDLENIVAIHCKGGT | 324 |
| | | |
| SEQ_ID_19 | DRTGTMVCAFLIASEICSTAKESLYYFGERRTDKTHSEKFQGVETPSQKRYVAYFAQVKH | 402 |
| SEQ_ID_20 | DRTGTMVCAFLIASEICSTAKESLYYFGERRTDKTHSEKFQGVETPSQKRYVAYFAQVKH | 384 |
| SEQ_ID_21 | DRTGTMVCAFLIASEICSTAKESLYYFGERRTDKTHSEKFQGVETPSQKRYVAYFAQVKH | 420 |
| SEQ_ID_58 | DRTGTMVCAFLIASEICSTAKESLYYFGERRTDKTHSEKFQGVETPSQVMYVI------- | 395 |
| SEQ_ID_59 | G----------------------------------------------------------- | 343 |
| SEQ_ID_60 | DRTGTMVCAFLIASEICSTAKESLYYFGERRTDKTHSEKFQGVETP-------------- | 370 |
| SEQ_ID_61 | G----------------------------------------------------------- | 325 |
| | | |
| SEQ_ID_19 | LYNWNLPPRRILFIKHFIIYSIPRYVRDLKIQIEMEKKVVFSTISLGKCSVLDNITTDKI | 462 |
| SEQ_ID_20 | LYNWNLPPRRILFIKHFIIYSIPRYVRDLKIQIEMEKKVVFSTISLGKCSVLDNITTDKI | 444 |
| SEQ_ID_21 | LYNWNLPPRRILFIKHFIIYSIPRYVRDLKIQIEMEKKVVFSTISLGKCSVLDNITTDKI | 460 |
| SEQ_ID_58 | ------------------------------------------------------------ | |
| SEQ_ID_59 | ------------------------YVRDLKIQIEMEKKVVFSTISLGKCSVLDNITTDKI | 379 |
| SEQ_ID_60 | -------------------------------------------------SVLDNITTDKI | 381 |
| SEQ_ID_61 | ------------------------YVRDLKIQIEMEKKVVFSTISLGKCSVLDNITTDKI | 361 |
| | | |
| SEQ_ID_19 | LIDVFDGPPLYDDVKVQFFYSNLPTYYDNCSFYFWLHTSFIENNRLYLPKNELDNLHKQK | 522 |
| SEQ_ID_20 | LIDVFDGPPLYDDVKVQFFYSNLPTYYDNCSFYFWLHTSFIENNRLYLPKNELDNLHKQK | 504 |
| SEQ_ID_21 | LIDVFDGPPLYDDVKVQFFYSNLPTYYDNCSFYFWLHTSFIENNRLYLPKNELDNLHKQK | 540 |
| SEQ_ID_58 | ------------------------------------------------------------ | |
| SEQ_ID_59 | LIDVFDGPPLYDDVKVQFFYSNLPTYYDNCSFYFWLHTSFIENNRLYLPKNELDNLHKQK | 439 |
| SEQ_ID_60 | LIDVFDGPPLYDDVKVQFFYSNLPTYYDNCSFYFWLHTSFIENNRLYLPKNELDNLHKQK | 441 |
| SEQ_ID_61 | LIDVFDGPPLYDDVKVQFFYSNLPTYYDNCSFYFWLHTSFIENNRLYLPKNELDNLHKQK | 421 |
| | | |
| SEQ_ID_19 | ARRIYPSDFAVEILFGEKMTSSDVVAGSD | 551 |
| SEQ_ID_20 | ARRIYPSDFAVEILFGEKMTSSDVVAGSD | 533 |
| SEQ_ID_21 | ARRIYPSDFAVEILFGEKMTSSDVVAGSD | 569 |
| SEQ_ID_58 | ----------------------------- | |
| SEQ_ID_59 | ARRIYPSDFAVEILFGEKMTSSDVVAGSD | 468 |
| SEQ_ID_60 | ARRIYPSDFAVEILFGEKMTSSDVVAGSD | 470 |
| SEQ_ID_61 | ARRIYPSDFAVEILFGEKMTSSDVVAGSD | 450 |

Figure 6

```
1 SEQ_31     ATGACAGTCTTGGAAATAACTTTGGCTGTCATCCTGACTCTACTGGGACTTGCCATCCTGGCTATTTTGTTAACAAGATGGGCACGATGT    90
2 SEQ_32     ATGACAGTCTTGGAAATAACTTTGGCTGTCATCCTGACTCTACTGGGACTTGCCATCCTGGCTATTTTGTTAACAAGATGGGCACGA CGT   90
3 SEQ_33     ATGACAGTCTTGGAAATAACTTTGGCTGTCATCCTGACTCTACTGGGACTTGCCATCCTGGCTATTTTGTTAACAAGATGGGCACGATGT    90
4 SEQ_29     ATGACAGTCTTGGAAATAACTTTGGCTGTCATCCTGACTCTACTGGGACTTGCCATCCTGGCTATTTTGTTAACAAGATGGGCACGACGT    90

1 SEQ_31     AAGCAAAGTGAAATGTATATCTCCAGATACAGTTCAGA ACAAAGTGCTAGACTTCTGGACTATGAGGATGGTAGAGGATCCCGACATGCA   180
2 SEQ_32     AAGCAAAGTGAAATGCATATCTCCAGATACAGTTCAGAACAAAGTGCTAGACTTCTGGACTATGAGGATGGTAGAGGATCCCGACATGCA    180
3 SEQ_33     AAGCAAAGTGAAATGTATATCTCCAGATACAGTTCAGAACAAAGTGCTAGACTTCTGGACTATGAG GATGGTAGAGGATCCCGACATGCA   180
4 NM_006781  AAGCAAAGTGAAATGTATATCTCCAGATACAGTTCAGAACAAAGTGCTAGACTTCTGGACTATGAGGATGGTAGAGGATCCCGACATGCA    180

1 SEQ_31     TATTCAACACAAAGTGACACTTCATATGATAACCGAGAGAGATCCAAAA-GAGATTACACACCATCAACCAACTCTCTAGCACTGTCTCG    269
2 SEQ_32     TATTCAACACAAAGTGACACTTCAT GTGATAACCGAGAGAGATCCAAAA-GAGATTACACACCATCAACCAACTCTCTAGCACTGTCTCG   269
3 SEQ_33     TATTCAACACAAAGTG---------------------AGAGATCCAAAA-GAGATTACACACCATCAACCAACTCTCTAGCACTGTCTCG    248
4 SEQ_29     TAT-CAACACAAAGTGACACTTCATATGATAACCGAGAGAGATCCAAAA AGAGATTACACACCATCAACCAACTCTCTAGCACTGTCTCG   269

1 SEQ_31     ATCAAGTATTGCTTTACCTCAAGGATCCATGAGTAGTATAAAATGTTTACAAACAACTGAAGAACCTCCTTCCAGAACTGCAGGAGCCAT    359
2 SEQ_32     ATCAAGTATTGCTTTACCTCAAGGATCCATGA GTAGTATAAAATGTTTACAAACAACTGAAGAAC TTCCTTCCAGAACTGCAGGAGCCAT  359
3 SEQ_33     ATCAAGTATTGCTTTACCTCAAGGATCCATGAGTAGTATAAAATGTTTACAAACAACTGAAGAACCTCCTTCCAGAACTGCAGGAGCCAT    338
4 SEQ_29     ATCAAGTATTGCTTTACCTCAAGGATCCATGAGTAGTATAAAATGTTTACAAACAACTGA AGAACCTCCTTCCAGAACTGCAGGAGCCAT   359

1 SEQ_31     GATGCAATTCACAGCCCCTATTCCCGGAGCTACAGGACCTATCAAGCTCTCTCAAAAAACCATTGTGCAAACTCCAGGACCTATTGTACA    449
2 SEQ_32     GATGCAATTCACAGCCCCTATTCCCGGAGCTACAGGACCTATCAAGCTCTCTCAAAAAACCATTGTGCAAACTCCAGGACCTATTG TACA   449
3 SEQ_33     GATGCAATTCACAGCCCCTATTCCCGGAGCTACAGGACCTATCAAGCTCTCTCAAAAAACCATTGTGCAAACTCCAGGACCTATTGTACA    428
4 SEQ_29     GATGCAATTCACAGCCC-TATTCCCGGAGCTACAGGACCTATCAAGCTCTCTCAAAAAACCATTGTGCAAACTCCAGGACCTATTGTACA    448

1 SEQ_31     ATATCCTGGATCCAATG------------------------CTGGTCCACCTTCAGCACCCCGCGGTCCACCCATGGCACCCATAATAAT    515
2 SEQ_32     ATATCCTGGACCCAATGTCAGATCGCATCCTCACACAATCACTGGTCCACCTTCAGCACCCCGCGGTCCACCCATGGCACCCATAATAAT    539
3 SEQ_33     ATATCCTGGATCCAATG------------------------CTGGTCCACCTTCAGCACCCCGCGGTCCACCCATGGCACCCATAATAAT    494
4 SEQ_29     ATATC-TGGATCCAATGTCAGATCGCATC-TCACACAATCACTGGTC-ACCTTCAGCACCC-GCGGTC-ACCCATGGCACCCATAATAAT    533

1 SEQ_31     TTCACAGAGAACCGCAAGTCAGCTGGCAGCACCTATAATAATTTCGCAGAGA ACTGCAAGAATACCTCAAGTTCACACTATGGACAGTTC  605
2 SEQ_32     TTCACAGAGAACCGCAAGTCAGCTGGCAGCACCTATAATAATTTCGCAGAGAACTGCAAGAATACCTCAAGTTCACACTATGGACAGTTC    629
3 SEQ_33     TTCACAGAGAACCGCAAGTCAGCTGGCAGCACCTATAATAATTTCGCAGAGAACTGCAAGAATACCTCAAGTTCACACTA TGGACAGTTC   584
4 SEQ_29     TTCACAGAGAACCGCAAGTCAGCTGGCAGCACCTATAA---------------------GAATACCTCAAGTTCACACTATGGACAGTTC    602
```

Fig. 7a

```
1 SEQ_31   TGGAAAAATCACACTGACTCCTGTGGTTATATTAACAGGTTACATGGATGAAGAACTTGCAAAAAAATCTTGTTCCAAAATCCAGATTCT   695
2 SEQ_32   TGGAAAAACCACACTGACTCCTGTGGTTATATTAACAGGTTACATGGATGAAGAACTTGCAAAAAAATCTTGTTCCAAAATCCAGATTCT   719
3 SEQ_33   TGGAAAAATCACACTGACTCCTGTGGTTATATTAACAGGTTACATGGATGAAGAACTTGCAAAAAAATCTTGTTCCAAAATCCAGATTCT   674
4 SEQ_29   TGGAAAAATCACACTGACTCCTGTGGTTATATTAACAGGTTACATGGACGAAGAACTTCGAAAAAAATCTTGTTCCAAAATCCAGATTCT   692

1 SEQ_31   AAAATGTGGAGGCACTGCAAGGTCTCAGAATAGCCGAGAAGAAAACAAGGAAGCA-CTAAAGAATGACATCATATTTACGAATTCTGTAG   784
2 SEQ_32   AAAATGTGGAGGCACTGCAAGGTCTCAGAATAGCCGAGAAGAAAACAAGGAAGCA-CTAAAGAATGACATCATATTTACGAATTCTGTAG   808
3 SEQ_33   AAAATGTGGAGGCACTGCAAGGTCTCAGAATAGCCGAGAAGAAAACAAGGAAGCA-CTAAAGAATGACATCATATTTACGAATTCTGTAG   763
4 SEQ_29   AAAATGTGGAGGCACTGCAAGGTCTCAGA-TAGCCGAGAAGAAAACAAGGAAGCAACTAAAGAATGACATCATATTTACGAATTCTGTAG   781

1 SEQ_31   AATCCTTGAAATCAGCACACATAAAGGAGCCAGAAAGAGAAGGAAAAGGCACTGATTTAGAGAAAGACAAAATAGGAATGGAGGTCAAGG   874
2 SEQ_32   AATCCTTGAAATCAGCACACATAAAGGAGCCAGAAAGAGAAGGAAAAGGCACTGATTTAGAGAAAGACAAAATAGGAATGGAGGTCAAGG   898
3 SEQ_33   AATCCTTGAAATCAGCACACATAAAGGAGCCAGAAAGAGAAGGAAAAGGCACTGATTTAGAGAAAGACAAAATAGGAATGGAGGTCAAGG   853
4 SEQ_29   AATCCTTGAAATCAGCACACATAAAGGAGCCAGAAAGAGAAGGAAAAGGCACTGATTTAGAGAAAGACAAAATAGGAATGGAGGTCAAGG   871

1 SEQ_31   TAGACAGTGACGCTGGAATACCAAAAAGACAGGAAACCCAACTAAAAATCAGTGA-GATGAGTATACCACAAGGACAGGGAGCCCAAATA   963
2 SEQ_32   TAGACAGTGACGCTGGAATACCAAAAAGACAGGAAACCCAACTAAAAATCAGTGA-GATGAGTATACCACAAGGACAGGGAGCCCAAATA   987
3 SEQ_33   TAGACAGTGACGCTGGAATACCAAAAAGACAGGAAACCCAACTAAAAATCAGTGA-GATGAGTATACCACAAGGACAGGGAGCCCAAATA   942
4 SEQ_29   TAGACAGTGACGCTGGAATACCAAAAAGACAGGAAACCCAACTAAAAATCAGTGAAGATGAGTATACCACAAGGACAGGGAGCCCAAATA   961

1 SEQ_31   AAGAAAAGTGTGTCAGATGTACCAAGAGGACAGGAGTCCCAAGTAAAGAAGAGTGAGTCAGGTGTCCCAAAAGGACAAGAAGCCCAAGTA   1053
2 SEQ_32   AAGAAAAGTGTGTCAGATGTACCAAGAGGACAGGAGTCCCAAGTAAAGAAGAGTGAGTCAGGTGTCCCAAAAGGACAAGAAGCCCAAGTA   1077
3 SEQ_33   AAGAAAAGTGTGTCAGATGTACCAAGAGGACAGGAGTCCCAAGTAAAGAAGAGTGAGTCAGGTGTCCCAAAAGGACAAGAAGCCCAAGTA   1032
4 SEQ_29   AAGAAAAGTGTGTCAGATGTACCAAGAGGACAGGAGTCC-AAGTAAAGAAGAGTGAGTCAGGTGTCCCAAAAGGACAAGAAGCCCAAGTA   1050

1 SEQ_31   ACGAAGAGTGGGTTGGTTGTACTGAAAGGACAGGAAGCCCAGGTAGAGAAGAGTGAGATGGGTGTGCCAAGAAGACAGGAATCCCAAGTA   1143
2 SEQ_32   ACGAAGAGTGGGTTGGTTGTACTGAAAGGACAGGAAGCCCAGGTAGAGAAGAGTGAGATGGGTGTGCCAAGAAGACAGGAATCCCAAGTA   1167
3 SEQ_33   ACGAAGAGTGGGTTGGTTGTACTGAAAGGACAGGAAGCCCAGGTAGAGAAGAGTGAGATGGGTGTGCCAAGAAGACAGGAATCCCAAGTA   1122
4 SEQ_29   ACGAAGAGTGGGTTGGTTGTACTGAAAGGACAGGAAGCCCAGGTAGAGAAGAGTGAGATGGGTGTGCCAAGAAGACAGGAATCCCAAGTA   1140

1 SEQ_31   AAGAAGAGTCAGTCTGGTGTCTCAAAGGGACAGGAAGCCCAGGTAAAGAAGAGGGAGTCAGTTGTACTGAAAGGACAGGAAGCCCAGGTA   1233
2 SEQ_32   AAGAAGAGTCAGTCTGGTGTCTCAAAGGGACAGGAAGCCCAGGTAAAGAAGAGGGAGTCAGTTGTACTGAAAGGACAGGAAGCCCAGGTA   1257
3 SEQ_33   AAGAAGAGTCAGTCTGGTGTCTCAAAGGGACAGGAAGCCCAGGTAAAGAAGAGGGAGTCAGTTGTACTGAAAGGACAGGAAGCCCAGGTA   1212
4 SEQ_29   AAGAAGAGTCAGTCTGGTGTCTCAAAGGGACAGGAAGCCCAGGTAAAGAAGAGGGAGTCAGTTGTACTGAAAGGACAGGAAGCCCAGGTA   1230
```

Fig. 7b

```
1 SEQ_36      MTVLEITLAVILTLLGLAILAILLTRWARCKQSEMYISRYSSEQSARLLDYEDGRGSRHAYSTQS --------ERSKRDYTPSTNSLALSR   83
2 SEQ_34      MTVLEITLAVILTLLGLAILAILLTRWARCKQSEMYISRYSSEQSARLLDYEDGRGSRHAYSTQSDTSYDNRERSKRDYTPSTNSLALSR   90
3 SEQ_35      MTVLEITLAVIL TLLGLAILAILLTRWARRKQSEMHISRYSSEQSARLLDYEDGRGSRHAYSTQSDTS CDNRERSKRDYTPSTNSLALSR   90
4 NM_006781 MTVLEITLAVILTLLGLAILAILLTRWAR RKQSEMYISRYSSEQSARLLDYEDGRGSRHAY QHKVTLHMITERDPKRDYTPSTNSLALSR   90

1 SEQ_36      SSIALPQGSMSSIKCLQTTEEPPSRTAGAMMQFTAPIP GATGPIKLSQKTIVQTPGPIVQYPGSN--------AGPPSAPRGPPMAPIII   165
2 SEQ_34      SSIALPQGSMSSIKCLQTTEEPPSRTAGAMMQFTAPIPGATGPIKLSQKTIVQTPGPIVQYPGSN ---------AGPPSAPRGPPMAPIII   172
3 SEQ_35      SSIALPQGSMSSIKCLQTTEE LPSRTAGAMMQFTAPIPGATGPIKLSQKTIVQTPGPIVQYPG PNVRSHPHTITGPPSAPRGPPMAPIII   180
4 NM_006781 SSIALPQGSMSSIKCLQTTEEPPSRTAGAMMQFTA LFPELQDLSSSLKKPLCKLQDLLYNIWIQCQIAS --HTITGHLQHPRSPMAPIII   178

1 SEQ_36      SQRTASQLAAPIIISQRTARIPQVHTMDSSGKITLTPVVILTGYMDEELAKKSCSKIQILKCGGTARSQNSREENKEALKNDIIFTNSVE   255
2 SEQ_34      SQRTASQLAAPIIISQRTARIPQVHTMDSSGKITLTPVVILTGYMDEELAKKSCSKIQILKCGGTARSQNSREENKEALKNDIIFTNSVE   262
3 SEQ_35      SQRTASQLAAPIIISQRTARIPQVHTMDSSGK TTLTPVVILTGYMDEELAKKSCSKIQILKCGGTARSQNSREENKEALKNDIIFTNSVE   270
4 NM_006781 SQRTASQLAAPI-------RIPQVRTMDSSGKITLTPVVILTGYMDEELRKKSCSKIQILKCGGTARSQ IAEKKTRKQLKNDIIFTNSVE   261

1 SEQ_36      SLKSAHIKEPEREGKGTDLEKDKIGMEVKVDSDAGIPKRQETQLKISEMSIPQGQGAQIKKSVSDVPRGQESQVKKSESGVPKGQEAQVT   345
2 SEQ_34      SLKSAHIKEPEREGKGTDLEKDKIGMEVKVDS DAGIPKRQETQLKISEMSIPQGQGAQIKKSVSDVPRGQESQVKKSESGVPKGQEAQVT   352
3 SEQ_35      SLKSAHIKEPEREGKGTDLEKDKIGMEVKVDSDAGIPKRQETQLKISEMSIPQGQGAQIKKSVSDVPRGQESQVKKSESGVPKGQEAQVT   360
4 NM_006781 SLKSAHIKEPEREGKGTDLEKDKIGMEVKVDSDAGIPKRQETQLKISE DEYTTRTGSPNKEKCVRCTKRTGVQVKKSESGVPKGQEAQVT   351

1 SEQ_36      KSGLVVLKGQEAQVEKSEMGVPRRQESQVKKSQSGVSKGQEAQVKKRESVVLKGQEAQVEKSELKVPKGQEGQVEKTEADVPKEQEVQEK   435
2 SEQ_34      KSGLVVLKGQEAQVEKSEMGVPRRQESQVKKSQSGVSKGQEAQVKKRESVVLKGQEAQVEKSELKVPKGQEGQVEKTEADVPKEQE VQEK   442
3 SEQ_35      KSGLVVLKGQEAQVEKSEMGVPRRQESQVKKSQSGVSKGQEAQVKKRESVVLKGQEAQVEKSELKVPKGQEGQVEKTEADVPKEQEVQEK   450
4 NM_006781 KSGLVVLKGQEAQVEKSEMGVPRRQESQVKKSQSGVSKGQEAQVKKRESVVLKGQEAQVEKSELKVPKGQEGQVEKTEADVPKEQEVQEK   441

1 SEQ_36      KSEAGVLKGPESQVKNTEVSVPETLESQVKKSESGVLKGQEAQEKKESFEDKGNNDKEKERDAEKDPNKKEKGDKNTKGDKGKDKVKGKR   525
2 SEQ_34      KSEAGVLKGPESQVKNTEVSVPETLESQVKKSESGVLKGQEAQEKKESFEDKGNNDKEKERDAEKDPNKKEKGDKNTKGDKGKDKVKGKR   532
3 SEQ_35      KSEAGVLKGPESQVKNTEVSVPETLE SQVKKSESGVLKGQEAQEKKESFEDKGNNDKEKERDAEKDPNKKEKGDKNTKGDKGKDKVKGKR   540
4 NM_006781 KSEAGVLKGPESQVKNTEVSVPETLESQVKKSESGVLKGQEAQEKKESFEDKGNNDKEKERDAEKDPNKKEKGDKNTKGDKGKDKVKGKR   531

1 SEQ_36      ESEINGEKSKGSKRAKANTGRKYNKKVEE --------   554
2 SEQ_34      ESEINGEKSKGSKRAKANTGRKYNKKVEE --------   561
3 SEQ_35      ESEINGEKSKGSKRAKANTGRKYNKKVEE --------   569
4 NM_006781 ESEINGEKSKGSKRRRQIQEGSTTKKWKSKDKFFKGP   568
```

Fig. 8

N Colon, normal
T Colorectal tumors

Tumors

Normal tissue

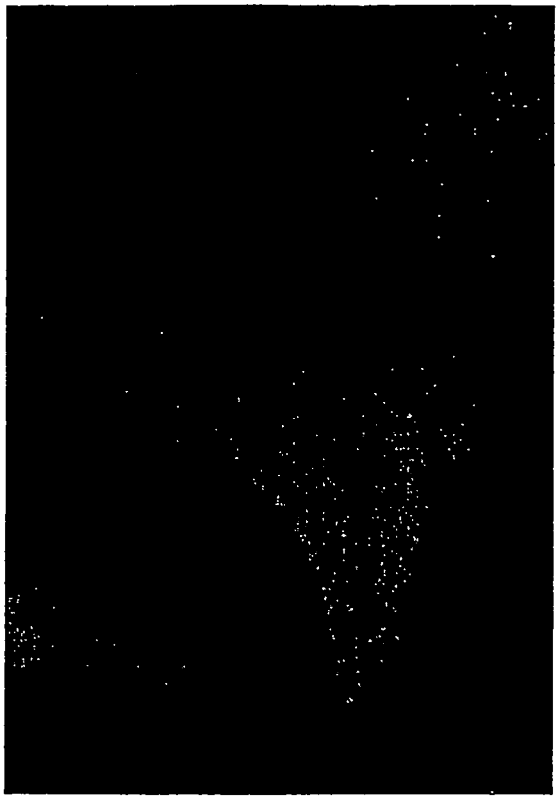
HCT 116 DKO
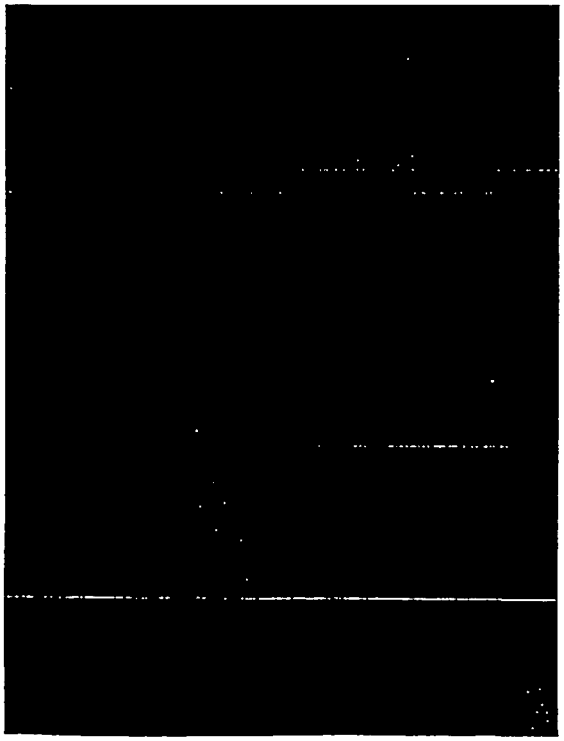
HCT 116 P
Fig. 16

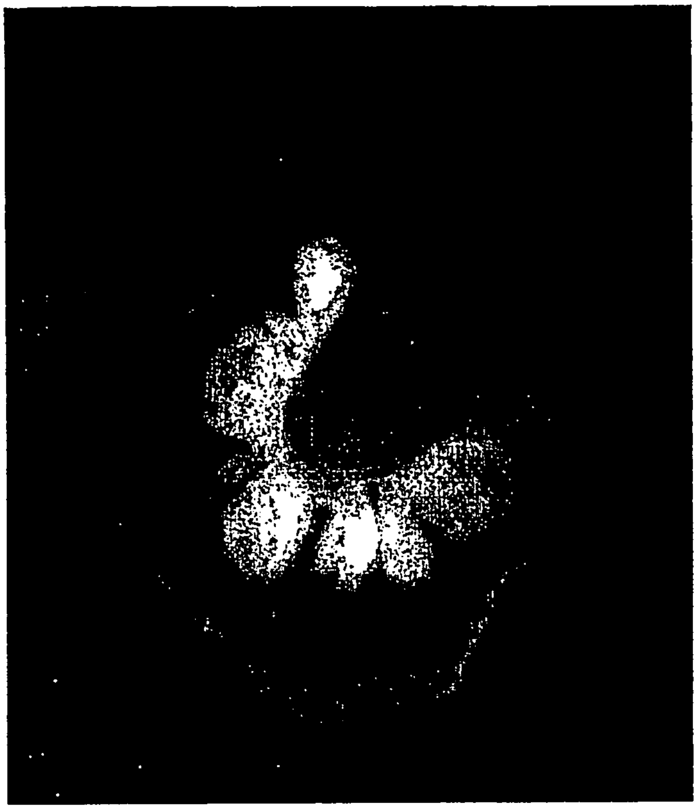
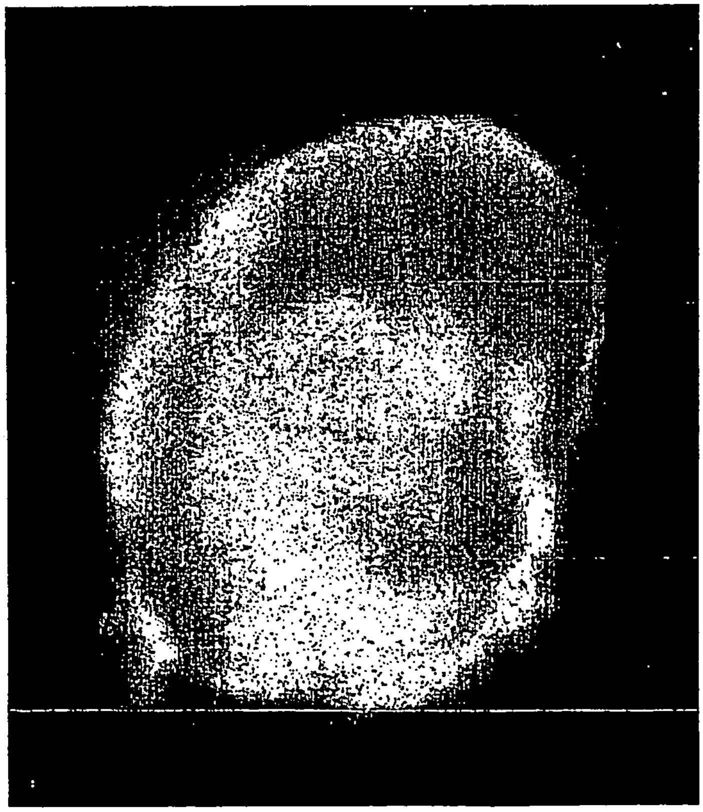
Fig. 18

| | Lymph node metastasis | | Metastasis in other organs | |
|---|---|---|---|---|
| | N- | N+ | M- | M+ |
| TPTE-negative | 16/25<br>64% | 9/25<br>36% | 25/25<br>100% | 0/25<br>0% |
| TPTE-positive | 8/33<br>24% | 25/33<br>75% | 26/33<br>78% | 7/33<br>21% |
| | p<0,01 | | p<0,02 | |

Fig. 24

HCT 116 DKO
HCT 116 P
Fig. 25

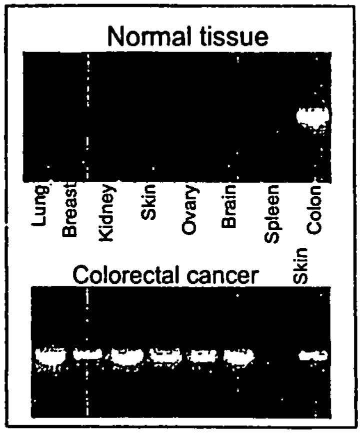
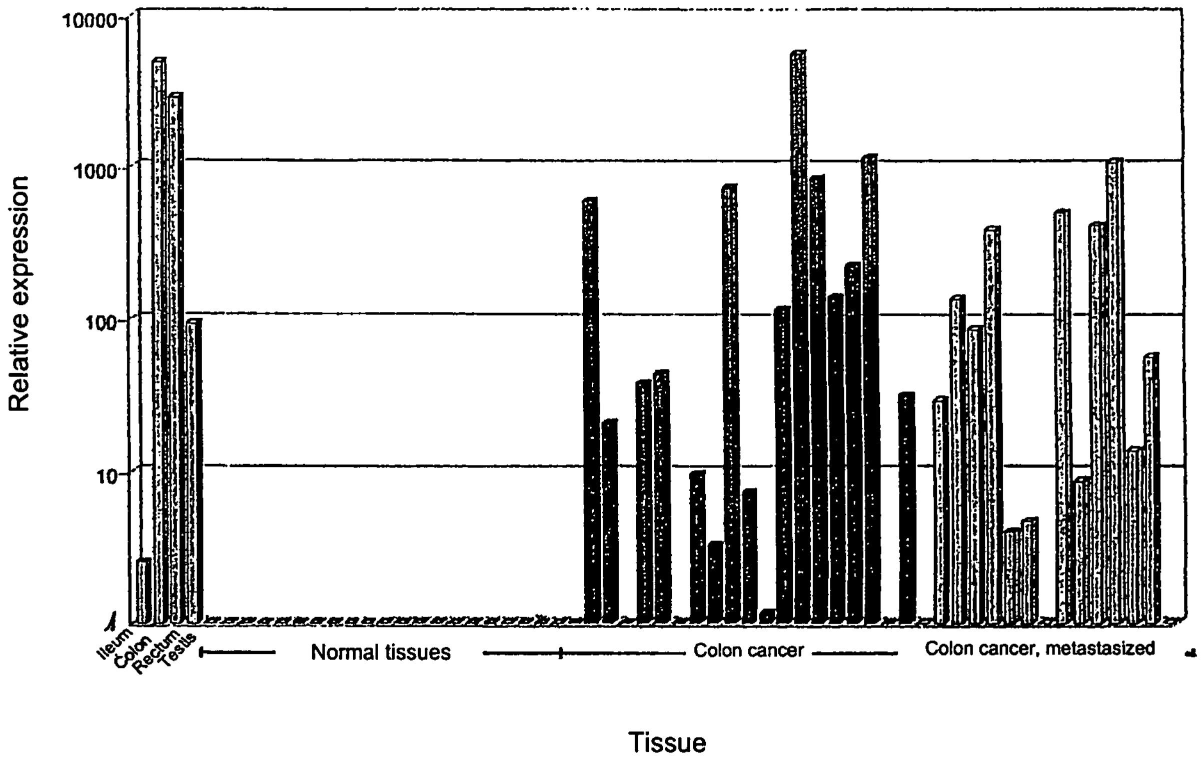
Fig. 26
| Cancer type | Expression |
|---|---|
| Colorectal, primary | 80% |
| Colorectal, metast. | 80% |
| Esophagus | 28% |

Colon cancer
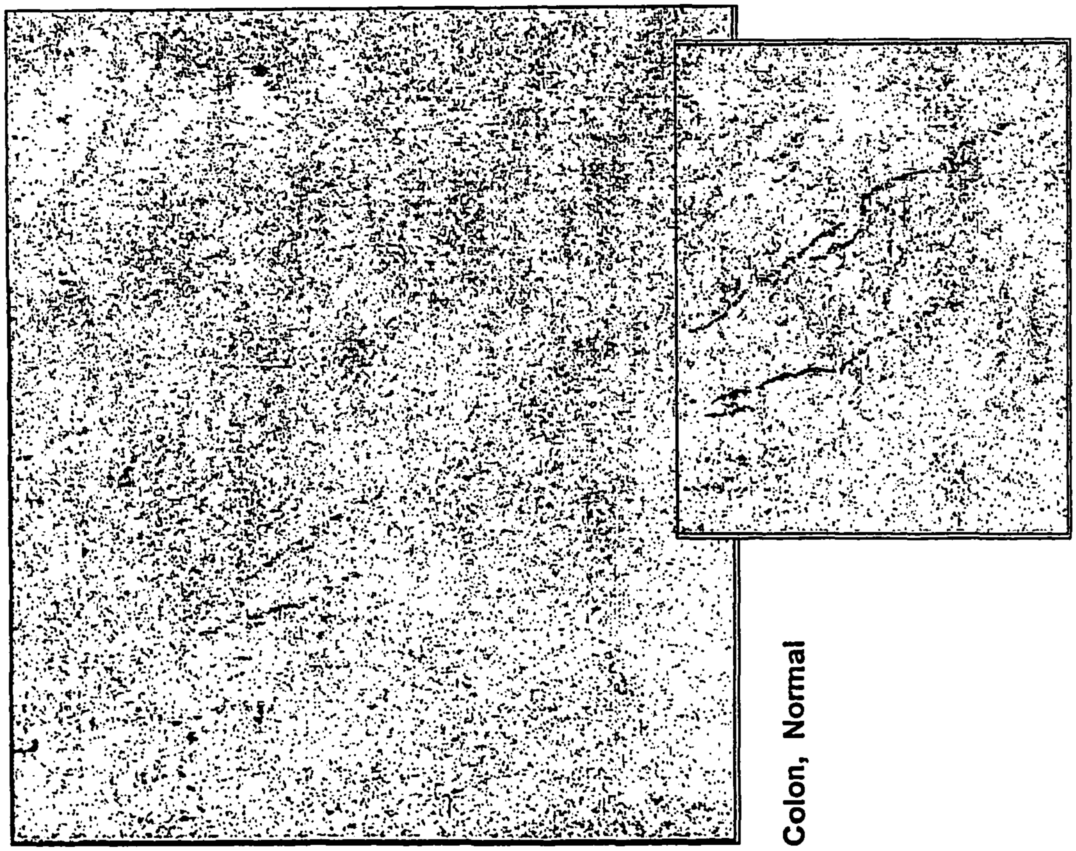
Colon, Normal
Fig. 29

SEQUENCE LISTING

```
<160> NUMBER OF SEQ ID NOS: 830

<210> SEQ ID NO 1
<211> LENGTH: 1171
<212> TYPE: DNA
<213> ORGANISM: Homo sapiens

<400> SEQUENCE: 1

ctgtcgttgg tgtatttttc tggtgtcact tctgtgcctt ccttcaaagg ttctccaaat      60

gtcaactgtc aaggagcagc taattgagaa gctaattgag gatgatgaaa actcccagtg     120

taaaattact attgttggaa ctggtgccgt aggcatggct tgtgctatta gtatcttact     180

gaaggatttg gctgatgaac ttgcccttgt tgatgttgca ttggacaaac tgaagggaga     240

aatgatggat cttcagcatg gcagtctttt ctttagtact tcaaagatta cttctggaaa     300

agattacagt gtatctgcaa actccagaat agttattgtc acagcaggtg caaggcagca     360

ggagggagaa actcgccttg ccctggtcca acgtaatgtg gctataatga aatcaatcat     420

tcctgccata gtccattata gtcctgattg taaaattctt gttgtttcaa atccagtgga     480

tattttgaca tatatagtct ggaagataag tggcttacct gtaactcgtg taattggaag     540

tggttgtaat ctagactctg cccgtttccg ttacctaatt ggagaaaagt tgggtgtcca     600

ccccacaagc tgccatggtt ggattattgg agaacatggt gattctagtg tgcccttatg     660

gagtggggtg aatgttgctg gtgttgctct gaagactctg gaccctaaat taggaacgga     720

ttcagataag gaacactgga aaaatatcca taaacaagtt attcaaagtg cctatgaaat     780

tatcaagctg aaggggtata cctcttgggc tattggactg tctgtgatgg atctggtagg     840

atccattttg aaaaatctta ggagagtgca cccagtttcc accatggtta agggattata     900

tggaataaaa gaagaactct ttctcagtat cccttgtgtc ttggggcgga atggtgtctc     960

agatgttgtg aaaattaact tgaattctga ggaggaggcc cttttcaaga agagtgcaga    1020

aacactttgg aatattcaaa aggatctaat attttaaatt aaagccttct aatgttccac    1080
```

tgtttggaga acagaagata gcaggctgtg tattttaaat tttgaaagta ttttcattga 1140
tcttaaaaaa taaaaacaaa ttggagacct g 1171

<210> SEQ ID NO 2
<211> LENGTH: 1053
<212> TYPE: DNA
<213> ORGANISM: Homo sapiens

<400> SEQUENCE: 2
ctgtcgttgg tgtatttttc tggtgtcact tctgtgcctt ccttcaaagg ttctccaaat 60
gtcaactgtc aaggagcagc taattgagaa gctaattgag gatgatgaaa actcccagtg 120
taaaattact attgttggaa ctggtgccgt aggcatggct tgtgctatta gtatcttact 180
gaagattaca gtgtatctgc aaactccaga atagttattg tcacagcagg tgcaaggcag 240
caggagggag aaactcgcct tgccctggtc caacgtaatg tggctataat gaaatcaatc 300
attcctgcca tagtccatta tagtcctgat tgtaaaattc ttgttgtttc aaatccagtg 360
gatattttga catatatagt ctggaagata agtggcttac ctgtaactcg tgtaattgga 420
agtggttgta atctagactc tgcccgtttc cgttacctaa ttggagaaaa gttgggtgtc 480
caccccacaa gctgccatgg ttggattatt ggagaacatg gtgattctag tgtgccctta 540
tggagtgggg tgaatgttgc tggtgttgct ctgaagactc tggaccctaa attaggaacg 600
gattcagata aggaacactg gaaaaatatc cataaacaag ttattcaaag tgcctatgaa 660
attatcaagc tgaaggggta tacctcttgg gctattggac tgtctgtgat ggatctggta 720
ggatccattt tgaaaaatct taggagagtg cacccagttt ccaccatggt taagggatta 780
tatggaataa aagaagaact ctttctcagt atcccttgtg tcttggggcg gaatggtgtc 840
tcagatgttg tgaaaattaa cttgaattct gaggaggagg cccttttcaa gaagagtgca 900
gaaacacttt ggaatattca aaaggatcta atattttaaa ttaaagcctt ctaatgttcc 960
actgtttgga gaacagaaga tagcaggctg tgtattttaa attttgaaag tattttcatt 1020
gatcttaaaa aataaaaaca aattggagac ctg 1053

<210> SEQ ID NO 3
<211> LENGTH: 879
<212> TYPE: DNA
<213> ORGANISM: Homo sapiens

<400> SEQUENCE: 3
ctgtcgttgg tgtatttttc tggtgtcact tctgtgcctt ccttcaaagg ttctccaaat 60
gtcaactgtc aaggagcagc taattgagaa gctaattgag gatgatgaaa actcccagtg 120
taaaattact attgttggaa ctggtgccgt aggcatggct tgtgctatta gtatcttact 180
gaagtggata ttttgacata tatagtctgg aagataagtg gcttacctgt aactcgtgta 240
attggaagtg gttgtaatct agactctgcc cgtttccgtt acctaattgg agaaaagttg 300
ggtgtccacc ccacaagctg ccatggttgg attattggag aacatggtga ttctagtgtg 360
cccttatgga gtggggtgaa tgttgctggt gttgctctga agactctgga ccctaaatta 420
ggaacggatt cagataagga acactggaaa aatatccata aacaagttat tcaaagtgcc 480
tatgaaatta tcaagctgaa ggggtatacc tcttgggcta ttggactgtc tgtgatggat 540
ctggtaggat ccattttgaa aaatcttagg agagtgcacc cagtttccac catggttaag 600
ggattatatg gaataaaaga agaactcttt ctcagtatcc cttgtgtctt ggggcggaat 660
ggtgtctcag atgttgtgaa aattaacttg aattctgagg aggaggccct tttcaagaag 720
agtgcagaaa cactttggaa tattcaaaag gatctaatat tttaaattaa agccttctaa 780
tgttccactg tttggagaac agaagatagc aggctgtgta ttttaaattt tgaaagtatt 840
ttcattgatc ttaaaaaata aaaacaaatt ggagacctg 879

<210> SEQ ID NO 4
<211> LENGTH: 811
<212> TYPE: DNA
<213> ORGANISM: Homo sapiens

<400> SEQUENCE: 4
ctgtcgttgg tgtatttttc tggtgtcact tctgtgcctt ccttcaaagg ttctccaaat 60
gtcaactgtc aaggagcagc taattgagaa gctaattgag gatgatgaaa actcccagtg 120
taaaattact attgttggaa ctggtgccgt aggcatggct tgtgctatta gtatcttact 180
gaagattaca gtgtatctgc aaactccaga atagttattg tcacagcagg tgcaaggcag 240
caggagggag aaactcgcct tgccctggtc caacgtaatg tggctataat gaaatcaatc 300
attcctgcca tagtccatta tagtcctgat tgtaaaattc ttgttgtttc aaatccagtg 360
gatattttga catatatagt ctggaagata agtggcttac ctgtaactcg tgtaattgga 420
agtggttgta atctagactc tgcccgtttc cgttacctaa ttggagaaaa gttgggtgtc 480
caccccacaa gctgccatgg ttggattatt ggagaacatg gtgattctag tgggattata 540
tggaataaaa gaagaactct ttctcagtat cccttgtgtc ttggggcgga atggtgtctc 600
agatgttgtg aaaattaact tgaattctga ggaggaggcc cttttcaaga agagtgcaga 660
aacactttgg aatattcaaa aggatctaat attttaaatt aaagccttct aatgttccac 720
tgtttggaga acagaagata gcaggctgtg tattttaaat tttgaaagta ttttcattga 780
tcttaaaaaa taaaaacaaa ttggagacct g 811

<210> SEQ ID NO 5
<211> LENGTH: 1047
<212> TYPE: DNA
<213> ORGANISM: Homo sapiens

<400> SEQUENCE: 5
ctgtcgttgg tgtatttttc tggtgtcact tctgtgcctt ccttcaaagg ttctccaaat 60
gtcaactgtc aaggagcagc taattgagaa gctaattgag gatgatgaaa actcccagtg 120
taaaattact attgttggaa ctggtgccgt aggcatggct tgtgctatta gtatcttact 180
gaaggatttg gctgatgaac ttgcccttgt tgatgttgca ttggacaaac tgaagggaga 240
aatgatggat cttcagcatg gcagtctttt ctttagtact tcaaagatta cttctggaaa 300
agattacagt gtatctgcaa actccagaat agttattgtc acagcaggtg caaggcagca 360
ggagggagaa actcgccttg ccctggtcca acgtaatgtg gctataatga aatcaatcat 420
tcctgccata gtccattata gtcctgattg taaaattctt gttgtttcaa atccagtgga 480
tattttgaca tatatagtct ggaagataag tggcttacct gtaactcgtg taattggaag 540
tggttgtaat ctagactctg cccgtttccg ttacctaatt ggagaaaagt tgggtgtcca 600
ccccacaagc tgccatggtt ggattattgg agaacatggt gattctagtg tgcccttatg 660
gagtggggtg aatgttgctg gtgttgctct gaagactctg gaccctaaat taggaacgga 720
ttcagataag gaacactgga aaaatatcca taaacaagtt attcaaaggg attatatgga 780
ataaaagaag aactctttct cagtatccct tgtgtcttgg ggcggaatgg tgtctcagat 840

-continued

```
gttgtgaaaa ttaacttgaa ttctgaggag gaggcccttt tcaagaagag tgcagaaaca    900

ctttggaata ttcaaaagga tctaatattt taaattaaag ccttctaatg ttccactgtt    960

tggagaacag aagatagcag gctgtgtatt ttaaattttg aaagtatttt cattgatctt   1020

aaaaaataaa aacaaattgg agacctg                                       1047


<210> SEQ ID NO 6
<211> LENGTH: 332
<212> TYPE: PRT
<213> ORGANISM: Homo sapiens

<400> SEQUENCE: 6

Met Ser Thr Val Lys Glu Gln Leu Ile Glu Lys Leu Ile Glu Asp Asp
1               5                   10                  15

Glu Asn Ser Gln Cys Lys Ile Thr Ile Val Gly Thr Gly Ala Val Gly
            20                  25                  30

Met Ala Cys Ala Ile Ser Ile Leu Leu Lys Asp Leu Ala Asp Glu Leu
        35                  40                  45

Ala Leu Val Asp Val Ala Leu Asp Lys Leu Lys Gly Glu Met Met Asp
    50                  55                  60

Leu Gln His Gly Ser Leu Phe Phe Ser Thr Ser Lys Ile Thr Ser Gly
65                  70                  75                  80

Lys Asp Tyr Ser Val Ser Ala Asn Ser Arg Ile Val Ile Val Thr Ala
                85                  90                  95

Gly Ala Arg Gln Gln Glu Gly Glu Thr Arg Leu Ala Leu Val Gln Arg
            100                 105                 110

Asn Val Ala Ile Met Lys Ser Ile Ile Pro Ala Ile Val His Tyr Ser
        115                 120                 125

Pro Asp Cys Lys Ile Leu Val Val Ser Asn Pro Val Asp Ile Leu Thr
    130                 135                 140

Tyr Ile Val Trp Lys Ile Ser Gly Leu Pro Val Thr Arg Val Ile Gly
145                 150                 155                 160

Ser Gly Cys Asn Leu Asp Ser Ala Arg Phe Arg Tyr Leu Ile Gly Glu
                165                 170                 175

Lys Leu Gly Val His Pro Thr Ser Cys His Gly Trp Ile Ile Gly Glu
            180                 185                 190

His Gly Asp Ser Ser Val Pro Leu Trp Ser Gly Val Asn Val Ala Gly
        195                 200                 205

Val Ala Leu Lys Thr Leu Asp Pro Lys Leu Gly Thr Asp Ser Asp Lys
    210                 215                 220

Glu His Trp Lys Asn Ile His Lys Gln Val Ile Gln Ser Ala Tyr Glu
225                 230                 235                 240

Ile Ile Lys Leu Lys Gly Tyr Thr Ser Trp Ala Ile Gly Leu Ser Val
                245                 250                 255

Met Asp Leu Val Gly Ser Ile Leu Lys Asn Leu Arg Arg Val His Pro
            260                 265                 270

Val Ser Thr Met Val Lys Gly Leu Tyr Gly Ile Lys Glu Glu Leu Phe
        275                 280                 285

Leu Ser Ile Pro Cys Val Leu Gly Arg Asn Gly Val Ser Asp Val Val
    290                 295                 300

Lys Ile Asn Leu Asn Ser Glu Glu Glu Ala Leu Phe Lys Lys Ser Ala
305                 310                 315                 320

Glu Thr Leu Trp Asn Ile Gln Lys Asp Leu Ile Phe
                325                 330
```

<210> SEQ ID NO 7
<211> LENGTH: 51
<212> TYPE: PRT
<213> ORGANISM: Homo sapiens

<400> SEQUENCE: 7

```
Met Ser Thr Val Lys Glu Gln Leu Ile Glu Lys Leu Ile Glu Asp Asp
1               5                   10                  15

Glu Asn Ser Gln Cys Lys Ile Thr Ile Val Gly Thr Gly Ala Val Gly
            20                  25                  30

Met Ala Cys Ala Ile Ser Ile Leu Leu Lys Ile Thr Val Tyr Leu Gln
        35                  40                  45

Thr Pro Glu
    50
```

<210> SEQ ID NO 8
<211> LENGTH: 216
<212> TYPE: PRT
<213> ORGANISM: Homo sapiens

<400> SEQUENCE: 8

```
Met Lys Ser Ile Ile Pro Ala Ile Val His Tyr Ser Pro Asp Cys Lys
1               5                   10                  15

Ile Leu Val Val Ser Asn Pro Val Asp Ile Leu Thr Tyr Ile Val Trp
            20                  25                  30

Lys Ile Ser Gly Leu Pro Val Thr Arg Val Ile Gly Ser Gly Cys Asn
        35                  40                  45

Leu Asp Ser Ala Arg Phe Arg Tyr Leu Ile Gly Glu Lys Leu Gly Val
    50                  55                  60

His Pro Thr Ser Cys His Gly Trp Ile Ile Gly Glu His Gly Asp Ser
65                  70                  75                  80

Ser Val Pro Leu Trp Ser Gly Val Asn Val Ala Gly Val Ala Leu Lys
                85                  90                  95

Thr Leu Asp Pro Lys Leu Gly Thr Asp Ser Asp Lys Glu His Trp Lys
            100                 105                 110

Asn Ile His Lys Gln Val Ile Gln Ser Ala Tyr Glu Ile Ile Lys Leu
        115                 120                 125

Lys Gly Tyr Thr Ser Trp Ala Ile Gly Leu Ser Val Met Asp Leu Val
    130                 135                 140

Gly Ser Ile Leu Lys Asn Leu Arg Arg Val His Pro Val Ser Thr Met
145                 150                 155                 160

Val Lys Gly Leu Tyr Gly Ile Lys Glu Glu Leu Phe Leu Ser Ile Pro
                165                 170                 175

Cys Val Leu Gly Arg Asn Gly Val Ser Asp Val Val Lys Ile Asn Leu
            180                 185                 190

Asn Ser Glu Glu Glu Ala Leu Phe Lys Lys Ser Ala Glu Thr Leu Trp
        195                 200                 205

Asn Ile Gln Lys Asp Leu Ile Phe
    210                 215
```

<210> SEQ ID NO 9
<211> LENGTH: 45
<212> TYPE: PRT
<213> ORGANISM: Homo sapiens

<400> SEQUENCE: 9

```
Met Ser Thr Val Lys Glu Gln Leu Ile Glu Lys Leu Ile Glu Asp Asp
```

```
1               5                   10                  15

Glu Asn Ser Gln Cys Lys Ile Thr Ile Val Gly Thr Gly Ala Val Gly
            20                  25                  30

Met Ala Cys Ala Ile Ser Ile Leu Leu Lys Trp Ile Phe
        35                  40                  45


<210> SEQ ID NO 10
<211> LENGTH: 76
<212> TYPE: PRT
<213> ORGANISM: Homo sapiens

<400> SEQUENCE: 10

Met Asp Leu Val Gly Ser Ile Leu Lys Asn Leu Arg Arg Val His Pro
1               5                   10                  15

Val Ser Thr Met Val Lys Gly Leu Tyr Gly Ile Lys Glu Glu Leu Phe
            20                  25                  30

Leu Ser Ile Pro Cys Val Leu Gly Arg Asn Gly Val Ser Asp Val Val
        35                  40                  45

Lys Ile Asn Leu Asn Ser Glu Glu Glu Ala Leu Phe Lys Lys Ser Ala
    50                  55                  60

Glu Thr Leu Trp Asn Ile Gln Lys Asp Leu Ile Phe
65                  70                  75


<210> SEQ ID NO 11
<211> LENGTH: 109
<212> TYPE: PRT
<213> ORGANISM: Homo sapiens

<400> SEQUENCE: 11

Met Lys Ser Ile Ile Pro Ala Ile Val His Tyr Ser Pro Asp Cys Lys
1               5                   10                  15

Ile Leu Val Val Ser Asn Pro Val Asp Ile Leu Thr Tyr Ile Val Trp
            20                  25                  30

Lys Ile Ser Gly Leu Pro Val Thr Arg Val Ile Gly Ser Gly Cys Asn
        35                  40                  45

Leu Asp Ser Ala Arg Phe Arg Tyr Leu Ile Gly Glu Lys Leu Gly Val
    50                  55                  60

His Pro Thr Ser Cys His Gly Trp Ile Ile Gly Glu His Gly Asp Ser
65                  70                  75                  80

Ser Gly Ile Ile Trp Asn Lys Arg Arg Thr Leu Ser Gln Tyr Pro Leu
                85                  90                  95

Cys Leu Gly Ala Glu Trp Cys Leu Arg Cys Cys Glu Asn
            100                 105


<210> SEQ ID NO 12
<211> LENGTH: 66
<212> TYPE: PRT
<213> ORGANISM: Homo sapiens

<400> SEQUENCE: 12

Met Val Gly Leu Leu Glu Asn Met Val Ile Leu Val Gly Leu Tyr Gly
1               5                   10                  15

Ile Lys Glu Glu Leu Phe Leu Ser Ile Pro Cys Val Leu Gly Arg Asn
            20                  25                  30

Gly Val Ser Asp Val Val Lys Ile Asn Leu Asn Ser Glu Glu Glu Ala
        35                  40                  45

Leu Phe Lys Lys Ser Ala Glu Thr Leu Trp Asn Ile Gln Lys Asp Leu
    50                  55                  60
```

Ile Phe
65

<210> SEQ ID NO 13
<211> LENGTH: 241
<212> TYPE: PRT
<213> ORGANISM: Homo sapiens

<400> SEQUENCE: 13

Met Ser Thr Val Lys Glu Gln Leu Ile Glu Lys Leu Ile Glu Asp Asp
1               5                   10                  15

Glu Asn Ser Gln Cys Lys Ile Thr Ile Val Gly Thr Gly Ala Val Gly
            20                  25                  30

Met Ala Cys Ala Ile Ser Ile Leu Leu Lys Asp Leu Ala Asp Glu Leu
        35                  40                  45

Ala Leu Val Asp Val Ala Leu Asp Lys Leu Lys Gly Glu Met Met Asp
    50                  55                  60

Leu Gln His Gly Ser Leu Phe Phe Ser Thr Ser Lys Ile Thr Ser Gly
65                  70                  75                  80

Lys Asp Tyr Ser Val Ser Ala Asn Ser Arg Ile Val Ile Val Thr Ala
                85                  90                  95

Gly Ala Arg Gln Gln Glu Gly Glu Thr Arg Leu Ala Leu Val Gln Arg
            100                 105                 110

Asn Val Ala Ile Met Lys Ser Ile Ile Pro Ala Ile Val His Tyr Ser
        115                 120                 125

Pro Asp Cys Lys Ile Leu Val Val Ser Asn Pro Val Asp Ile Leu Thr
    130                 135                 140

Tyr Ile Val Trp Lys Ile Ser Gly Leu Pro Val Thr Arg Val Ile Gly
145                 150                 155                 160

Ser Gly Cys Asn Leu Asp Ser Ala Arg Phe Arg Tyr Leu Ile Gly Glu
                165                 170                 175

Lys Leu Gly Val His Pro Thr Ser Cys His Gly Trp Ile Ile Gly Glu
            180                 185                 190

His Gly Asp Ser Ser Val Pro Leu Trp Ser Gly Val Asn Val Ala Gly
        195                 200                 205

Val Ala Leu Lys Thr Leu Asp Pro Lys Leu Gly Thr Asp Ser Asp Lys
    210                 215                 220

Glu His Trp Lys Asn Ile His Lys Gln Val Ile Gln Arg Asp Tyr Met
225                 230                 235                 240

Glu

<210> SEQ ID NO 14
<211> LENGTH: 23
<212> TYPE: PRT
<213> ORGANISM: Homo sapiens

<400> SEQUENCE: 14

Gly Ala Val Gly Met Ala Cys Ala Ile Ser Ile Leu Leu Lys Ile Thr
1               5                   10                  15

Val Tyr Leu Gln Thr Pro Glu
            20

<210> SEQ ID NO 15
<211> LENGTH: 17
<212> TYPE: PRT
<213> ORGANISM: Homo sapiens

<400> SEQUENCE: 15

Gly Ala Val Gly Met Ala Cys Ala Ile Ser Ile Leu Leu Lys Trp Ile
1 5 10 15

Phe

<210> SEQ ID NO 16
<211> LENGTH: 39
<212> TYPE: PRT
<213> ORGANISM: Homo sapiens

<400> SEQUENCE: 16

Gly Trp Ile Ile Gly Glu His Gly Asp Ser Ser Gly Ile Ile Trp Asn
1 5 10 15

Lys Arg Arg Thr Leu Ser Gln Tyr Pro Leu Cys Leu Gly Ala Glu Trp
20 25 30

Cys Leu Arg Cys Cys Glu Asn
35

<210> SEQ ID NO 17
<211> LENGTH: 23
<212> TYPE: PRT
<213> ORGANISM: Homo sapiens

<400> SEQUENCE: 17

Met Val Gly Leu Leu Glu Asn Met Val Ile Leu Val Gly Leu Tyr Gly
1 5 10 15

Ile Lys Glu Glu Leu Phe Leu
20

<210> SEQ ID NO 18
<211> LENGTH: 17
<212> TYPE: PRT
<213> ORGANISM: Homo sapiens

<400> SEQUENCE: 18

Glu His Trp Lys Asn Ile His Lys Gln Val Ile Gln Arg Asp Tyr Met
1 5 10 15

Glu

<210> SEQ ID NO 19
<211> LENGTH: 2168
<212> TYPE: DNA
<213> ORGANISM: Homo sapiens

<400> SEQUENCE: 19
gaatccgcgg ggagggcaca acagctgcta cctgaacagt ttctgaccca acagttaccc 60
agcgccggac tcgctgcgcc ccggcggctc tagggacccc cggcgcctac acttagctcc 120
gcgcccgaga gaatgttgga ccgacgacac aagacctcag acttgtgtta ttctagcagc 180
tgaacacacc ccaggctctt ctgaccggca gtggctctgg aagcagtctg gtgtatagag 240
ttatggattc actaccagat tctactgtat gctcttgaca actatgacca caatggtcca 300
cccacaaatg aattatcagg agtgaaccca gaggcacgta tgaatgaaag tcctgatccg 360
actgacctgg cgggagtcat cattgagctc ggccccaatg acagtccaca gacaagtgaa 420
tttaaaggag caaccgagga ggcacctgcg aaagaaagcc cacacacaag tgaatttaaa 480
ggagcagccc gggtgtcacc tatcagtgaa agtgtgttag cacgactttc caagtttgaa 540
gttgaagatg ctgaaaatgt tgcttcatat gacagcaaga ttaagaaaat tgtgcattca 600

-continued attgtatcat cctttgcatt tggactattt ggagttttcc tggtcttact ggatgtcact 660
ctcatccttg ccgacctaat tttcactgac agcaaacttt atattccttt ggagtatcgt 720
tctatttctc tagctattgc cttatttttt ctcatggatg ttcttcttcg agtatttgta 780
gaaaggagac agcagtattt ttctgactta tttaacattt tagatactgc cattattgtg 840
attcttctgc tggttgatgt cgtttacatt ttttttgaca ttaagttgct taggaatatt 900
cccagatgga cacatttact tcgacttcta cgacttatta ttctgttaag aatttttcat 960
ctgtttcatc aaaaaagaca acttgaaaag ctgataagaa ggcgggtttc agaaaacaaa 1020
aggcgataca caagggatgg atttgaccta gacctcactt acgttacaga acgtattatt 1080
gctatgtcat ttccatcttc tggaaggcag tctttctata gaaatccaat caaggaagtt 1140
gtgcggtttc tagataagaa acaccgaaac cactatcgag tctacaatct atgcagtgaa 1200
agagcttacg atcctaagca cttccataat agggtcgtta gaatcatgat tgatgatcat 1260
aatgtcccca ctctacatca gatggtggtt ttcaccaagg aagtaaatga gtggatggct 1320
caagatcttg aaaacatcgt agcgattcac tgtaaaggag gcacagatag aacaggaact 1380
atggtttgtg ccttccttat tgcctctgaa atatgttcaa ctgcaaagga aagcctgtat 1440
tattttggag aaaggcgaac agataaaacc cacagcgaaa aatttcaggg agtagaaact 1500
ccttctcaga agagatatgt tgcatatttt gcacaagtga aacatctcta caactggaat 1560
ctccctccaa gacggatact ctttataaaa cacttcatta tttattcgat tcctcgttat 1620
gtacgtgatc taaaaatcca aatagaaatg gagaaaaagg ttgtcttttc cactatttca 1680
ttaggaaaat gttcggtact tgataacatt acaacagaca aaatattaat tgatgtattc 1740
gacggtccac ctctgtatga tgatgtgaaa gtgcagtttt tctattcgaa tcttcctaca 1800
tactatgaca attgctcatt ttacttctgg ttgcacacat cttttattga aaataacagg 1860
ctttatctac caaaaaatga attggataat ctacataaac aaaaagcacg gagaatttat 1920
ccatcagatt ttgccgtgga gatacttttt ggcgagaaaa tgacttccag tgatgttgta 1980
gctggatccg attaagtata gctcccccctt cccccttctgg gaaagaatta tgttctttcc 2040
aaccctgcca catgttcata tatcctaaat ctatcctaaa tgttcccttg aagtatttat 2100
ttatgtttat atatgtttat acatgttctt caataaatct attacatata tataaaaaaa 2160
aaaaaaaa 2168

<210> SEQ ID NO 20
<211> LENGTH: 2114
<212> TYPE: DNA
<213> ORGANISM: Homo sapiens

<400> SEQUENCE: 20
gaatccgcgg ggagggcaca acagctgcta cctgaacagt ttctgaccca acagttaccc 60
agcgccggac tcgctgcgcc ccggcggctc tagggacccc cggcgcctac acttagctcc 120
gcgcccgaga gaatgttgga ccgacgacac aagacctcag acttgtgtta ttctagcagc 180
tgaacacacc ccaggctctt ctgaccggca gtggctctgg aagcagtctg gtgtatagag 240
ttatggattc actaccagat tctactgtat gctcttgaca actatgacca caatggtcca 300
cccacaaatg aattatcagg agtgaaccca gaggcacgta tgaatgaaag tcctgatccg 360
actgacctgg cgggagtcat cattgagctc ggccccaatg acagtccaca gacaagtgaa 420
tttaaaggag caaccgagga ggcacctgcg aaagaaagtg tgttagcacg actttccaag 480
tttgaagttg aagatgctga aaatgttgct tcatatgaca gcaagattaa gaaaattgtg 540

```
cattcaattg tatcatcctt tgcatttgga ctatttggag ttttcctggt cttactggat    600

gtcactctca tccttgccga cctaattttc actgacagca aactttatat tcctttggag    660

tatcgttcta tttctctagc tattgcctta ttttttctca tggatgttct tcttcgagta    720

tttgtagaaa ggagacagca gtatttttct gacttattta acattttaga tactgccatt    780

attgtgattc ttctgctggt tgatgtcgtt tacatttttt ttgacattaa gttgcttagg    840

aatattccca gatggacaca tttacttcga cttctacgac ttattattct gttaagaatt    900

tttcatctgt ttcatcaaaa aagacaactt gaaaagctga taagaaggcg ggtttcagaa    960

aacaaaaggc gatacacaag ggatggattt gacctagacc tcacttacgt tacagaacgt   1020

attattgcta tgtcatttcc atcttctgga aggcagtctt tctatagaaa tccaatcaag   1080

gaagttgtgc ggtttctaga taagaaacac cgaaaccact atcgagtcta caatctatgc   1140

agtgaaagag cttacgatcc taagcacttc cataataggg tcgttagaat catgattgat   1200

gatcataatg tccccactct acatcagatg gtggttttca ccaaggaagt aaatgagtgg   1260

atggctcaag atcttgaaaa catcgtagcg attcactgta aaggaggcac agatagaaca   1320

ggaactatgg tttgtgcctt ccttattgcc tctgaaatat gttcaactgc aaaggaaagc   1380

ctgtattatt ttggagaaag gcgaacagat aaaacccaca gcgaaaaatt tcagggagta   1440

gaaactcctt ctcagaagag atatgttgca tattttgcac aagtgaaaca tctctacaac   1500

tggaatctcc ctccaagacg gatactcttt ataaaacact tcattattta ttcgattcct   1560

cgttatgtac gtgatctaaa aatccaaata gaaatggaga aaaaggttgt cttttccact   1620

atttcattag gaaaatgttc ggtacttgat aacattacaa cagacaaaat attaattgat   1680

gtattcgacg gtccacctct gtatgatgat gtgaaagtgc agtttttcta ttcgaatctt   1740

cctacatact atgacaattg ctcattttac ttctggttgc acacatcttt tattgaaaat   1800

aacaggcttt atctaccaaa aaatgaattg gataatctac ataaacaaaa agcacggaga   1860

atttatccat cagattttgc cgtggagata ctttttggcg agaaaatgac ttccagtgat   1920

gttgtagctg gatccgatta agtatagctc ccccttcccc ttctgggaaa gaattatgtt   1980

ctttccaacc ctgccacatg ttcatatatc ctaaatctat cctaaatgtt cccttgaagt   2040

atttatttat gtttatatat gtttatacat gttcttcaat aaatctatta catatatata   2100

aaaaaaaaaa aaaa                                                     2114
```

<210> SEQ ID NO 21
<211> LENGTH: 2222
<212> TYPE: DNA
<213> ORGANISM: Homo sapiens

<400> SEQUENCE: 21

```
gaatccgcgg ggagggcaca acagctgcta cctgaacagt ttctgaccca acagttaccc     60

agcgccggac tcgctgcgcc ccggcggctc tagggacccc cggcgcctac acttagctcc    120

gcgcccgaga gaatgttgga ccgacgacac aagacctcag acttgtgtta ttctagcagc    180

tgaacacacc ccaggctctt ctgaccggca gtggctctgg aagcagtctg gtgtatagag    240

ttatggattc actaccagat tctactgtat gctcttgaca actatgacca caatggtcca    300

cccacaaatg aattatcagg agtgaaccca gaggcacgta tgaatgaaag tcctgatccg    360

actgacctgg cgggagtcat cattgagctc ggccccaatg acagtccaca gacaagtgaa    420

tttaaaggag caaccgagga ggcacctgcg aaagaaagcc cacacacaag tgaatttaaa    480
```

-continued

```
ggagcagccc gggtgtcacc tatcagtgaa agtgtgttag cacgactttc caagtttgaa    540

gttgaagatg ctgaaaatgt tgcttcatat gacagcaaga ttaagaaaat tgtgcattca    600

attgtatcat cctttgcatt tggactattt ggagttttcc tggtcttact ggatgtcact    660

ctcatccttg ccgacctaat tttcactgac agcaaacttt atattccttt ggagtatcgt    720

tctatttctc tagctattgc cttatttttt ctcatggatg ttcttcttcg agtatttgta    780

gaaaggagac agcagtattt ttctgactta tttaacattt tagatactgc cattattgtg    840

attcttctgc tggttgatgt cgtttacatt ttttttgaca ttaagttgct taggaatatt    900

cccagatgga cacatttact tcgacttcta cgacttatta ttctgttaag aatttttcat    960

ctgtttcatc aaaaaagaca acttgaaaag ctgataagaa ggcgggtttc agaaaacaaa   1020

aggcgataca caagggatgg atttgaccta gacctcactt acgttacaga acgtattatt   1080

gctatgtcat ttccatcttc tggaaggcag tctttctata gaaatccaat caaggaagtt   1140

gtgcggtttc tagataagaa acaccgaaac cactatcgag tctacaatct atgcagtatg   1200

tacattactc tatattgtgc tactgtagat agaaaacaga ttactgcacg tgaaagagct   1260

tacgatccta agcacttcca taatagggtc gttagaatca tgattgatga tcataatgtc   1320

cccactctac atcagatggt ggttttcacc aaggaagtaa atgagtggat ggctcaagat   1380

cttgaaaaca tcgtagcgat tcactgtaaa ggaggcacag atagaacagg aactatggtt   1440

tgtgccttcc ttattgcctc tgaaatatgt tcaactgcaa aggaaagcct gtattatttt   1500

ggagaaaggc gaacagataa aacccacagc gaaaaatttc agggagtaga aactccttct   1560

cagaagagat atgttgcata ttttgcacaa gtgaaacatc tctacaactg gaatctccct   1620

ccaagacgga tactctttat aaaacacttc attatttatt cgattcctcg ttatgtacgt   1680

gatctaaaaa tccaaataga aatggagaaa aaggttgtct tttccactat ttcattagga   1740

aaatgttcgg tacttgataa cattacaaca gacaaaatat taattgatgt attcgacggt   1800

ccacctctgt atgatgatgt gaaagtgcag tttttctatt cgaatcttcc tacatactat   1860

gacaattgct cattttactt ctggttgcac acatctttta ttgaaaataa caggctttat   1920

ctaccaaaaa atgaattgga taatctacat aaacaaaaag cacggagaat ttatccatca   1980

gattttgccg tggagatact tttggcgag aaaatgactt ccagtgatgt tgtagctgga   2040

tccgattaag tatagctccc ccttcccctt ctgggaaaga attatgttct ttccaaccct   2100

gccacatgtt catatatcct aaatctatcc taaatgttcc cttgaagtat ttatttatgt   2160

ttatatatgt ttatacatgt tcttcaataa atctattaca tatatataaa aaaaaaaaaa   2220

aa                                                                  2222
```

<210> SEQ ID NO 22
<211> LENGTH: 551
<212> TYPE: PRT
<213> ORGANISM: Homo sapiens

<400> SEQUENCE: 22

```
Met Asn Glu Ser Pro Asp Pro Thr Asp Leu Ala Gly Val Ile Ile Glu
1               5                   10                  15

Leu Gly Pro Asn Asp Ser Pro Gln Thr Ser Glu Phe Lys Gly Ala Thr
            20                  25                  30

Glu Glu Ala Pro Ala Lys Glu Ser Pro His Thr Ser Glu Phe Lys Gly
        35                  40                  45

Ala Ala Arg Val Ser Pro Ile Ser Glu Ser Val Leu Ala Arg Leu Ser
    50                  55                  60
```

-continued

```
Lys Phe Glu Val Glu Asp Ala Glu Asn Val Ala Ser Tyr Asp Ser Lys
65                  70                  75                  80

Ile Lys Lys Ile Val His Ser Ile Val Ser Ser Phe Ala Phe Gly Leu
                85                  90                  95

Phe Gly Val Phe Leu Val Leu Leu Asp Val Thr Leu Ile Leu Ala Asp
            100                 105                 110

Leu Ile Phe Thr Asp Ser Lys Leu Tyr Ile Pro Leu Glu Tyr Arg Ser
        115                 120                 125

Ile Ser Leu Ala Ile Ala Leu Phe Phe Leu Met Asp Val Leu Leu Arg
    130                 135                 140

Val Phe Val Glu Arg Arg Gln Gln Tyr Phe Ser Asp Leu Phe Asn Ile
145                 150                 155                 160

Leu Asp Thr Ala Ile Ile Val Ile Leu Leu Leu Val Asp Val Val Tyr
                165                 170                 175

Ile Phe Phe Asp Ile Lys Leu Leu Arg Asn Ile Pro Arg Trp Thr His
            180                 185                 190

Leu Leu Arg Leu Leu Arg Leu Ile Ile Leu Leu Arg Ile Phe His Leu
        195                 200                 205

Phe His Gln Lys Arg Gln Leu Glu Lys Leu Ile Arg Arg Arg Val Ser
    210                 215                 220

Glu Asn Lys Arg Arg Tyr Thr Arg Asp Gly Phe Asp Leu Asp Leu Thr
225                 230                 235                 240

Tyr Val Thr Glu Arg Ile Ile Ala Met Ser Phe Pro Ser Ser Gly Arg
                245                 250                 255

Gln Ser Phe Tyr Arg Asn Pro Ile Lys Glu Val Val Arg Phe Leu Asp
            260                 265                 270

Lys Lys His Arg Asn His Tyr Arg Val Tyr Asn Leu Cys Ser Glu Arg
        275                 280                 285

Ala Tyr Asp Pro Lys His Phe His Asn Arg Val Val Arg Ile Met Ile
    290                 295                 300

Asp Asp His Asn Val Pro Thr Leu His Gln Met Val Val Phe Thr Lys
305                 310                 315                 320

Glu Val Asn Glu Trp Met Ala Gln Asp Leu Glu Asn Ile Val Ala Ile
                325                 330                 335

His Cys Lys Gly Gly Thr Asp Arg Thr Gly Thr Met Val Cys Ala Phe
            340                 345                 350

Leu Ile Ala Ser Glu Ile Cys Ser Thr Ala Lys Glu Ser Leu Tyr Tyr
        355                 360                 365

Phe Gly Glu Arg Arg Thr Asp Lys Thr His Ser Glu Lys Phe Gln Gly
    370                 375                 380

Val Glu Thr Pro Ser Gln Lys Arg Tyr Val Ala Tyr Phe Ala Gln Val
385                 390                 395                 400

Lys His Leu Tyr Asn Trp Asn Leu Pro Pro Arg Arg Ile Leu Phe Ile
                405                 410                 415

Lys His Phe Ile Ile Tyr Ser Ile Pro Arg Tyr Val Arg Asp Leu Lys
            420                 425                 430

Ile Gln Ile Glu Met Glu Lys Lys Val Val Phe Ser Thr Ile Ser Leu
        435                 440                 445

Gly Lys Cys Ser Val Leu Asp Asn Ile Thr Thr Asp Lys Ile Leu Ile
    450                 455                 460

Asp Val Phe Asp Gly Pro Pro Leu Tyr Asp Asp Val Lys Val Gln Phe
465                 470                 475                 480
```

-continued

```
Phe Tyr Ser Asn Leu Pro Thr Tyr Tyr Asp Asn Cys Ser Phe Tyr Phe
                485                 490                 495

Trp Leu His Thr Ser Phe Ile Glu Asn Asn Arg Leu Tyr Leu Pro Lys
            500                 505                 510

Asn Glu Leu Asp Asn Leu His Lys Gln Lys Ala Arg Arg Ile Tyr Pro
        515                 520                 525

Ser Asp Phe Ala Val Glu Ile Leu Phe Gly Glu Lys Met Thr Ser Ser
    530                 535                 540

Asp Val Val Ala Gly Ser Asp
545                 550


<210> SEQ ID NO 23
<211> LENGTH: 533
<212> TYPE: PRT
<213> ORGANISM: Homo sapiens

<400> SEQUENCE: 23

Met Asn Glu Ser Pro Asp Pro Thr Asp Leu Ala Gly Val Ile Ile Glu
1               5                   10                  15

Leu Gly Pro Asn Asp Ser Pro Gln Thr Ser Glu Phe Lys Gly Ala Thr
            20                  25                  30

Glu Glu Ala Pro Ala Lys Glu Ser Val Leu Ala Arg Leu Ser Lys Phe
        35                  40                  45

Glu Val Glu Asp Ala Glu Asn Val Ala Ser Tyr Asp Ser Lys Ile Lys
    50                  55                  60

Lys Ile Val His Ser Ile Val Ser Ser Phe Ala Phe Gly Leu Phe Gly
65                  70                  75                  80

Val Phe Leu Val Leu Leu Asp Val Thr Leu Ile Leu Ala Asp Leu Ile
                85                  90                  95

Phe Thr Asp Ser Lys Leu Tyr Ile Pro Leu Glu Tyr Arg Ser Ile Ser
            100                 105                 110

Leu Ala Ile Ala Leu Phe Phe Leu Met Asp Val Leu Leu Arg Val Phe
        115                 120                 125

Val Glu Arg Arg Gln Gln Tyr Phe Ser Asp Leu Phe Asn Ile Leu Asp
    130                 135                 140

Thr Ala Ile Ile Val Ile Leu Leu Leu Val Asp Val Val Tyr Ile Phe
145                 150                 155                 160

Phe Asp Ile Lys Leu Leu Arg Asn Ile Pro Arg Trp Thr His Leu Leu
                165                 170                 175

Arg Leu Leu Arg Leu Ile Ile Leu Leu Arg Ile Phe His Leu Phe His
            180                 185                 190

Gln Lys Arg Gln Leu Glu Lys Leu Ile Arg Arg Arg Val Ser Glu Asn
        195                 200                 205

Lys Arg Arg Tyr Thr Arg Asp Gly Phe Asp Leu Asp Leu Thr Tyr Val
    210                 215                 220

Thr Glu Arg Ile Ile Ala Met Ser Phe Pro Ser Ser Gly Arg Gln Ser
225                 230                 235                 240

Phe Tyr Arg Asn Pro Ile Lys Glu Val Val Arg Phe Leu Asp Lys Lys
                245                 250                 255

His Arg Asn His Tyr Arg Val Tyr Asn Leu Cys Ser Glu Arg Ala Tyr
            260                 265                 270

Asp Pro Lys His Phe His Asn Arg Val Val Arg Ile Met Ile Asp Asp
        275                 280                 285

His Asn Val Pro Thr Leu His Gln Met Val Val Phe Thr Lys Glu Val
    290                 295                 300
```

Asn Glu Trp Met Ala Gln Asp Leu Glu Asn Ile Val Ala Ile His Cys
305 310 315 320

Lys Gly Gly Thr Asp Arg Thr Gly Thr Met Val Cys Ala Phe Leu Ile
325 330 335

Ala Ser Glu Ile Cys Ser Thr Ala Lys Glu Ser Leu Tyr Tyr Phe Gly
340 345 350

Glu Arg Arg Thr Asp Lys Thr His Ser Glu Lys Phe Gln Gly Val Glu
355 360 365

Thr Pro Ser Gln Lys Arg Tyr Val Ala Tyr Phe Ala Gln Val Lys His
370 375 380

Leu Tyr Asn Trp Asn Leu Pro Pro Arg Arg Ile Leu Phe Ile Lys His
385 390 395 400

Phe Ile Ile Tyr Ser Ile Pro Arg Tyr Val Arg Asp Leu Lys Ile Gln
405 410 415

Ile Glu Met Glu Lys Lys Val Val Phe Ser Thr Ile Ser Leu Gly Lys
420 425 430

Cys Ser Val Leu Asp Asn Ile Thr Thr Asp Lys Ile Leu Ile Asp Val
435 440 445

Phe Asp Gly Pro Pro Leu Tyr Asp Asp Val Lys Val Gln Phe Phe Tyr
450 455 460

Ser Asn Leu Pro Thr Tyr Tyr Asp Asn Cys Ser Phe Tyr Phe Trp Leu
465 470 475 480

His Thr Ser Phe Ile Glu Asn Asn Arg Leu Tyr Leu Pro Lys Asn Glu
485 490 495

Leu Asp Asn Leu His Lys Gln Lys Ala Arg Arg Ile Tyr Pro Ser Asp
500 505 510

Phe Ala Val Glu Ile Leu Phe Gly Glu Lys Met Thr Ser Ser Asp Val
515 520 525

Val Ala Gly Ser Asp
530

<210> SEQ ID NO 24
<211> LENGTH: 569
<212> TYPE: PRT
<213> ORGANISM: Homo sapiens

<400> SEQUENCE: 24

Met Asn Glu Ser Pro Asp Pro Thr Asp Leu Ala Gly Val Ile Ile Glu
1 5 10 15

Leu Gly Pro Asn Asp Ser Pro Gln Thr Ser Glu Phe Lys Gly Ala Thr
20 25 30

Glu Glu Ala Pro Ala Lys Glu Ser Pro His Thr Ser Glu Phe Lys Gly
35 40 45

Ala Ala Arg Val Ser Pro Ile Ser Glu Ser Val Leu Ala Arg Leu Ser
50 55 60

Lys Phe Glu Val Glu Asp Ala Glu Asn Val Ala Ser Tyr Asp Ser Lys
65 70 75 80

Ile Lys Lys Ile Val His Ser Ile Val Ser Ser Phe Ala Phe Gly Leu
85 90 95

Phe Gly Val Phe Leu Val Leu Leu Asp Val Thr Leu Ile Leu Ala Asp
100 105 110

Leu Ile Phe Thr Asp Ser Lys Leu Tyr Ile Pro Leu Glu Tyr Arg Ser
115 120 125

Ile Ser Leu Ala Ile Ala Leu Phe Phe Leu Met Asp Val Leu Leu Arg

-continued

```
    130                 135                 140

Val Phe Val Glu Arg Arg Gln Gln Tyr Phe Ser Asp Leu Phe Asn Ile
145                 150                 155                 160

Leu Asp Thr Ala Ile Ile Val Ile Leu Leu Leu Val Asp Val Val Tyr
                165                 170                 175

Ile Phe Phe Asp Ile Lys Leu Leu Arg Asn Ile Pro Arg Trp Thr His
            180                 185                 190

Leu Leu Arg Leu Leu Arg Leu Ile Ile Leu Leu Arg Ile Phe His Leu
        195                 200                 205

Phe His Gln Lys Arg Gln Leu Glu Lys Leu Ile Arg Arg Arg Val Ser
    210                 215                 220

Glu Asn Lys Arg Arg Tyr Thr Arg Asp Gly Phe Asp Leu Asp Leu Thr
225                 230                 235                 240

Tyr Val Thr Glu Arg Ile Ile Ala Met Ser Phe Pro Ser Ser Gly Arg
                245                 250                 255

Gln Ser Phe Tyr Arg Asn Pro Ile Lys Glu Val Val Arg Phe Leu Asp
            260                 265                 270

Lys Lys His Arg Asn His Tyr Arg Val Tyr Asn Leu Cys Ser Met Tyr
        275                 280                 285

Ile Thr Leu Tyr Cys Ala Thr Val Asp Arg Lys Gln Ile Thr Ala Arg
    290                 295                 300

Glu Arg Ala Tyr Asp Pro Lys His Phe His Asn Arg Val Val Arg Ile
305                 310                 315                 320

Met Ile Asp Asp His Asn Val Pro Thr Leu His Gln Met Val Val Phe
                325                 330                 335

Thr Lys Glu Val Asn Glu Trp Met Ala Gln Asp Leu Glu Asn Ile Val
            340                 345                 350

Ala Ile His Cys Lys Gly Gly Thr Asp Arg Thr Gly Thr Met Val Cys
        355                 360                 365

Ala Phe Leu Ile Ala Ser Glu Ile Cys Ser Thr Ala Lys Glu Ser Leu
    370                 375                 380

Tyr Tyr Phe Gly Glu Arg Arg Thr Asp Lys Thr His Ser Glu Lys Phe
385                 390                 395                 400

Gln Gly Val Glu Thr Pro Ser Gln Lys Arg Tyr Val Ala Tyr Phe Ala
                405                 410                 415

Gln Val Lys His Leu Tyr Asn Trp Asn Leu Pro Pro Arg Arg Ile Leu
            420                 425                 430

Phe Ile Lys His Phe Ile Ile Tyr Ser Ile Pro Arg Tyr Val Arg Asp
        435                 440                 445

Leu Lys Ile Gln Ile Glu Met Glu Lys Lys Val Val Phe Ser Thr Ile
    450                 455                 460

Ser Leu Gly Lys Cys Ser Val Leu Asp Asn Ile Thr Thr Asp Lys Ile
465                 470                 475                 480

Leu Ile Asp Val Phe Asp Gly Pro Pro Leu Tyr Asp Asp Val Lys Val
                485                 490                 495

Gln Phe Phe Tyr Ser Asn Leu Pro Thr Tyr Tyr Asp Asn Cys Ser Phe
            500                 505                 510

Tyr Phe Trp Leu His Thr Ser Phe Ile Glu Asn Asn Arg Leu Tyr Leu
        515                 520                 525

Pro Lys Asn Glu Leu Asp Asn Leu His Lys Gln Lys Ala Arg Arg Ile
    530                 535                 540

Tyr Pro Ser Asp Phe Ala Val Glu Ile Leu Phe Gly Glu Lys Met Thr
545                 550                 555                 560
```

Ser Ser Asp Val Val Ala Gly Ser Asp
565

<210> SEQ ID NO 25
<211> LENGTH: 21
<212> TYPE: DNA
<213> ORGANISM: Artificial sequence
<220> FEATURE:
<223> OTHER INFORMATION: Description of the artificial sequence:
oligonucleotide

<400> SEQUENCE: 25
tgccgtaggc atggcttgtg c 21

<210> SEQ ID NO 26
<211> LENGTH: 21
<212> TYPE: DNA
<213> ORGANISM: Artificial sequence
<220> FEATURE:
<223> OTHER INFORMATION: Description of the artificial sequence:
oligonucleotide

<400> SEQUENCE: 26
caacatctga gacaccattc c 21

<210> SEQ ID NO 27
<211> LENGTH: 21
<212> TYPE: DNA
<213> ORGANISM: Artificial sequence
<220> FEATURE:
<223> OTHER INFORMATION: Description of the artificial sequence:
oligonucleotide

<400> SEQUENCE: 27
tggatgtcac tctcatcctt g 21

<210> SEQ ID NO 28
<211> LENGTH: 21
<212> TYPE: DNA
<213> ORGANISM: Artificial sequence
<220> FEATURE:
<223> OTHER INFORMATION: Description of the artificial sequence:
oligonucleotide

<400> SEQUENCE: 28
ccatagttcc tgttctatct g 21

<210> SEQ ID NO 29
<211> LENGTH: 2192
<212> TYPE: DNA
<213> ORGANISM: Homo sapiens

<400> SEQUENCE: 29
agctcagctg ggagcgcaga ggctcacgcc tgtaatccca tcatttgctt aggtctgatc 60
aatctgctcc acacaatttc tcagtgatcc tctgcatctc tgcctacaag ggcctccctg 120
acacccaagt tcatattgct cagaaacagt gaacttgagt ttttcgtttt accttgatct 180
ctctctgaca aagaaatcca gatgatgcaa cacctgatga agacaataca tggaaaatga 240
cagtcttgga aataactttg gctgtcatcc tgactctact gggacttgcc atcctggcta 300
ttttgttaac aagatgggca cgacgtaagc aaagtgaaat gtatatctcc agatacagtt 360
cagaacaaag tgctagactt ctggactatg aggatggtag aggatcccga catgcatatc 420
aacacaaagt gacacttcat atgataaccg agagagatcc aaaaagagat tacacaccat 480

```
caaccaactc tctagcactg tctcgatcaa gtattgcttt acctcaagga tccatgagta    540
gtataaaatg tttacaaaca actgaagaac ctccttccag aactgcagga gccatgatgc    600
aattcacagc cctattcccg gagctacagg acctatcaag ctctctcaaa aaaccattgt    660
gcaaactcca ggacctattg tacaatatct ggatccaatg tcagatcgca tctcacacaa    720
tcactggtca ccttcagcac ccgcggtcac ccatggcacc cataataatt tcacagagaa    780
ccgcaagtca gctggcagca cctataagaa tacctcaagt tcacactatg gacagttctg    840
gaaaaatcac actgactcct gtggttatat taacaggtta catggacgaa gaacttcgaa    900
aaaaatcttg ttccaaaatc cagattctaa aatgtggagg cactgcaagg tctcagatag    960
ccgagaagaa aacaaggaag caactaaaga atgacatcat atttacgaat tctgtagaat   1020
ccttgaaatc agcacacata aaggagccag aaagagaagg aaaaggcact gatttagaga   1080
aagacaaaat aggaatggag gtcaaggtag acagtgacgc tggaatacca aaaagacagg   1140
aaacccaact aaaaatcagt gaagatgagt ataccacaag gacagggagc ccaaataaag   1200
aaaagtgtgt cagatgtacc aagaggacag gagtccaagt aaagaagagt gagtcaggtg   1260
tcccaaaagg acaagaagcc caagtaacga agagtgggtt ggttgtactg aaaggacagg   1320
aagcccaggt agagaagagt gagatgggtg tgccaagaag acaggaatcc caagtaaaga   1380
agagtcagtc tggtgtctca aagggacagg aagcccaggt aaagaagagg gagtcagttg   1440
tactgaaagg acaggaagcc caggtagaga agagtgagtt gaaggtacca aaaggacaag   1500
aaggccaagt agagaagact gaggcagatg tgccaaagga acaagaggtc caagaaaaga   1560
agagtgaggc aggtgtactg aaaggaccag aatcccaagt aaagaacact gaggtgagtg   1620
taccagaaac actggaatcc caagtaaaga agagtgagtc aggtgtacta aaaggacagg   1680
aagcccaaga aaagaaggag agttttgagg ataaaggaaa taatgataaa gaaaaggaga   1740
gagatgcaga gaaagatcca aataaaaaag aaaaaggtga caaaaacaca aaaggtgaca   1800
aaggaaagga caaagttaaa ggaaagagag aatcagaaat caatggtgaa aaatcaaaag   1860
gctcgaaaag gcgaaggcaa atacaggaag gaagtacaac aaaaaagtgg aagagtaagg   1920
ataaattttt taaaggccca taagacaagt gattattatg attcccatac tccagataca   1980
aaccatatcc cagccattgc ctaaacagat tacaattata aaatcccttt catcttcata   2040
tcacagtttc tgctcttcag aagtttcacc ctttttaatc tctcagccac aaacctcagt   2100
tccaatattg ttataagtta agacgtatat gattccgtca agaaagactg gatactttct   2160
gaagtaaaac attttaatta aagaaaaaaa aa                                  2192
```

<210> SEQ ID NO 30
<211> LENGTH: 568
<212> TYPE: PRT
<213> ORGANISM: Homo sapiens

<400> SEQUENCE: 30

```
Met Thr Val Leu Glu Ile Thr Leu Ala Val Ile Leu Thr Leu Leu Gly
1               5                   10                  15

Leu Ala Ile Leu Ala Ile Leu Leu Thr Arg Trp Ala Arg Arg Lys Gln
            20                  25                  30

Ser Glu Met Tyr Ile Ser Arg Tyr Ser Ser Glu Gln Ser Ala Arg Leu
        35                  40                  45

Leu Asp Tyr Glu Asp Gly Arg Gly Ser Arg His Ala Tyr Gln His Lys
    50                  55                  60
```

-continued

```
Val Thr Leu His Met Ile Thr Glu Arg Asp Pro Lys Arg Asp Tyr Thr
65                  70                  75                  80

Pro Ser Thr Asn Ser Leu Ala Leu Ser Arg Ser Ser Ile Ala Leu Pro
                85                  90                  95

Gln Gly Ser Met Ser Ser Ile Lys Cys Leu Gln Thr Thr Glu Glu Pro
            100                 105                 110

Pro Ser Arg Thr Ala Gly Ala Met Met Gln Phe Thr Ala Leu Phe Pro
        115                 120                 125

Glu Leu Gln Asp Leu Ser Ser Ser Leu Lys Lys Pro Leu Cys Lys Leu
    130                 135                 140

Gln Asp Leu Leu Tyr Asn Ile Trp Ile Gln Cys Gln Ile Ala Ser His
145                 150                 155                 160

Thr Ile Thr Gly His Leu Gln His Pro Arg Ser Pro Met Ala Pro Ile
                165                 170                 175

Ile Ile Ser Gln Arg Thr Ala Ser Gln Leu Ala Ala Pro Ile Arg Ile
            180                 185                 190

Pro Gln Val His Thr Met Asp Ser Ser Gly Lys Ile Thr Leu Thr Pro
        195                 200                 205

Val Val Ile Leu Thr Gly Tyr Met Asp Glu Glu Leu Arg Lys Lys Ser
    210                 215                 220

Cys Ser Lys Ile Gln Ile Leu Lys Cys Gly Gly Thr Ala Arg Ser Gln
225                 230                 235                 240

Ile Ala Glu Lys Lys Thr Arg Lys Gln Leu Lys Asn Asp Ile Ile Phe
                245                 250                 255

Thr Asn Ser Val Glu Ser Leu Lys Ser Ala His Ile Lys Glu Pro Glu
            260                 265                 270

Arg Glu Gly Lys Gly Thr Asp Leu Glu Lys Asp Lys Ile Gly Met Glu
        275                 280                 285

Val Lys Val Asp Ser Asp Ala Gly Ile Pro Lys Arg Gln Glu Thr Gln
    290                 295                 300

Leu Lys Ile Ser Glu Asp Glu Tyr Thr Thr Arg Thr Gly Ser Pro Asn
305                 310                 315                 320

Lys Glu Lys Cys Val Arg Cys Thr Lys Arg Thr Gly Val Gln Val Lys
                325                 330                 335

Lys Ser Glu Ser Gly Val Pro Lys Gly Gln Glu Ala Gln Val Thr Lys
            340                 345                 350

Ser Gly Leu Val Val Leu Lys Gly Gln Glu Ala Gln Val Glu Lys Ser
        355                 360                 365

Glu Met Gly Val Pro Arg Arg Gln Glu Ser Gln Val Lys Lys Ser Gln
    370                 375                 380

Ser Gly Val Ser Lys Gly Gln Glu Ala Gln Val Lys Lys Arg Glu Ser
385                 390                 395                 400

Val Val Leu Lys Gly Gln Glu Ala Gln Val Glu Lys Ser Glu Leu Lys
                405                 410                 415

Val Pro Lys Gly Gln Glu Gly Gln Val Glu Lys Thr Glu Ala Asp Val
            420                 425                 430

Pro Lys Glu Gln Glu Val Gln Glu Lys Lys Ser Glu Ala Gly Val Leu
        435                 440                 445

Lys Gly Pro Glu Ser Gln Val Lys Asn Thr Glu Val Ser Val Pro Glu
    450                 455                 460

Thr Leu Glu Ser Gln Val Lys Lys Ser Glu Ser Gly Val Leu Lys Gly
465                 470                 475                 480

Gln Glu Ala Gln Glu Lys Lys Glu Ser Phe Glu Asp Lys Gly Asn Asn
```

-continued

```
                485                 490                 495

Asp Lys Glu Lys Glu Arg Asp Ala Glu Lys Asp Pro Asn Lys Lys Glu
            500                 505                 510

Lys Gly Asp Lys Asn Thr Lys Gly Asp Lys Gly Lys Asp Lys Val Lys
        515                 520                 525

Gly Lys Arg Glu Ser Glu Ile Asn Gly Glu Lys Ser Lys Gly Ser Lys
    530                 535                 540

Arg Arg Arg Gln Ile Gln Glu Gly Ser Thr Thr Lys Lys Trp Lys Ser
545                 550                 555                 560

Lys Asp Lys Phe Phe Lys Gly Pro
                565
```

<210> SEQ ID NO 31
<211> LENGTH: 1686
<212> TYPE: DNA
<213> ORGANISM: Homo sapiens

<400> SEQUENCE: 31

```
atgacagtct tggaaataac tttggctgtc atcctgactc tactgggact tgccatcctg      60

gctattttgt taacaagatg ggcacgatgt aagcaaagtg aaatgtatat ctccagatac     120

agttcagaac aaagtgctag acttctggac tatgaggatg gtagaggatc ccgacatgca     180

tattcaacac aaagtgacac ttcatatgat aaccgagaga gatccaaaag agattacaca     240

ccatcaacca actctctagc actgtctcga tcaagtattg ctttacctca aggatccatg     300

agtagtataa aatgtttaca aacaactgaa gaacctcctt ccagaactgc aggagccatg     360

atgcaattca cagcccctat tcccggagct acaggaccta tcaagctctc tcaaaaaacc     420

attgtgcaaa ctccaggacc tattgtacaa tatcctggat ccaatgctgg tccaccttca     480

gcaccccgcg gtccacccat ggcacccata ataatttcac agagaaccgc aagtcagctg     540

gcagcaccta taataatttc gcagagaact gcaagaatac ctcaagttca cactatggac     600

agttctggaa aaatcacact gactcctgtg gttatattaa caggttacat ggatgaagaa     660

cttgcaaaaa aatcttgttc caaaatccag attctaaaat gtggaggcac tgcaaggtct     720

cagaatagcc gagaagaaaa caaggaagca ctaaagaatg acatcatatt tacgaattct     780

gtagaatcct tgaaatcagc acacataaag gagccagaaa gagaaggaaa aggcactgat     840

ttagagaaag acaaaatagg aatggaggtc aaggtagaca gtgacgctgg aataccaaaa     900

agacaggaaa cccaactaaa aatcagtgag atgagtatac cacaaggaca gggagcccaa     960

ataaagaaaa gtgtgtcaga tgtaccaaga ggacaggagt cccaagtaaa gaagagtgag    1020

tcaggtgtcc caaaaggaca agaagcccaa gtaacgaaga gtgggttggt tgtactgaaa    1080

ggacaggaag cccaggtaga gaagagtgag atgggtgtgc caagaagaca ggaatcccaa    1140

gtaaagaaga gtcagtctgg tgtctcaaag ggacaggaag cccaggtaaa gaagagggag    1200

tcagttgtac tgaaaggaca ggaagcccag gtagagaaga gtgagttgaa ggtaccaaaa    1260

ggacaagaag gccaagtaga gaagactgag gcagatgtgc caaaggaaca agaggtccaa    1320

gaaaagaaga gtgaggcagg tgtactgaaa ggaccagaat cccaagtaaa gaacactgag    1380

gtgagtgtac cagaaacact ggaatcccaa gtaaagaaga gtgagtcagg tgtactaaaa    1440

ggacaggaag cccaagaaaa gaaggagagt tttgaggata aaggaaataa tgataaagaa    1500

aaggagagag atgcagagaa agatccaaat aaaaaagaaa aaggtgacaa aaacacaaaa    1560

ggtgacaaag gaaaggacaa agttaaagga aagagagaat cagaaatcaa tggtgaaaaa    1620
```

-continued tcaaaaggct cgaaaagggc gaaggcaaat acaggaagga agtacaacaa aaaagtggaa 1680
gagtaa 1686

<210> SEQ ID NO 32
<211> LENGTH: 1710
<212> TYPE: DNA
<213> ORGANISM: Homo sapiens

<400> SEQUENCE: 32
atgacagtct tggaaataac tttggctgtc atcctgactc tactgggact tgccatcctg 60
gctattttgt taacaagatg ggcacgacgt aagcaaagtg aaatgcatat ctccagatac 120
agttcagaac aaagtgctag acttctggac tatgaggatg gtagaggatc ccgacatgca 180
tattcaacac aaagtgacac ttcatgtgat aaccgagaga gatccaaaag agattacaca 240
ccatcaacca actctctagc actgtctcga tcaagtattg ctttacctca aggatccatg 300
agtagtataa aatgtttaca aacaactgaa gaacttcctt ccagaactgc aggagccatg 360
atgcaattca cagcccctat tcccggagct acaggaccta tcaagctctc tcaaaaaacc 420
attgtgcaaa ctccaggacc tattgtacaa tatcctggac ccaatgtcag atcgcatcct 480
cacacaatca ctggtccacc ttcagcaccc cgcggtccac ccatggcacc cataataatt 540
tcacagagaa ccgcaagtca gctggcagca cctataataa tttcgcagag aactgcaaga 600
atacctcaag ttcacactat ggacagttct ggaaaaacca cactgactcc tgtggttata 660
ttaacaggtt acatggatga agaacttgca aaaaaatctt gttccaaaat ccagattcta 720
aaatgtggag gcactgcaag gtctcagaat agccgagaag aaaacaagga agcactaaag 780
aatgacatca tatttacgaa ttctgtagaa tccttgaaat cagcacacat aaaggagcca 840
gaaagagaag gaaaaggcac tgatttagag aaagacaaaa taggaatgga ggtcaaggta 900
gacagtgacg ctggaatacc aaaaagacag gaaacccaac taaaaatcag tgagatgagt 960
ataccacaag gacagggagc ccaaataaag aaaagtgtgt cagatgtacc aagaggacag 1020
gagtcccaag taaagaagag tgagtcaggt gtcccaaaag gacaagaagc ccaagtaacg 1080
aagagtgggt tggttgtact gaaaggacag gaagcccagg tagagaagag tgagatgggt 1140
gtgccaagaa gacaggaatc ccaagtaaag aagagtcagt ctggtgtctc aaagggacag 1200
gaagcccagg taaagaagag ggagtcagtt gtactgaaag gacaggaagc ccaggtagag 1260
aagagtgagt tgaaggtacc aaaaggacaa gaaggccaag tagagaagac tgaggcagat 1320
gtgccaaagg aacaagaggt ccaagaaaag aagagtgagg caggtgtact gaaaggacca 1380
gaatcccaag taaagaacac tgaggtgagt gtaccagaaa cactggaatc ccaagtaaag 1440
aagagtgagt caggtgtact aaaaggacag gaagcccaag aaaagaagga gagttttgag 1500
gataaaggaa ataatgataa agaaaaggag agagatgcag agaaagatcc aaataaaaaa 1560
gaaaaaggtg acaaaaacac aaaaggtgac aaaggaaagg acaaagttaa aggaaagaga 1620
gaatcagaaa tcaatggtga aaaatcaaaa ggctcgaaaa gggcgaaggc aaatacagga 1680
aggaagtaca acaaaaaagt ggaagagtaa 1710

<210> SEQ ID NO 33
<211> LENGTH: 1665
<212> TYPE: DNA
<213> ORGANISM: Homo sapiens

<400> SEQUENCE: 33
atgacagtct tggaaataac tttggctgtc atcctgactc tactgggact tgccatcctg 60

-continued

```
gctattttgt taacaagatg ggcacgatgt aagcaaagtg aaatgtatat ctccagatac    120

agttcagaac aaagtgctag acttctggac tatgaggatg gtagaggatc ccgacatgca    180

tattcaacac aaagtgagag atccaaaaga gattacacac catcaaccaa ctctctagca    240

ctgtctcgat caagtattgc tttacctcaa ggatccatga gtagtataaa atgtttacaa    300

acaactgaag aacctccttc cagaactgca ggagccatga tgcaattcac agcccctatt    360

cccggagcta caggacctat caagctctct caaaaaacca ttgtgcaaac tccaggacct    420

attgtacaat atcctggatc caatgctggt ccaccttcag caccccgcgg tccacccatg    480

gcacccataa taatttcaca gagaaccgca agtcagctgg cagcacctat aataatttcg    540

cagagaactg caagaatacc tcaagttcac actatggaca gttctggaaa aatcacactg    600

actcctgtgg ttatattaac aggttacatg gatgaagaac ttgcaaaaaa atcttgttcc    660

aaaatccaga ttctaaaatg tggaggcact gcaaggtctc agaatagccg agaagaaaac    720

aaggaagcac taaagaatga catcatattt acgaattctg tagaatcctt gaaatcagca    780

cacataaagg agccagaaag agaaggaaaa ggcactgatt tagagaaaga caaaatagga    840

atggaggtca aggtagacag tgacgctgga ataccaaaaa gacaggaaac ccaactaaaa    900

atcagtgaga tgagtatacc acaaggacag ggagcccaaa taaagaaaag tgtgtcagat    960

gtaccaagag gacaggagtc ccaagtaaag aagagtgagt caggtgtccc aaaaggacaa   1020

gaagcccaag taacgaagag tgggttggtt gtactgaaag gacaggaagc ccaggtagag   1080

aagagtgaga tgggtgtgcc aagaagacag gaatcccaag taaagaagag tcagtctggt   1140

gtctcaaagg gacaggaagc ccaggtaaag aagagggagt cagttgtact gaaaggacag   1200

gaagcccagg tagagaagag tgagttgaag gtaccaaaag gacaagaagg ccaagtagag   1260

aagactgagg cagatgtgcc aaaggaacaa gaggtccaag aaaagaagag tgaggcaggt   1320

gtactgaaag gaccagaatc ccaagtaaag aacactgagg tgagtgtacc agaaacactg   1380

gaatcccaag taaagaagag tgagtcaggt gtactaaaag gacaggaagc ccaagaaaag   1440

aaggagagtt ttgaggataa aggaaataat gataaagaaa aggagagaga tgcagagaaa   1500

gatccaaata aaaaagaaaa aggtgacaaa aacacaaaag gtgacaaagg aaaggacaaa   1560

gttaaaggaa agagagaatc agaaatcaat ggtgaaaaat caaaaggctc gaaaagggcg   1620

aaggcaaata caggaaggaa gtacaacaaa aaagtggaag agtaa                   1665
```

```
<210> SEQ ID NO 34
<211> LENGTH: 561
<212> TYPE: PRT
<213> ORGANISM: Homo sapiens

<400> SEQUENCE: 34

Met Thr Val Leu Glu Ile Thr Leu Ala Val Ile Leu Thr Leu Leu Gly
1               5                   10                  15

Leu Ala Ile Leu Ala Ile Leu Leu Thr Arg Trp Ala Arg Cys Lys Gln
            20                  25                  30

Ser Glu Met Tyr Ile Ser Arg Tyr Ser Ser Glu Gln Ser Ala Arg Leu
        35                  40                  45

Leu Asp Tyr Glu Asp Gly Arg Gly Ser Arg His Ala Tyr Ser Thr Gln
    50                  55                  60

Ser Asp Thr Ser Tyr Asp Asn Arg Glu Arg Ser Lys Arg Asp Tyr Thr
65                  70                  75                  80

Pro Ser Thr Asn Ser Leu Ala Leu Ser Arg Ser Ser Ile Ala Leu Pro
```

-continued

```
                85                  90                  95

Gln Gly Ser Met Ser Ser Ile Lys Cys Leu Gln Thr Thr Glu Glu Pro
            100                 105                 110

Pro Ser Arg Thr Ala Gly Ala Met Met Gln Phe Thr Ala Pro Ile Pro
        115                 120                 125

Gly Ala Thr Gly Pro Ile Lys Leu Ser Gln Lys Thr Ile Val Gln Thr
    130                 135                 140

Pro Gly Pro Ile Val Gln Tyr Pro Gly Ser Asn Ala Gly Pro Pro Ser
145                 150                 155                 160

Ala Pro Arg Gly Pro Pro Met Ala Pro Ile Ile Ile Ser Gln Arg Thr
                165                 170                 175

Ala Ser Gln Leu Ala Ala Pro Ile Ile Ile Ser Gln Arg Thr Ala Arg
            180                 185                 190

Ile Pro Gln Val His Thr Met Asp Ser Ser Gly Lys Ile Thr Leu Thr
        195                 200                 205

Pro Val Val Ile Leu Thr Gly Tyr Met Asp Glu Glu Leu Ala Lys Lys
    210                 215                 220

Ser Cys Ser Lys Ile Gln Ile Leu Lys Cys Gly Gly Thr Ala Arg Ser
225                 230                 235                 240

Gln Asn Ser Arg Glu Glu Asn Lys Glu Ala Leu Lys Asn Asp Ile Ile
                245                 250                 255

Phe Thr Asn Ser Val Glu Ser Leu Lys Ser Ala His Ile Lys Glu Pro
            260                 265                 270

Glu Arg Glu Gly Lys Gly Thr Asp Leu Glu Lys Asp Lys Ile Gly Met
        275                 280                 285

Glu Val Lys Val Asp Ser Asp Ala Gly Ile Pro Lys Arg Gln Glu Thr
    290                 295                 300

Gln Leu Lys Ile Ser Glu Met Ser Ile Pro Gln Gly Gln Gly Ala Gln
305                 310                 315                 320

Ile Lys Lys Ser Val Ser Asp Val Pro Arg Gly Gln Glu Ser Gln Val
                325                 330                 335

Lys Lys Ser Glu Ser Gly Val Pro Lys Gly Gln Glu Ala Gln Val Thr
            340                 345                 350

Lys Ser Gly Leu Val Val Leu Lys Gly Gln Glu Ala Gln Val Glu Lys
        355                 360                 365

Ser Glu Met Gly Val Pro Arg Arg Gln Glu Ser Gln Val Lys Lys Ser
    370                 375                 380

Gln Ser Gly Val Ser Lys Gly Gln Glu Ala Gln Val Lys Lys Arg Glu
385                 390                 395                 400

Ser Val Val Leu Lys Gly Gln Glu Ala Gln Val Glu Lys Ser Glu Leu
                405                 410                 415

Lys Val Pro Lys Gly Gln Glu Gly Gln Val Glu Lys Thr Glu Ala Asp
            420                 425                 430

Val Pro Lys Glu Gln Glu Val Gln Glu Lys Lys Ser Glu Ala Gly Val
        435                 440                 445

Leu Lys Gly Pro Glu Ser Gln Val Lys Asn Thr Glu Val Ser Val Pro
    450                 455                 460

Glu Thr Leu Glu Ser Gln Val Lys Lys Ser Glu Ser Gly Val Leu Lys
465                 470                 475                 480

Gly Gln Glu Ala Gln Glu Lys Lys Glu Ser Phe Glu Asp Lys Gly Asn
                485                 490                 495

Asn Asp Lys Glu Lys Glu Arg Asp Ala Glu Lys Asp Pro Asn Lys Lys
            500                 505                 510
```

```
Glu Lys Gly Asp Lys Asn Thr Lys Gly Asp Lys Gly Lys Asp Lys Val
        515                 520                 525

Lys Gly Lys Arg Glu Ser Glu Ile Asn Gly Glu Lys Ser Lys Gly Ser
    530                 535                 540

Lys Arg Ala Lys Ala Asn Thr Gly Arg Lys Tyr Asn Lys Lys Val Glu
545                 550                 555                 560

Glu


<210> SEQ ID NO 35
<211> LENGTH: 569
<212> TYPE: PRT
<213> ORGANISM: Homo sapiens

<400> SEQUENCE: 35

Met Thr Val Leu Glu Ile Thr Leu Ala Val Ile Leu Thr Leu Leu Gly
1               5                   10                  15

Leu Ala Ile Leu Ala Ile Leu Leu Thr Arg Trp Ala Arg Arg Lys Gln
            20                  25                  30

Ser Glu Met His Ile Ser Arg Tyr Ser Ser Glu Gln Ser Ala Arg Leu
        35                  40                  45

Leu Asp Tyr Glu Asp Gly Arg Gly Ser Arg His Ala Tyr Ser Thr Gln
    50                  55                  60

Ser Asp Thr Ser Cys Asp Asn Arg Glu Arg Ser Lys Arg Asp Tyr Thr
65                  70                  75                  80

Pro Ser Thr Asn Ser Leu Ala Leu Ser Arg Ser Ser Ile Ala Leu Pro
                85                  90                  95

Gln Gly Ser Met Ser Ser Ile Lys Cys Leu Gln Thr Thr Glu Glu Leu
            100                 105                 110

Pro Ser Arg Thr Ala Gly Ala Met Met Gln Phe Thr Ala Pro Ile Pro
        115                 120                 125

Gly Ala Thr Gly Pro Ile Lys Leu Ser Gln Lys Thr Ile Val Gln Thr
    130                 135                 140

Pro Gly Pro Ile Val Gln Tyr Pro Gly Pro Asn Val Arg Ser His Pro
145                 150                 155                 160

His Thr Ile Thr Gly Pro Pro Ser Ala Pro Arg Gly Pro Pro Met Ala
                165                 170                 175

Pro Ile Ile Ile Ser Gln Arg Thr Ala Ser Gln Leu Ala Ala Pro Ile
            180                 185                 190

Ile Ile Ser Gln Arg Thr Ala Arg Ile Pro Gln Val His Thr Met Asp
        195                 200                 205

Ser Ser Gly Lys Thr Thr Leu Thr Pro Val Val Ile Leu Thr Gly Tyr
    210                 215                 220

Met Asp Glu Glu Leu Ala Lys Lys Ser Cys Ser Lys Ile Gln Ile Leu
225                 230                 235                 240

Lys Cys Gly Gly Thr Ala Arg Ser Gln Asn Ser Arg Glu Glu Asn Lys
                245                 250                 255

Glu Ala Leu Lys Asn Asp Ile Ile Phe Thr Asn Ser Val Glu Ser Leu
            260                 265                 270

Lys Ser Ala His Ile Lys Glu Pro Glu Arg Glu Gly Lys Gly Thr Asp
        275                 280                 285

Leu Glu Lys Asp Lys Ile Gly Met Glu Val Lys Val Asp Ser Asp Ala
    290                 295                 300

Gly Ile Pro Lys Arg Gln Glu Thr Gln Leu Lys Ile Ser Glu Met Ser
305                 310                 315                 320
```

```
Ile Pro Gln Gly Gln Gly Ala Gln Ile Lys Lys Ser Val Ser Asp Val
                325                 330                 335

Pro Arg Gly Gln Glu Ser Gln Val Lys Lys Ser Glu Ser Gly Val Pro
            340                 345                 350

Lys Gly Gln Glu Ala Gln Val Thr Lys Ser Gly Leu Val Val Leu Lys
        355                 360                 365

Gly Gln Glu Ala Gln Val Glu Lys Ser Glu Met Gly Val Pro Arg Arg
    370                 375                 380

Gln Glu Ser Gln Val Lys Lys Ser Gln Ser Gly Val Ser Lys Gly Gln
385                 390                 395                 400

Glu Ala Gln Val Lys Lys Arg Glu Ser Val Val Leu Lys Gly Gln Glu
                405                 410                 415

Ala Gln Val Glu Lys Ser Glu Leu Lys Val Pro Lys Gly Gln Glu Gly
            420                 425                 430

Gln Val Glu Lys Thr Glu Ala Asp Val Pro Lys Glu Gln Glu Val Gln
        435                 440                 445

Glu Lys Lys Ser Glu Ala Gly Val Leu Lys Gly Pro Glu Ser Gln Val
    450                 455                 460

Lys Asn Thr Glu Val Ser Val Pro Glu Thr Leu Glu Ser Gln Val Lys
465                 470                 475                 480

Lys Ser Glu Ser Gly Val Leu Lys Gly Gln Glu Ala Gln Glu Lys Lys
                485                 490                 495

Glu Ser Phe Glu Asp Lys Gly Asn Asn Asp Lys Glu Lys Glu Arg Asp
            500                 505                 510

Ala Glu Lys Asp Pro Asn Lys Lys Glu Lys Gly Asp Lys Asn Thr Lys
        515                 520                 525

Gly Asp Lys Gly Lys Asp Lys Val Lys Gly Lys Arg Glu Ser Glu Ile
    530                 535                 540

Asn Gly Glu Lys Ser Lys Gly Ser Lys Arg Ala Lys Ala Asn Thr Gly
545                 550                 555                 560

Arg Lys Tyr Asn Lys Lys Val Glu Glu
                565


<210> SEQ ID NO 36
<211> LENGTH: 554
<212> TYPE: PRT
<213> ORGANISM: Homo sapiens

<400> SEQUENCE: 36

Met Thr Val Leu Glu Ile Thr Leu Ala Val Ile Leu Thr Leu Leu Gly
1               5                   10                  15

Leu Ala Ile Leu Ala Ile Leu Leu Thr Arg Trp Ala Arg Cys Lys Gln
            20                  25                  30

Ser Glu Met Tyr Ile Ser Arg Tyr Ser Ser Glu Gln Ser Ala Arg Leu
        35                  40                  45

Leu Asp Tyr Glu Asp Gly Arg Gly Ser Arg His Ala Tyr Ser Thr Gln
    50                  55                  60

Ser Glu Arg Ser Lys Arg Asp Tyr Thr Pro Ser Thr Asn Ser Leu Ala
65                  70                  75                  80

Leu Ser Arg Ser Ser Ile Ala Leu Pro Gln Gly Ser Met Ser Ser Ile
                85                  90                  95

Lys Cys Leu Gln Thr Thr Glu Glu Pro Pro Ser Arg Thr Ala Gly Ala
            100                 105                 110

Met Met Gln Phe Thr Ala Pro Ile Pro Gly Ala Thr Gly Pro Ile Lys
```

-continued

```
        115                 120                 125

Leu Ser Gln Lys Thr Ile Val Gln Thr Pro Gly Pro Ile Val Gln Tyr
    130                 135                 140

Pro Gly Ser Asn Ala Gly Pro Pro Ser Ala Pro Arg Gly Pro Pro Met
145                 150                 155                 160

Ala Pro Ile Ile Ile Ser Gln Arg Thr Ala Ser Gln Leu Ala Ala Pro
                165                 170                 175

Ile Ile Ile Ser Gln Arg Thr Ala Arg Ile Pro Gln Val His Thr Met
            180                 185                 190

Asp Ser Ser Gly Lys Ile Thr Leu Thr Pro Val Val Ile Leu Thr Gly
        195                 200                 205

Tyr Met Asp Glu Glu Leu Ala Lys Lys Ser Cys Ser Lys Ile Gln Ile
    210                 215                 220

Leu Lys Cys Gly Gly Thr Ala Arg Ser Gln Asn Ser Arg Glu Glu Asn
225                 230                 235                 240

Lys Glu Ala Leu Lys Asn Asp Ile Ile Phe Thr Asn Ser Val Glu Ser
                245                 250                 255

Leu Lys Ser Ala His Ile Lys Glu Pro Glu Arg Glu Gly Lys Gly Thr
            260                 265                 270

Asp Leu Glu Lys Asp Lys Ile Gly Met Glu Val Lys Val Asp Ser Asp
        275                 280                 285

Ala Gly Ile Pro Lys Arg Gln Glu Thr Gln Leu Lys Ile Ser Glu Met
    290                 295                 300

Ser Ile Pro Gln Gly Gln Gly Ala Gln Ile Lys Lys Ser Val Ser Asp
305                 310                 315                 320

Val Pro Arg Gly Gln Glu Ser Gln Val Lys Lys Ser Glu Ser Gly Val
                325                 330                 335

Pro Lys Gly Gln Glu Ala Gln Val Thr Lys Ser Gly Leu Val Val Leu
            340                 345                 350

Lys Gly Gln Glu Ala Gln Val Glu Lys Ser Glu Met Gly Val Pro Arg
        355                 360                 365

Arg Gln Glu Ser Gln Val Lys Lys Ser Gln Ser Gly Val Ser Lys Gly
    370                 375                 380

Gln Glu Ala Gln Val Lys Lys Arg Glu Ser Val Val Leu Lys Gly Gln
385                 390                 395                 400

Glu Ala Gln Val Glu Lys Ser Glu Leu Lys Val Pro Lys Gly Gln Glu
                405                 410                 415

Gly Gln Val Glu Lys Thr Glu Ala Asp Val Pro Lys Glu Gln Glu Val
            420                 425                 430

Gln Glu Lys Lys Ser Glu Ala Gly Val Leu Lys Gly Pro Glu Ser Gln
        435                 440                 445

Val Lys Asn Thr Glu Val Ser Val Pro Glu Thr Leu Glu Ser Gln Val
    450                 455                 460

Lys Lys Ser Glu Ser Gly Val Leu Lys Gly Gln Glu Ala Gln Glu Lys
465                 470                 475                 480

Lys Glu Ser Phe Glu Asp Lys Gly Asn Asn Asp Lys Glu Lys Glu Arg
                485                 490                 495

Asp Ala Glu Lys Asp Pro Asn Lys Lys Glu Lys Gly Asp Lys Asn Thr
            500                 505                 510

Lys Gly Asp Lys Gly Lys Asp Lys Val Lys Gly Lys Arg Glu Ser Glu
        515                 520                 525

Ile Asn Gly Glu Lys Ser Lys Gly Ser Lys Arg Ala Lys Ala Asn Thr
    530                 535                 540
```

Gly Arg Lys Tyr Asn Lys Lys Val Glu Glu
545 550

<210> SEQ ID NO 37
<211> LENGTH: 1182
<212> TYPE: DNA
<213> ORGANISM: Homo sapiens

<400> SEQUENCE: 37
acacaggttg gagcagagaa agaggaaaca tagaggtgcc aaaggaacaa agacataatg 60
atgtcatcca agccaacaag ccatgctgaa gtaaatgaaa ccatacccaa cccttaccca 120
ccaggcagct ttatggctcc tggatttcaa cagcctctgg gttcaatcaa cttagaaaac 180
caagctcagg gtgctcagcg tgctcagccc tacggcatca catctccggg aatctttgct 240
agcagtcaac cgggtcaagg aaatatacaa atgataaatc caagtgtggg aacagcagta 300
atgaacttta aagaagaagc aaaggcacta ggggtgatcc agatcatggt tggattgatg 360
cacattggtt ttggaattgt tttgtgttta atatccttct cttttagaga agtattaggt 420
tttgcctcta ctgctgttat tggtggatac ccattctggg gtggcctttc ttttattatc 480
tctggctctc tctctgtgtc agcatccaag gagctttccc gttgtctggt gaaaggcagc 540
ctgggaatga acattgttag ttctatcttg gccttcattg gagtgattct gctgctggtg 600
gatatgtgca tcaatggggt agctggccaa gactactggg ccgtgctttc tggaaaaggc 660
atttcagcca cgctgatgat cttctccctc ttggagttct tcgtagcttg tgccacagcc 720
cattttgcca accaagcaaa caccacaacc aatatgtctg tcctggttat tccaaatatg 780
tatgaaagca accctgtgac accagcgtct tcttcagctc ctcccagatg caacaactac 840
tcagctaatg cccctaaata gtaaaagaaa aaggggtatc agtctaatct catggagaaa 900
aactacttgc aaaaacttct taagaagatg tcttttattg tctacaatga tttctagtct 960
ttaaaaactg tgtttgagat ttgtttttag gttggtcgct aatgatggct gtatctccct 1020
tcactgtctc ttcctacatt accactacta catgctggca aaggtgaagg atcagaggac 1080
tgaaaaatga ttctgcaact ctcttaaagt tagaaatgtt tctgttcata ttactttttc 1140
cttaataaaa tgtcattaga aacaaaaaaa aaaaaaaaaa aa 1182

<210> SEQ ID NO 38
<211> LENGTH: 267
<212> TYPE: PRT
<213> ORGANISM: Homo sapiens

<400> SEQUENCE: 38

Met Met Ser Ser Lys Pro Thr Ser His Ala Glu Val Asn Glu Thr Ile
1 5 10 15

Pro Asn Pro Tyr Pro Pro Gly Ser Phe Met Ala Pro Gly Phe Gln Gln
20 25 30

Pro Leu Gly Ser Ile Asn Leu Glu Asn Gln Ala Gln Gly Ala Gln Arg
35 40 45

Ala Gln Pro Tyr Gly Ile Thr Ser Pro Gly Ile Phe Ala Ser Ser Gln
50 55 60

Pro Gly Gln Gly Asn Ile Gln Met Ile Asn Pro Ser Val Gly Thr Ala
65 70 75 80

Val Met Asn Phe Lys Glu Glu Ala Lys Ala Leu Gly Val Ile Gln Ile
85 90 95

Met Val Gly Leu Met His Ile Gly Phe Gly Ile Val Leu Cys Leu Ile

```
            100                 105                 110

Ser Phe Ser Phe Arg Glu Val Leu Gly Phe Ala Ser Thr Ala Val Ile
        115                 120                 125

Gly Gly Tyr Pro Phe Trp Gly Gly Leu Ser Phe Ile Ile Ser Gly Ser
    130                 135                 140

Leu Ser Val Ser Ala Ser Lys Glu Leu Ser Arg Cys Leu Val Lys Gly
145                 150                 155                 160

Ser Leu Gly Met Asn Ile Val Ser Ser Ile Leu Ala Phe Ile Gly Val
                165                 170                 175

Ile Leu Leu Leu Val Asp Met Cys Ile Asn Gly Val Ala Gly Gln Asp
            180                 185                 190

Tyr Trp Ala Val Leu Ser Gly Lys Gly Ile Ser Ala Thr Leu Met Ile
        195                 200                 205

Phe Ser Leu Leu Glu Phe Phe Val Ala Cys Ala Thr Ala His Phe Ala
    210                 215                 220

Asn Gln Ala Asn Thr Thr Thr Asn Met Ser Val Leu Val Ile Pro Asn
225                 230                 235                 240

Met Tyr Glu Ser Asn Pro Val Thr Pro Ala Ser Ser Ser Ala Pro Pro
                245                 250                 255

Arg Cys Asn Asn Tyr Ser Ala Asn Ala Pro Lys
            260                 265


<210> SEQ ID NO 39
<211> LENGTH: 1948
<212> TYPE: DNA
<213> ORGANISM: Homo sapiens

<400> SEQUENCE: 39

gcacgaggtt ttgaggacca gcaacacagc aatacttcca gatctccata taacctctgt     60

tcatttggga ggggctttgt attttcaaca ggagagttca aagttcattt ttttttcagc    120

aactacagtt ctaagtgaaa tctattttta ttgatacatg gtattttaca tgtttatggg    180

atacatatga gtcataatct attttaaata ataccttagt gttgtaaaat caacagtgct    240

ttttaaaaga aatatacctt gttaattatc ccacatgtgt ctccagaagt acagcttgaa    300

caaatccacc ttctgtggac caagcaccac cctgggcatt tctagcatga gcaaaatcca    360

aggtcctggc tggactccag agatgctatt tacctcagaa gcatgacaat aggaggcaga    420

aggagcaggc aaatccaagt cctttcttgt agtttccttg tttggggagg aaaagttgag    480

ttttactatt atggaaaaga aacaggaaat agagacagac aaagagatat gacaatacag    540

tcctgccacc cagatactca tttccaccta ccattccatg catttgtttt gaatatataa    600

gtatgtacat aaaggtaggt actctcaagt ccatcagggc ttggctgtcc actgtttttg    660

aagttccaga atgtttttgc taagttgagg aaataccaaa tcaggactat gaaaattatg    720

gtatatattg atgtgtcaca gaacacagat gtgacataat aaagatgtgt aagattatat    780

atataacttg tgtgtacacc tacctcatct ggggataaca cctcaagttt aattttgagg    840

cttgggtcaa tcgtgcttcc cttccctttc ataggtcctc tatgagatat tgtcatagat    900

tccatgttat gcaatagcca tagaatatga catctctcta tgataattct atattacttt    960

aattgctgca cagaagttca ttgtatgtaa gtgccacagt atattataga tcttcttgtg   1020

ggacatctat ttctagttta tgtgatagta tagcactttc atgaatgttc ttgtacttga   1080

tctttacaca ttttcttttt tccttaggat gaattctgag agatgtaatt gatggggcaa   1140

aatgtactca ctgtttgagg tttgaaattt ttccatcaaa agctggtact cttggttttt   1200
```

-continued

```
taagacaaag agcaaatcct cccctgccag gattgacttt tggctctttt ttttcaaacc   1260

tcactgcttt ttggtttagt tgtcataaaa tgccaagcac catgaacagg gctccatgaa   1320

ggggctcaga ggtaggaggg ctgtgattag gagaaggctt ggactgatgg gcaatttgag   1380

tgctcagaat tagagtgagg gggtgggggt gctgcaggga cagatgctgg ggaaagacac   1440

cctgaagggc aaagggagca acaatggctg cagtacatgt ggcctttcag ctagcgcaga   1500

ggatggaaac cagagtgggc tgatgattgg atgccaggcc tgagccagca actgtgatcc   1560

tgagctgtgc acacttctgg ttgggattat ttctggtttc tacttcctgt ttgaagatgt   1620

ggcatggaga gtgctctgct ttgacctgaa gtattttatc tatcctcagt ctcaggacac   1680

tgttgatgga attaaggcca agcacatctg caaaaaagac attgctggag gaggtgcaaa   1740

gagctggaaa ccaagtctcc agtcctggga aaagcagtgg tatggaaaag caatggaaag   1800

agcattttga aaatgccatt ccactgtttt ctggccttta tgatttctgc tgagaaatcc   1860

actgttagtc tgatggggtc tccttcatag caccaatgac ctgaagagcc ttgttgaagg   1920

aagactccat ctgatgactc agagcaag                                      1948
```

<210> SEQ ID NO 40
<211> LENGTH: 1406
<212> TYPE: DNA
<213> ORGANISM: Homo sapiens

<400> SEQUENCE: 40

```
cggtgagagg ggcgcgcagc agcagctcct caacgccgca acgcgccggc ccaactgcag     60

gaaggtctgt gctctggagc cagggtaaat ggttataaaa ttatacacca tggccctcct    120

aaagacactc taggaaaacc atgtcatcct gatcttaaaa cacctgcaag aaagagcaca    180

gtacttcacc attaataaag tagatatttc atcctgctca gaaaaccaac atttccagca    240

atggctttac taccggtgtt gtttctggtt actgtgctgc ttccatcttt acctgcagaa    300

ggaaaggatc ccgcttttac tgctttgtta accacccagt tgcaagtgca aagggagatt    360

gtaaataaac acaatgaact aaggaaagca gtctctccac ctgccagtaa catgctaaag    420

atggaatgga gcagagaggt aacaacgaat gcccaaaggt gggcaaacaa gtgcacttta    480

caacatagtg atccagagga ccgcaaaacc agtacaagat gtggtgagaa tctctatatg    540

tcaagtgacc ctacttcctg gtcttctgca atccaaagct ggtatgacga gatcctagat    600

tttgtctatg gtgtaggacc aaagagtccc aatgcagttg ttggacatta tactcagctt    660

gtttggtact cgacttacca ggtaggctgt ggaattgcct actgtcccaa tcaagatagt    720

ctaaaatact actatgtttg ccaatattgt cctgctggta ataatatgaa tagaaagaat    780

accccgtacc aacaaggaac accttgtgcc ggttgccctg atgactgtga caaaggacta    840

tgcaccaata gttgccagta tcaagatctc ctaagtaact gtgattcctt gaagaataca    900

gctggctgtg aacatgagtt actcaaggaa aagtgcaagg ctacttgcct atgtgagaac    960

aaaatttact gatttaccta gtgagcattg tgcaagactg catggataag ggctgcatca   1020

tttaattgcg acataccagt ggaaattgta tgtatgttag tgacaaattt gatttcaaag   1080

agcaatgcat cttctccccc agatcatcac agaaatcact ttcaggcaat gatttacaaa   1140

agtagcatag tagatgatga caactgtgaa ctctgacata aatttagtgc tttataacga   1200

actgaatcag gttgaggatt ttgaaaactg tataaccata ggatttaggt cactaggact   1260

ttggatcaaa atggtgcatt acgtatttcc tgaaacatgc taaagaagaa gactgtaaca   1320
```

```
tcattgccat tcctactacc tgagttttta cttgcataaa caataaattc aaagctttac   1380

atctgcaaaa aaaaaaaaaa aaaaaa                                         1406


<210> SEQ ID NO 41
<211> LENGTH: 243
<212> TYPE: PRT
<213> ORGANISM: Homo sapiens

<400> SEQUENCE: 41

Met Ala Leu Leu Pro Val Leu Phe Leu Val Thr Val Leu Leu Pro Ser
1               5                   10                  15

Leu Pro Ala Glu Gly Lys Asp Pro Ala Phe Thr Ala Leu Leu Thr Thr
            20                  25                  30

Gln Leu Gln Val Gln Arg Glu Ile Val Asn Lys His Asn Glu Leu Arg
        35                  40                  45

Lys Ala Val Ser Pro Pro Ala Ser Asn Met Leu Lys Met Glu Trp Ser
    50                  55                  60

Arg Glu Val Thr Thr Asn Ala Gln Arg Trp Ala Asn Lys Cys Thr Leu
65                  70                  75                  80

Gln His Ser Asp Pro Glu Asp Arg Lys Thr Ser Thr Arg Cys Gly Glu
                85                  90                  95

Asn Leu Tyr Met Ser Ser Asp Pro Thr Ser Trp Ser Ser Ala Ile Gln
            100                 105                 110

Ser Trp Tyr Asp Glu Ile Leu Asp Phe Val Tyr Gly Val Gly Pro Lys
        115                 120                 125

Ser Pro Asn Ala Val Val Gly His Tyr Thr Gln Leu Val Trp Tyr Ser
    130                 135                 140

Thr Tyr Gln Val Gly Cys Gly Ile Ala Tyr Cys Pro Asn Gln Asp Ser
145                 150                 155                 160

Leu Lys Tyr Tyr Tyr Val Cys Gln Tyr Cys Pro Ala Gly Asn Asn Met
                165                 170                 175

Asn Arg Lys Asn Thr Pro Tyr Gln Gln Gly Thr Pro Cys Ala Gly Cys
            180                 185                 190

Pro Asp Asp Cys Asp Lys Gly Leu Cys Thr Asn Ser Cys Gln Tyr Gln
        195                 200                 205

Asp Leu Leu Ser Asn Cys Asp Ser Leu Lys Asn Thr Ala Gly Cys Glu
    210                 215                 220

His Glu Leu Leu Lys Glu Lys Cys Lys Ala Thr Cys Leu Cys Glu Asn
225                 230                 235                 240

Lys Ile Tyr


<210> SEQ ID NO 42
<211> LENGTH: 21
<212> TYPE: DNA
<213> ORGANISM: Artificial sequence
<220> FEATURE:
<223> OTHER INFORMATION: Description of the artificial sequence:
      oligonucleotide

<400> SEQUENCE: 42

tctagcactg tctcgatcaa g                                                21


<210> SEQ ID NO 43
<211> LENGTH: 21
<212> TYPE: DNA
<213> ORGANISM: Artificial sequence
<220> FEATURE:
<223> OTHER INFORMATION: Description of the artificial sequence:
```

oligonucleotide

<400> SEQUENCE: 43
tgtcctcttg gtacatctga c 21

<210> SEQ ID NO 44
<211> LENGTH: 21
<212> TYPE: DNA
<213> ORGANISM: Artificial sequence
<220> FEATURE:
<223> OTHER INFORMATION: Description of the artificial sequence: oligonucleotide

<400> SEQUENCE: 44
ctgtgtcagc atccaaggag c 21

<210> SEQ ID NO 45
<211> LENGTH: 21
<212> TYPE: DNA
<213> ORGANISM: Artificial sequence
<220> FEATURE:
<223> OTHER INFORMATION: Description of the artificial sequence: oligonucleotide

<400> SEQUENCE: 45
ttcacctttg ccagcatgta g 21

<210> SEQ ID NO 46
<211> LENGTH: 21
<212> TYPE: DNA
<213> ORGANISM: Artificial sequence
<220> FEATURE:
<223> OTHER INFORMATION: Description of the artificial sequence: oligonucleotide

<400> SEQUENCE: 46
cttgctctga gtcatcagat g 21

<210> SEQ ID NO 47
<211> LENGTH: 21
<212> TYPE: DNA
<213> ORGANISM: Artificial sequence
<220> FEATURE:
<223> OTHER INFORMATION: Description of the artificial sequence: oligonucleotide

<400> SEQUENCE: 47
cacagaatat gagccataca g 21

<210> SEQ ID NO 48
<211> LENGTH: 22
<212> TYPE: DNA
<213> ORGANISM: Artificial sequence
<220> FEATURE:
<223> OTHER INFORMATION: Description of the artificial sequence: oligonucleotide

<400> SEQUENCE: 48
ggtgtcactt ctgtgccttc ct 22

<210> SEQ ID NO 49
<211> LENGTH: 21
<212> TYPE: DNA
<213> ORGANISM: Artificial sequence
<220> FEATURE:
<223> OTHER INFORMATION: Description of the artificial sequence: oligonucleotide

<400> SEQUENCE: 49
cggcaccagt tccaacaata g    21

<210> SEQ ID NO 50
<211> LENGTH: 18
<212> TYPE: DNA
<213> ORGANISM: Artificial sequence
<220> FEATURE:
<223> OTHER INFORMATION: Description of the artificial sequence:
      oligonucleotide

<400> SEQUENCE: 50
caaaggttct ccaaatgt    18

<210> SEQ ID NO 51
<211> LENGTH: 21
<212> TYPE: DNA
<213> ORGANISM: Artificial sequence
<220> FEATURE:
<223> OTHER INFORMATION: Description of the artificial sequence:
      oligonucleotide

<400> SEQUENCE: 51
tagcgcctca actgtcgttg g    21

<210> SEQ ID NO 52
<211> LENGTH: 23
<212> TYPE: DNA
<213> ORGANISM: Artificial sequence
<220> FEATURE:
<223> OTHER INFORMATION: Description of the artificial sequence:
      oligonucleotide

<400> SEQUENCE: 52
cgtgagcgct tcgagatgtt ccg    23

<210> SEQ ID NO 53
<211> LENGTH: 23
<212> TYPE: DNA
<213> ORGANISM: Artificial sequence
<220> FEATURE:
<223> OTHER INFORMATION: Description of the artificial sequence:
      oligonucleotide

<400> SEQUENCE: 53
cctaaccagc tgcccaactg tag    23

<210> SEQ ID NO 54
<211> LENGTH: 1550
<212> TYPE: DNA
<213> ORGANISM: Homo sapiens

<400> SEQUENCE: 54
atgaatgaaa gtcctgatcc gactgacctg gcgggagtca tcattgagct cggccccaat    60
gacagtccac agacaagtga atttaaagga gcaaccgagg aggcacctgc gaaagaaagc    120
ccacacacaa gtgaatttaa aggagcagcc cgggtgtcac ctatcagtga aagtgtgtta    180
gcacgacttt ccaagtttga agttgaagat gctgaaaatg ttgcttcata tgacagcaag    240
attaagaaaa ttgtgcattc aattgtatca tcctttgcat ttggactatt tggagttttc    300
ctggtcttac tggatgtcac tctcatcctt gccgacctaa ttttcactga cagcaaactt    360
tatattcctt tggagtatcg ttctatttct ctagctattg ccttattttt tctcatggat    420

-continued gttcttcttc gagtatttgt agaaaggaga cagcagtatt tttctgactt atttaacatt 480
ttagatactg ccattattgt gattcttctg ctggttgatg tcgtttacat ttttttgac 540 attaagttgc ttaggaatat tcccagatgg acacatttac ttcgacttct acgacttatt 600
attctgttaa gaatttttca tctgtttcat caaaaaagac aacttgaaaa gctgataaga 660
aggcgggttt cagaaaacaa aaggcgatac acaagggatg gatttgacct agacctcact 720
tacgttacag aacgtattat tgctatgtca tttccatctt ctggaaggca gtctttctat 780
agaaatccaa tcaaggaagt tgtgcggttt ctagataaga aacaccgaaa ccactatcga 840
gtctacaatc tatgcagtga aagagcttac gatcctaagc acttccataa tagggtcgtt 900
agaatcatga ttgatgatca taatgtcccc actctacatc agatggtggt tttcaccaag 960
gaagtaaatg agtggatggc tcaagatctt gaaaacatcg tagcgattca ctgtaaagga 1020
ggcacagata gaacaggaac tatggtttgt gccttcctta ttgcctctga aatatgttca 1080
actgcaaagg aaagcctgta ttattttgga gaaaggcgaa cagataaaac ccacagcgaa 1140
aaatttcagg gagtagaaac tccttctcag gttatgtacg tgatctaaaa atccaaatag 1200
aaatggagaa aaaggttgtc ttttccacta tttcattagg aaaatgttcg gtacttgata 1260
acattacaac agacaaaata ttaattgatg tattcgacgg tccacctctg tatgatgatg 1320
tgaaagtgca gtttttctat tcgaatcttc ctacatacta tgacaattgc tcattttact 1380
tctggttgca cacatctttt attgaaaata acaggcttta tctaccaaaa aatgaattgg 1440
ataatctaca taaacaaaaa gcacggagaa tttatccatc agattttgcc gtggagatac 1500
tttttggcga gaaaatgact tccagtgatg ttgtagctgg atccgattaa 1550

<210> SEQ ID NO 55
<211> LENGTH: 1407
<212> TYPE: DNA
<213> ORGANISM: Homo sapiens

<400> SEQUENCE: 55
atgaatgaaa gtcctgatcc gactgacctg gcgggagtca tcattgagct cggccccaat 60
gacagtccac agacaagtga atttaaagga gcaaccgagg aggcacctgc gaaagaaagc 120
ccacacacaa gtgaatttaa aggagcagcc cgggtgtcac ctatcagtga aagtgtgtta 180
gcacgacttt ccaagtttga agttgaagat gctgaaaatg ttgcttcata tgacagcaag 240
attaagaaaa ttgtgcattc aattgtatca tcctttgcat ttggactatt tggagttttc 300
ctggtcttac tggatgtcac tctcatcctt gccgacctaa ttttcactga cagcaaactt 360
tatattcctt tggagtatcg ttctatttct ctagctattg ccttattttt tctcatggat 420
gttcttcttc gagtatttgt agaaaggaga cagcagtatt tttctgactt atttaacatt 480
ttagatactg ccattattgt gattcttctg ctggttgatg tcgtttacat ttttttgac 540 attaagttgc ttaggaatat tcccagatgg acacatttac ttcgacttct acgacttatt 600
attctgttaa gaatttttca tctgtttcat caaaaaagac aacttgaaaa gctgataaga 660
aggcgggttt cagaaaacaa aaggcgatac acaagggatg gatttgacct agacctcact 720
tacgttacag aacgtattat tgctatgtca tttccatctt ctggaaggca gtctttctat 780
agaaatccaa tcaaggaagt tgtgcggttt ctagataaga aacaccgaaa ccactatcga 840
gtctacaatc tatgcagtga aagagcttac gatcctaagc acttccataa tagggtcgtt 900
agaatcatga ttgatgatca taatgtcccc actctacatc agatggtggt tttcaccaag 960
gaagtaaatg agtggatggc tcaagatctt gaaaacatcg tagcgattca ctgtaaagga 1020

-continued

```
ggcacaggtt atgtacgtga tctaaaaatc caaatagaaa tggagaaaaa ggttgtcttt   1080
tccactattt cattaggaaa atgttcggta cttgataaca ttacaacaga caaaatatta   1140
attgatgtat tcgacggtcc acctctgtat gatgatgtga aagtgcagtt tttctattcg   1200
aatcttccta catactatga caattgctca ttttacttct ggttgcacac atcttttatt   1260
gaaaataaca ggctttatct accaaaaaat gaattggata atctacataa acaaaaagca   1320
cggagaattt atccatcaga ttttgccgtg gagatacttt ttggcgagaa aatgacttcc   1380
agtgatgttg tagctggatc cgattaa                                       1407
```

<210> SEQ ID NO 56
<211> LENGTH: 1413
<212> TYPE: DNA
<213> ORGANISM: Homo sapiens

<400> SEQUENCE: 56

```
atgaatgaaa gtcctgatcc gactgacctg gcgggagtca tcattgagct cggccccaat     60
gacagtccac agacaagtga atttaaagga gcaaccgagg aggcacctgc gaaagaaagt    120
gtgttagcac gactttccaa gtttgaagtt gaagatgctg aaaatgttgc ttcatatgac    180
agcaagatta agaaaattgt gcattcaatt gtatcatcct ttgcatttgg actatttgga    240
gttttcctgg tcttactgga tgtcactctc atccttgccg acctaatttt cactgacagc    300
aaactttata ttcctttgga gtatcgttct atttctctag ctattgcctt atttttctc     360
atggatgttc ttcttcgagt atttgtagaa aggagacagc agtatttttc tgacttattt    420
aacattttag atactgccat tattgtgatt cttctgctgg ttgatgtcgt ttacattttt    480
tttgacatta agttgcttag gaatattccc agatggacac atttacttcg acttctacga    540
cttattattc tgttaagaat ttttcatctg tttcatcaaa aaagacaact tgaaaagctg    600
ataagaaggc gggtttcaga aaacaaaagg cgatacacaa gggatggatt tgacctagac    660
ctcacttacg ttacagaacg tattattgct atgtcatttc catcttctgg aaggcagtct    720
ttctatagaa atccaatcaa ggaagttgtg cggtttctag ataagaaaca ccgaaaccac    780
tatcgagtct acaatctatg cagtgaaaga gcttacgatc ctaagcactt ccataatagg    840
gtcgttagaa tcatgattga tgatcataat gtccccactc tacatcagat ggtggttttc    900
accaaggaag taaatgagtg gatggctcaa gatcttgaaa acatcgtagc gattcactgt    960
aaaggaggca cagatagaac aggaactatg gtttgtgcct tccttattgc ctctgaaata   1020
tgttcaactg caaaggaaag cctgtattat tttggagaaa ggcgaacaga taaaacccac   1080
agcgaaaaat ttcagggagt agaaactcct tctgtacttg ataacattac aacagacaaa   1140
atattaattg atgtattcga cggtccacct ctgtatgatg atgtgaaagt gcagtttttc   1200
tattcgaatc ttcctacata ctatgacaat tgctcatttt acttctggtt gcacacatct   1260
tttattgaaa ataacaggct ttatctacca aaaaatgaat tggataatct acataaacaa   1320
aaagcacgga gaatttatcc atcagatttt gccgtggaga tactttttgg cgagaaaatg   1380
acttccagtg atgttgtagc tggatccgat taa                                1413
```

<210> SEQ ID NO 57
<211> LENGTH: 1353
<212> TYPE: DNA
<213> ORGANISM: Homo sapiens

<400> SEQUENCE: 57

-continued

```
atgaatgaaa gtcctgatcc gactgacctg gcgggagtca tcattgagct cggccccaat      60
gacagtccac agacaagtga atttaaagga gcaaccgagg aggcacctgc gaaagaaagt     120
gtgttagcac gactttccaa gtttgaagtt gaagatgctg aaaatgttgc ttcatatgac     180
agcaagatta agaaaattgt gcattcaatt gtatcatcct ttgcatttgg actatttgga     240
gttttcctgg tcttactgga tgtcactctc atccttgccg acctaatttt cactgacagc     300
aaactttata ttcctttgga gtatcgttct atttctctag ctattgcctt attttttctc     360
atggatgttc ttcttcgagt atttgtagaa aggagacagc agtatttttc tgacttattt     420
aacattttag atactgccat tattgtgatt cttctgctgg ttgatgtcgt ttacattttt     480
tttgacatta agttgcttag gaatattccc agatggacac atttacttcg acttctacga     540
cttattattc tgttaagaat tttttcatctg tttcatcaaa aaagacaact tgaaaagctg    600
ataagaaggc gggtttcaga aaacaaaagg cgatacacaa gggatggatt tgacctagac     660
ctcacttacg ttacagaacg tattattgct atgtcatttc catcttctgg aaggcagtct     720
ttctatagaa atccaatcaa ggaagttgtg cggtttctag ataagaaaca ccgaaaccac     780
tatcgagtct acaatctatg cagtgaaaga gcttacgatc ctaagcactt ccataatagg     840
gtcgttagaa tcatgattga tgatcataat gtccccactc tacatcagat ggtggttttc     900
accaaggaag taaatgagtg gatggctcaa gatcttgaaa acatcgtagc gattcactgt     960
aaaggaggca caggttatgt acgtgatcta aaaatccaaa tagaaatgga gaaaaaggtt    1020
gtcttttcca ctatttcatt aggaaaatgt tcggtacttg ataacattac aacagacaaa    1080
atattaattg atgtattcga cggtccacct ctgtatgatg atgtgaaagt gcagtttttc    1140
tattcgaatc ttcctacata ctatgacaat tgctcatttt acttctggtt gcacacatct    1200
tttattgaaa ataacaggct ttatctacca aaaaatgaat tggataatct acataaacaa    1260
aaagcacgga gaatttatcc atcagatttt gccgtggaga tactttttgg cgagaaaatg    1320
acttccagtg atgttgtagc tggatccgat taa                                 1353
```

<210> SEQ ID NO 58
<211> LENGTH: 395
<212> TYPE: PRT
<213> ORGANISM: Homo sapiens

<400> SEQUENCE: 58

```
Met Asn Glu Ser Pro Asp Pro Thr Asp Leu Ala Gly Val Ile Ile Glu
1               5                   10                  15

Leu Gly Pro Asn Asp Ser Pro Gln Thr Ser Glu Phe Lys Gly Ala Thr
            20                  25                  30

Glu Glu Ala Pro Ala Lys Glu Ser Pro His Thr Ser Glu Phe Lys Gly
        35                  40                  45

Ala Ala Arg Val Ser Pro Ile Ser Glu Ser Val Leu Ala Arg Leu Ser
    50                  55                  60

Lys Phe Glu Val Glu Asp Ala Glu Asn Val Ala Ser Tyr Asp Ser Lys
65                  70                  75                  80

Ile Lys Lys Ile Val His Ser Ile Val Ser Ser Phe Ala Phe Gly Leu
                85                  90                  95

Phe Gly Val Phe Leu Val Leu Leu Asp Val Thr Leu Ile Leu Ala Asp
            100                 105                 110

Leu Ile Phe Thr Asp Ser Lys Leu Tyr Ile Pro Leu Glu Tyr Arg Ser
        115                 120                 125

Ile Ser Leu Ala Ile Ala Leu Phe Phe Leu Met Asp Val Leu Leu Arg
```

-continued

```
    130                 135                 140

Val Phe Val Glu Arg Arg Gln Gln Tyr Phe Ser Asp Leu Phe Asn Ile
145                 150                 155                 160

Leu Asp Thr Ala Ile Ile Val Ile Leu Leu Leu Val Asp Val Val Tyr
                165                 170                 175

Ile Phe Phe Asp Ile Lys Leu Leu Arg Asn Ile Pro Arg Trp Thr His
            180                 185                 190

Leu Leu Arg Leu Leu Arg Leu Ile Ile Leu Leu Arg Ile Phe His Leu
        195                 200                 205

Phe His Gln Lys Arg Gln Leu Glu Lys Leu Ile Arg Arg Arg Val Ser
    210                 215                 220

Glu Asn Lys Arg Arg Tyr Thr Arg Asp Gly Phe Asp Leu Asp Leu Thr
225                 230                 235                 240

Tyr Val Thr Glu Arg Ile Ile Ala Met Ser Phe Pro Ser Ser Gly Arg
                245                 250                 255

Gln Ser Phe Tyr Arg Asn Pro Ile Lys Glu Val Val Arg Phe Leu Asp
            260                 265                 270

Lys Lys His Arg Asn His Tyr Arg Val Tyr Asn Leu Cys Ser Glu Arg
        275                 280                 285

Ala Tyr Asp Pro Lys His Phe His Asn Arg Val Val Arg Ile Met Ile
    290                 295                 300

Asp Asp His Asn Val Pro Thr Leu His Gln Met Val Val Phe Thr Lys
305                 310                 315                 320

Glu Val Asn Glu Trp Met Ala Gln Asp Leu Glu Asn Ile Val Ala Ile
                325                 330                 335

His Cys Lys Gly Gly Thr Asp Arg Thr Gly Thr Met Val Cys Ala Phe
            340                 345                 350

Leu Ile Ala Ser Glu Ile Cys Ser Thr Ala Lys Glu Ser Leu Tyr Tyr
        355                 360                 365

Phe Gly Glu Arg Arg Thr Asp Lys Thr His Ser Glu Lys Phe Gln Gly
    370                 375                 380

Val Glu Thr Pro Ser Gln Val Met Tyr Val Ile
385                 390                 395


<210> SEQ ID NO 59
<211> LENGTH: 468
<212> TYPE: PRT
<213> ORGANISM: Homo sapiens

<400> SEQUENCE: 59

Met Asn Glu Ser Pro Asp Pro Thr Asp Leu Ala Gly Val Ile Ile Glu
1               5                   10                  15

Leu Gly Pro Asn Asp Ser Pro Gln Thr Ser Glu Phe Lys Gly Ala Thr
            20                  25                  30

Glu Glu Ala Pro Ala Lys Glu Ser Pro His Thr Ser Glu Phe Lys Gly
        35                  40                  45

Ala Ala Arg Val Ser Pro Ile Ser Glu Ser Val Leu Ala Arg Leu Ser
    50                  55                  60

Lys Phe Glu Val Glu Asp Ala Glu Asn Val Ala Ser Tyr Asp Ser Lys
65                  70                  75                  80

Ile Lys Lys Ile Val His Ser Ile Val Ser Ser Phe Ala Phe Gly Leu
                85                  90                  95

Phe Gly Val Phe Leu Val Leu Leu Asp Val Thr Leu Ile Leu Ala Asp
            100                 105                 110
```

```
Leu Ile Phe Thr Asp Ser Lys Leu Tyr Ile Pro Leu Glu Tyr Arg Ser
        115                 120                 125

Ile Ser Leu Ala Ile Ala Leu Phe Phe Leu Met Asp Val Leu Leu Arg
    130                 135                 140

Val Phe Val Glu Arg Arg Gln Gln Tyr Phe Ser Asp Leu Phe Asn Ile
145                 150                 155                 160

Leu Asp Thr Ala Ile Ile Val Ile Leu Leu Leu Val Asp Val Val Tyr
                165                 170                 175

Ile Phe Phe Asp Ile Lys Leu Leu Arg Asn Ile Pro Arg Trp Thr His
            180                 185                 190

Leu Leu Arg Leu Leu Arg Leu Ile Ile Leu Leu Arg Ile Phe His Leu
        195                 200                 205

Phe His Gln Lys Arg Gln Leu Glu Lys Leu Ile Arg Arg Arg Val Ser
    210                 215                 220

Glu Asn Lys Arg Arg Tyr Thr Arg Asp Gly Phe Asp Leu Asp Leu Thr
225                 230                 235                 240

Tyr Val Thr Glu Arg Ile Ile Ala Met Ser Phe Pro Ser Ser Gly Arg
                245                 250                 255

Gln Ser Phe Tyr Arg Asn Pro Ile Lys Glu Val Val Arg Phe Leu Asp
            260                 265                 270

Lys Lys His Arg Asn His Tyr Arg Val Tyr Asn Leu Cys Ser Glu Arg
        275                 280                 285

Ala Tyr Asp Pro Lys His Phe His Asn Arg Val Val Arg Ile Met Ile
    290                 295                 300

Asp Asp His Asn Val Pro Thr Leu His Gln Met Val Val Phe Thr Lys
305                 310                 315                 320

Glu Val Asn Glu Trp Met Ala Gln Asp Leu Glu Asn Ile Val Ala Ile
                325                 330                 335

His Cys Lys Gly Gly Thr Gly Tyr Val Arg Asp Leu Lys Ile Gln Ile
            340                 345                 350

Glu Met Glu Lys Lys Val Val Phe Ser Thr Ile Ser Leu Gly Lys Cys
        355                 360                 365

Ser Val Leu Asp Asn Ile Thr Thr Asp Lys Ile Leu Ile Asp Val Phe
    370                 375                 380

Asp Gly Pro Pro Leu Tyr Asp Asp Val Lys Val Gln Phe Phe Tyr Ser
385                 390                 395                 400

Asn Leu Pro Thr Tyr Tyr Asp Asn Cys Ser Phe Tyr Phe Trp Leu His
                405                 410                 415

Thr Ser Phe Ile Glu Asn Asn Arg Leu Tyr Leu Pro Lys Asn Glu Leu
            420                 425                 430

Asp Asn Leu His Lys Gln Lys Ala Arg Arg Ile Tyr Pro Ser Asp Phe
        435                 440                 445

Ala Val Glu Ile Leu Phe Gly Glu Lys Met Thr Ser Ser Asp Val Val
    450                 455                 460

Ala Gly Ser Asp
465


<210> SEQ ID NO 60
<211> LENGTH: 470
<212> TYPE: PRT
<213> ORGANISM: Homo sapiens

<400> SEQUENCE: 60

Met Asn Glu Ser Pro Asp Pro Thr Asp Leu Ala Gly Val Ile Ile Glu
1               5                   10                  15
```

-continued

```
Leu Gly Pro Asn Asp Ser Pro Gln Thr Ser Glu Phe Lys Gly Ala Thr
            20                  25                  30

Glu Glu Ala Pro Ala Lys Glu Ser Val Leu Ala Arg Leu Ser Lys Phe
        35                  40                  45

Glu Val Glu Asp Ala Glu Asn Val Ala Ser Tyr Asp Ser Lys Ile Lys
    50                  55                  60

Lys Ile Val His Ser Ile Val Ser Ser Phe Ala Phe Gly Leu Phe Gly
65                  70                  75                  80

Val Phe Leu Val Leu Leu Asp Val Thr Leu Ile Leu Ala Asp Leu Ile
                85                  90                  95

Phe Thr Asp Ser Lys Leu Tyr Ile Pro Leu Glu Tyr Arg Ser Ile Ser
            100                 105                 110

Leu Ala Ile Ala Leu Phe Phe Leu Met Asp Val Leu Leu Arg Val Phe
        115                 120                 125

Val Glu Arg Arg Gln Gln Tyr Phe Ser Asp Leu Phe Asn Ile Leu Asp
    130                 135                 140

Thr Ala Ile Ile Val Ile Leu Leu Leu Val Asp Val Val Tyr Ile Phe
145                 150                 155                 160

Phe Asp Ile Lys Leu Leu Arg Asn Ile Pro Arg Trp Thr His Leu Leu
                165                 170                 175

Arg Leu Leu Arg Leu Ile Ile Leu Leu Arg Ile Phe His Leu Phe His
            180                 185                 190

Gln Lys Arg Gln Leu Glu Lys Leu Ile Arg Arg Arg Val Ser Glu Asn
        195                 200                 205

Lys Arg Arg Tyr Thr Arg Asp Gly Phe Asp Leu Asp Leu Thr Tyr Val
    210                 215                 220

Thr Glu Arg Ile Ile Ala Met Ser Phe Pro Ser Ser Gly Arg Gln Ser
225                 230                 235                 240

Phe Tyr Arg Asn Pro Ile Lys Glu Val Val Arg Phe Leu Asp Lys Lys
                245                 250                 255

His Arg Asn His Tyr Arg Val Tyr Asn Leu Cys Ser Glu Arg Ala Tyr
            260                 265                 270

Asp Pro Lys His Phe His Asn Arg Val Val Arg Ile Met Ile Asp Asp
        275                 280                 285

His Asn Val Pro Thr Leu His Gln Met Val Val Phe Thr Lys Glu Val
    290                 295                 300

Asn Glu Trp Met Ala Gln Asp Leu Glu Asn Ile Val Ala Ile His Cys
305                 310                 315                 320

Lys Gly Gly Thr Asp Arg Thr Gly Thr Met Val Cys Ala Phe Leu Ile
                325                 330                 335

Ala Ser Glu Ile Cys Ser Thr Ala Lys Glu Ser Leu Tyr Tyr Phe Gly
            340                 345                 350

Glu Arg Arg Thr Asp Lys Thr His Ser Glu Lys Phe Gln Gly Val Glu
        355                 360                 365

Thr Pro Ser Val Leu Asp Asn Ile Thr Thr Asp Lys Ile Leu Ile Asp
    370                 375                 380

Val Phe Asp Gly Pro Pro Leu Tyr Asp Asp Val Lys Val Gln Phe Phe
385                 390                 395                 400

Tyr Ser Asn Leu Pro Thr Tyr Tyr Asp Asn Cys Ser Phe Tyr Phe Trp
                405                 410                 415

Leu His Thr Ser Phe Ile Glu Asn Asn Arg Leu Tyr Leu Pro Lys Asn
            420                 425                 430
```

```
Glu Leu Asp Asn Leu His Lys Gln Lys Ala Arg Arg Ile Tyr Pro Ser
        435                 440                 445

Asp Phe Ala Val Glu Ile Leu Phe Gly Glu Lys Met Thr Ser Ser Asp
    450                 455                 460

Val Val Ala Gly Ser Asp
465                 470


<210> SEQ ID NO 61
<211> LENGTH: 450
<212> TYPE: PRT
<213> ORGANISM: Homo sapiens

<400> SEQUENCE: 61

Met Asn Glu Ser Pro Asp Pro Thr Asp Leu Ala Gly Val Ile Ile Glu
1               5                   10                  15

Leu Gly Pro Asn Asp Ser Pro Gln Thr Ser Glu Phe Lys Gly Ala Thr
            20                  25                  30

Glu Glu Ala Pro Ala Lys Glu Ser Val Leu Ala Arg Leu Ser Lys Phe
        35                  40                  45

Glu Val Glu Asp Ala Glu Asn Val Ala Ser Tyr Asp Ser Lys Ile Lys
    50                  55                  60

Lys Ile Val His Ser Ile Val Ser Ser Phe Ala Phe Gly Leu Phe Gly
65                  70                  75                  80

Val Phe Leu Val Leu Leu Asp Val Thr Leu Ile Leu Ala Asp Leu Ile
                85                  90                  95

Phe Thr Asp Ser Lys Leu Tyr Ile Pro Leu Glu Tyr Arg Ser Ile Ser
            100                 105                 110

Leu Ala Ile Ala Leu Phe Phe Leu Met Asp Val Leu Leu Arg Val Phe
        115                 120                 125

Val Glu Arg Arg Gln Gln Tyr Phe Ser Asp Leu Phe Asn Ile Leu Asp
    130                 135                 140

Thr Ala Ile Ile Val Ile Leu Leu Leu Val Asp Val Val Tyr Ile Phe
145                 150                 155                 160

Phe Asp Ile Lys Leu Leu Arg Asn Ile Pro Arg Trp Thr His Leu Leu
                165                 170                 175

Arg Leu Leu Arg Leu Ile Ile Leu Leu Arg Ile Phe His Leu Phe His
            180                 185                 190

Gln Lys Arg Gln Leu Glu Lys Leu Ile Arg Arg Arg Val Ser Glu Asn
        195                 200                 205

Lys Arg Arg Tyr Thr Arg Asp Gly Phe Asp Leu Asp Leu Thr Tyr Val
    210                 215                 220

Thr Glu Arg Ile Ile Ala Met Ser Phe Pro Ser Ser Gly Arg Gln Ser
225                 230                 235                 240

Phe Tyr Arg Asn Pro Ile Lys Glu Val Val Arg Phe Leu Asp Lys Lys
                245                 250                 255

His Arg Asn His Tyr Arg Val Tyr Asn Leu Cys Ser Glu Arg Ala Tyr
            260                 265                 270

Asp Pro Lys His Phe His Asn Arg Val Val Arg Ile Met Ile Asp Asp
        275                 280                 285

His Asn Val Pro Thr Leu His Gln Met Val Val Phe Thr Lys Glu Val
    290                 295                 300

Asn Glu Trp Met Ala Gln Asp Leu Glu Asn Ile Val Ala Ile His Cys
305                 310                 315                 320

Lys Gly Gly Thr Gly Tyr Val Arg Asp Leu Lys Ile Gln Ile Glu Met
                325                 330                 335
```

```
Glu Lys Lys Val Val Phe Ser Thr Ile Ser Leu Gly Lys Cys Ser Val
            340                 345                 350

Leu Asp Asn Ile Thr Thr Asp Lys Ile Leu Ile Asp Val Phe Asp Gly
        355                 360                 365

Pro Pro Leu Tyr Asp Asp Val Lys Val Gln Phe Phe Tyr Ser Asn Leu
    370                 375                 380

Pro Thr Tyr Tyr Asp Asn Cys Ser Phe Tyr Phe Trp Leu His Thr Ser
385                 390                 395                 400

Phe Ile Glu Asn Asn Arg Leu Tyr Leu Pro Lys Asn Glu Leu Asp Asn
                405                 410                 415

Leu His Lys Gln Lys Ala Arg Arg Ile Tyr Pro Ser Asp Phe Ala Val
            420                 425                 430

Glu Ile Leu Phe Gly Glu Lys Met Thr Ser Ser Asp Val Val Ala Gly
        435                 440                 445

Ser Asp
    450


<210> SEQ ID NO 62
<211> LENGTH: 1299
<212> TYPE: DNA
<213> ORGANISM: Homo sapiens

<400> SEQUENCE: 62

cgcccttaga catggctcag atgtgcagcc acagtgagct tctgaacatt tcttctcaga     60

ctaagctctt acacacagtt gcagttgaaa gaaagaattg cttgacatgg ccacaggagc    120

aggcagcttc ctgcagacat gacagtcaac gcaaactcat gtcactgtgg gcagacacat    180

gtttgcaaag agactcagag ccaaacaagc acactcaatg tgctttgccc aaatttaccc    240

attaggtaaa tcttccctcc tcccaagaag aaagtggaga gagcatgagt cctcacatgg    300

gaacttgaag tcagggaaat gaaggctcac caattatttg tgcatgggtt taagttttcc    360

ttgaaattaa gttcaggttt gtctttgtgt gtaccaatta atgacaagag gttagataga    420

agtatgctag atggcaaaga gaaatatgtt ttgtgtcttc aattttgcta aaaataaccc    480

agaacatgga taattcattt attaattgat tttggtaagc caagtcctat ttggagaaaa    540

ttaatagttt ttctaaaaaa gaattttctc aatatcacct ggcttgataa catttttctc    600

cttcgagttc ctttttctgg agtttaacaa acttgttctt tacaaataga ttatattgac    660

tacctctcac tgatgttatg atattagttt ctattgctta ctttgtattt ctaattttag    720

gattcacaat ttagctggag aactattttt taacctgttg cacctaaaca tgattgagct    780

agaagacagt tttaccatat gcatgcattt tctctgagtt atattttaaa atctatacat    840

ttctcctaaa tatggaggaa atcactggca tcaaatgcca gtctcagacg gaagacctaa    900

agcccatttc tggcctggag ctacttggct ttgtgaccta tggtgaggca taagtgctct    960

gagtttgtgt tgcctctttt gtaaaatgag ggtttgactt aatcagtgat tttcatagct   1020

taaaattttt ttgaagaaca gaactttttt taaaaacagt tagatgcaac catattatat   1080

aaaacagaac agatacaagt agagctaact tgctaaagaa aggatggagg ctctgaagct   1140

gtgacttcat tatcccttaa tactgctatg tcctctgtag taccttagat ttctatggga   1200

catcgtttaa aaactattgt ttatgcgaga gccttgctaa tttcctaaaa attgtggata   1260

catttttctt cccatgtata attttctcac cttctattt                           1299


<210> SEQ ID NO 63
```

<211> LENGTH: 405
<212> TYPE: DNA
<213> ORGANISM: Homo sapiens

<400> SEQUENCE: 63
gcacaaggcc tgctcttact ccaaaaagat ggacccaggt ccgaaggggc actgccactg 60 tgggggcat ggccatcctc caggtcactg cgggccaccc cctggccatg gcccagggcc 120
ctgcgggcca ccccccacca tggtccaggg ccctgcgggc cacccccctgg ccatggccca 180 gggccctgcg ggccaccccc ccaccatggt ccagggccct gcgggcctcc ccctggccat 240
ggcccaggtc acccaccccc tggtccacat cactgaggaa gtagaagaaa acaggacaca 300
agatggcaag cctgagagaa ttgcccagct gacctggaat gaggcctaaa ccacaatctt 360
ctcttcctaa taaacagcct cctagaggcc acattctatt ctgta 405

<210> SEQ ID NO 64
<211> LENGTH: 106
<212> TYPE: PRT
<213> ORGANISM: Homo sapiens

<400> SEQUENCE: 64

Met Asp Pro Gly Pro Lys Gly His Cys His Cys Gly Gly His Gly His
1 5 10 15

Pro Pro Gly His Cys Gly Pro Pro Pro Gly His Gly Pro Gly Pro Cys
20 25 30

Gly Pro Pro Pro Thr Met Val Gln Gly Pro Ala Gly His Pro Leu Ala
35 40 45

Met Ala Gln Gly Pro Ala Gly His Pro Pro Thr Met Val Gln Gly Pro
50 55 60

Ala Gly Leu Pro Leu Ala Met Ala Gln Val Thr His Pro Leu Val His
65 70 75 80

Ile Thr Glu Glu Val Glu Glu Asn Arg Thr Gln Asp Gly Lys Pro Glu
85 90 95

Arg Ile Ala Gln Leu Thr Trp Asn Glu Ala
100 105

<210> SEQ ID NO 65
<211> LENGTH: 71
<212> TYPE: PRT
<213> ORGANISM: Homo sapiens

<400> SEQUENCE: 65

Met Ala Ile Leu Gln Val Thr Ala Gly His Pro Leu Ala Met Ala Gln
1 5 10 15

Gly Pro Ala Gly His Pro Pro Pro Trp Ser Arg Ala Leu Arg Ala Thr
20 25 30

Pro Trp Pro Trp Pro Arg Ala Leu Arg Ala Thr Pro Pro Pro Trp Ser
35 40 45

Arg Ala Leu Arg Ala Ser Pro Trp Pro Trp Pro Arg Ser Pro Thr Pro
50 55 60

Trp Ser Thr Ser Leu Arg Lys
65 70

<210> SEQ ID NO 66
<211> LENGTH: 21
<212> TYPE: DNA
<213> ORGANISM: Artificial sequence
<220> FEATURE:
<223> OTHER INFORMATION: Description of the artificial sequence:

oligonucleotide

<400> SEQUENCE: 66
agacatggct cagatgtgca g 21

<210> SEQ ID NO 67
<211> LENGTH: 21
<212> TYPE: DNA
<213> ORGANISM: Artificial sequence
<220> FEATURE:
<223> OTHER INFORMATION: Description of the artificial sequence: oligonucleotide

<400> SEQUENCE: 67
ggaaattagc aaggctctcg c 21

<210> SEQ ID NO 68
<211> LENGTH: 21
<212> TYPE: DNA
<213> ORGANISM: Artificial sequence
<220> FEATURE:
<223> OTHER INFORMATION: Description of the artificial sequence: oligonucleotide

<400> SEQUENCE: 68
tcaggtattc cctgctctta c 21

<210> SEQ ID NO 69
<211> LENGTH: 21
<212> TYPE: DNA
<213> ORGANISM: Artificial sequence
<220> FEATURE:
<223> OTHER INFORMATION: Description of the artificial sequence: oligonucleotide

<400> SEQUENCE: 69
tgggcaattc tctcaggctt g 21

<210> SEQ ID NO 70
<211> LENGTH: 908
<212> TYPE: DNA
<213> ORGANISM: Homo sapiens

<400> SEQUENCE: 70
aaaattcggc acgaggccgg gctgtggtct agcataaagg cggagcccag aagaaggggc 60
ggggtatggg agaagcctcc ccacctgccc ccgcaaggcg gcatctgctg gtcctgctgc 120
tgctcctctc taccctggtg atcccctccg ctgcagctcc tatccatgat gctgacgccc 180
aagagagctc cttgggtctc acaggcctcc agagcctact ccaaggcttc agccgacttt 240
tcctgaaagg taacctgctt cggggcatag acagcttatt ctctgccccc atggacttcc 300
ggggcctccc tgggaactac cacaaagagg agaaccagga gcaccagctg gggaacaaca 360
ccctctccag ccacctccag atcgacaaga tgaccgacaa caagacagga gaggtgctga 420
tctccgagaa tgtggtggca tccattcaac cagcggaggg gagcttcgag ggtgatttga 480
aggtacccag gatggaggag aaggaggccc tggtacccat ccagaaggcc acggacagct 540
tccacacaga actccatccc cgggtggcct tctggatcat taagctgcca cggcggaggt 600
cccaccagga tgccctggag ggcggccact ggctcagcga gaagcgacac cgcctgcagg 660
ccatccggga tggactccgc aaggggaccc acaaggacgt cctagaagag gggaccgaga 720
gctcctccca ctccaggctg tccccccgaa agacccactt actgtacatc ctcaggccct 780

```
ctcggcagct gtaggggtgg ggaccgggga gcacctgcct gtagccccca tcagaccctg    840

ccccaagcac catatggaaa taaagttctt tcttacatct aaaaaaaaaa aaaaaaaaaa    900

aaaaaaaa                                                              908


<210> SEQ ID NO 71
<211> LENGTH: 242
<212> TYPE: PRT
<213> ORGANISM: Homo sapiens

<400> SEQUENCE: 71

Met Gly Glu Ala Ser Pro Pro Ala Pro Ala Arg Arg His Leu Leu Val
1               5                   10                  15

Leu Leu Leu Leu Leu Ser Thr Leu Val Ile Pro Ser Ala Ala Ala Pro
            20                  25                  30

Ile His Asp Ala Asp Ala Gln Glu Ser Ser Leu Gly Leu Thr Gly Leu
        35                  40                  45

Gln Ser Leu Leu Gln Gly Phe Ser Arg Leu Phe Leu Lys Gly Asn Leu
    50                  55                  60

Leu Arg Gly Ile Asp Ser Leu Phe Ser Ala Pro Met Asp Phe Arg Gly
65                  70                  75                  80

Leu Pro Gly Asn Tyr His Lys Glu Glu Asn Gln Glu His Gln Leu Gly
                85                  90                  95

Asn Asn Thr Leu Ser Ser His Leu Gln Ile Asp Lys Met Thr Asp Asn
            100                 105                 110

Lys Thr Gly Glu Val Leu Ile Ser Glu Asn Val Val Ala Ser Ile Gln
        115                 120                 125

Pro Ala Glu Gly Ser Phe Glu Gly Asp Leu Lys Val Pro Arg Met Glu
    130                 135                 140

Glu Lys Glu Ala Leu Val Pro Ile Gln Lys Ala Thr Asp Ser Phe His
145                 150                 155                 160

Thr Glu Leu His Pro Arg Val Ala Phe Trp Ile Ile Lys Leu Pro Arg
                165                 170                 175

Arg Arg Ser His Gln Asp Ala Leu Glu Gly Gly His Trp Leu Ser Glu
            180                 185                 190

Lys Arg His Arg Leu Gln Ala Ile Arg Asp Gly Leu Arg Lys Gly Thr
        195                 200                 205

His Lys Asp Val Leu Glu Glu Gly Thr Glu Ser Ser Ser His Ser Arg
    210                 215                 220

Leu Ser Pro Arg Lys Thr His Leu Leu Tyr Ile Leu Arg Pro Ser Arg
225                 230                 235                 240

Gln Leu


<210> SEQ ID NO 72
<211> LENGTH: 21
<212> TYPE: DNA
<213> ORGANISM: Artificial sequence
<220> FEATURE:
<223> OTHER INFORMATION: Description of the artificial sequence:
      oligonucleotide

<400> SEQUENCE: 72

ctcctatcca tgatgctgac g                                                21


<210> SEQ ID NO 73
<211> LENGTH: 21
<212> TYPE: DNA
<213> ORGANISM: Artificial sequence
```

<220> FEATURE:
<223> OTHER INFORMATION: Description of the artificial sequence:
oligonucleotide

<400> SEQUENCE: 73
cctgaggatg tacagtaagt g 21

<210> SEQ ID NO 74
<211> LENGTH: 2987
<212> TYPE: DNA
<213> ORGANISM: Homo sapiens

<400> SEQUENCE: 74
tttcccagcg aggtggtcat tcagagccta cacatctgtt ctgtatttta acccatggat 60
gagaatattc attcaagcca agagagttaa aactaaacat ctttgctatt gcctctacag 120
acccagaaag tatctttatg tcacatcttc ttttaaagga gcatttaaag atgaagttaa 180
aaaggcagaa gaagcagtaa agattgctga atccatattg aaagaagcac aaatcaaagt 240
aaaccagtgt gacagaacct ctttatcttc tgccaaggat gtattacaga gagctttgga 300
agatgtagaa gcaaagcaaa agaatcttaa agagaaacaa agagaattaa aaacagcaag 360
aacgctctcc ctgttctatg gagtgaacgt agaaaaccga agccaagctg gaatgttcat 420
ttacagtaat aaccgtttga tcaaaatgca tgaaaaagtg ggctcacagt tgaaactgaa 480
gtccttactt ggcgcaggcg tggttggaat tgttaatata cccttggagg tcatggaacc 540
atcccataat aaacaggaat ttctcaatgt ccaagagtat aatcatctac taaaagtcat 600
gggacagtac ttggtccagt actgtaagga caccggcatc aataatagaa atttaacatt 660
gttttgcaat gaatttggat accagaatga catcgatgtg gagaaacctt taaattcttt 720
tcaatatcaa agaagacaag ccatgggtat cccattcatc atacaatgtg atctttgtct 780
taaatggaga gtcttgcctt cctctactaa ttatcaggaa aaagaatttt ttgacatttg 840
gatttgtgct aataatccca accgcttgga aaacagttgt catcaggtag aatgtctacc 900
ttccatccca ctgggcacca tgagcacaat atcaccatca aaaaatgaga aagagaagca 960
acttagagag tcggtcataa agtatcaaaa tagactggca gaacagcagc cacagcctca 1020
atttatacca gtggacgaaa tcactgtcac ttccacctgc ctaacttcag cacataagga 1080
aaataccaaa acccagaaaa tcaggctttt gggcgatgac ttgaagcatg aatctctttc 1140
atcctttgag ctttcagcga gccgtagagg acagaaaaga aacatagaag agacagactc 1200
tgatgtagag tatatttcag aaacaaaaat tatgaaaaag tctatggagg agaaaatgaa 1260
ctctcaacag cagagaattc cagtagctct gccagaaaat gtcaaactag ctgagagatc 1320
ccagagaagt cagattgcta atattaccac tgtctggaga gctcaaccaa ctgaagggtg 1380
cctgaagaat gcccaggccg cttcttggga aatgaaaagg aagcagagtc tgaactttgt 1440
agaggaatgt aaggtattga ctgaagatga gaacacgagt gattcagata taatcctggt 1500
ttcagataaa agcaacactg atgtttcatt gaaacaagaa aaaaaggaaa ttcctctttt 1560
aaaccaagaa aaacaggagc tgtgcaatga tgttctagca atgaaaagaa gctcttcatt 1620
acctagctgg aaaagcttgc tcaatgtgcc gatggaagat gtgaatctaa gttctggaca 1680
catagccaga gtttctgtga gtggcagttg taaagttgct tcttcgccag cgtcttctca 1740
aagcacacct gtcaaggaaa cagtgagaaa actgaagtct aagttaaggg agattcttct 1800
gtattttttt cctgagcatc agctaccatc agaattggaa gaacctgcat taagttgtga 1860
gctggagcag tgcccagagc agatgaacaa aaagctgaaa atgtgtttca accagataca 1920

-continued

```
gaatacttac atggtccaat atgaaaaaaa aataaagagg aaattgcagt ccattatcta   1980

tgattcaaat acaagaggaa tacataatga aatctctctg gggcaatgtg aaaataaaag   2040

aaaaatctct gaggataagc tgaagaatct tcgtataaaa ctggcactat tgttgcagaa   2100

actccaactg ggtggtccag aaggtgacct ggagcagact gacacttatt tagaagcttt   2160

gcttaaagaa gataatcttc tcttccagaa caatttaaat aaagtaacta tagatgcaag   2220

acatagactc cctttagaaa aaaatgaaaa gacttcggaa aattaagtca gagatggtat   2280

taccttttaa aaaatgctaa taagaaaatt ggaagattct tttaaaaatt tttctttttt   2340

gttgttgtta ctgtaaagtc tattctgttt aacaataaga aataagaaat aatttttttc   2400

aaataagaaa attgtgtact ctagaaatgg agaccgattt acaatttatg tattccctaa   2460

tccaattatc taaatcttcc ttttctttca gaaatattaa taatatctag agttctctaa   2520

ttttcatgtg agctactgaa aaaaatgaaa atgtcactca agcttaactt ttgttattcc   2580

ttaaaagatt gttattgtaa ttttgttatt ccttaaaaac atttaaaagc agatttttttc  2640

aaaatcgata tgtgaaggac tacagaatca cctcctcttg aagatattga aaaagaaaga   2700

cattatgccc tttctccact atagccaaca ctcagtcaag cagaaaatac aaatcccccc   2760

aaaactttga gacatagctt atataatttt attatttagt catagtaaaa gaataaatct   2820

cctaagcata atatgtatac atattacaca tatgtaaaaa ttgttgtttt acatttacat   2880

atacgtaaag aagtatgttt ttacactttt cttgataagt gttttttttt tgtttagaaa   2940

tgtctgaaac tttagacaaa aacagtaaaa catttaatat tcatttg                 2987
```

<210> SEQ ID NO 75
<211> LENGTH: 735
<212> TYPE: PRT
<213> ORGANISM: Homo sapiens

<400> SEQUENCE: 75

```
Met Arg Ile Phe Ile Gln Ala Lys Arg Val Lys Thr Lys His Leu Cys
1               5                   10                  15

Tyr Cys Leu Tyr Arg Pro Arg Lys Tyr Leu Tyr Val Thr Ser Ser Phe
            20                  25                  30

Lys Gly Ala Phe Lys Asp Glu Val Lys Lys Ala Glu Glu Ala Val Lys
        35                  40                  45

Ile Ala Glu Ser Ile Leu Lys Glu Ala Gln Ile Lys Val Asn Gln Cys
    50                  55                  60

Asp Arg Thr Ser Leu Ser Ser Ala Lys Asp Val Leu Gln Arg Ala Leu
65                  70                  75                  80

Glu Asp Val Glu Ala Lys Gln Lys Asn Leu Lys Glu Lys Gln Arg Glu
                85                  90                  95

Leu Lys Thr Ala Arg Thr Leu Ser Leu Phe Tyr Gly Val Asn Val Glu
            100                 105                 110

Asn Arg Ser Gln Ala Gly Met Phe Ile Tyr Ser Asn Asn Arg Leu Ile
        115                 120                 125

Lys Met His Glu Lys Val Gly Ser Gln Leu Lys Leu Lys Ser Leu Leu
    130                 135                 140

Gly Ala Gly Val Val Gly Ile Val Asn Ile Pro Leu Glu Val Met Glu
145                 150                 155                 160

Pro Ser His Asn Lys Gln Glu Phe Leu Asn Val Gln Glu Tyr Asn His
                165                 170                 175

Leu Leu Lys Val Met Gly Gln Tyr Leu Val Gln Tyr Cys Lys Asp Thr
```

-continued

```
            180                 185                 190

Gly Ile Asn Asn Arg Asn Leu Thr Leu Phe Cys Asn Glu Phe Gly Tyr
        195                 200                 205

Gln Asn Asp Ile Asp Val Glu Lys Pro Leu Asn Ser Phe Gln Tyr Gln
    210                 215                 220

Arg Arg Gln Ala Met Gly Ile Pro Phe Ile Ile Gln Cys Asp Leu Cys
225                 230                 235                 240

Leu Lys Trp Arg Val Leu Pro Ser Ser Thr Asn Tyr Gln Glu Lys Glu
                245                 250                 255

Phe Phe Asp Ile Trp Ile Cys Ala Asn Asn Pro Asn Arg Leu Glu Asn
            260                 265                 270

Ser Cys His Gln Val Glu Cys Leu Pro Ser Ile Pro Leu Gly Thr Met
        275                 280                 285

Ser Thr Ile Ser Pro Ser Lys Asn Glu Lys Glu Lys Gln Leu Arg Glu
    290                 295                 300

Ser Val Ile Lys Tyr Gln Asn Arg Leu Ala Glu Gln Gln Pro Gln Pro
305                 310                 315                 320

Gln Phe Ile Pro Val Asp Glu Ile Thr Val Thr Ser Thr Cys Leu Thr
                325                 330                 335

Ser Ala His Lys Glu Asn Thr Lys Thr Gln Lys Ile Arg Leu Leu Gly
            340                 345                 350

Asp Asp Leu Lys His Glu Ser Leu Ser Ser Phe Glu Leu Ser Ala Ser
        355                 360                 365

Arg Arg Gly Gln Lys Arg Asn Ile Glu Glu Thr Asp Ser Asp Val Glu
    370                 375                 380

Tyr Ile Ser Glu Thr Lys Ile Met Lys Lys Ser Met Glu Glu Lys Met
385                 390                 395                 400

Asn Ser Gln Gln Gln Arg Ile Pro Val Ala Leu Pro Glu Asn Val Lys
                405                 410                 415

Leu Ala Glu Arg Ser Gln Arg Ser Gln Ile Ala Asn Ile Thr Thr Val
            420                 425                 430

Trp Arg Ala Gln Pro Thr Glu Gly Cys Leu Lys Asn Ala Gln Ala Ala
        435                 440                 445

Ser Trp Glu Met Lys Arg Lys Gln Ser Leu Asn Phe Val Glu Glu Cys
    450                 455                 460

Lys Val Leu Thr Glu Asp Glu Asn Thr Ser Asp Ser Asp Ile Ile Leu
465                 470                 475                 480

Val Ser Asp Lys Ser Asn Thr Asp Val Ser Leu Lys Gln Glu Lys Lys
                485                 490                 495

Glu Ile Pro Leu Leu Asn Gln Glu Lys Gln Glu Leu Cys Asn Asp Val
            500                 505                 510

Leu Ala Met Lys Arg Ser Ser Ser Leu Pro Ser Trp Lys Ser Leu Leu
        515                 520                 525

Asn Val Pro Met Glu Asp Val Asn Leu Ser Ser Gly His Ile Ala Arg
    530                 535                 540

Val Ser Val Ser Gly Ser Cys Lys Val Ala Ser Ser Pro Ala Ser Ser
545                 550                 555                 560

Gln Ser Thr Pro Val Lys Glu Thr Val Arg Lys Leu Lys Ser Lys Leu
                565                 570                 575

Arg Glu Ile Leu Leu Tyr Phe Phe Pro Glu His Gln Leu Pro Ser Glu
            580                 585                 590

Leu Glu Glu Pro Ala Leu Ser Cys Glu Leu Glu Gln Cys Pro Glu Gln
        595                 600                 605
```

```
Met Asn Lys Lys Leu Lys Met Cys Phe Asn Gln Ile Gln Asn Thr Tyr
    610                 615                 620

Met Val Gln Tyr Glu Lys Lys Ile Lys Arg Lys Leu Gln Ser Ile Ile
625                 630                 635                 640

Tyr Asp Ser Asn Thr Arg Gly Ile His Asn Glu Ile Ser Leu Gly Gln
                645                 650                 655

Cys Glu Asn Lys Arg Lys Ile Ser Glu Asp Lys Leu Lys Asn Leu Arg
            660                 665                 670

Ile Lys Leu Ala Leu Leu Leu Gln Lys Leu Gln Leu Gly Gly Pro Glu
        675                 680                 685

Gly Asp Leu Glu Gln Thr Asp Thr Tyr Leu Glu Ala Leu Leu Lys Glu
    690                 695                 700

Asp Asn Leu Leu Phe Gln Asn Asn Leu Asn Lys Val Thr Ile Asp Ala
705                 710                 715                 720

Arg His Arg Leu Pro Leu Glu Lys Asn Glu Lys Thr Ser Glu Asn
                725                 730                 735
```

<210> SEQ ID NO 76
<211> LENGTH: 21
<212> TYPE: DNA
<213> ORGANISM: Artificial sequence
<220> FEATURE:
<223> OTHER INFORMATION: Description of the artificial sequence: oligonucleotide

<400> SEQUENCE: 76
ctgagtatca gctaccatca g 21

<210> SEQ ID NO 77
<211> LENGTH: 21
<212> TYPE: DNA
<213> ORGANISM: Artificial sequence
<220> FEATURE:
<223> OTHER INFORMATION: Description of the artificial sequence: oligonucleotide

<400> SEQUENCE: 77
tctgtagtcc ttcacatatc g 21

<210> SEQ ID NO 78
<211> LENGTH: 21
<212> TYPE: DNA
<213> ORGANISM: Artificial sequence
<220> FEATURE:
<223> OTHER INFORMATION: Description of the artificial sequence: oligonucleotide

<400> SEQUENCE: 78
ttttgtctat ggtgtaggac c 21

<210> SEQ ID NO 79
<211> LENGTH: 21
<212> TYPE: DNA
<213> ORGANISM: Artificial sequence
<220> FEATURE:
<223> OTHER INFORMATION: Description of the artificial sequence: oligonucleotide

<400> SEQUENCE: 79
ggaatggcaa tgatgttaca g 21

<210> SEQ ID NO 80

<211> LENGTH: 20
<212> TYPE: PRT
<213> ORGANISM: Homo sapiens

<400> SEQUENCE: 80

Met Ser Thr Val Lys Glu Gln Leu Ile Glu Lys Leu Ile Glu Asp Asp
1 5 10 15

Glu Asn Ser Gln
20

<210> SEQ ID NO 81
<211> LENGTH: 14
<212> TYPE: PRT
<213> ORGANISM: Homo sapiens

<400> SEQUENCE: 81

Phe Thr Asp Ser Lys Leu Tyr Ile Pro Leu Glu Tyr Arg Ser
1 5 10

<210> SEQ ID NO 82
<211> LENGTH: 13
<212> TYPE: PRT
<213> ORGANISM: Homo sapiens

<400> SEQUENCE: 82

Phe Asp Ile Lys Leu Leu Arg Asn Ile Pro Arg Trp Thr
1 5 10

<210> SEQ ID NO 83
<211> LENGTH: 15
<212> TYPE: PRT
<213> ORGANISM: Homo sapiens

<400> SEQUENCE: 83

Gly Val Ala Gly Gln Asp Tyr Trp Ala Val Leu Ser Gly Lys Gly
1 5 10 15

<210> SEQ ID NO 84
<211> LENGTH: 10
<212> TYPE: PRT
<213> ORGANISM: Homo sapiens

<400> SEQUENCE: 84

Ser Arg Glu Val Thr Thr Asn Ala Gln Arg
1 5 10

<210> SEQ ID NO 85
<211> LENGTH: 216
<212> TYPE: DNA
<213> ORGANISM: Homo sapiens

<400> SEQUENCE: 85
tgctcttact ccaaaaagat ggacccaggg ccctgcgggc ctccccctgg ccatggccca 60
ggtcacccac cccctggtcc acatcactga ggaagtagaa gaaaacagga cacaagatgg 120
caagcctgag agaattgccc agctgacctg gaaggaggcc taaaccgcaa tattctcttc 180
ctaataaaca gcctcctaga ggccacattc tattct 216

<210> SEQ ID NO 86
<211> LENGTH: 227
<212> TYPE: DNA
<213> ORGANISM: Homo sapiens

<400> SEQUENCE: 86
tgctcttact ccaaaaagat ggacccaggt ccgaaggggc actgccactg tggggggcat 60
ggccatcctc caggtcaccc accccctggt ccacatcact gaggaagtag aagaaaacag 120
gacacaagat ggcaagcctg agagaattgc ccagctgacc tggaatgagg cctaaaccac 180
aatcttctct tcctaataaa cagcctccta gaggccacat tctattc 227

<210> SEQ ID NO 87
<211> LENGTH: 261
<212> TYPE: DNA
<213> ORGANISM: Homo sapiens

<400> SEQUENCE: 87
tgctcttact ccaaaaagat ggacccaggt ccgaaggggc actgccactg tggggggcat 60
ggccatcctc caggtcactg cgggcctccc cctggccatg gcccaggtca cccacccccct 120 ggtccacatc actgaggaag tagaagaaaa caggacacaa gatggcaagc ctgagagaat 180
tgcccagctg acctggaatg aggcctaaac cacaatcttc tcttcctaat aaacagcctc 240
ctagaggcca cattctattc t 261

<210> SEQ ID NO 88
<211> LENGTH: 327
<212> TYPE: DNA
<213> ORGANISM: Homo sapiens

<400> SEQUENCE: 88
tgctcttact ccaaaaagat ggacccaggt ccgaaggggc actgccactg tggggggcat 60
ggccatcctc caggtcactg cgggccaccc ccccaccatg gtccagggcc ctgcgggcca 120 ccccccacc atggtccagg gccctgcggg cctccccctg gccatggccc aggtcaccca 180 cccccctggtc cacatcactg aggaagtaga agaaaacagg acacaagatg gcaagcctga 240
gagaattgcc cagctgacct ggaatgaggc ctaaaccaca atcttctctt cctaataaac 300
agcctcctag aggccacatt ctattct 327

<210> SEQ ID NO 89
<211> LENGTH: 31
<212> TYPE: PRT
<213> ORGANISM: Homo sapiens

<400> SEQUENCE: 89

Leu Leu Leu Gln Lys Asp Gly Pro Arg Ala Leu Arg Ala Ser Pro Trp
1               5                   10                  15

Pro Trp Pro Arg Ser Pro Thr Pro Trp Ser Thr Ser Leu Arg Lys
            20                  25                  30

<210> SEQ ID NO 90
<211> LENGTH: 23
<212> TYPE: PRT
<213> ORGANISM: Homo sapiens

<400> SEQUENCE: 90

Met Asp Pro Gly Pro Cys Gly Pro Pro Pro Gly His Gly Pro Gly His
1               5                   10                  15

Pro Pro Pro Gly Pro His His
            20

<210> SEQ ID NO 91
<211> LENGTH: 36
<212> TYPE: PRT

<213> ORGANISM: Homo sapiens

<400> SEQUENCE: 91

Met Ala Gln Val Thr His Pro Leu Val His Ile Thr Glu Glu Val Glu
1 5 10 15

Glu Asn Arg Thr Gln Asp Gly Lys Pro Glu Arg Ile Ala Gln Leu Thr
20 25 30

Trp Lys Glu Ala
35

<210> SEQ ID NO 92
<211> LENGTH: 34
<212> TYPE: PRT
<213> ORGANISM: Homo sapiens

<400> SEQUENCE: 92

Leu Leu Gln Lys Asp Gly Pro Arg Ser Glu Gly Ala Leu Pro Leu Trp
1 5 10 15

Gly Ala Trp Pro Ser Ser Arg Ser Pro Thr Pro Trp Ser Thr Ser Leu
20 25 30

Arg Lys

<210> SEQ ID NO 93
<211> LENGTH: 27
<212> TYPE: PRT
<213> ORGANISM: Homo sapiens

<400> SEQUENCE: 93

Met Asp Pro Gly Pro Lys Gly His Cys His Cys Gly Gly His Gly His
1 5 10 15

Pro Pro Gly His Pro Pro Pro Gly Pro His His
20 25

<210> SEQ ID NO 94
<211> LENGTH: 38
<212> TYPE: PRT
<213> ORGANISM: Homo sapiens

<400> SEQUENCE: 94

Met Ala Ile Leu Gln Val Thr His Pro Leu Val His Ile Thr Glu Glu
1 5 10 15

Val Glu Glu Asn Arg Thr Gln Asp Gly Lys Pro Glu Arg Ile Ala Gln
20 25 30

Leu Thr Trp Asn Glu Ala
35

<210> SEQ ID NO 95
<211> LENGTH: 46
<212> TYPE: PRT
<213> ORGANISM: Homo sapiens

<400> SEQUENCE: 95

Leu Leu Leu Gln Lys Asp Gly Pro Arg Ser Glu Gly Ala Leu Pro Leu
1 5 10 15

Trp Gly Ala Trp Pro Ser Ser Arg Ser Leu Arg Ala Ser Pro Trp Pro
20 25 30

Trp Pro Arg Ser Pro Thr Pro Trp Ser Thr Ser Leu Arg Lys
35 40 45

<210> SEQ ID NO 96

<211> LENGTH: 38
<212> TYPE: PRT
<213> ORGANISM: Homo sapiens

<400> SEQUENCE: 96

```
Met Asp Pro Gly Pro Lys Gly His Cys His Cys Gly Gly His Gly His
1               5                   10                  15

Pro Pro Gly His Cys Gly Pro Pro Pro Gly His Gly Pro Gly His Pro
            20                  25                  30

Pro Pro Gly Pro His His
        35
```

<210> SEQ ID NO 97
<211> LENGTH: 49
<212> TYPE: PRT
<213> ORGANISM: Homo sapiens

<400> SEQUENCE: 97

```
Met Ala Ile Leu Gln Val Thr Ala Gly Leu Pro Leu Ala Met Ala Gln
1               5                   10                  15

Val Thr His Pro Leu Val His Ile Thr Glu Glu Val Glu Glu Asn Arg
            20                  25                  30

Thr Gln Asp Gly Lys Pro Glu Arg Ile Ala Gln Leu Thr Trp Asn Glu
        35                  40                  45

Ala
```

<210> SEQ ID NO 98
<211> LENGTH: 68
<212> TYPE: PRT
<213> ORGANISM: Homo sapiens

<400> SEQUENCE: 98

```
Leu Leu Leu Gln Lys Asp Gly Pro Arg Ser Glu Gly Ala Leu Pro Leu
1               5                   10                  15

Trp Gly Ala Trp Pro Ser Ser Arg Ser Leu Arg Ala Thr Pro Pro Pro
            20                  25                  30

Trp Ser Arg Ala Leu Arg Ala Thr Pro Pro Pro Trp Ser Arg Ala Leu
        35                  40                  45

Arg Ala Ser Pro Trp Pro Trp Pro Arg Ser Pro Thr Pro Trp Ser Thr
    50                  55                  60

Ser Leu Arg Lys
65
```

<210> SEQ ID NO 99
<211> LENGTH: 60
<212> TYPE: PRT
<213> ORGANISM: Homo sapiens

<400> SEQUENCE: 99

```
Met Asp Pro Gly Pro Lys Gly His Cys His Cys Gly Gly His Gly His
1               5                   10                  15

Pro Pro Gly His Cys Gly Pro Pro Pro His His Gly Pro Gly Pro Cys
            20                  25                  30

Gly Pro Pro Pro His His Gly Pro Gly Pro Cys Gly Pro Pro Pro Gly
        35                  40                  45

His Gly Pro Gly His Pro Pro Pro Gly Pro His His
    50                  55                  60
```

<210> SEQ ID NO 100

-continued

<211> LENGTH: 71
<212> TYPE: PRT
<213> ORGANISM: Homo sapiens

<400> SEQUENCE: 100

```
Met Ala Ile Leu Gln Val Thr Ala Gly His Pro Pro Thr Met Val Gln
1               5                   10                  15

Gly Pro Ala Gly His Pro Pro Thr Met Val Gln Gly Pro Ala Gly Leu
            20                  25                  30

Pro Leu Ala Met Ala Gln Val Thr His Pro Leu Val His Ile Thr Glu
        35                  40                  45

Glu Val Glu Glu Asn Arg Thr Gln Asp Gly Lys Pro Glu Arg Ile Ala
    50                  55                  60

Gln Leu Thr Trp Asn Glu Ala
65                  70
```

<210> SEQ ID NO 101
<211> LENGTH: 15
<212> TYPE: PRT
<213> ORGANISM: Homo sapiens

<400> SEQUENCE: 101

```
Arg Asn Gly Val Ser Asp Val Val Lys Ile Asn Leu Asn Ser Glu
1               5                   10                  15
```

<210> SEQ ID NO 102
<211> LENGTH: 15
<212> TYPE: PRT
<213> ORGANISM: Homo sapiens

<400> SEQUENCE: 102

```
Gly Ile Ile Trp Asn Lys Arg Arg Thr Leu Ser Gln Tyr Pro Leu
1               5                   10                  15
```

<210> SEQ ID NO 103
<211> LENGTH: 15
<212> TYPE: PRT
<213> ORGANISM: Homo sapiens

<400> SEQUENCE: 103

```
Phe Thr Asp Ser Lys Leu Tyr Ile Pro Leu Glu Tyr Arg Ser Cys
1               5                   10                  15
```

<210> SEQ ID NO 104
<211> LENGTH: 14
<212> TYPE: PRT
<213> ORGANISM: Homo sapiens

<400> SEQUENCE: 104

```
Cys Phe Asp Ile Lys Leu Leu Arg Asn Ile Pro Arg Trp Thr
1               5                   10
```

<210> SEQ ID NO 105
<211> LENGTH: 54
<212> TYPE: PRT
<213> ORGANISM: Homo sapiens

<400> SEQUENCE: 105

```
Met Asn Glu Ser Pro Asp Pro Thr Asp Leu Ala Gly Val Ile Ile Glu
1               5                   10                  15

Leu Gly Pro Asn Asp Ser Pro Gln Thr Ser Glu Phe Lys Gly Ala Thr
            20                  25                  30
```

```
Glu Glu Ala Pro Ala Lys Glu Ser Pro His Thr Ser Glu Phe Lys Gly
        35                  40                  45

Ala Ala Arg Val Ser Pro
    50


<210> SEQ ID NO 106
<211> LENGTH: 16
<212> TYPE: PRT
<213> ORGANISM: Homo sapiens

<400> SEQUENCE: 106

Cys Tyr Gln His Lys Val Thr Leu His Met Ile Thr Glu Arg Asp Pro
1               5                   10                  15


<210> SEQ ID NO 107
<211> LENGTH: 15
<212> TYPE: PRT
<213> ORGANISM: Homo sapiens

<400> SEQUENCE: 107

Cys Arg Ile Pro Gln Val His Thr Met Asp Ser Ser Gly Lys Ile
1               5                   10                  15


<210> SEQ ID NO 108
<211> LENGTH: 541
<212> TYPE: PRT
<213> ORGANISM: Homo sapiens

<400> SEQUENCE: 108

Arg Arg Lys Gln Ser Glu Met His Ile Ser Arg Tyr Ser Ser Glu Gln
1               5                   10                  15

Ser Ala Arg Leu Leu Asp Tyr Glu Asp Gly Arg Gly Ser Arg His Ala
            20                  25                  30

Tyr Ser Thr Gln Ser Asp Thr Ser Cys Asp Asn Arg Glu Arg Ser Lys
        35                  40                  45

Arg Asp Tyr Thr Pro Ser Thr Asn Ser Leu Ala Leu Ser Arg Ser Ser
    50                  55                  60

Ile Ala Leu Pro Gln Gly Ser Met Ser Ser Ile Lys Cys Leu Gln Thr
65                  70                  75                  80

Thr Glu Glu Leu Pro Ser Arg Thr Ala Gly Ala Met Met Gln Phe Thr
                85                  90                  95

Ala Pro Ile Pro Gly Ala Thr Gly Pro Ile Lys Leu Ser Gln Lys Thr
            100                 105                 110

Ile Val Gln Thr Pro Gly Pro Ile Val Gln Tyr Pro Gly Pro Asn Val
        115                 120                 125

Arg Ser His Pro His Thr Ile Thr Gly Pro Pro Ser Ala Pro Arg Gly
    130                 135                 140

Pro Pro Met Ala Pro Ile Ile Ile Ser Gln Arg Thr Ala Ser Gln Leu
145                 150                 155                 160

Ala Ala Pro Ile Ile Ile Ser Gln Arg Thr Ala Arg Ile Pro Gln Val
                165                 170                 175

His Thr Met Asp Ser Ser Gly Lys Thr Thr Leu Thr Pro Val Val Ile
            180                 185                 190

Leu Thr Gly Tyr Met Asp Glu Glu Leu Ala Lys Lys Ser Cys Ser Lys
        195                 200                 205

Ile Gln Ile Leu Lys Cys Gly Gly Thr Ala Arg Ser Gln Asn Ser Arg
    210                 215                 220

Glu Glu Asn Lys Glu Ala Leu Lys Asn Asp Ile Ile Phe Thr Asn Ser
```

```
225                 230                 235                 240

Val Glu Ser Leu Lys Ser Ala His Ile Lys Glu Pro Glu Arg Glu Gly
                245                 250                 255

Lys Gly Thr Asp Leu Glu Lys Asp Lys Ile Gly Met Glu Val Lys Val
            260                 265                 270

Asp Ser Asp Ala Gly Ile Pro Lys Arg Gln Glu Thr Gln Leu Lys Ile
        275                 280                 285

Ser Glu Met Ser Ile Pro Gln Gly Gln Gly Ala Gln Ile Lys Lys Ser
    290                 295                 300

Val Ser Asp Val Pro Arg Gly Gln Glu Ser Gln Val Lys Lys Ser Glu
305                 310                 315                 320

Ser Gly Val Pro Lys Gly Gln Glu Ala Gln Val Thr Lys Ser Gly Leu
                325                 330                 335

Val Val Leu Lys Gly Gln Glu Ala Gln Val Glu Lys Ser Glu Met Gly
            340                 345                 350

Val Pro Arg Arg Gln Glu Ser Gln Val Lys Lys Ser Gln Ser Gly Val
        355                 360                 365

Ser Lys Gly Gln Glu Ala Gln Val Lys Lys Arg Glu Ser Val Val Leu
    370                 375                 380

Lys Gly Gln Glu Ala Gln Val Glu Lys Ser Glu Leu Lys Val Pro Lys
385                 390                 395                 400

Gly Gln Glu Gly Gln Val Glu Lys Thr Glu Ala Asp Val Pro Lys Glu
                405                 410                 415

Gln Glu Val Gln Glu Lys Lys Ser Glu Ala Gly Val Leu Lys Gly Pro
            420                 425                 430

Glu Ser Gln Val Lys Asn Thr Glu Val Ser Val Pro Glu Thr Leu Glu
        435                 440                 445

Ser Gln Val Lys Lys Ser Glu Ser Gly Val Leu Lys Gly Gln Glu Ala
    450                 455                 460

Gln Glu Lys Lys Glu Ser Phe Glu Asp Lys Gly Asn Asn Asp Lys Glu
465                 470                 475                 480

Lys Glu Arg Asp Ala Glu Lys Asp Pro Asn Lys Lys Glu Lys Gly Asp
                485                 490                 495

Lys Asn Thr Lys Gly Asp Lys Gly Lys Asp Lys Val Lys Gly Lys Arg
            500                 505                 510

Glu Ser Glu Ile Asn Gly Glu Lys Ser Lys Gly Ser Lys Arg Ala Lys
        515                 520                 525

Ala Asn Thr Gly Arg Lys Tyr Asn Lys Lys Val Glu Glu
    530                 535                 540


<210> SEQ ID NO 109
<211> LENGTH: 16
<212> TYPE: PRT
<213> ORGANISM: Homo sapiens

<400> SEQUENCE: 109

Met Met Ser Ser Lys Pro Thr Ser His Ala Glu Val Asn Glu Thr Cys
1               5                   10                  15


<210> SEQ ID NO 110
<211> LENGTH: 16
<212> TYPE: PRT
<213> ORGANISM: Homo sapiens

<400> SEQUENCE: 110

Cys Gly Val Ala Gly Gln Asp Tyr Trp Ala Val Leu Ser Gly Lys Gly
```

1 5 10 15

<210> SEQ ID NO 111
<211> LENGTH: 63
<212> TYPE: PRT
<213> ORGANISM: Homo sapiens

<400> SEQUENCE: 111

Met Met Ser Ser Lys Pro Thr Ser His Ala Glu Val Asn Glu Thr Ile
1 5 10 15

Pro Asn Pro Tyr Pro Pro Gly Ser Phe Met Ala Pro Gly Phe Gln Gln
20 25 30

Pro Leu Gly Ser Ile Asn Leu Glu Asn Gln Ala Gln Gly Ala Gln Arg
35 40 45

Ala Gln Pro Tyr Gly Ile Thr Ser Pro Gly Ile Phe Ala Ser Ser
50 55 60

<210> SEQ ID NO 112
<211> LENGTH: 13
<212> TYPE: PRT
<213> ORGANISM: Homo sapiens

<400> SEQUENCE: 112

Gly His Gly Pro Gly His Pro Pro Pro Gly Pro His His
1 5 10

<210> SEQ ID NO 113
<211> LENGTH: 13
<212> TYPE: PRT
<213> ORGANISM: Homo sapiens

<400> SEQUENCE: 113

Lys Pro Glu Arg Ile Ala Gln Leu Thr Trp Asn Glu Ala
1 5 10

<210> SEQ ID NO 114
<211> LENGTH: 13
<212> TYPE: PRT
<213> ORGANISM: Homo sapiens

<400> SEQUENCE: 114

Pro Arg Ser Pro Thr Pro Trp Ser Thr Ser Leu Arg Lys
1 5 10

<210> SEQ ID NO 115
<211> LENGTH: 13
<212> TYPE: PRT
<213> ORGANISM: Homo sapiens

<400> SEQUENCE: 115

Ile Ala Pro Asn Thr Arg Gly Gln Gln Thr Ile Val Leu
1 5 10

<210> SEQ ID NO 116
<211> LENGTH: 14
<212> TYPE: PRT
<213> ORGANISM: Homo sapiens

<400> SEQUENCE: 116

Val Trp Lys Ser Asn Gly Lys Ser Ile Leu Lys Met Pro Phe
1 5 10

<210> SEQ ID NO 117

```
<211> LENGTH: 91
<212> TYPE: PRT
<213> ORGANISM: Homo sapiens

<400> SEQUENCE: 117

Ala Gln Gly Leu Leu Leu Leu Gln Lys Asp Gly Pro Arg Ser Glu Gly
1               5                   10                  15

Ala Leu Pro Leu Trp Gly Ala Trp Pro Ser Ser Arg Ser Leu Arg Ala
            20                  25                  30

Thr Pro Trp Pro Trp Pro Arg Ala Leu Arg Ala Thr Pro His His Gly
        35                  40                  45

Pro Gly Pro Cys Gly Pro Pro Pro Gly His Gly Pro Gly Pro Cys Gly
    50                  55                  60

Pro Pro Pro His His Gly Pro Gly Pro Cys Gly Pro Pro Pro Gly His
65                  70                  75                  80

Gly Pro Gly His Pro Pro Pro Gly Pro His His
                85                  90


<210> SEQ ID NO 118
<211> LENGTH: 8
<212> TYPE: PRT
<213> ORGANISM: Homo sapiens

<400> SEQUENCE: 118

Ile Thr Ile Val Gly Thr Gly Ala
1               5


<210> SEQ ID NO 119
<211> LENGTH: 8
<212> TYPE: PRT
<213> ORGANISM: Homo sapiens

<400> SEQUENCE: 119

Gly Thr Gly Ala Val Gly Met Ala
1               5


<210> SEQ ID NO 120
<211> LENGTH: 8
<212> TYPE: PRT
<213> ORGANISM: Homo sapiens

<400> SEQUENCE: 120

Gly Ala Val Gly Met Ala Cys Ala
1               5


<210> SEQ ID NO 121
<211> LENGTH: 8
<212> TYPE: PRT
<213> ORGANISM: Homo sapiens

<400> SEQUENCE: 121

Ser Ile Leu Leu Lys Asp Leu Ala
1               5


<210> SEQ ID NO 122
<211> LENGTH: 8
<212> TYPE: PRT
<213> ORGANISM: Homo sapiens

<400> SEQUENCE: 122

Lys Asp Leu Ala Asp Glu Leu Ala
1               5
```

<210> SEQ ID NO 123
<211> LENGTH: 8
<212> TYPE: PRT
<213> ORGANISM: Homo sapiens

<400> SEQUENCE: 123

Glu Leu Ala Leu Val Asp Val Ala
1 5

<210> SEQ ID NO 124
<211> LENGTH: 8
<212> TYPE: PRT
<213> ORGANISM: Homo sapiens

<400> SEQUENCE: 124

Gly Lys Asp Tyr Ser Val Ser Ala
1 5

<210> SEQ ID NO 125
<211> LENGTH: 8
<212> TYPE: PRT
<213> ORGANISM: Homo sapiens

<400> SEQUENCE: 125

Ser Arg Ile Val Ile Val Thr Ala
1 5

<210> SEQ ID NO 126
<211> LENGTH: 8
<212> TYPE: PRT
<213> ORGANISM: Homo sapiens

<400> SEQUENCE: 126

Ile Val Ile Val Thr Ala Gly Ala
1 5

<210> SEQ ID NO 127
<211> LENGTH: 8
<212> TYPE: PRT
<213> ORGANISM: Homo sapiens

<400> SEQUENCE: 127

Gln Glu Gly Glu Thr Arg Leu Ala
1 5

<210> SEQ ID NO 128
<211> LENGTH: 8
<212> TYPE: PRT
<213> ORGANISM: Homo sapiens

<400> SEQUENCE: 128

Ala Leu Val Gln Arg Asn Val Ala
1 5

<210> SEQ ID NO 129
<211> LENGTH: 8
<212> TYPE: PRT
<213> ORGANISM: Homo sapiens

<400> SEQUENCE: 129

Ile Met Lys Ser Ile Ile Pro Ala
1 5

<210> SEQ ID NO 130

<211> LENGTH: 8
<212> TYPE: PRT
<213> ORGANISM: Homo sapiens

<400> SEQUENCE: 130

Ser Gly Cys Asn Leu Asp Ser Ala
1 5

<210> SEQ ID NO 131
<211> LENGTH: 8
<212> TYPE: PRT
<213> ORGANISM: Homo sapiens

<400> SEQUENCE: 131

Leu Trp Ser Gly Val Asn Val Ala
1 5

<210> SEQ ID NO 132
<211> LENGTH: 8
<212> TYPE: PRT
<213> ORGANISM: Homo sapiens

<400> SEQUENCE: 132

Gly Val Asn Val Ala Gly Val Ala
1 5

<210> SEQ ID NO 133
<211> LENGTH: 8
<212> TYPE: PRT
<213> ORGANISM: Homo sapiens

<400> SEQUENCE: 133

His Lys Gln Val Ile Gln Ser Ala
1 5

<210> SEQ ID NO 134
<211> LENGTH: 8
<212> TYPE: PRT
<213> ORGANISM: Homo sapiens

<400> SEQUENCE: 134

Leu Lys Gly Tyr Thr Ser Trp Ala
1 5

<210> SEQ ID NO 135
<211> LENGTH: 8
<212> TYPE: PRT
<213> ORGANISM: Homo sapiens

<400> SEQUENCE: 135

Asn Leu Asn Ser Glu Glu Glu Ala
1 5

<210> SEQ ID NO 136
<211> LENGTH: 8
<212> TYPE: PRT
<213> ORGANISM: Homo sapiens

<400> SEQUENCE: 136

Glu Ala Leu Phe Lys Lys Ser Ala
1 5

<210> SEQ ID NO 137
<211> LENGTH: 9
<212> TYPE: PRT

<213> ORGANISM: Homo sapiens

<400> SEQUENCE: 137

Asp Leu Ala Asp Glu Leu Ala Leu Val
1               5

<210> SEQ ID NO 138
<211> LENGTH: 9
<212> TYPE: PRT
<213> ORGANISM: Homo sapiens

<400> SEQUENCE: 138

Tyr Leu Ile Gly Glu Lys Leu Gly Val
1               5

<210> SEQ ID NO 139
<211> LENGTH: 9
<212> TYPE: PRT
<213> ORGANISM: Homo sapiens

<400> SEQUENCE: 139

Tyr Ile Val Trp Lys Ile Ser Gly Leu
1               5

<210> SEQ ID NO 140
<211> LENGTH: 9
<212> TYPE: PRT
<213> ORGANISM: Homo sapiens

<400> SEQUENCE: 140

Ser Ile Leu Lys Asn Leu Arg Arg Val
1               5

<210> SEQ ID NO 141
<211> LENGTH: 9
<212> TYPE: PRT
<213> ORGANISM: Homo sapiens

<400> SEQUENCE: 141

Gly Leu Tyr Gly Ile Lys Glu Glu Leu
1               5

<210> SEQ ID NO 142
<211> LENGTH: 9
<212> TYPE: PRT
<213> ORGANISM: Homo sapiens

<400> SEQUENCE: 142

Gly Met Ala Cys Ala Ile Ser Ile Leu
1               5

<210> SEQ ID NO 143
<211> LENGTH: 9
<212> TYPE: PRT
<213> ORGANISM: Homo sapiens

<400> SEQUENCE: 143

Leu Leu Lys Asp Leu Ala Asp Glu Leu
1               5

<210> SEQ ID NO 144
<211> LENGTH: 9
<212> TYPE: PRT
<213> ORGANISM: Homo sapiens

<400> SEQUENCE: 144

Ala Leu Lys Thr Leu Asp Pro Lys Leu
1 5

<210> SEQ ID NO 145
<211> LENGTH: 9
<212> TYPE: PRT
<213> ORGANISM: Homo sapiens

<400> SEQUENCE: 145

Ala Ile Ser Ile Leu Leu Lys Asp Leu
1 5

<210> SEQ ID NO 146
<211> LENGTH: 9
<212> TYPE: PRT
<213> ORGANISM: Homo sapiens

<400> SEQUENCE: 146

Ser Leu Phe Phe Ser Thr Ser Lys Ile
1 5

<210> SEQ ID NO 147
<211> LENGTH: 9
<212> TYPE: PRT
<213> ORGANISM: Homo sapiens

<400> SEQUENCE: 147

Ile Leu Thr Tyr Ile Val Trp Lys Ile
1 5

<210> SEQ ID NO 148
<211> LENGTH: 9
<212> TYPE: PRT
<213> ORGANISM: Homo sapiens

<400> SEQUENCE: 148

Ala Ile Gly Leu Ser Val Met Asp Leu
1 5

<210> SEQ ID NO 149
<211> LENGTH: 9
<212> TYPE: PRT
<213> ORGANISM: Homo sapiens

<400> SEQUENCE: 149

Thr Met Val Lys Gly Leu Tyr Gly Ile
1 5

<210> SEQ ID NO 150
<211> LENGTH: 9
<212> TYPE: PRT
<213> ORGANISM: Homo sapiens

<400> SEQUENCE: 150

Ile Thr Ile Val Gly Thr Gly Ala Val
1 5

<210> SEQ ID NO 151
<211> LENGTH: 9
<212> TYPE: PRT
<213> ORGANISM: Homo sapiens

<400> SEQUENCE: 151

-continued

Ser Ala Asn Ser Arg Ile Val Ile Val
1 5

<210> SEQ ID NO 152
<211> LENGTH: 9
<212> TYPE: PRT
<213> ORGANISM: Homo sapiens

<400> SEQUENCE: 152

Ala Leu Val Gln Arg Asn Val Ala Ile
1 5

<210> SEQ ID NO 153
<211> LENGTH: 9
<212> TYPE: PRT
<213> ORGANISM: Homo sapiens

<400> SEQUENCE: 153

Ile Met Lys Ser Ile Ile Pro Ala Ile
1 5

<210> SEQ ID NO 154
<211> LENGTH: 9
<212> TYPE: PRT
<213> ORGANISM: Homo sapiens

<400> SEQUENCE: 154

Ser Val Met Asp Leu Val Gly Ser Ile
1 5

<210> SEQ ID NO 155
<211> LENGTH: 9
<212> TYPE: PRT
<213> ORGANISM: Homo sapiens

<400> SEQUENCE: 155

Glu Leu Phe Leu Ser Ile Pro Cys Val
1 5

<210> SEQ ID NO 156
<211> LENGTH: 9
<212> TYPE: PRT
<213> ORGANISM: Homo sapiens

<400> SEQUENCE: 156

Glu Leu Ala Leu Val Asp Val Ala Leu
1 5

<210> SEQ ID NO 157
<211> LENGTH: 9
<212> TYPE: PRT
<213> ORGANISM: Homo sapiens

<400> SEQUENCE: 157

Leu Val Asp Val Ala Leu Asp Lys Leu
1 5

<210> SEQ ID NO 158
<211> LENGTH: 9
<212> TYPE: PRT
<213> ORGANISM: Homo sapiens

<400> SEQUENCE: 158

Lys Leu Lys Gly Glu Met Met Asp Leu
1 5

<210> SEQ ID NO 159
<211> LENGTH: 9
<212> TYPE: PRT
<213> ORGANISM: Homo sapiens

<400> SEQUENCE: 159

Ile Thr Ser Gly Lys Asp Tyr Ser Val
1 5

<210> SEQ ID NO 160
<211> LENGTH: 9
<212> TYPE: PRT
<213> ORGANISM: Homo sapiens

<400> SEQUENCE: 160

Arg Leu Ala Leu Val Gln Arg Asn Val
1 5

<210> SEQ ID NO 161
<211> LENGTH: 9
<212> TYPE: PRT
<213> ORGANISM: Homo sapiens

<400> SEQUENCE: 161

Lys Ile Leu Val Val Ser Asn Pro Val
1 5

<210> SEQ ID NO 162
<211> LENGTH: 9
<212> TYPE: PRT
<213> ORGANISM: Homo sapiens

<400> SEQUENCE: 162

Asn Leu Asn Ser Glu Glu Glu Ala Leu
1 5

<210> SEQ ID NO 163
<211> LENGTH: 9
<212> TYPE: PRT
<213> ORGANISM: Homo sapiens

<400> SEQUENCE: 163

Ala Leu Phe Lys Lys Ser Ala Glu Thr
1 5

<210> SEQ ID NO 164
<211> LENGTH: 9
<212> TYPE: PRT
<213> ORGANISM: Homo sapiens

<400> SEQUENCE: 164

Gln Leu Ile Glu Lys Leu Ile Glu Asp
1 5

<210> SEQ ID NO 165
<211> LENGTH: 9
<212> TYPE: PRT
<213> ORGANISM: Homo sapiens

<400> SEQUENCE: 165

Ile Leu Leu Lys Asp Leu Ala Asp Glu
1 5

<210> SEQ ID NO 166
<211> LENGTH: 9
<212> TYPE: PRT
<213> ORGANISM: Homo sapiens

<400> SEQUENCE: 166

Met Met Asp Leu Gln His Gly Ser Leu
1 5

<210> SEQ ID NO 167
<211> LENGTH: 9
<212> TYPE: PRT
<213> ORGANISM: Homo sapiens

<400> SEQUENCE: 167

Ser Ile Ile Pro Ala Ile Val His Tyr
1 5

<210> SEQ ID NO 168
<211> LENGTH: 9
<212> TYPE: PRT
<213> ORGANISM: Homo sapiens

<400> SEQUENCE: 168

Val Val Ser Asn Pro Val Asp Ile Leu
1 5

<210> SEQ ID NO 169
<211> LENGTH: 9
<212> TYPE: PRT
<213> ORGANISM: Homo sapiens

<400> SEQUENCE: 169

Val Ala Gly Val Ala Leu Lys Thr Leu
1 5

<210> SEQ ID NO 170
<211> LENGTH: 9
<212> TYPE: PRT
<213> ORGANISM: Homo sapiens

<400> SEQUENCE: 170

Thr Leu Trp Asn Ile Gln Lys Asp Leu
1 5

<210> SEQ ID NO 171
<211> LENGTH: 9
<212> TYPE: PRT
<213> ORGANISM: Homo sapiens

<400> SEQUENCE: 171

Ala Leu Asp Lys Leu Lys Gly Glu Met
1 5

<210> SEQ ID NO 172
<211> LENGTH: 9
<212> TYPE: PRT
<213> ORGANISM: Homo sapiens

<400> SEQUENCE: 172

Ala Ile Met Lys Ser Ile Ile Pro Ala
1 5

<210> SEQ ID NO 173
<211> LENGTH: 9

<212> TYPE: PRT
<213> ORGANISM: Homo sapiens

<400> SEQUENCE: 173

Pro Leu Trp Ser Gly Val Asn Val Ala
1 5

<210> SEQ ID NO 174
<211> LENGTH: 9
<212> TYPE: PRT
<213> ORGANISM: Homo sapiens

<400> SEQUENCE: 174

Gly Val Asn Val Ala Gly Val Ala Leu
1 5

<210> SEQ ID NO 175
<211> LENGTH: 9
<212> TYPE: PRT
<213> ORGANISM: Homo sapiens

<400> SEQUENCE: 175

Thr Leu Asp Pro Lys Leu Gly Thr Asp
1 5

<210> SEQ ID NO 176
<211> LENGTH: 9
<212> TYPE: PRT
<213> ORGANISM: Homo sapiens

<400> SEQUENCE: 176

Lys Leu Lys Gly Tyr Thr Ser Trp Ala
1 5

<210> SEQ ID NO 177
<211> LENGTH: 9
<212> TYPE: PRT
<213> ORGANISM: Homo sapiens

<400> SEQUENCE: 177

Val Met Asp Leu Val Gly Ser Ile Leu
1 5

<210> SEQ ID NO 178
<211> LENGTH: 9
<212> TYPE: PRT
<213> ORGANISM: Homo sapiens

<400> SEQUENCE: 178

Leu Val Gly Ser Ile Leu Lys Asn Leu
1 5

<210> SEQ ID NO 179
<211> LENGTH: 9
<212> TYPE: PRT
<213> ORGANISM: Homo sapiens

<400> SEQUENCE: 179

Ser Pro Asp Cys Lys Ile Leu Val Val
1 5

<210> SEQ ID NO 180
<211> LENGTH: 9
<212> TYPE: PRT
<213> ORGANISM: Homo sapiens

<400> SEQUENCE: 180

Arg Val Ile Gly Ser Gly Cys Asn Leu
1 5

<210> SEQ ID NO 181
<211> LENGTH: 9
<212> TYPE: PRT
<213> ORGANISM: Homo sapiens

<400> SEQUENCE: 181

Asp Leu Val Gly Ser Ile Leu Lys Asn
1 5

<210> SEQ ID NO 182
<211> LENGTH: 9
<212> TYPE: PRT
<213> ORGANISM: Homo sapiens

<400> SEQUENCE: 182

Lys Asn Leu Arg Arg Val His Pro Val
1 5

<210> SEQ ID NO 183
<211> LENGTH: 9
<212> TYPE: PRT
<213> ORGANISM: Homo sapiens

<400> SEQUENCE: 183

Leu Gly Arg Asn Gly Val Ser Asp Val
1 5

<210> SEQ ID NO 184
<211> LENGTH: 10
<212> TYPE: PRT
<213> ORGANISM: Homo sapiens

<400> SEQUENCE: 184

Ala Leu Val Asp Val Ala Leu Asp Lys Leu
1 5 10

<210> SEQ ID NO 185
<211> LENGTH: 10
<212> TYPE: PRT
<213> ORGANISM: Homo sapiens

<400> SEQUENCE: 185

Ile Leu Leu Lys Asp Leu Ala Asp Glu Leu
1 5 10

<210> SEQ ID NO 186
<211> LENGTH: 10
<212> TYPE: PRT
<213> ORGANISM: Homo sapiens

<400> SEQUENCE: 186

Ala Ile Met Lys Ser Ile Ile Pro Ala Ile
1 5 10

<210> SEQ ID NO 187
<211> LENGTH: 10
<212> TYPE: PRT
<213> ORGANISM: Homo sapiens

<400> SEQUENCE: 187

Lys Ile Ser Gly Leu Pro Val Thr Arg Val
1 5 10

<210> SEQ ID NO 188
<211> LENGTH: 10
<212> TYPE: PRT
<213> ORGANISM: Homo sapiens

<400> SEQUENCE: 188

Val Leu Gly Arg Asn Gly Val Ser Asp Val
1 5 10

<210> SEQ ID NO 189
<211> LENGTH: 10
<212> TYPE: PRT
<213> ORGANISM: Homo sapiens

<400> SEQUENCE: 189

Ala Leu Phe Lys Lys Ser Ala Glu Thr Leu
1 5 10

<210> SEQ ID NO 190
<211> LENGTH: 10
<212> TYPE: PRT
<213> ORGANISM: Homo sapiens

<400> SEQUENCE: 190

Leu Ala Asp Glu Leu Ala Leu Val Asp Val
1 5 10

<210> SEQ ID NO 191
<211> LENGTH: 10
<212> TYPE: PRT
<213> ORGANISM: Homo sapiens

<400> SEQUENCE: 191

Ile Ile Gly Glu His Gly Asp Ser Ser Val
1 5 10

<210> SEQ ID NO 192
<211> LENGTH: 10
<212> TYPE: PRT
<213> ORGANISM: Homo sapiens

<400> SEQUENCE: 192

Asp Leu Val Gly Ser Ile Leu Lys Asn Leu
1 5 10

<210> SEQ ID NO 193
<211> LENGTH: 10
<212> TYPE: PRT
<213> ORGANISM: Homo sapiens

<400> SEQUENCE: 193

Asp Ile Leu Thr Tyr Ile Val Trp Lys Ile
1 5 10

<210> SEQ ID NO 194
<211> LENGTH: 10
<212> TYPE: PRT
<213> ORGANISM: Homo sapiens

<400> SEQUENCE: 194

Asn Val Ala Gly Val Ala Leu Lys Thr Leu

-continued 1 5 10

<210> SEQ ID NO 195
<211> LENGTH: 10
<212> TYPE: PRT
<213> ORGANISM: Homo sapiens

<400> SEQUENCE: 195

Ala Leu Val Gln Arg Asn Val Ala Ile Met
1 5 10

<210> SEQ ID NO 196
<211> LENGTH: 10
<212> TYPE: PRT
<213> ORGANISM: Homo sapiens

<400> SEQUENCE: 196

Ile Leu Val Val Ser Asn Pro Val Asp Ile
1 5 10

<210> SEQ ID NO 197
<211> LENGTH: 10
<212> TYPE: PRT
<213> ORGANISM: Homo sapiens

<400> SEQUENCE: 197

Trp Ala Ile Gly Leu Ser Val Met Asp Leu
1 5 10

<210> SEQ ID NO 198
<211> LENGTH: 10
<212> TYPE: PRT
<213> ORGANISM: Homo sapiens

<400> SEQUENCE: 198

Thr Val Lys Glu Gln Leu Ile Glu Lys Leu
1 5 10

<210> SEQ ID NO 199
<211> LENGTH: 10
<212> TYPE: PRT
<213> ORGANISM: Homo sapiens

<400> SEQUENCE: 199

Gly Met Ala Cys Ala Ile Ser Ile Leu Leu
1 5 10

<210> SEQ ID NO 200
<211> LENGTH: 10
<212> TYPE: PRT
<213> ORGANISM: Homo sapiens

<400> SEQUENCE: 200

Lys Ile Thr Ser Gly Lys Asp Tyr Ser Val
1 5 10

<210> SEQ ID NO 201
<211> LENGTH: 10
<212> TYPE: PRT
<213> ORGANISM: Homo sapiens

<400> SEQUENCE: 201

Ile Met Lys Ser Ile Ile Pro Ala Ile Val
1 5 10

<210> SEQ ID NO 202
<211> LENGTH: 10
<212> TYPE: PRT
<213> ORGANISM: Homo sapiens

<400> SEQUENCE: 202

Leu Trp Ser Gly Val Asn Val Ala Gly Val
1 5 10

<210> SEQ ID NO 203
<211> LENGTH: 10
<212> TYPE: PRT
<213> ORGANISM: Homo sapiens

<400> SEQUENCE: 203

Lys Leu Lys Gly Tyr Thr Ser Trp Ala Ile
1 5 10

<210> SEQ ID NO 204
<211> LENGTH: 10
<212> TYPE: PRT
<213> ORGANISM: Homo sapiens

<400> SEQUENCE: 204

Ser Thr Met Val Lys Gly Leu Tyr Gly Ile
1 5 10

<210> SEQ ID NO 205
<211> LENGTH: 10
<212> TYPE: PRT
<213> ORGANISM: Homo sapiens

<400> SEQUENCE: 205

Gly Ile Lys Glu Glu Leu Phe Leu Ser Ile
1 5 10

<210> SEQ ID NO 206
<211> LENGTH: 10
<212> TYPE: PRT
<213> ORGANISM: Homo sapiens

<400> SEQUENCE: 206

Leu Val Val Ser Asn Pro Val Asp Ile Leu
1 5 10

<210> SEQ ID NO 207
<211> LENGTH: 10
<212> TYPE: PRT
<213> ORGANISM: Homo sapiens

<400> SEQUENCE: 207

Asn Leu Asp Ser Ala Arg Phe Arg Tyr Leu
1 5 10

<210> SEQ ID NO 208
<211> LENGTH: 10
<212> TYPE: PRT
<213> ORGANISM: Homo sapiens

<400> SEQUENCE: 208

Tyr Leu Ile Gly Glu Lys Leu Gly Val His
1 5 10

<210> SEQ ID NO 209

<211> LENGTH: 10
<212> TYPE: PRT
<213> ORGANISM: Homo sapiens

<400> SEQUENCE: 209

Val Ala Leu Lys Thr Leu Asp Pro Lys Leu
1               5                   10

<210> SEQ ID NO 210
<211> LENGTH: 10
<212> TYPE: PRT
<213> ORGANISM: Homo sapiens

<400> SEQUENCE: 210

Ala Ile Gly Leu Ser Val Met Asp Leu Val
1               5                   10

<210> SEQ ID NO 211
<211> LENGTH: 10
<212> TYPE: PRT
<213> ORGANISM: Homo sapiens

<400> SEQUENCE: 211

Lys Ile Thr Ile Val Gly Thr Gly Ala Val
1               5                   10

<210> SEQ ID NO 212
<211> LENGTH: 10
<212> TYPE: PRT
<213> ORGANISM: Homo sapiens

<400> SEQUENCE: 212

Cys Ala Ile Ser Ile Leu Leu Lys Asp Leu
1               5                   10

<210> SEQ ID NO 213
<211> LENGTH: 10
<212> TYPE: PRT
<213> ORGANISM: Homo sapiens

<400> SEQUENCE: 213

Lys Asp Leu Ala Asp Glu Leu Ala Leu Val
1               5                   10

<210> SEQ ID NO 214
<211> LENGTH: 10
<212> TYPE: PRT
<213> ORGANISM: Homo sapiens

<400> SEQUENCE: 214

Glu Met Met Asp Leu Gln His Gly Ser Leu
1               5                   10

<210> SEQ ID NO 215
<211> LENGTH: 10
<212> TYPE: PRT
<213> ORGANISM: Homo sapiens

<400> SEQUENCE: 215

Val Ser Ala Asn Ser Arg Ile Val Ile Val
1               5                   10

<210> SEQ ID NO 216
<211> LENGTH: 10
<212> TYPE: PRT

<213> ORGANISM: Homo sapiens

<400> SEQUENCE: 216

Leu Ala Leu Val Gln Arg Asn Val Ala Ile
1 5 10

<210> SEQ ID NO 217
<211> LENGTH: 10
<212> TYPE: PRT
<213> ORGANISM: Homo sapiens

<400> SEQUENCE: 217

Ser Ile Ile Pro Ala Ile Val His Tyr Ser
1 5 10

<210> SEQ ID NO 218
<211> LENGTH: 10
<212> TYPE: PRT
<213> ORGANISM: Homo sapiens

<400> SEQUENCE: 218

Tyr Thr Ser Trp Ala Ile Gly Leu Ser Val
1 5 10

<210> SEQ ID NO 219
<211> LENGTH: 10
<212> TYPE: PRT
<213> ORGANISM: Homo sapiens

<400> SEQUENCE: 219

Thr Leu Trp Asn Ile Gln Lys Asp Leu Ile
1 5 10

<210> SEQ ID NO 220
<211> LENGTH: 10
<212> TYPE: PRT
<213> ORGANISM: Homo sapiens

<400> SEQUENCE: 220

Gln Leu Ile Glu Lys Leu Ile Glu Asp Asp
1 5 10

<210> SEQ ID NO 221
<211> LENGTH: 10
<212> TYPE: PRT
<213> ORGANISM: Homo sapiens

<400> SEQUENCE: 221

Lys Leu Ile Glu Asp Asp Glu Asn Ser Gln
1 5 10

<210> SEQ ID NO 222
<211> LENGTH: 10
<212> TYPE: PRT
<213> ORGANISM: Homo sapiens

<400> SEQUENCE: 222

Ser Ile Leu Leu Lys Asp Leu Ala Asp Glu
1 5 10

<210> SEQ ID NO 223
<211> LENGTH: 10
<212> TYPE: PRT
<213> ORGANISM: Homo sapiens

<400> SEQUENCE: 223

Gln Glu Gly Glu Thr Arg Leu Ala Leu Val
1 5 10

<210> SEQ ID NO 224
<211> LENGTH: 10
<212> TYPE: PRT
<213> ORGANISM: Homo sapiens

<400> SEQUENCE: 224

Tyr Ser Pro Asp Cys Lys Ile Leu Val Val
1 5 10

<210> SEQ ID NO 225
<211> LENGTH: 10
<212> TYPE: PRT
<213> ORGANISM: Homo sapiens

<400> SEQUENCE: 225

Ile Val Trp Lys Ile Ser Gly Leu Pro Val
1 5 10

<210> SEQ ID NO 226
<211> LENGTH: 10
<212> TYPE: PRT
<213> ORGANISM: Homo sapiens

<400> SEQUENCE: 226

Ser Val Pro Leu Trp Ser Gly Val Asn Val
1 5 10

<210> SEQ ID NO 227
<211> LENGTH: 10
<212> TYPE: PRT
<213> ORGANISM: Homo sapiens

<400> SEQUENCE: 227

Asn Ile His Lys Gln Val Ile Gln Ser Ala
1 5 10

<210> SEQ ID NO 228
<211> LENGTH: 10
<212> TYPE: PRT
<213> ORGANISM: Homo sapiens

<400> SEQUENCE: 228

Ile Gln Ser Ala Tyr Glu Ile Ile Lys Leu
1 5 10

<210> SEQ ID NO 229
<211> LENGTH: 10
<212> TYPE: PRT
<213> ORGANISM: Homo sapiens

<400> SEQUENCE: 229

Gly Leu Ser Val Met Asp Leu Val Gly Ser
1 5 10

<210> SEQ ID NO 230
<211> LENGTH: 10
<212> TYPE: PRT
<213> ORGANISM: Homo sapiens

<400> SEQUENCE: 230

Ser Val Met Asp Leu Val Gly Ser Ile Leu
1 5 10

<210> SEQ ID NO 231
<211> LENGTH: 10
<212> TYPE: PRT
<213> ORGANISM: Homo sapiens

<400> SEQUENCE: 231

Leu Lys Asn Leu Arg Arg Val His Pro Val
1 5 10

<210> SEQ ID NO 232
<211> LENGTH: 10
<212> TYPE: PRT
<213> ORGANISM: Homo sapiens

<400> SEQUENCE: 232

Asn Leu Arg Arg Val His Pro Val Ser Thr
1 5 10

<210> SEQ ID NO 233
<211> LENGTH: 10
<212> TYPE: PRT
<213> ORGANISM: Homo sapiens

<400> SEQUENCE: 233

Glu Leu Phe Leu Ser Ile Pro Cys Val Leu
1 5 10

<210> SEQ ID NO 234
<211> LENGTH: 9
<212> TYPE: PRT
<213> ORGANISM: Homo sapiens

<400> SEQUENCE: 234

Leu Tyr Gly Ile Lys Glu Glu Leu Phe
1 5

<210> SEQ ID NO 235
<211> LENGTH: 9
<212> TYPE: PRT
<213> ORGANISM: Homo sapiens

<400> SEQUENCE: 235

His Tyr Ser Pro Asp Cys Lys Ile Leu
1 5

<210> SEQ ID NO 236
<211> LENGTH: 9
<212> TYPE: PRT
<213> ORGANISM: Homo sapiens

<400> SEQUENCE: 236

Gly Tyr Thr Ser Trp Ala Ile Gly Leu
1 5

<210> SEQ ID NO 237
<211> LENGTH: 9
<212> TYPE: PRT
<213> ORGANISM: Homo sapiens

<400> SEQUENCE: 237

Leu Phe Leu Ser Ile Pro Cys Val Leu
1 5

<210> SEQ ID NO 238
<211> LENGTH: 9
<212> TYPE: PRT
<213> ORGANISM: Homo sapiens

<400> SEQUENCE: 238

Leu Phe Lys Lys Ser Ala Glu Thr Leu
1               5

<210> SEQ ID NO 239
<211> LENGTH: 9
<212> TYPE: PRT
<213> ORGANISM: Homo sapiens

<400> SEQUENCE: 239

Val Lys Glu Gln Leu Ile Glu Lys Leu
1               5

<210> SEQ ID NO 240
<211> LENGTH: 9
<212> TYPE: PRT
<213> ORGANISM: Homo sapiens

<400> SEQUENCE: 240

Met Asp Leu Gln His Gly Ser Leu Phe
1               5

<210> SEQ ID NO 241
<211> LENGTH: 9
<212> TYPE: PRT
<213> ORGANISM: Homo sapiens

<400> SEQUENCE: 241

Lys Glu Gln Leu Ile Glu Lys Leu Ile
1               5

<210> SEQ ID NO 242
<211> LENGTH: 9
<212> TYPE: PRT
<213> ORGANISM: Homo sapiens

<400> SEQUENCE: 242

Val His Tyr Ser Pro Asp Cys Lys Ile
1               5

<210> SEQ ID NO 243
<211> LENGTH: 9
<212> TYPE: PRT
<213> ORGANISM: Homo sapiens

<400> SEQUENCE: 243

Ile Leu Thr Tyr Ile Val Trp Lys Ile
1               5

<210> SEQ ID NO 244
<211> LENGTH: 10
<212> TYPE: PRT
<213> ORGANISM: Homo sapiens

<400> SEQUENCE: 244

Thr Tyr Ile Val Trp Lys Ile Ser Gly Leu
1               5                   10

-continued

<210> SEQ ID NO 245
<211> LENGTH: 10
<212> TYPE: PRT
<213> ORGANISM: Homo sapiens

<400> SEQUENCE: 245

Asp Tyr Ser Val Ser Ala Asn Ser Arg Ile
1 5 10

<210> SEQ ID NO 246
<211> LENGTH: 10
<212> TYPE: PRT
<213> ORGANISM: Homo sapiens

<400> SEQUENCE: 246

Leu Tyr Gly Ile Lys Glu Glu Leu Phe Leu
1 5 10

<210> SEQ ID NO 247
<211> LENGTH: 10
<212> TYPE: PRT
<213> ORGANISM: Homo sapiens

<400> SEQUENCE: 247

Arg Phe Arg Tyr Leu Ile Gly Glu Lys Leu
1 5 10

<210> SEQ ID NO 248
<211> LENGTH: 10
<212> TYPE: PRT
<213> ORGANISM: Homo sapiens

<400> SEQUENCE: 248

Val Ala Leu Lys Thr Leu Asp Pro Lys Leu
1 5 10

<210> SEQ ID NO 249
<211> LENGTH: 10
<212> TYPE: PRT
<213> ORGANISM: Homo sapiens

<400> SEQUENCE: 249

Thr Val Lys Glu Gln Leu Ile Glu Lys Leu
1 5 10

<210> SEQ ID NO 250
<211> LENGTH: 10
<212> TYPE: PRT
<213> ORGANISM: Homo sapiens

<400> SEQUENCE: 250

Asp Ile Leu Thr Tyr Ile Val Trp Lys Ile
1 5 10

<210> SEQ ID NO 251
<211> LENGTH: 10
<212> TYPE: PRT
<213> ORGANISM: Homo sapiens

<400> SEQUENCE: 251

Val His Pro Thr Ser Cys His Gly Trp Ile
1 5 10

<210> SEQ ID NO 252
<211> LENGTH: 10

<212> TYPE: PRT
<213> ORGANISM: Homo sapiens

<400> SEQUENCE: 252

Val Lys Glu Gln Leu Ile Glu Lys Leu Ile
1 5 10

<210> SEQ ID NO 253
<211> LENGTH: 10
<212> TYPE: PRT
<213> ORGANISM: Homo sapiens

<400> SEQUENCE: 253

Glu Asp Asp Glu Asn Ser Gln Cys Lys Ile
1 5 10

<210> SEQ ID NO 254
<211> LENGTH: 9
<212> TYPE: PRT
<213> ORGANISM: Homo sapiens

<400> SEQUENCE: 254

Asn Leu Asp Ser Ala Arg Phe Arg Tyr
1 5

<210> SEQ ID NO 255
<211> LENGTH: 9
<212> TYPE: PRT
<213> ORGANISM: Homo sapiens

<400> SEQUENCE: 255

Val Ser Thr Met Val Lys Gly Leu Tyr
1 5

<210> SEQ ID NO 256
<211> LENGTH: 9
<212> TYPE: PRT
<213> ORGANISM: Homo sapiens

<400> SEQUENCE: 256

Ser Asn Pro Val Asp Ile Leu Thr Tyr
1 5

<210> SEQ ID NO 257
<211> LENGTH: 9
<212> TYPE: PRT
<213> ORGANISM: Homo sapiens

<400> SEQUENCE: 257

Ser Ile Ile Pro Ala Ile Val His Tyr
1 5

<210> SEQ ID NO 258
<211> LENGTH: 9
<212> TYPE: PRT
<213> ORGANISM: Homo sapiens

<400> SEQUENCE: 258

Val Ser Asp Val Val Lys Ile Asn Leu
1 5

<210> SEQ ID NO 259
<211> LENGTH: 9
<212> TYPE: PRT
<213> ORGANISM: Homo sapiens

<400> SEQUENCE: 259

Asn Ser Glu Glu Glu Ala Leu Phe Lys
1               5

<210> SEQ ID NO 260
<211> LENGTH: 9
<212> TYPE: PRT
<213> ORGANISM: Homo sapiens

<400> SEQUENCE: 260

Ser Pro Asp Cys Lys Ile Leu Val Val
1               5

<210> SEQ ID NO 261
<211> LENGTH: 9
<212> TYPE: PRT
<213> ORGANISM: Homo sapiens

<400> SEQUENCE: 261

Ala Tyr Glu Ile Ile Lys Leu Lys Gly
1               5

<210> SEQ ID NO 262
<211> LENGTH: 9
<212> TYPE: PRT
<213> ORGANISM: Homo sapiens

<400> SEQUENCE: 262

Ile Lys Glu Glu Leu Phe Leu Ser Ile
1               5

<210> SEQ ID NO 263
<211> LENGTH: 9
<212> TYPE: PRT
<213> ORGANISM: Homo sapiens

<400> SEQUENCE: 263

Ser Lys Ile Thr Ser Gly Lys Asp Tyr
1               5

<210> SEQ ID NO 264
<211> LENGTH: 9
<212> TYPE: PRT
<213> ORGANISM: Homo sapiens

<400> SEQUENCE: 264

Leu Ala Asp Glu Leu Ala Leu Val Asp
1               5

<210> SEQ ID NO 265
<211> LENGTH: 9
<212> TYPE: PRT
<213> ORGANISM: Homo sapiens

<400> SEQUENCE: 265

Val Ser Asn Pro Val Asp Ile Leu Thr
1               5

<210> SEQ ID NO 266
<211> LENGTH: 9
<212> TYPE: PRT
<213> ORGANISM: Homo sapiens

<400> SEQUENCE: 266

Tyr Glu Ile Ile Lys Leu Lys Gly Tyr
1 5

<210> SEQ ID NO 267
<211> LENGTH: 9
<212> TYPE: PRT
<213> ORGANISM: Homo sapiens

<400> SEQUENCE: 267

Lys Gly Glu Met Met Asp Leu Gln His
1 5

<210> SEQ ID NO 268
<211> LENGTH: 9
<212> TYPE: PRT
<213> ORGANISM: Homo sapiens

<400> SEQUENCE: 268

Gly Thr Asp Ser Asp Lys Glu His Trp
1 5

<210> SEQ ID NO 269
<211> LENGTH: 9
<212> TYPE: PRT
<213> ORGANISM: Homo sapiens

<400> SEQUENCE: 269

Asp Ser Asp Lys Glu His Trp Lys Asn
1 5

<210> SEQ ID NO 270
<211> LENGTH: 9
<212> TYPE: PRT
<213> ORGANISM: Homo sapiens

<400> SEQUENCE: 270

Thr Leu Asp Pro Lys Leu Gly Thr Asp
1 5

<210> SEQ ID NO 271
<211> LENGTH: 9
<212> TYPE: PRT
<213> ORGANISM: Homo sapiens

<400> SEQUENCE: 271

His Lys Gln Val Ile Gln Ser Ala Tyr
1 5

<210> SEQ ID NO 272
<211> LENGTH: 9
<212> TYPE: PRT
<213> ORGANISM: Homo sapiens

<400> SEQUENCE: 272

Ser Thr Met Val Lys Gly Leu Tyr Gly
1 5

<210> SEQ ID NO 273
<211> LENGTH: 9
<212> TYPE: PRT
<213> ORGANISM: Homo sapiens

<400> SEQUENCE: 273

Leu Ser Ile Pro Cys Val Leu Gly Arg

-continued 1 5

<210> SEQ ID NO 274
<211> LENGTH: 9
<212> TYPE: PRT
<213> ORGANISM: Homo sapiens

<400> SEQUENCE: 274

Glu Glu Glu Ala Leu Phe Lys Lys Ser
1 5

<210> SEQ ID NO 275
<211> LENGTH: 10
<212> TYPE: PRT
<213> ORGANISM: Homo sapiens

<400> SEQUENCE: 275

Val Ser Asn Pro Val Asp Ile Leu Thr Tyr
1 5 10

<210> SEQ ID NO 276
<211> LENGTH: 10
<212> TYPE: PRT
<213> ORGANISM: Homo sapiens

<400> SEQUENCE: 276

Ala Tyr Glu Ile Ile Lys Leu Lys Gly Tyr
1 5 10

<210> SEQ ID NO 277
<211> LENGTH: 10
<212> TYPE: PRT
<213> ORGANISM: Homo sapiens

<400> SEQUENCE: 277

Thr Ser Lys Ile Thr Ser Gly Lys Asp Tyr
1 5 10

<210> SEQ ID NO 278
<211> LENGTH: 10
<212> TYPE: PRT
<213> ORGANISM: Homo sapiens

<400> SEQUENCE: 278

Lys Ser Ile Ile Pro Ala Ile Val His Tyr
1 5 10

<210> SEQ ID NO 279
<211> LENGTH: 10
<212> TYPE: PRT
<213> ORGANISM: Homo sapiens

<400> SEQUENCE: 279

Gln Gln Glu Gly Glu Thr Arg Leu Ala Leu
1 5 10

<210> SEQ ID NO 280
<211> LENGTH: 10
<212> TYPE: PRT
<213> ORGANISM: Homo sapiens

<400> SEQUENCE: 280

Glu Gly Glu Thr Arg Leu Ala Leu Val Gln
1 5 10

<210> SEQ ID NO 281
<211> LENGTH: 10
<212> TYPE: PRT
<213> ORGANISM: Homo sapiens

<400> SEQUENCE: 281

Val Met Asp Leu Val Gly Ser Ile Leu Lys
1 5 10

<210> SEQ ID NO 282
<211> LENGTH: 10
<212> TYPE: PRT
<213> ORGANISM: Homo sapiens

<400> SEQUENCE: 282

Pro Val Ser Thr Met Val Lys Gly Leu Tyr
1 5 10

<210> SEQ ID NO 283
<211> LENGTH: 10
<212> TYPE: PRT
<213> ORGANISM: Homo sapiens

<400> SEQUENCE: 283

Val Ser Asp Val Val Lys Ile Asn Leu Asn
1 5 10

<210> SEQ ID NO 284
<211> LENGTH: 10
<212> TYPE: PRT
<213> ORGANISM: Homo sapiens

<400> SEQUENCE: 284

Ser Glu Glu Glu Ala Leu Phe Lys Lys Ser
1 5 10

<210> SEQ ID NO 285
<211> LENGTH: 10
<212> TYPE: PRT
<213> ORGANISM: Homo sapiens

<400> SEQUENCE: 285

Ser Ala Glu Thr Leu Trp Asn Ile Gln Lys
1 5 10

<210> SEQ ID NO 286
<211> LENGTH: 10
<212> TYPE: PRT
<213> ORGANISM: Homo sapiens

<400> SEQUENCE: 286

Leu Lys Asp Leu Ala Asp Glu Leu Ala Leu
1 5 10

<210> SEQ ID NO 287
<211> LENGTH: 10
<212> TYPE: PRT
<213> ORGANISM: Homo sapiens

<400> SEQUENCE: 287

Cys Asn Leu Asp Ser Ala Arg Phe Arg Tyr
1 5 10

<210> SEQ ID NO 288

<211> LENGTH: 10
<212> TYPE: PRT
<213> ORGANISM: Homo sapiens

<400> SEQUENCE: 288

His Gly Asp Ser Ser Val Pro Leu Trp Ser
1 5 10

<210> SEQ ID NO 289
<211> LENGTH: 10
<212> TYPE: PRT
<213> ORGANISM: Homo sapiens

<400> SEQUENCE: 289

Thr Leu Asp Pro Lys Leu Gly Thr Asp Ser
1 5 10

<210> SEQ ID NO 290
<211> LENGTH: 10
<212> TYPE: PRT
<213> ORGANISM: Homo sapiens

<400> SEQUENCE: 290

Gly Thr Asp Ser Asp Lys Glu His Trp Lys
1 5 10

<210> SEQ ID NO 291
<211> LENGTH: 10
<212> TYPE: PRT
<213> ORGANISM: Homo sapiens

<400> SEQUENCE: 291

Asn Ser Glu Glu Glu Ala Leu Phe Lys Lys
1 5 10

<210> SEQ ID NO 292
<211> LENGTH: 10
<212> TYPE: PRT
<213> ORGANISM: Homo sapiens

<400> SEQUENCE: 292

Pro Val Asp Ile Leu Thr Tyr Ile Val Trp
1 5 10

<210> SEQ ID NO 293
<211> LENGTH: 10
<212> TYPE: PRT
<213> ORGANISM: Homo sapiens

<400> SEQUENCE: 293

Asp Lys Glu His Trp Lys Asn Ile His Lys
1 5 10

<210> SEQ ID NO 294
<211> LENGTH: 10
<212> TYPE: PRT
<213> ORGANISM: Homo sapiens

<400> SEQUENCE: 294

Ile His Lys Gln Val Ile Gln Ser Ala Tyr
1 5 10

<210> SEQ ID NO 295
<211> LENGTH: 10
<212> TYPE: PRT

<213> ORGANISM: Homo sapiens

<400> SEQUENCE: 295

Tyr Thr Ser Trp Ala Ile Gly Leu Ser Val
1 5 10

<210> SEQ ID NO 296
<211> LENGTH: 9
<212> TYPE: PRT
<213> ORGANISM: Homo sapiens

<400> SEQUENCE: 296

Ala Leu Val Asp Val Ala Leu Asp Lys
1 5

<210> SEQ ID NO 297
<211> LENGTH: 9
<212> TYPE: PRT
<213> ORGANISM: Homo sapiens

<400> SEQUENCE: 297

Lys Ile Ser Gly Leu Pro Val Thr Arg
1 5

<210> SEQ ID NO 298
<211> LENGTH: 9
<212> TYPE: PRT
<213> ORGANISM: Homo sapiens

<400> SEQUENCE: 298

Ser Ile Ile Pro Ala Ile Val His Tyr
1 5

<210> SEQ ID NO 299
<211> LENGTH: 9
<212> TYPE: PRT
<213> ORGANISM: Homo sapiens

<400> SEQUENCE: 299

Asp Ile Leu Thr Tyr Ile Val Trp Lys
1 5

<210> SEQ ID NO 300
<211> LENGTH: 9
<212> TYPE: PRT
<213> ORGANISM: Homo sapiens

<400> SEQUENCE: 300

Ile Val Ile Val Thr Ala Gly Ala Arg
1 5

<210> SEQ ID NO 301
<211> LENGTH: 9
<212> TYPE: PRT
<213> ORGANISM: Homo sapiens

<400> SEQUENCE: 301

Met Val Lys Gly Leu Tyr Gly Ile Lys
1 5

<210> SEQ ID NO 302
<211> LENGTH: 9
<212> TYPE: PRT
<213> ORGANISM: Homo sapiens

<400> SEQUENCE: 302

Ile Val His Tyr Ser Pro Asp Cys Lys
1               5

<210> SEQ ID NO 303
<211> LENGTH: 9
<212> TYPE: PRT
<213> ORGANISM: Homo sapiens

<400> SEQUENCE: 303

Ile Leu Lys Asn Leu Arg Arg Val His
1               5

<210> SEQ ID NO 304
<211> LENGTH: 9
<212> TYPE: PRT
<213> ORGANISM: Homo sapiens

<400> SEQUENCE: 304

Thr Val Lys Glu Gln Leu Ile Glu Lys
1               5

<210> SEQ ID NO 305
<211> LENGTH: 9
<212> TYPE: PRT
<213> ORGANISM: Homo sapiens

<400> SEQUENCE: 305

Ile Val Thr Ala Gly Ala Arg Gln Gln
1               5

<210> SEQ ID NO 306
<211> LENGTH: 9
<212> TYPE: PRT
<213> ORGANISM: Homo sapiens

<400> SEQUENCE: 306

Arg Val Ile Gly Ser Gly Cys Asn Leu
1               5

<210> SEQ ID NO 307
<211> LENGTH: 9
<212> TYPE: PRT
<213> ORGANISM: Homo sapiens

<400> SEQUENCE: 307

Val Leu Gly Arg Asn Gly Val Ser Asp
1               5

<210> SEQ ID NO 308
<211> LENGTH: 9
<212> TYPE: PRT
<213> ORGANISM: Homo sapiens

<400> SEQUENCE: 308

Arg Asn Gly Val Ser Asp Val Val Lys
1               5

<210> SEQ ID NO 309
<211> LENGTH: 9
<212> TYPE: PRT
<213> ORGANISM: Homo sapiens

<400> SEQUENCE: 309

Ile Val Gly Thr Gly Ala Val Gly Met
1 5

<210> SEQ ID NO 310
<211> LENGTH: 9
<212> TYPE: PRT
<213> ORGANISM: Homo sapiens

<400> SEQUENCE: 310

Asn Leu Arg Arg Val His Pro Val Ser
1 5

<210> SEQ ID NO 311
<211> LENGTH: 9
<212> TYPE: PRT
<213> ORGANISM: Homo sapiens

<400> SEQUENCE: 311

Cys Val Leu Gly Arg Asn Gly Val Ser
1 5

<210> SEQ ID NO 312
<211> LENGTH: 9
<212> TYPE: PRT
<213> ORGANISM: Homo sapiens

<400> SEQUENCE: 312

Thr Ile Val Gly Thr Gly Ala Val Gly
1 5

<210> SEQ ID NO 313
<211> LENGTH: 9
<212> TYPE: PRT
<213> ORGANISM: Homo sapiens

<400> SEQUENCE: 313

Ala Leu Val Gln Arg Asn Val Ala Ile
1 5

<210> SEQ ID NO 314
<211> LENGTH: 9
<212> TYPE: PRT
<213> ORGANISM: Homo sapiens

<400> SEQUENCE: 314

Asn Val Ala Gly Val Ala Leu Lys Thr
1 5

<210> SEQ ID NO 315
<211> LENGTH: 9
<212> TYPE: PRT
<213> ORGANISM: Homo sapiens

<400> SEQUENCE: 315

Ile Ile Lys Leu Lys Gly Tyr Thr Ser
1 5

<210> SEQ ID NO 316
<211> LENGTH: 9
<212> TYPE: PRT
<213> ORGANISM: Homo sapiens

<400> SEQUENCE: 316

Lys Leu Lys Gly Tyr Thr Ser Trp Ala
1 5

<210> SEQ ID NO 317
<211> LENGTH: 9
<212> TYPE: PRT
<213> ORGANISM: Homo sapiens

<400> SEQUENCE: 317

Arg Val His Pro Val Ser Thr Met Val
1               5

<210> SEQ ID NO 318
<211> LENGTH: 9
<212> TYPE: PRT
<213> ORGANISM: Homo sapiens

<400> SEQUENCE: 318

Asp Leu Gln His Gly Ser Leu Phe Phe
1               5

<210> SEQ ID NO 319
<211> LENGTH: 9
<212> TYPE: PRT
<213> ORGANISM: Homo sapiens

<400> SEQUENCE: 319

Val Gln Arg Asn Val Ala Ile Met Lys
1               5

<210> SEQ ID NO 320
<211> LENGTH: 9
<212> TYPE: PRT
<213> ORGANISM: Homo sapiens

<400> SEQUENCE: 320

Leu Ile Gly Glu Lys Leu Gly Val His
1               5

<210> SEQ ID NO 321
<211> LENGTH: 9
<212> TYPE: PRT
<213> ORGANISM: Homo sapiens

<400> SEQUENCE: 321

Thr Leu Asp Pro Lys Leu Gly Thr Asp
1               5

<210> SEQ ID NO 322
<211> LENGTH: 9
<212> TYPE: PRT
<213> ORGANISM: Homo sapiens

<400> SEQUENCE: 322

Ala Cys Ala Ile Ser Ile Leu Leu Lys
1               5

<210> SEQ ID NO 323
<211> LENGTH: 9
<212> TYPE: PRT
<213> ORGANISM: Homo sapiens

<400> SEQUENCE: 323

Glu Leu Ala Leu Val Asp Val Ala Leu
1               5

<210> SEQ ID NO 324
<211> LENGTH: 9
<212> TYPE: PRT
<213> ORGANISM: Homo sapiens

<400> SEQUENCE: 324

Lys Ser Ile Ile Pro Ala Ile Val His
1 5

<210> SEQ ID NO 325
<211> LENGTH: 9
<212> TYPE: PRT
<213> ORGANISM: Homo sapiens

<400> SEQUENCE: 325

Arg Phe Arg Tyr Leu Ile Gly Glu Lys
1 5

<210> SEQ ID NO 326
<211> LENGTH: 9
<212> TYPE: PRT
<213> ORGANISM: Homo sapiens

<400> SEQUENCE: 326

Tyr Leu Ile Gly Glu Lys Leu Gly Val
1 5

<210> SEQ ID NO 327
<211> LENGTH: 9
<212> TYPE: PRT
<213> ORGANISM: Homo sapiens

<400> SEQUENCE: 327

Gly Val Asn Val Ala Gly Val Ala Leu
1 5

<210> SEQ ID NO 328
<211> LENGTH: 9
<212> TYPE: PRT
<213> ORGANISM: Homo sapiens

<400> SEQUENCE: 328

Gln Val Ile Gln Ser Ala Tyr Glu Ile
1 5

<210> SEQ ID NO 329
<211> LENGTH: 10
<212> TYPE: PRT
<213> ORGANISM: Homo sapiens

<400> SEQUENCE: 329

Arg Val His Pro Val Ser Thr Met Val Lys
1 5 10

<210> SEQ ID NO 330
<211> LENGTH: 10
<212> TYPE: PRT
<213> ORGANISM: Homo sapiens

<400> SEQUENCE: 330

Leu Val Gln Arg Asn Val Ala Ile Met Lys
1 5 10

<210> SEQ ID NO 331
<211> LENGTH: 10

<212> TYPE: PRT
<213> ORGANISM: Homo sapiens

<400> SEQUENCE: 331

Tyr Leu Ile Gly Glu Lys Leu Gly Val His
1 5 10

<210> SEQ ID NO 332
<211> LENGTH: 10
<212> TYPE: PRT
<213> ORGANISM: Homo sapiens

<400> SEQUENCE: 332

Gly Val Asn Val Ala Gly Val Ala Leu Lys
1 5 10

<210> SEQ ID NO 333
<211> LENGTH: 10
<212> TYPE: PRT
<213> ORGANISM: Homo sapiens

<400> SEQUENCE: 333

Asn Leu Arg Arg Val His Pro Val Ser Thr
1 5 10

<210> SEQ ID NO 334
<211> LENGTH: 10
<212> TYPE: PRT
<213> ORGANISM: Homo sapiens

<400> SEQUENCE: 334

Cys Val Leu Gly Arg Asn Gly Val Ser Asp
1 5 10

<210> SEQ ID NO 335
<211> LENGTH: 10
<212> TYPE: PRT
<213> ORGANISM: Homo sapiens

<400> SEQUENCE: 335

Asp Leu Ala Asp Glu Leu Ala Leu Val Asp
1 5 10

<210> SEQ ID NO 336
<211> LENGTH: 10
<212> TYPE: PRT
<213> ORGANISM: Homo sapiens

<400> SEQUENCE: 336

Arg Ile Val Ile Val Thr Ala Gly Ala Arg
1 5 10

<210> SEQ ID NO 337
<211> LENGTH: 10
<212> TYPE: PRT
<213> ORGANISM: Homo sapiens

<400> SEQUENCE: 337

Ala Ile Val His Tyr Ser Pro Asp Cys Lys
1 5 10

<210> SEQ ID NO 338
<211> LENGTH: 10
<212> TYPE: PRT
<213> ORGANISM: Homo sapiens

<400> SEQUENCE: 338

Gly Val Ala Leu Lys Thr Leu Asp Pro Lys
1 5 10

<210> SEQ ID NO 339
<211> LENGTH: 10
<212> TYPE: PRT
<213> ORGANISM: Homo sapiens

<400> SEQUENCE: 339

Ile Val Ile Val Thr Ala Gly Ala Arg Gln
1 5 10

<210> SEQ ID NO 340
<211> LENGTH: 10
<212> TYPE: PRT
<213> ORGANISM: Homo sapiens

<400> SEQUENCE: 340

Arg Leu Ala Leu Val Gln Arg Asn Val Ala
1 5 10

<210> SEQ ID NO 341
<211> LENGTH: 10
<212> TYPE: PRT
<213> ORGANISM: Homo sapiens

<400> SEQUENCE: 341

Leu Val Asp Val Ala Leu Asp Lys Leu Lys
1 5 10

<210> SEQ ID NO 342
<211> LENGTH: 10
<212> TYPE: PRT
<213> ORGANISM: Homo sapiens

<400> SEQUENCE: 342

Lys Leu Gly Val His Pro Thr Ser Cys His
1 5 10

<210> SEQ ID NO 343
<211> LENGTH: 10
<212> TYPE: PRT
<213> ORGANISM: Homo sapiens

<400> SEQUENCE: 343

Ser Ile Leu Lys Asn Leu Arg Arg Val His
1 5 10

<210> SEQ ID NO 344
<211> LENGTH: 10
<212> TYPE: PRT
<213> ORGANISM: Homo sapiens

<400> SEQUENCE: 344

Gly Leu Tyr Gly Ile Lys Glu Glu Leu Phe
1 5 10

<210> SEQ ID NO 345
<211> LENGTH: 10
<212> TYPE: PRT
<213> ORGANISM: Homo sapiens

<400> SEQUENCE: 345

Gly Arg Asn Gly Val Ser Asp Val Val Lys
1 5 10

<210> SEQ ID NO 346
<211> LENGTH: 10
<212> TYPE: PRT
<213> ORGANISM: Homo sapiens

<400> SEQUENCE: 346

Ala Leu Phe Lys Lys Ser Ala Glu Thr Leu
1 5 10

<210> SEQ ID NO 347
<211> LENGTH: 10
<212> TYPE: PRT
<213> ORGANISM: Homo sapiens

<400> SEQUENCE: 347

Lys Leu Ile Glu Asp Asp Glu Asn Ser Gln
1 5 10

<210> SEQ ID NO 348
<211> LENGTH: 10
<212> TYPE: PRT
<213> ORGANISM: Homo sapiens

<400> SEQUENCE: 348

Val Asp Ile Leu Thr Tyr Ile Val Trp Lys
1 5 10

<210> SEQ ID NO 349
<211> LENGTH: 10
<212> TYPE: PRT
<213> ORGANISM: Homo sapiens

<400> SEQUENCE: 349

Pro Val Thr Arg Val Ile Gly Ser Gly Cys
1 5 10

<210> SEQ ID NO 350
<211> LENGTH: 10
<212> TYPE: PRT
<213> ORGANISM: Homo sapiens

<400> SEQUENCE: 350

Arg Val Ile Gly Ser Gly Cys Asn Leu Asp
1 5 10

<210> SEQ ID NO 351
<211> LENGTH: 10
<212> TYPE: PRT
<213> ORGANISM: Homo sapiens

<400> SEQUENCE: 351

Ser Val Pro Leu Trp Ser Gly Val Asn Val
1 5 10

<210> SEQ ID NO 352
<211> LENGTH: 10
<212> TYPE: PRT
<213> ORGANISM: Homo sapiens

<400> SEQUENCE: 352

Ile Leu Lys Asn Leu Arg Arg Val His Pro 1 5 10

<210> SEQ ID NO 353
<211> LENGTH: 10
<212> TYPE: PRT
<213> ORGANISM: Homo sapiens

<400> SEQUENCE: 353

Ala Val Gly Met Ala Cys Ala Ile Ser Ile
1 5 10

<210> SEQ ID NO 354
<211> LENGTH: 10
<212> TYPE: PRT
<213> ORGANISM: Homo sapiens

<400> SEQUENCE: 354

Leu Ala Leu Val Asp Val Ala Leu Asp Lys
1 5 10

<210> SEQ ID NO 355
<211> LENGTH: 10
<212> TYPE: PRT
<213> ORGANISM: Homo sapiens

<400> SEQUENCE: 355

Ser Val Ser Ala Asn Ser Arg Ile Val Ile
1 5 10

<210> SEQ ID NO 356
<211> LENGTH: 10
<212> TYPE: PRT
<213> ORGANISM: Homo sapiens

<400> SEQUENCE: 356

Ile Val Thr Ala Gly Ala Arg Gln Gln Glu
1 5 10

<210> SEQ ID NO 357
<211> LENGTH: 10
<212> TYPE: PRT
<213> ORGANISM: Homo sapiens

<400> SEQUENCE: 357

Ile Val Trp Lys Ile Ser Gly Leu Pro Val
1 5 10

<210> SEQ ID NO 358
<211> LENGTH: 10
<212> TYPE: PRT
<213> ORGANISM: Homo sapiens

<400> SEQUENCE: 358

Trp Ile Ile Gly Glu His Gly Asp Ser Ser
1 5 10

<210> SEQ ID NO 359
<211> LENGTH: 10
<212> TYPE: PRT
<213> ORGANISM: Homo sapiens

<400> SEQUENCE: 359

Val Ile Gln Ser Ala Tyr Glu Ile Ile Lys
1 5 10

<210> SEQ ID NO 360
<211> LENGTH: 10
<212> TYPE: PRT
<213> ORGANISM: Homo sapiens

<400> SEQUENCE: 360

Glu Ile Ile Lys Leu Lys Gly Tyr Thr Ser
1 5 10

<210> SEQ ID NO 361
<211> LENGTH: 10
<212> TYPE: PRT
<213> ORGANISM: Homo sapiens

<400> SEQUENCE: 361

Ser Val Met Asp Leu Val Gly Ser Ile Leu
1 5 10

<210> SEQ ID NO 362
<211> LENGTH: 10
<212> TYPE: PRT
<213> ORGANISM: Homo sapiens

<400> SEQUENCE: 362

Phe Leu Ser Ile Pro Cys Val Leu Gly Arg
1 5 10

<210> SEQ ID NO 363
<211> LENGTH: 9
<212> TYPE: PRT
<213> ORGANISM: Homo sapiens

<400> SEQUENCE: 363

Ser Pro Asp Cys Lys Ile Leu Val Val
1 5

<210> SEQ ID NO 364
<211> LENGTH: 9
<212> TYPE: PRT
<213> ORGANISM: Homo sapiens

<400> SEQUENCE: 364

Val Pro Leu Trp Ser Gly Val Asn Val
1 5

<210> SEQ ID NO 365
<211> LENGTH: 9
<212> TYPE: PRT
<213> ORGANISM: Homo sapiens

<400> SEQUENCE: 365

Asn Pro Val Asp Ile Leu Thr Tyr Ile
1 5

<210> SEQ ID NO 366
<211> LENGTH: 9
<212> TYPE: PRT
<213> ORGANISM: Homo sapiens

<400> SEQUENCE: 366

Val Val Ser Asn Pro Val Asp Ile Leu
1 5

<210> SEQ ID NO 367

<211> LENGTH: 9
<212> TYPE: PRT
<213> ORGANISM: Homo sapiens

<400> SEQUENCE: 367

His Pro Thr Ser Cys His Gly Trp Ile
1               5

<210> SEQ ID NO 368
<211> LENGTH: 9
<212> TYPE: PRT
<213> ORGANISM: Homo sapiens

<400> SEQUENCE: 368

Lys Asp Leu Ala Asp Glu Leu Ala Leu
1               5

<210> SEQ ID NO 369
<211> LENGTH: 9
<212> TYPE: PRT
<213> ORGANISM: Homo sapiens

<400> SEQUENCE: 369

Glu Leu Ala Leu Val Asp Val Ala Leu
1               5

<210> SEQ ID NO 370
<211> LENGTH: 9
<212> TYPE: PRT
<213> ORGANISM: Homo sapiens

<400> SEQUENCE: 370

Gln Glu Gly Glu Thr Arg Leu Ala Leu
1               5

<210> SEQ ID NO 371
<211> LENGTH: 9
<212> TYPE: PRT
<213> ORGANISM: Homo sapiens

<400> SEQUENCE: 371

Glu His Gly Asp Ser Ser Val Pro Leu
1               5

<210> SEQ ID NO 372
<211> LENGTH: 9
<212> TYPE: PRT
<213> ORGANISM: Homo sapiens

<400> SEQUENCE: 372

Ala Ile Ser Ile Leu Leu Lys Asp Leu
1               5

<210> SEQ ID NO 373
<211> LENGTH: 10
<212> TYPE: PRT
<213> ORGANISM: Homo sapiens

<400> SEQUENCE: 373

His Pro Val Ser Thr Met Val Lys Gly Leu
1               5                   10

<210> SEQ ID NO 374
<211> LENGTH: 10
<212> TYPE: PRT

<213> ORGANISM: Homo sapiens

<400> SEQUENCE: 374

Val Pro Leu Trp Ser Gly Val Asn Val Ala
1 5 10

<210> SEQ ID NO 375
<211> LENGTH: 10
<212> TYPE: PRT
<213> ORGANISM: Homo sapiens

<400> SEQUENCE: 375

Ile Pro Cys Val Leu Gly Arg Asn Gly Val
1 5 10

<210> SEQ ID NO 376
<211> LENGTH: 10
<212> TYPE: PRT
<213> ORGANISM: Homo sapiens

<400> SEQUENCE: 376

Asn Pro Val Asp Ile Leu Thr Tyr Ile Val
1 5 10

<210> SEQ ID NO 377
<211> LENGTH: 10
<212> TYPE: PRT
<213> ORGANISM: Homo sapiens

<400> SEQUENCE: 377

Gln Gln Glu Gly Glu Thr Arg Leu Ala Leu
1 5 10

<210> SEQ ID NO 378
<211> LENGTH: 10
<212> TYPE: PRT
<213> ORGANISM: Homo sapiens

<400> SEQUENCE: 378

His Pro Thr Ser Cys His Gly Trp Ile Ile
1 5 10

<210> SEQ ID NO 379
<211> LENGTH: 10
<212> TYPE: PRT
<213> ORGANISM: Homo sapiens

<400> SEQUENCE: 379

Gly Glu His Gly Asp Ser Ser Val Pro Leu
1 5 10

<210> SEQ ID NO 380
<211> LENGTH: 10
<212> TYPE: PRT
<213> ORGANISM: Homo sapiens

<400> SEQUENCE: 380

Leu Lys Asp Leu Ala Asp Glu Leu Ala Leu
1 5 10

<210> SEQ ID NO 381
<211> LENGTH: 10
<212> TYPE: PRT
<213> ORGANISM: Homo sapiens

<400> SEQUENCE: 381

Asp Glu Leu Ala Leu Val Asp Val Ala Leu
1 5 10

<210> SEQ ID NO 382
<211> LENGTH: 10
<212> TYPE: PRT
<213> ORGANISM: Homo sapiens

<400> SEQUENCE: 382

Ser Pro Asp Cys Lys Ile Leu Val Val Ser
1 5 10

<210> SEQ ID NO 383
<211> LENGTH: 8
<212> TYPE: PRT
<213> ORGANISM: Homo sapiens

<400> SEQUENCE: 383

Ser Pro Asp Pro Thr Asp Leu Ala
1 5

<210> SEQ ID NO 384
<211> LENGTH: 8
<212> TYPE: PRT
<213> ORGANISM: Homo sapiens

<400> SEQUENCE: 384

Gln Thr Ser Glu Phe Lys Gly Ala
1 5

<210> SEQ ID NO 385
<211> LENGTH: 8
<212> TYPE: PRT
<213> ORGANISM: Homo sapiens

<400> SEQUENCE: 385

Phe Lys Gly Ala Thr Glu Glu Ala
1 5

<210> SEQ ID NO 386
<211> LENGTH: 8
<212> TYPE: PRT
<213> ORGANISM: Homo sapiens

<400> SEQUENCE: 386

Gly Ala Thr Glu Glu Ala Pro Ala
1 5

<210> SEQ ID NO 387
<211> LENGTH: 8
<212> TYPE: PRT
<213> ORGANISM: Homo sapiens

<400> SEQUENCE: 387

His Thr Ser Glu Phe Lys Gly Ala
1 5

<210> SEQ ID NO 388
<211> LENGTH: 8
<212> TYPE: PRT
<213> ORGANISM: Homo sapiens

<400> SEQUENCE: 388

Thr Ser Glu Phe Lys Gly Ala Ala
1 5

<210> SEQ ID NO 389
<211> LENGTH: 8
<212> TYPE: PRT
<213> ORGANISM: Homo sapiens

<400> SEQUENCE: 389

Pro Ile Ser Glu Ser Val Leu Ala
1 5

<210> SEQ ID NO 390
<211> LENGTH: 8
<212> TYPE: PRT
<213> ORGANISM: Homo sapiens

<400> SEQUENCE: 390

Ser Lys Phe Glu Val Glu Asp Ala
1 5

<210> SEQ ID NO 391
<211> LENGTH: 8
<212> TYPE: PRT
<213> ORGANISM: Homo sapiens

<400> SEQUENCE: 391

Val Glu Asp Ala Glu Asn Val Ala
1 5

<210> SEQ ID NO 392
<211> LENGTH: 8
<212> TYPE: PRT
<213> ORGANISM: Homo sapiens

<400> SEQUENCE: 392

His Ser Ile Val Ser Ser Phe Ala
1 5

<210> SEQ ID NO 393
<211> LENGTH: 8
<212> TYPE: PRT
<213> ORGANISM: Homo sapiens

<400> SEQUENCE: 393

Leu Asp Val Thr Leu Ile Leu Ala
1 5

<210> SEQ ID NO 394
<211> LENGTH: 8
<212> TYPE: PRT
<213> ORGANISM: Homo sapiens

<400> SEQUENCE: 394

Glu Tyr Arg Ser Ile Ser Leu Ala
1 5

<210> SEQ ID NO 395
<211> LENGTH: 8
<212> TYPE: PRT
<213> ORGANISM: Homo sapiens

<400> SEQUENCE: 395

Arg Ser Ile Ser Leu Ala Ile Ala
1 5

<210> SEQ ID NO 396
<211> LENGTH: 8
<212> TYPE: PRT
<213> ORGANISM: Homo sapiens

<400> SEQUENCE: 396

Leu Phe Asn Ile Leu Asp Thr Ala
1               5

<210> SEQ ID NO 397
<211> LENGTH: 8
<212> TYPE: PRT
<213> ORGANISM: Homo sapiens

<400> SEQUENCE: 397

Tyr Val Thr Glu Arg Ile Ile Ala
1               5

<210> SEQ ID NO 398
<211> LENGTH: 8
<212> TYPE: PRT
<213> ORGANISM: Homo sapiens

<400> SEQUENCE: 398

Tyr Asn Leu Cys Ser Glu Arg Ala
1               5

<210> SEQ ID NO 399
<211> LENGTH: 8
<212> TYPE: PRT
<213> ORGANISM: Homo sapiens

<400> SEQUENCE: 399

Lys Glu Val Asn Glu Trp Met Ala
1               5

<210> SEQ ID NO 400
<211> LENGTH: 8
<212> TYPE: PRT
<213> ORGANISM: Homo sapiens

<400> SEQUENCE: 400

Gln Asp Leu Glu Asn Ile Val Ala
1               5

<210> SEQ ID NO 401
<211> LENGTH: 8
<212> TYPE: PRT
<213> ORGANISM: Homo sapiens

<400> SEQUENCE: 401

Arg Thr Gly Thr Met Val Cys Ala
1               5

<210> SEQ ID NO 402
<211> LENGTH: 8
<212> TYPE: PRT
<213> ORGANISM: Homo sapiens

<400> SEQUENCE: 402

Met Val Cys Ala Phe Leu Ile Ala
1               5

<210> SEQ ID NO 403
<211> LENGTH: 8
<212> TYPE: PRT
<213> ORGANISM: Homo sapiens

<400> SEQUENCE: 403

Ala Ser Glu Ile Cys Ser Thr Ala
1               5

<210> SEQ ID NO 404
<211> LENGTH: 8
<212> TYPE: PRT
<213> ORGANISM: Homo sapiens

<400> SEQUENCE: 404

Pro Ser Gln Lys Arg Tyr Val Ala
1               5

<210> SEQ ID NO 405
<211> LENGTH: 8
<212> TYPE: PRT
<213> ORGANISM: Homo sapiens

<400> SEQUENCE: 405

Lys Arg Tyr Val Ala Tyr Phe Ala
1               5

<210> SEQ ID NO 406
<211> LENGTH: 8
<212> TYPE: PRT
<213> ORGANISM: Homo sapiens

<400> SEQUENCE: 406

Asp Asn Leu His Lys Gln Lys Ala
1               5

<210> SEQ ID NO 407
<211> LENGTH: 8
<212> TYPE: PRT
<213> ORGANISM: Homo sapiens

<400> SEQUENCE: 407

Arg Ile Tyr Pro Ser Asp Phe Ala
1               5

<210> SEQ ID NO 408
<211> LENGTH: 8
<212> TYPE: PRT
<213> ORGANISM: Homo sapiens

<400> SEQUENCE: 408

Met Thr Ser Ser Asp Val Val Ala
1               5

<210> SEQ ID NO 409
<211> LENGTH: 9
<212> TYPE: PRT
<213> ORGANISM: Homo sapiens

<400> SEQUENCE: 409

Asp Leu Ala Gly Val Ile Ile Glu Leu
1               5

<210> SEQ ID NO 410
<211> LENGTH: 9

<212> TYPE: PRT
<213> ORGANISM: Homo sapiens

<400> SEQUENCE: 410

Ser Leu Ala Ile Ala Leu Phe Phe Leu
1 5

<210> SEQ ID NO 411
<211> LENGTH: 9
<212> TYPE: PRT
<213> ORGANISM: Homo sapiens

<400> SEQUENCE: 411

Phe Leu Met Asp Val Leu Leu Arg Val
1 5

<210> SEQ ID NO 412
<211> LENGTH: 9
<212> TYPE: PRT
<213> ORGANISM: Homo sapiens

<400> SEQUENCE: 412

Leu Leu Leu Val Asp Val Val Tyr Ile
1 5

<210> SEQ ID NO 413
<211> LENGTH: 9
<212> TYPE: PRT
<213> ORGANISM: Homo sapiens

<400> SEQUENCE: 413

Val Leu Leu Asp Val Thr Leu Ile Leu
1 5

<210> SEQ ID NO 414
<211> LENGTH: 9
<212> TYPE: PRT
<213> ORGANISM: Homo sapiens

<400> SEQUENCE: 414

Ala Ile Ile Val Ile Leu Leu Leu Val
1 5

<210> SEQ ID NO 415
<211> LENGTH: 9
<212> TYPE: PRT
<213> ORGANISM: Homo sapiens

<400> SEQUENCE: 415

Arg Leu Leu Arg Leu Ile Ile Leu Leu
1 5

<210> SEQ ID NO 416
<211> LENGTH: 9
<212> TYPE: PRT
<213> ORGANISM: Homo sapiens

<400> SEQUENCE: 416

Phe Leu Val Leu Leu Asp Val Thr Leu
1 5

<210> SEQ ID NO 417
<211> LENGTH: 9
<212> TYPE: PRT
<213> ORGANISM: Homo sapiens

<400> SEQUENCE: 417

Val Ile Leu Leu Leu Val Asp Val Val
1 5

<210> SEQ ID NO 418
<211> LENGTH: 9
<212> TYPE: PRT
<213> ORGANISM: Homo sapiens

<400> SEQUENCE: 418

Ile Ile Leu Leu Arg Ile Phe His Leu
1 5

<210> SEQ ID NO 419
<211> LENGTH: 9
<212> TYPE: PRT
<213> ORGANISM: Homo sapiens

<400> SEQUENCE: 419

Gly Leu Phe Gly Val Phe Leu Val Leu
1 5

<210> SEQ ID NO 420
<211> LENGTH: 9
<212> TYPE: PRT
<213> ORGANISM: Homo sapiens

<400> SEQUENCE: 420

Ile Val Ile Leu Leu Leu Val Asp Val
1 5

<210> SEQ ID NO 421
<211> LENGTH: 9
<212> TYPE: PRT
<213> ORGANISM: Homo sapiens

<400> SEQUENCE: 421

His Leu Leu Arg Leu Leu Arg Leu Ile
1 5

<210> SEQ ID NO 422
<211> LENGTH: 9
<212> TYPE: PRT
<213> ORGANISM: Homo sapiens

<400> SEQUENCE: 422

Ser Ile Pro Arg Tyr Val Arg Asp Leu
1 5

<210> SEQ ID NO 423
<211> LENGTH: 9
<212> TYPE: PRT
<213> ORGANISM: Homo sapiens

<400> SEQUENCE: 423

Arg Leu Tyr Leu Pro Lys Asn Glu Leu
1 5

<210> SEQ ID NO 424
<211> LENGTH: 9
<212> TYPE: PRT
<213> ORGANISM: Homo sapiens

<400> SEQUENCE: 424

Ile Leu Asp Thr Ala Ile Ile Val Ile
1 5

<210> SEQ ID NO 425
<211> LENGTH: 9
<212> TYPE: PRT
<213> ORGANISM: Homo sapiens

<400> SEQUENCE: 425

Lys Ile Lys Lys Ile Val His Ser Ile
1 5

<210> SEQ ID NO 426
<211> LENGTH: 9
<212> TYPE: PRT
<213> ORGANISM: Homo sapiens

<400> SEQUENCE: 426

Ala Leu Phe Phe Leu Met Asp Val Leu
1 5

<210> SEQ ID NO 427
<211> LENGTH: 9
<212> TYPE: PRT
<213> ORGANISM: Homo sapiens

<400> SEQUENCE: 427

Tyr Ile Phe Phe Asp Ile Lys Leu Leu
1 5

<210> SEQ ID NO 428
<211> LENGTH: 9
<212> TYPE: PRT
<213> ORGANISM: Homo sapiens

<400> SEQUENCE: 428

Ile Leu Ala Asp Leu Ile Phe Thr Asp
1 5

<210> SEQ ID NO 429
<211> LENGTH: 9
<212> TYPE: PRT
<213> ORGANISM: Homo sapiens

<400> SEQUENCE: 429

Asp Leu Ile Phe Thr Asp Ser Lys Leu
1 5

<210> SEQ ID NO 430
<211> LENGTH: 9
<212> TYPE: PRT
<213> ORGANISM: Homo sapiens

<400> SEQUENCE: 430

Ile Ala Leu Phe Phe Leu Met Asp Val
1 5

<210> SEQ ID NO 431
<211> LENGTH: 9
<212> TYPE: PRT
<213> ORGANISM: Homo sapiens

<400> SEQUENCE: 431

Leu Leu Arg Leu Leu Arg Leu Ile Ile 1 5

<210> SEQ ID NO 432
<211> LENGTH: 9
<212> TYPE: PRT
<213> ORGANISM: Homo sapiens

<400> SEQUENCE: 432

Gln Met Val Val Phe Thr Lys Glu Val
1 5

<210> SEQ ID NO 433
<211> LENGTH: 9
<212> TYPE: PRT
<213> ORGANISM: Homo sapiens

<400> SEQUENCE: 433

Trp Met Ala Gln Asp Leu Glu Asn Ile
1 5

<210> SEQ ID NO 434
<211> LENGTH: 9
<212> TYPE: PRT
<213> ORGANISM: Homo sapiens

<400> SEQUENCE: 434

Leu Ile Ala Ser Glu Ile Cys Ser Thr
1 5

<210> SEQ ID NO 435
<211> LENGTH: 9
<212> TYPE: PRT
<213> ORGANISM: Homo sapiens

<400> SEQUENCE: 435

Ile Leu Phe Ile Lys His Phe Ile Ile
1 5

<210> SEQ ID NO 436
<211> LENGTH: 9
<212> TYPE: PRT
<213> ORGANISM: Homo sapiens

<400> SEQUENCE: 436

Thr Ile Ser Leu Gly Lys Cys Ser Val
1 5

<210> SEQ ID NO 437
<211> LENGTH: 9
<212> TYPE: PRT
<213> ORGANISM: Homo sapiens

<400> SEQUENCE: 437

Arg Ile Tyr Pro Ser Asp Phe Ala Val
1 5

<210> SEQ ID NO 438
<211> LENGTH: 9
<212> TYPE: PRT
<213> ORGANISM: Homo sapiens

<400> SEQUENCE: 438

Gly Val Phe Leu Val Leu Leu Asp Val
1 5

<210> SEQ ID NO 439
<211> LENGTH: 9
<212> TYPE: PRT
<213> ORGANISM: Homo sapiens

<400> SEQUENCE: 439

Asn Ile Leu Asp Thr Ala Ile Ile Val
1               5

<210> SEQ ID NO 440
<211> LENGTH: 9
<212> TYPE: PRT
<213> ORGANISM: Homo sapiens

<400> SEQUENCE: 440

Thr Ala Ile Ile Val Ile Leu Leu Leu
1               5

<210> SEQ ID NO 441
<211> LENGTH: 9
<212> TYPE: PRT
<213> ORGANISM: Homo sapiens

<400> SEQUENCE: 441

Asn Ile Pro Arg Trp Thr His Leu Leu
1               5

<210> SEQ ID NO 442
<211> LENGTH: 9
<212> TYPE: PRT
<213> ORGANISM: Homo sapiens

<400> SEQUENCE: 442

His Leu Phe His Gln Lys Arg Gln Leu
1               5

<210> SEQ ID NO 443
<211> LENGTH: 9
<212> TYPE: PRT
<213> ORGANISM: Homo sapiens

<400> SEQUENCE: 443

Ile Ile Tyr Ser Ile Pro Arg Tyr Val
1               5

<210> SEQ ID NO 444
<211> LENGTH: 9
<212> TYPE: PRT
<213> ORGANISM: Homo sapiens

<400> SEQUENCE: 444

Ser Phe Ala Phe Gly Leu Phe Gly Val
1               5

<210> SEQ ID NO 445
<211> LENGTH: 9
<212> TYPE: PRT
<213> ORGANISM: Homo sapiens

<400> SEQUENCE: 445

Leu Val Leu Leu Asp Val Thr Leu Ile
1               5

<210> SEQ ID NO 446

<211> LENGTH: 9
<212> TYPE: PRT
<213> ORGANISM: Homo sapiens

<400> SEQUENCE: 446

Leu Leu Asp Val Thr Leu Ile Leu Ala
1 5

<210> SEQ ID NO 447
<211> LENGTH: 9
<212> TYPE: PRT
<213> ORGANISM: Homo sapiens

<400> SEQUENCE: 447

Leu Ile Leu Ala Asp Leu Ile Phe Thr
1 5

<210> SEQ ID NO 448
<211> LENGTH: 9
<212> TYPE: PRT
<213> ORGANISM: Homo sapiens

<400> SEQUENCE: 448

Tyr Ile Pro Leu Glu Tyr Arg Ser Ile
1 5

<210> SEQ ID NO 449
<211> LENGTH: 9
<212> TYPE: PRT
<213> ORGANISM: Homo sapiens

<400> SEQUENCE: 449

Asp Leu Phe Asn Ile Leu Asp Thr Ala
1 5

<210> SEQ ID NO 450
<211> LENGTH: 9
<212> TYPE: PRT
<213> ORGANISM: Homo sapiens

<400> SEQUENCE: 450

Pro Ile Lys Glu Val Val Arg Phe Leu
1 5

<210> SEQ ID NO 451
<211> LENGTH: 9
<212> TYPE: PRT
<213> ORGANISM: Homo sapiens

<400> SEQUENCE: 451

Arg Ile Met Ile Asp Asp His Asn Val
1 5

<210> SEQ ID NO 452
<211> LENGTH: 9
<212> TYPE: PRT
<213> ORGANISM: Homo sapiens

<400> SEQUENCE: 452

Thr Leu His Gln Met Val Val Phe Thr
1 5

<210> SEQ ID NO 453
<211> LENGTH: 9
<212> TYPE: PRT

<213> ORGANISM: Homo sapiens

<400> SEQUENCE: 453

Leu Phe Gly Val Phe Leu Val Leu Leu
1 5

<210> SEQ ID NO 454
<211> LENGTH: 9
<212> TYPE: PRT
<213> ORGANISM: Homo sapiens

<400> SEQUENCE: 454

Asp Thr Ala Ile Ile Val Ile Leu Leu
1 5

<210> SEQ ID NO 455
<211> LENGTH: 9
<212> TYPE: PRT
<213> ORGANISM: Homo sapiens

<400> SEQUENCE: 455

Ile Asp Asp His Asn Val Pro Thr Leu
1 5

<210> SEQ ID NO 456
<211> LENGTH: 9
<212> TYPE: PRT
<213> ORGANISM: Homo sapiens

<400> SEQUENCE: 456

Gln Asp Leu Glu Asn Ile Val Ala Ile
1 5

<210> SEQ ID NO 457
<211> LENGTH: 9
<212> TYPE: PRT
<213> ORGANISM: Homo sapiens

<400> SEQUENCE: 457

Phe Ile Glu Asn Asn Arg Leu Tyr Leu
1 5

<210> SEQ ID NO 458
<211> LENGTH: 9
<212> TYPE: PRT
<213> ORGANISM: Homo sapiens

<400> SEQUENCE: 458

Arg Val Ser Pro Ile Ser Glu Ser Val
1 5

<210> SEQ ID NO 459
<211> LENGTH: 9
<212> TYPE: PRT
<213> ORGANISM: Homo sapiens

<400> SEQUENCE: 459

Leu Ala Arg Leu Ser Lys Phe Glu Val
1 5

<210> SEQ ID NO 460
<211> LENGTH: 9
<212> TYPE: PRT
<213> ORGANISM: Homo sapiens

<400> SEQUENCE: 460

Ile Val Ser Ser Phe Ala Phe Gly Leu
1               5

<210> SEQ ID NO 461
<211> LENGTH: 9
<212> TYPE: PRT
<213> ORGANISM: Homo sapiens

<400> SEQUENCE: 461

Phe Gly Leu Phe Gly Val Phe Leu Val
1               5

<210> SEQ ID NO 462
<211> LENGTH: 9
<212> TYPE: PRT
<213> ORGANISM: Homo sapiens

<400> SEQUENCE: 462

Asp Val Thr Leu Ile Leu Ala Asp Leu
1               5

<210> SEQ ID NO 463
<211> LENGTH: 9
<212> TYPE: PRT
<213> ORGANISM: Homo sapiens

<400> SEQUENCE: 463

Leu Leu Val Asp Val Val Tyr Ile Phe
1               5

<210> SEQ ID NO 464
<211> LENGTH: 9
<212> TYPE: PRT
<213> ORGANISM: Homo sapiens

<400> SEQUENCE: 464

Lys Leu Leu Arg Asn Ile Pro Arg Trp
1               5

<210> SEQ ID NO 465
<211> LENGTH: 9
<212> TYPE: PRT
<213> ORGANISM: Homo sapiens

<400> SEQUENCE: 465

Leu Arg Leu Leu Arg Leu Ile Ile Leu
1               5

<210> SEQ ID NO 466
<211> LENGTH: 9
<212> TYPE: PRT
<213> ORGANISM: Homo sapiens

<400> SEQUENCE: 466

Arg Ile Leu Phe Ile Lys His Phe Ile
1               5

<210> SEQ ID NO 467
<211> LENGTH: 9
<212> TYPE: PRT
<213> ORGANISM: Homo sapiens

<400> SEQUENCE: 467

Lys Val Val Phe Ser Thr Ile Ser Leu
1 5

<210> SEQ ID NO 468
<211> LENGTH: 9
<212> TYPE: PRT
<213> ORGANISM: Homo sapiens

<400> SEQUENCE: 468

Thr Thr Asp Lys Ile Leu Ile Asp Val
1 5

<210> SEQ ID NO 469
<211> LENGTH: 10
<212> TYPE: PRT
<213> ORGANISM: Homo sapiens

<400> SEQUENCE: 469

Gly Leu Phe Gly Val Phe Leu Val Leu Leu
1 5 10

<210> SEQ ID NO 470
<211> LENGTH: 10
<212> TYPE: PRT
<213> ORGANISM: Homo sapiens

<400> SEQUENCE: 470

Ile Leu Asp Thr Ala Ile Ile Val Ile Leu
1 5 10

<210> SEQ ID NO 471
<211> LENGTH: 10
<212> TYPE: PRT
<213> ORGANISM: Homo sapiens

<400> SEQUENCE: 471

Ile Leu Leu Leu Val Asp Val Val Tyr Ile
1 5 10

<210> SEQ ID NO 472
<211> LENGTH: 10
<212> TYPE: PRT
<213> ORGANISM: Homo sapiens

<400> SEQUENCE: 472

Ala Ile Ala Leu Phe Phe Leu Met Asp Val
1 5 10

<210> SEQ ID NO 473
<211> LENGTH: 10
<212> TYPE: PRT
<213> ORGANISM: Homo sapiens

<400> SEQUENCE: 473

Ile Ile Val Ile Leu Leu Leu Val Asp Val
1 5 10

<210> SEQ ID NO 474
<211> LENGTH: 10
<212> TYPE: PRT
<213> ORGANISM: Homo sapiens

<400> SEQUENCE: 474

Leu Leu Arg Leu Leu Arg Leu Ile Ile Leu
1 5 10

<210> SEQ ID NO 475
<211> LENGTH: 10
<212> TYPE: PRT
<213> ORGANISM: Homo sapiens

<400> SEQUENCE: 475

Leu Ile Ile Leu Leu Arg Ile Phe His Leu
1 5 10

<210> SEQ ID NO 476
<211> LENGTH: 10
<212> TYPE: PRT
<213> ORGANISM: Homo sapiens

<400> SEQUENCE: 476

Met Ile Asp Asp His Asn Val Pro Thr Leu
1 5 10

<210> SEQ ID NO 477
<211> LENGTH: 10
<212> TYPE: PRT
<213> ORGANISM: Homo sapiens

<400> SEQUENCE: 477

Tyr Leu Pro Lys Asn Glu Leu Asp Asn Leu
1 5 10

<210> SEQ ID NO 478
<211> LENGTH: 10
<212> TYPE: PRT
<213> ORGANISM: Homo sapiens

<400> SEQUENCE: 478

Val Leu Ala Arg Leu Ser Lys Phe Glu Val
1 5 10

<210> SEQ ID NO 479
<211> LENGTH: 10
<212> TYPE: PRT
<213> ORGANISM: Homo sapiens

<400> SEQUENCE: 479

Leu Leu Arg Leu Ile Ile Leu Leu Arg Ile
1 5 10

<210> SEQ ID NO 480
<211> LENGTH: 10
<212> TYPE: PRT
<213> ORGANISM: Homo sapiens

<400> SEQUENCE: 480

Asn Leu Pro Pro Arg Arg Ile Leu Phe Ile
1 5 10

<210> SEQ ID NO 481
<211> LENGTH: 10
<212> TYPE: PRT
<213> ORGANISM: Homo sapiens

<400> SEQUENCE: 481

Ala Leu Phe Phe Leu Met Asp Val Leu Leu
1 5 10

<210> SEQ ID NO 482
<211> LENGTH: 10
<212> TYPE: PRT
<213> ORGANISM: Homo sapiens

<400> SEQUENCE: 482

Pro Ile Ser Glu Ser Val Leu Ala Arg Leu
1 5 10

<210> SEQ ID NO 483
<211> LENGTH: 10
<212> TYPE: PRT
<213> ORGANISM: Homo sapiens

<400> SEQUENCE: 483

Phe Leu Val Leu Leu Asp Val Thr Leu Ile
1 5 10

<210> SEQ ID NO 484
<211> LENGTH: 10
<212> TYPE: PRT
<213> ORGANISM: Homo sapiens

<400> SEQUENCE: 484

Asn Ile Leu Asp Thr Ala Ile Ile Val Ile
1 5 10

<210> SEQ ID NO 485
<211> LENGTH: 10
<212> TYPE: PRT
<213> ORGANISM: Homo sapiens

<400> SEQUENCE: 485

Phe Leu Ile Ala Ser Glu Ile Cys Ser Thr
1 5 10

<210> SEQ ID NO 486
<211> LENGTH: 10
<212> TYPE: PRT
<213> ORGANISM: Homo sapiens

<400> SEQUENCE: 486

Phe Ile Lys His Phe Ile Ile Tyr Ser Ile
1 5 10

<210> SEQ ID NO 487
<211> LENGTH: 10
<212> TYPE: PRT
<213> ORGANISM: Homo sapiens

<400> SEQUENCE: 487

Val Leu Leu Asp Val Thr Leu Ile Leu Ala
1 5 10

<210> SEQ ID NO 488
<211> LENGTH: 10
<212> TYPE: PRT
<213> ORGANISM: Homo sapiens

<400> SEQUENCE: 488

Leu Met Asp Val Leu Leu Arg Val Phe Val
1 5 10

<210> SEQ ID NO 489
<211> LENGTH: 10

<212> TYPE: PRT
<213> ORGANISM: Homo sapiens

<400> SEQUENCE: 489

Ile Val Ile Leu Leu Leu Val Asp Val Val
1 5 10

<210> SEQ ID NO 490
<211> LENGTH: 10
<212> TYPE: PRT
<213> ORGANISM: Homo sapiens

<400> SEQUENCE: 490

Ser Pro Asp Pro Thr Asp Leu Ala Gly Val
1 5 10

<210> SEQ ID NO 491
<211> LENGTH: 10
<212> TYPE: PRT
<213> ORGANISM: Homo sapiens

<400> SEQUENCE: 491

Ser Ile Val Ser Ser Phe Ala Phe Gly Leu
1 5 10

<210> SEQ ID NO 492
<211> LENGTH: 10
<212> TYPE: PRT
<213> ORGANISM: Homo sapiens

<400> SEQUENCE: 492

Thr Ala Ile Ile Val Ile Leu Leu Leu Val
1 5 10

<210> SEQ ID NO 493
<211> LENGTH: 10
<212> TYPE: PRT
<213> ORGANISM: Homo sapiens

<400> SEQUENCE: 493

His Leu Leu Arg Leu Leu Arg Leu Ile Ile
1 5 10

<210> SEQ ID NO 494
<211> LENGTH: 10
<212> TYPE: PRT
<213> ORGANISM: Homo sapiens

<400> SEQUENCE: 494

Trp Met Ala Gln Asp Leu Glu Asn Ile Val
1 5 10

<210> SEQ ID NO 495
<211> LENGTH: 10
<212> TYPE: PRT
<213> ORGANISM: Homo sapiens

<400> SEQUENCE: 495

Val Leu Asp Asn Ile Thr Thr Asp Lys Ile
1 5 10

<210> SEQ ID NO 496
<211> LENGTH: 10
<212> TYPE: PRT
<213> ORGANISM: Homo sapiens

<400> SEQUENCE: 496

Leu Ile Asp Val Phe Asp Gly Pro Pro Leu
1               5                   10

<210> SEQ ID NO 497
<211> LENGTH: 10
<212> TYPE: PRT
<213> ORGANISM: Homo sapiens

<400> SEQUENCE: 497

Phe Ala Phe Gly Leu Phe Gly Val Phe Leu
1               5                   10

<210> SEQ ID NO 498
<211> LENGTH: 10
<212> TYPE: PRT
<213> ORGANISM: Homo sapiens

<400> SEQUENCE: 498

Thr Leu Ile Leu Ala Asp Leu Ile Phe Thr
1               5                   10

<210> SEQ ID NO 499
<211> LENGTH: 10
<212> TYPE: PRT
<213> ORGANISM: Homo sapiens

<400> SEQUENCE: 499

Leu Ile Phe Thr Asp Ser Lys Leu Tyr Ile
1               5                   10

<210> SEQ ID NO 500
<211> LENGTH: 10
<212> TYPE: PRT
<213> ORGANISM: Homo sapiens

<400> SEQUENCE: 500

Asp Thr Ala Ile Ile Val Ile Leu Leu Leu
1               5                   10

<210> SEQ ID NO 501
<211> LENGTH: 10
<212> TYPE: PRT
<213> ORGANISM: Homo sapiens

<400> SEQUENCE: 501

Phe Ile Ile Tyr Ser Ile Pro Arg Tyr Val
1               5                   10

<210> SEQ ID NO 502
<211> LENGTH: 10
<212> TYPE: PRT
<213> ORGANISM: Homo sapiens

<400> SEQUENCE: 502

Tyr Ser Ile Pro Arg Tyr Val Arg Asp Leu
1               5                   10

<210> SEQ ID NO 503
<211> LENGTH: 10
<212> TYPE: PRT
<213> ORGANISM: Homo sapiens

<400> SEQUENCE: 503

Lys Ile Gln Ile Glu Met Glu Lys Lys Val
1 5 10

<210> SEQ ID NO 504
<211> LENGTH: 10
<212> TYPE: PRT
<213> ORGANISM: Homo sapiens

<400> SEQUENCE: 504

Ser Thr Ile Ser Leu Gly Lys Cys Ser Val
1 5 10

<210> SEQ ID NO 505
<211> LENGTH: 10
<212> TYPE: PRT
<213> ORGANISM: Homo sapiens

<400> SEQUENCE: 505

Ile Thr Thr Asp Lys Ile Leu Ile Asp Val
1 5 10

<210> SEQ ID NO 506
<211> LENGTH: 10
<212> TYPE: PRT
<213> ORGANISM: Homo sapiens

<400> SEQUENCE: 506

Ser Lys Ile Lys Lys Ile Val His Ser Ile
1 5 10

<210> SEQ ID NO 507
<211> LENGTH: 10
<212> TYPE: PRT
<213> ORGANISM: Homo sapiens

<400> SEQUENCE: 507

Leu Val Leu Leu Asp Val Thr Leu Ile Leu
1 5 10

<210> SEQ ID NO 508
<211> LENGTH: 10
<212> TYPE: PRT
<213> ORGANISM: Homo sapiens

<400> SEQUENCE: 508

Asp Leu Phe Asn Ile Leu Asp Thr Ala Ile
1 5 10

<210> SEQ ID NO 509
<211> LENGTH: 10
<212> TYPE: PRT
<213> ORGANISM: Homo sapiens

<400> SEQUENCE: 509

Leu Leu Leu Val Asp Val Val Tyr Ile Phe
1 5 10

<210> SEQ ID NO 510
<211> LENGTH: 10
<212> TYPE: PRT
<213> ORGANISM: Homo sapiens

<400> SEQUENCE: 510

Trp Thr His Leu Leu Arg Leu Leu Arg Leu

-continued 1 5 10

<210> SEQ ID NO 511
<211> LENGTH: 10
<212> TYPE: PRT
<213> ORGANISM: Homo sapiens

<400> SEQUENCE: 511

Gln Leu Glu Lys Leu Ile Arg Arg Arg Val
1 5 10

<210> SEQ ID NO 512
<211> LENGTH: 10
<212> TYPE: PRT
<213> ORGANISM: Homo sapiens

<400> SEQUENCE: 512

Lys Leu Ile Arg Arg Arg Val Ser Glu Asn
1 5 10

<210> SEQ ID NO 513
<211> LENGTH: 10
<212> TYPE: PRT
<213> ORGANISM: Homo sapiens

<400> SEQUENCE: 513

Ile Met Ile Asp Asp His Asn Val Pro Thr
1 5 10

<210> SEQ ID NO 514
<211> LENGTH: 10
<212> TYPE: PRT
<213> ORGANISM: Homo sapiens

<400> SEQUENCE: 514

Thr Asp Leu Ala Gly Val Ile Ile Glu Leu
1 5 10

<210> SEQ ID NO 515
<211> LENGTH: 10
<212> TYPE: PRT
<213> ORGANISM: Homo sapiens

<400> SEQUENCE: 515

Arg Leu Ser Lys Phe Glu Val Glu Asp Ala
1 5 10

<210> SEQ ID NO 516
<211> LENGTH: 10
<212> TYPE: PRT
<213> ORGANISM: Homo sapiens

<400> SEQUENCE: 516

Lys Ile Lys Lys Ile Val His Ser Ile Val
1 5 10

<210> SEQ ID NO 517
<211> LENGTH: 10
<212> TYPE: PRT
<213> ORGANISM: Homo sapiens

<400> SEQUENCE: 517

Ser Ser Phe Ala Phe Gly Leu Phe Gly Val
1 5 10

<210> SEQ ID NO 518
<211> LENGTH: 10
<212> TYPE: PRT
<213> ORGANISM: Homo sapiens

<400> SEQUENCE: 518

Leu Leu Asp Val Thr Leu Ile Leu Ala Asp
1               5                   10

<210> SEQ ID NO 519
<211> LENGTH: 10
<212> TYPE: PRT
<213> ORGANISM: Homo sapiens

<400> SEQUENCE: 519

Leu Asp Val Thr Leu Ile Leu Ala Asp Leu
1               5                   10

<210> SEQ ID NO 520
<211> LENGTH: 10
<212> TYPE: PRT
<213> ORGANISM: Homo sapiens

<400> SEQUENCE: 520

Leu Ile Leu Ala Asp Leu Ile Phe Thr Asp
1               5                   10

<210> SEQ ID NO 521
<211> LENGTH: 10
<212> TYPE: PRT
<213> ORGANISM: Homo sapiens

<400> SEQUENCE: 521

Ile Pro Leu Glu Tyr Arg Ser Ile Ser Leu
1               5                   10

<210> SEQ ID NO 522
<211> LENGTH: 10
<212> TYPE: PRT
<213> ORGANISM: Homo sapiens

<400> SEQUENCE: 522

Ile Ser Leu Ala Ile Ala Leu Phe Phe Leu
1               5                   10

<210> SEQ ID NO 523
<211> LENGTH: 10
<212> TYPE: PRT
<213> ORGANISM: Homo sapiens

<400> SEQUENCE: 523

Ser Leu Ala Ile Ala Leu Phe Phe Leu Met
1               5                   10

<210> SEQ ID NO 524
<211> LENGTH: 10
<212> TYPE: PRT
<213> ORGANISM: Homo sapiens

<400> SEQUENCE: 524

Phe Phe Leu Met Asp Val Leu Leu Arg Val
1               5                   10

<210> SEQ ID NO 525

<211> LENGTH: 10
<212> TYPE: PRT
<213> ORGANISM: Homo sapiens

<400> SEQUENCE: 525

Val Val Tyr Ile Phe Phe Asp Ile Lys Leu
1 5 10

<210> SEQ ID NO 526
<211> LENGTH: 10
<212> TYPE: PRT
<213> ORGANISM: Homo sapiens

<400> SEQUENCE: 526

Leu Arg Leu Leu Arg Leu Ile Ile Leu Leu
1 5 10

<210> SEQ ID NO 527
<211> LENGTH: 10
<212> TYPE: PRT
<213> ORGANISM: Homo sapiens

<400> SEQUENCE: 527

Tyr Thr Arg Asp Gly Phe Asp Leu Asp Leu
1 5 10

<210> SEQ ID NO 528
<211> LENGTH: 10
<212> TYPE: PRT
<213> ORGANISM: Homo sapiens

<400> SEQUENCE: 528

Ser Phe Tyr Arg Asn Pro Ile Lys Glu Val
1 5 10

<210> SEQ ID NO 529
<211> LENGTH: 10
<212> TYPE: PRT
<213> ORGANISM: Homo sapiens

<400> SEQUENCE: 529

Leu Ile Ala Ser Glu Ile Cys Ser Thr Ala
1 5 10

<210> SEQ ID NO 530
<211> LENGTH: 10
<212> TYPE: PRT
<213> ORGANISM: Homo sapiens

<400> SEQUENCE: 530

Val Ala Tyr Phe Ala Gln Val Lys His Leu
1 5 10

<210> SEQ ID NO 531
<211> LENGTH: 10
<212> TYPE: PRT
<213> ORGANISM: Homo sapiens

<400> SEQUENCE: 531

Thr Ile Ser Leu Gly Lys Cys Ser Val Leu
1 5 10

<210> SEQ ID NO 532
<211> LENGTH: 10
<212> TYPE: PRT

<213> ORGANISM: Homo sapiens

<400> SEQUENCE: 532

Asn Leu His Lys Gln Lys Ala Arg Arg Ile
1 5 10

<210> SEQ ID NO 533
<211> LENGTH: 9
<212> TYPE: PRT
<213> ORGANISM: Homo sapiens

<400> SEQUENCE: 533

Val Tyr Ile Phe Phe Asp Ile Lys Leu
1 5

<210> SEQ ID NO 534
<211> LENGTH: 9
<212> TYPE: PRT
<213> ORGANISM: Homo sapiens

<400> SEQUENCE: 534

Ser Tyr Asp Ser Lys Ile Lys Lys Ile
1 5

<210> SEQ ID NO 535
<211> LENGTH: 9
<212> TYPE: PRT
<213> ORGANISM: Homo sapiens

<400> SEQUENCE: 535

Ala Tyr Phe Ala Gln Val Lys His Leu
1 5

<210> SEQ ID NO 536
<211> LENGTH: 9
<212> TYPE: PRT
<213> ORGANISM: Homo sapiens

<400> SEQUENCE: 536

Leu Tyr Asp Asp Val Lys Val Gln Phe
1 5

<210> SEQ ID NO 537
<211> LENGTH: 9
<212> TYPE: PRT
<213> ORGANISM: Homo sapiens

<400> SEQUENCE: 537

Gln Tyr Phe Ser Asp Leu Phe Asn Ile
1 5

<210> SEQ ID NO 538
<211> LENGTH: 9
<212> TYPE: PRT
<213> ORGANISM: Homo sapiens

<400> SEQUENCE: 538

Arg Tyr Thr Arg Asp Gly Phe Asp Leu
1 5

<210> SEQ ID NO 539
<211> LENGTH: 9
<212> TYPE: PRT
<213> ORGANISM: Homo sapiens

<400> SEQUENCE: 539

Tyr Tyr Asp Asn Cys Ser Phe Tyr Phe
1               5

<210> SEQ ID NO 540
<211> LENGTH: 9
<212> TYPE: PRT
<213> ORGANISM: Homo sapiens

<400> SEQUENCE: 540

Phe Tyr Phe Trp Leu His Thr Ser Phe
1               5

<210> SEQ ID NO 541
<211> LENGTH: 9
<212> TYPE: PRT
<213> ORGANISM: Homo sapiens

<400> SEQUENCE: 541

Glu Tyr Arg Ser Ile Ser Leu Ala Ile
1               5

<210> SEQ ID NO 542
<211> LENGTH: 9
<212> TYPE: PRT
<213> ORGANISM: Homo sapiens

<400> SEQUENCE: 542

Leu Phe Gly Val Phe Leu Val Leu Leu
1               5

<210> SEQ ID NO 543
<211> LENGTH: 9
<212> TYPE: PRT
<213> ORGANISM: Homo sapiens

<400> SEQUENCE: 543

Leu Phe Phe Leu Met Asp Val Leu Leu
1               5

<210> SEQ ID NO 544
<211> LENGTH: 9
<212> TYPE: PRT
<213> ORGANISM: Homo sapiens

<400> SEQUENCE: 544

Tyr Phe Ser Asp Leu Phe Asn Ile Leu
1               5

<210> SEQ ID NO 545
<211> LENGTH: 9
<212> TYPE: PRT
<213> ORGANISM: Homo sapiens

<400> SEQUENCE: 545

Ile Phe Thr Asp Ser Lys Leu Tyr Ile
1               5

<210> SEQ ID NO 546
<211> LENGTH: 9
<212> TYPE: PRT
<213> ORGANISM: Homo sapiens

<400> SEQUENCE: 546

Thr Ala Ile Ile Val Ile Leu Leu Leu
1 5

<210> SEQ ID NO 547
<211> LENGTH: 9
<212> TYPE: PRT
<213> ORGANISM: Homo sapiens

<400> SEQUENCE: 547

His Phe His Asn Arg Val Val Arg Ile
1 5

<210> SEQ ID NO 548
<211> LENGTH: 9
<212> TYPE: PRT
<213> ORGANISM: Homo sapiens

<400> SEQUENCE: 548

Tyr Phe Trp Leu His Thr Ser Phe Ile
1 5

<210> SEQ ID NO 549
<211> LENGTH: 9
<212> TYPE: PRT
<213> ORGANISM: Homo sapiens

<400> SEQUENCE: 549

Leu Tyr Leu Pro Lys Asn Glu Leu Asp
1 5

<210> SEQ ID NO 550
<211> LENGTH: 9
<212> TYPE: PRT
<213> ORGANISM: Homo sapiens

<400> SEQUENCE: 550

Ala Phe Gly Leu Phe Gly Val Phe Leu
1 5

<210> SEQ ID NO 551
<211> LENGTH: 9
<212> TYPE: PRT
<213> ORGANISM: Homo sapiens

<400> SEQUENCE: 551

Val Leu Leu Asp Val Thr Leu Ile Leu
1 5

<210> SEQ ID NO 552
<211> LENGTH: 9
<212> TYPE: PRT
<213> ORGANISM: Homo sapiens

<400> SEQUENCE: 552

Val Thr Leu Ile Leu Ala Asp Leu Ile
1 5

<210> SEQ ID NO 553
<211> LENGTH: 9
<212> TYPE: PRT
<213> ORGANISM: Homo sapiens

<400> SEQUENCE: 553

Leu Phe Asn Ile Leu Asp Thr Ala Ile
1 5

<210> SEQ ID NO 554
<211> LENGTH: 9
<212> TYPE: PRT
<213> ORGANISM: Homo sapiens

<400> SEQUENCE: 554

Ile Ile Leu Leu Arg Ile Phe His Leu
1 5

<210> SEQ ID NO 555
<211> LENGTH: 9
<212> TYPE: PRT
<213> ORGANISM: Homo sapiens

<400> SEQUENCE: 555

Ile Leu Leu Arg Ile Phe His Leu Phe
1 5

<210> SEQ ID NO 556
<211> LENGTH: 9
<212> TYPE: PRT
<213> ORGANISM: Homo sapiens

<400> SEQUENCE: 556

Asn Leu Pro Pro Arg Arg Ile Leu Phe
1 5

<210> SEQ ID NO 557
<211> LENGTH: 9
<212> TYPE: PRT
<213> ORGANISM: Homo sapiens

<400> SEQUENCE: 557

Ser Val Leu Ala Arg Leu Ser Lys Phe
1 5

<210> SEQ ID NO 558
<211> LENGTH: 9
<212> TYPE: PRT
<213> ORGANISM: Homo sapiens

<400> SEQUENCE: 558

Val Ser Ser Phe Ala Phe Gly Leu Phe
1 5

<210> SEQ ID NO 559
<211> LENGTH: 9
<212> TYPE: PRT
<213> ORGANISM: Homo sapiens

<400> SEQUENCE: 559

Leu Val Leu Leu Asp Val Thr Leu Ile
1 5

<210> SEQ ID NO 560
<211> LENGTH: 9
<212> TYPE: PRT
<213> ORGANISM: Homo sapiens

<400> SEQUENCE: 560

Arg Asn Ile Pro Arg Trp Thr His Leu
1 5

<210> SEQ ID NO 561
<211> LENGTH: 9
<212> TYPE: PRT
<213> ORGANISM: Homo sapiens

<400> SEQUENCE: 561

Arg Leu Leu Arg Leu Ile Ile Leu Leu
1               5

<210> SEQ ID NO 562
<211> LENGTH: 9
<212> TYPE: PRT
<213> ORGANISM: Homo sapiens

<400> SEQUENCE: 562

Ala Tyr Asp Pro Lys His Phe His Asn
1               5

<210> SEQ ID NO 563
<211> LENGTH: 9
<212> TYPE: PRT
<213> ORGANISM: Homo sapiens

<400> SEQUENCE: 563

Gln Asp Leu Glu Asn Ile Val Ala Ile
1               5

<210> SEQ ID NO 564
<211> LENGTH: 10
<212> TYPE: PRT
<213> ORGANISM: Homo sapiens

<400> SEQUENCE: 564

Val Tyr Ile Phe Phe Asp Ile Lys Leu Leu
1               5                   10

<210> SEQ ID NO 565
<211> LENGTH: 10
<212> TYPE: PRT
<213> ORGANISM: Homo sapiens

<400> SEQUENCE: 565

Leu Tyr Ile Pro Leu Glu Tyr Arg Ser Ile
1               5                   10

<210> SEQ ID NO 566
<211> LENGTH: 10
<212> TYPE: PRT
<213> ORGANISM: Homo sapiens

<400> SEQUENCE: 566

Thr Tyr Tyr Asp Asn Cys Ser Phe Tyr Phe
1               5                   10

<210> SEQ ID NO 567
<211> LENGTH: 10
<212> TYPE: PRT
<213> ORGANISM: Homo sapiens

<400> SEQUENCE: 567

Leu Tyr Asp Asp Val Lys Val Gln Phe Phe
1               5                   10

<210> SEQ ID NO 568
<211> LENGTH: 10

<212> TYPE: PRT
<213> ORGANISM: Homo sapiens

<400> SEQUENCE: 568

Ile Tyr Pro Ser Asp Phe Ala Val Glu Ile
1 5 10

<210> SEQ ID NO 569
<211> LENGTH: 10
<212> TYPE: PRT
<213> ORGANISM: Homo sapiens

<400> SEQUENCE: 569

Gln Tyr Phe Ser Asp Leu Phe Asn Ile Leu
1 5 10

<210> SEQ ID NO 570
<211> LENGTH: 10
<212> TYPE: PRT
<213> ORGANISM: Homo sapiens

<400> SEQUENCE: 570

Val Phe Leu Val Leu Leu Asp Val Thr Leu
1 5 10

<210> SEQ ID NO 571
<211> LENGTH: 10
<212> TYPE: PRT
<213> ORGANISM: Homo sapiens

<400> SEQUENCE: 571

Val Phe Val Glu Arg Arg Gln Gln Tyr Phe
1 5 10

<210> SEQ ID NO 572
<211> LENGTH: 10
<212> TYPE: PRT
<213> ORGANISM: Homo sapiens

<400> SEQUENCE: 572

Arg Tyr Val Arg Asp Leu Lys Ile Gln Ile
1 5 10

<210> SEQ ID NO 573
<211> LENGTH: 10
<212> TYPE: PRT
<213> ORGANISM: Homo sapiens

<400> SEQUENCE: 573

Phe Tyr Phe Trp Leu His Thr Ser Phe Ile
1 5 10

<210> SEQ ID NO 574
<211> LENGTH: 10
<212> TYPE: PRT
<213> ORGANISM: Homo sapiens

<400> SEQUENCE: 574

Ser Phe Ile Glu Asn Asn Arg Leu Tyr Leu
1 5 10

<210> SEQ ID NO 575
<211> LENGTH: 10
<212> TYPE: PRT
<213> ORGANISM: Homo sapiens

<400> SEQUENCE: 575

Ser Phe Pro Ser Ser Gly Arg Gln Ser Phe
1 5 10

<210> SEQ ID NO 576
<211> LENGTH: 10
<212> TYPE: PRT
<213> ORGANISM: Homo sapiens

<400> SEQUENCE: 576

Ser Phe Ala Phe Gly Leu Phe Gly Val Phe
1 5 10

<210> SEQ ID NO 577
<211> LENGTH: 10
<212> TYPE: PRT
<213> ORGANISM: Homo sapiens

<400> SEQUENCE: 577

Ser Phe Tyr Phe Trp Leu His Thr Ser Phe
1 5 10

<210> SEQ ID NO 578
<211> LENGTH: 10
<212> TYPE: PRT
<213> ORGANISM: Homo sapiens

<400> SEQUENCE: 578

Leu Phe Asn Ile Leu Asp Thr Ala Ile Ile
1 5 10

<210> SEQ ID NO 579
<211> LENGTH: 10
<212> TYPE: PRT
<213> ORGANISM: Homo sapiens

<400> SEQUENCE: 579

Phe Phe Asp Ile Lys Leu Leu Arg Asn Ile
1 5 10

<210> SEQ ID NO 580
<211> LENGTH: 10
<212> TYPE: PRT
<213> ORGANISM: Homo sapiens

<400> SEQUENCE: 580

Arg Ser Ile Ser Leu Ala Ile Ala Leu Phe
1 5 10

<210> SEQ ID NO 581
<211> LENGTH: 10
<212> TYPE: PRT
<213> ORGANISM: Homo sapiens

<400> SEQUENCE: 581

Arg Asn Ile Pro Arg Trp Thr His Leu Leu
1 5 10

<210> SEQ ID NO 582
<211> LENGTH: 10
<212> TYPE: PRT
<213> ORGANISM: Homo sapiens

<400> SEQUENCE: 582

Thr His Leu Leu Arg Leu Leu Arg Leu Ile
1 5 10

<210> SEQ ID NO 583
<211> LENGTH: 10
<212> TYPE: PRT
<213> ORGANISM: Homo sapiens

<400> SEQUENCE: 583

Leu Arg Leu Leu Arg Leu Ile Ile Leu Leu
1 5 10

<210> SEQ ID NO 584
<211> LENGTH: 10
<212> TYPE: PRT
<213> ORGANISM: Homo sapiens

<400> SEQUENCE: 584

Leu Ile Ile Leu Leu Arg Ile Phe His Leu
1 5 10

<210> SEQ ID NO 585
<211> LENGTH: 10
<212> TYPE: PRT
<213> ORGANISM: Homo sapiens

<400> SEQUENCE: 585

Ile Ile Leu Leu Arg Ile Phe His Leu Phe
1 5 10

<210> SEQ ID NO 586
<211> LENGTH: 10
<212> TYPE: PRT
<213> ORGANISM: Homo sapiens

<400> SEQUENCE: 586

Trp Asn Leu Pro Pro Arg Arg Ile Leu Phe
1 5 10

<210> SEQ ID NO 587
<211> LENGTH: 9
<212> TYPE: PRT
<213> ORGANISM: Homo sapiens

<400> SEQUENCE: 587

Ser Thr Ala Lys Glu Ser Leu Tyr Tyr
1 5

<210> SEQ ID NO 588
<211> LENGTH: 9
<212> TYPE: PRT
<213> ORGANISM: Homo sapiens

<400> SEQUENCE: 588

Ser Lys Leu Tyr Ile Pro Leu Glu Tyr
1 5

<210> SEQ ID NO 589
<211> LENGTH: 9
<212> TYPE: PRT
<213> ORGANISM: Homo sapiens

<400> SEQUENCE: 589

Ser Pro Asp Pro Thr Asp Leu Ala Gly

-continued 1 5

<210> SEQ ID NO 590
<211> LENGTH: 9
<212> TYPE: PRT
<213> ORGANISM: Homo sapiens

<400> SEQUENCE: 590

Phe Ser Asp Leu Phe Asn Ile Leu Asp
1 5

<210> SEQ ID NO 591
<211> LENGTH: 9
<212> TYPE: PRT
<213> ORGANISM: Homo sapiens

<400> SEQUENCE: 591

Leu Phe Ile Lys His Phe Ile Ile Tyr
1 5

<210> SEQ ID NO 592
<211> LENGTH: 9
<212> TYPE: PRT
<213> ORGANISM: Homo sapiens

<400> SEQUENCE: 592

Asp Gly Phe Asp Leu Asp Leu Thr Tyr
1 5

<210> SEQ ID NO 593
<211> LENGTH: 9
<212> TYPE: PRT
<213> ORGANISM: Homo sapiens

<400> SEQUENCE: 593

Cys Ser Thr Ala Lys Glu Ser Leu Tyr
1 5

<210> SEQ ID NO 594
<211> LENGTH: 9
<212> TYPE: PRT
<213> ORGANISM: Homo sapiens

<400> SEQUENCE: 594

Tyr Phe Ala Gln Val Lys His Leu Tyr
1 5

<210> SEQ ID NO 595
<211> LENGTH: 9
<212> TYPE: PRT
<213> ORGANISM: Homo sapiens

<400> SEQUENCE: 595

Pro Ser Ser Gly Arg Gln Ser Phe Tyr
1 5

<210> SEQ ID NO 596
<211> LENGTH: 9
<212> TYPE: PRT
<213> ORGANISM: Homo sapiens

<400> SEQUENCE: 596

Val Glu Thr Pro Ser Gln Lys Arg Tyr
1 5

<210> SEQ ID NO 597
<211> LENGTH: 9
<212> TYPE: PRT
<213> ORGANISM: Homo sapiens

<400> SEQUENCE: 597

Thr Thr Asp Lys Ile Leu Ile Asp Val
1               5

<210> SEQ ID NO 598
<211> LENGTH: 9
<212> TYPE: PRT
<213> ORGANISM: Homo sapiens

<400> SEQUENCE: 598

Ser Phe Ile Glu Asn Asn Arg Leu Tyr
1               5

<210> SEQ ID NO 599
<211> LENGTH: 9
<212> TYPE: PRT
<213> ORGANISM: Homo sapiens

<400> SEQUENCE: 599

Ala Thr Glu Glu Ala Pro Ala Lys Glu
1               5

<210> SEQ ID NO 600
<211> LENGTH: 9
<212> TYPE: PRT
<213> ORGANISM: Homo sapiens

<400> SEQUENCE: 600

Ile Leu Leu Leu Val Asp Val Val Tyr
1               5

<210> SEQ ID NO 601
<211> LENGTH: 9
<212> TYPE: PRT
<213> ORGANISM: Homo sapiens

<400> SEQUENCE: 601

Pro Ser Gln Lys Arg Tyr Val Ala Tyr
1               5

<210> SEQ ID NO 602
<211> LENGTH: 9
<212> TYPE: PRT
<213> ORGANISM: Homo sapiens

<400> SEQUENCE: 602

Asp Val Phe Asp Gly Pro Pro Leu Tyr
1               5

<210> SEQ ID NO 603
<211> LENGTH: 9
<212> TYPE: PRT
<213> ORGANISM: Homo sapiens

<400> SEQUENCE: 603

Val Phe Asp Gly Pro Pro Leu Tyr Asp
1               5

<210> SEQ ID NO 604

<211> LENGTH: 9
<212> TYPE: PRT
<213> ORGANISM: Homo sapiens

<400> SEQUENCE: 604

Val Thr Glu Arg Ile Ile Ala Met Ser
1 5

<210> SEQ ID NO 605
<211> LENGTH: 9
<212> TYPE: PRT
<213> ORGANISM: Homo sapiens

<400> SEQUENCE: 605

Gly Thr Asp Arg Thr Gly Thr Met Val
1 5

<210> SEQ ID NO 606
<211> LENGTH: 9
<212> TYPE: PRT
<213> ORGANISM: Homo sapiens

<400> SEQUENCE: 606

Phe Ile Glu Asn Asn Arg Leu Tyr Leu
1 5

<210> SEQ ID NO 607
<211> LENGTH: 9
<212> TYPE: PRT
<213> ORGANISM: Homo sapiens

<400> SEQUENCE: 607

Ser Ser Asp Val Val Ala Gly Ser Asp
1 5

<210> SEQ ID NO 608
<211> LENGTH: 9
<212> TYPE: PRT
<213> ORGANISM: Homo sapiens

<400> SEQUENCE: 608

Pro Thr Asp Leu Ala Gly Val Ile Ile
1 5

<210> SEQ ID NO 609
<211> LENGTH: 9
<212> TYPE: PRT
<213> ORGANISM: Homo sapiens

<400> SEQUENCE: 609

Leu Leu Asp Val Thr Leu Ile Leu Ala
1 5

<210> SEQ ID NO 610
<211> LENGTH: 9
<212> TYPE: PRT
<213> ORGANISM: Homo sapiens

<400> SEQUENCE: 610

Leu Ile Phe Thr Asp Ser Lys Leu Tyr
1 5

<210> SEQ ID NO 611
<211> LENGTH: 9
<212> TYPE: PRT

<213> ORGANISM: Homo sapiens

<400> SEQUENCE: 611

Phe Thr Asp Ser Lys Leu Tyr Ile Pro
1 5

<210> SEQ ID NO 612
<211> LENGTH: 9
<212> TYPE: PRT
<213> ORGANISM: Homo sapiens

<400> SEQUENCE: 612

Val Phe Val Glu Arg Arg Gln Gln Tyr
1 5

<210> SEQ ID NO 613
<211> LENGTH: 9
<212> TYPE: PRT
<213> ORGANISM: Homo sapiens

<400> SEQUENCE: 613

Phe Phe Asp Ile Lys Leu Leu Arg Asn
1 5

<210> SEQ ID NO 614
<211> LENGTH: 9
<212> TYPE: PRT
<213> ORGANISM: Homo sapiens

<400> SEQUENCE: 614

Thr Arg Asp Gly Phe Asp Leu Asp Leu
1 5

<210> SEQ ID NO 615
<211> LENGTH: 9
<212> TYPE: PRT
<213> ORGANISM: Homo sapiens

<400> SEQUENCE: 615

Tyr Asn Leu Cys Ser Glu Arg Ala Tyr
1 5

<210> SEQ ID NO 616
<211> LENGTH: 9
<212> TYPE: PRT
<213> ORGANISM: Homo sapiens

<400> SEQUENCE: 616

Ala Gln Asp Leu Glu Asn Ile Val Ala
1 5

<210> SEQ ID NO 617
<211> LENGTH: 9
<212> TYPE: PRT
<213> ORGANISM: Homo sapiens

<400> SEQUENCE: 617

Asp Asp Val Lys Val Gln Phe Phe Tyr
1 5

<210> SEQ ID NO 618
<211> LENGTH: 9
<212> TYPE: PRT
<213> ORGANISM: Homo sapiens

<400> SEQUENCE: 618

Lys Asn Glu Leu Asp Asn Leu His Lys
1               5

<210> SEQ ID NO 619
<211> LENGTH: 9
<212> TYPE: PRT
<213> ORGANISM: Homo sapiens

<400> SEQUENCE: 619

Ile Ser Glu Ser Val Leu Ala Arg Leu
1               5

<210> SEQ ID NO 620
<211> LENGTH: 9
<212> TYPE: PRT
<213> ORGANISM: Homo sapiens

<400> SEQUENCE: 620

Glu Asp Ala Glu Asn Val Ala Ser Tyr
1               5

<210> SEQ ID NO 621
<211> LENGTH: 9
<212> TYPE: PRT
<213> ORGANISM: Homo sapiens

<400> SEQUENCE: 621

Ile Leu Asp Thr Ala Ile Ile Val Ile
1               5

<210> SEQ ID NO 622
<211> LENGTH: 9
<212> TYPE: PRT
<213> ORGANISM: Homo sapiens

<400> SEQUENCE: 622

Leu Val Asp Val Val Tyr Ile Phe Phe
1               5

<210> SEQ ID NO 623
<211> LENGTH: 9
<212> TYPE: PRT
<213> ORGANISM: Homo sapiens

<400> SEQUENCE: 623

Val Ser Glu Asn Lys Arg Arg Tyr Thr
1               5

<210> SEQ ID NO 624
<211> LENGTH: 9
<212> TYPE: PRT
<213> ORGANISM: Homo sapiens

<400> SEQUENCE: 624

Leu Asp Lys Lys His Arg Asn His Tyr
1               5

<210> SEQ ID NO 625
<211> LENGTH: 9
<212> TYPE: PRT
<213> ORGANISM: Homo sapiens

<400> SEQUENCE: 625

```
Lys His Arg Asn His Tyr Arg Val Tyr
1               5


<210> SEQ ID NO 626
<211> LENGTH: 9
<212> TYPE: PRT
<213> ORGANISM: Homo sapiens

<400> SEQUENCE: 626

Arg Thr Asp Lys Thr His Ser Glu Lys
1               5


<210> SEQ ID NO 627
<211> LENGTH: 9
<212> TYPE: PRT
<213> ORGANISM: Homo sapiens

<400> SEQUENCE: 627

Phe Ile Ile Tyr Ser Ile Pro Arg Tyr
1               5


<210> SEQ ID NO 628
<211> LENGTH: 9
<212> TYPE: PRT
<213> ORGANISM: Homo sapiens

<400> SEQUENCE: 628

Phe Phe Tyr Ser Asn Leu Pro Thr Tyr
1               5


<210> SEQ ID NO 629
<211> LENGTH: 9
<212> TYPE: PRT
<213> ORGANISM: Homo sapiens

<400> SEQUENCE: 629

Phe Tyr Ser Asn Leu Pro Thr Tyr Tyr
1               5


<210> SEQ ID NO 630
<211> LENGTH: 9
<212> TYPE: PRT
<213> ORGANISM: Homo sapiens

<400> SEQUENCE: 630

His Lys Gln Lys Ala Arg Arg Ile Tyr
1               5


<210> SEQ ID NO 631
<211> LENGTH: 9
<212> TYPE: PRT
<213> ORGANISM: Homo sapiens

<400> SEQUENCE: 631

Thr Ser Glu Phe Lys Gly Ala Thr Glu
1               5


<210> SEQ ID NO 632
<211> LENGTH: 9
<212> TYPE: PRT
<213> ORGANISM: Homo sapiens

<400> SEQUENCE: 632

Thr Ser Glu Phe Lys Gly Ala Ala Arg
1               5
```

<210> SEQ ID NO 633
<211> LENGTH: 9
<212> TYPE: PRT
<213> ORGANISM: Homo sapiens

<400> SEQUENCE: 633

Pro Leu Glu Tyr Arg Ser Ile Ser Leu
1               5

<210> SEQ ID NO 634
<211> LENGTH: 9
<212> TYPE: PRT
<213> ORGANISM: Homo sapiens

<400> SEQUENCE: 634

Trp Thr His Leu Leu Arg Leu Leu Arg
1               5

<210> SEQ ID NO 635
<211> LENGTH: 9
<212> TYPE: PRT
<213> ORGANISM: Homo sapiens

<400> SEQUENCE: 635

Arg Val Ser Glu Asn Lys Arg Arg Tyr
1               5

<210> SEQ ID NO 636
<211> LENGTH: 9
<212> TYPE: PRT
<213> ORGANISM: Homo sapiens

<400> SEQUENCE: 636

Tyr Thr Arg Asp Gly Phe Asp Leu Asp
1               5

<210> SEQ ID NO 637
<211> LENGTH: 9
<212> TYPE: PRT
<213> ORGANISM: Homo sapiens

<400> SEQUENCE: 637

Ile Lys Glu Val Val Arg Phe Leu Asp
1               5

<210> SEQ ID NO 638
<211> LENGTH: 9
<212> TYPE: PRT
<213> ORGANISM: Homo sapiens

<400> SEQUENCE: 638

Ala Tyr Asp Pro Lys His Phe His Asn
1               5

<210> SEQ ID NO 639
<211> LENGTH: 9
<212> TYPE: PRT
<213> ORGANISM: Homo sapiens

<400> SEQUENCE: 639

Ala Ser Glu Ile Cys Ser Thr Ala Lys
1               5

<210> SEQ ID NO 640
<211> LENGTH: 9
<212> TYPE: PRT
<213> ORGANISM: Homo sapiens

<400> SEQUENCE: 640

His Ser Glu Lys Phe Gln Gly Val Glu
1               5

<210> SEQ ID NO 641
<211> LENGTH: 9
<212> TYPE: PRT
<213> ORGANISM: Homo sapiens

<400> SEQUENCE: 641

Thr Tyr Tyr Asp Asn Cys Ser Phe Tyr
1               5

<210> SEQ ID NO 642
<211> LENGTH: 9
<212> TYPE: PRT
<213> ORGANISM: Homo sapiens

<400> SEQUENCE: 642

Pro Ser Asp Phe Ala Val Glu Ile Leu
1               5

<210> SEQ ID NO 643
<211> LENGTH: 10
<212> TYPE: PRT
<213> ORGANISM: Homo sapiens

<400> SEQUENCE: 643

Phe Leu Asp Lys Lys His Arg Asn His Tyr
1               5                   10

<210> SEQ ID NO 644
<211> LENGTH: 10
<212> TYPE: PRT
<213> ORGANISM: Homo sapiens

<400> SEQUENCE: 644

Val Glu Asp Ala Glu Asn Val Ala Ser Tyr
1               5                   10

<210> SEQ ID NO 645
<211> LENGTH: 10
<212> TYPE: PRT
<213> ORGANISM: Homo sapiens

<400> SEQUENCE: 645

Tyr Asp Asp Val Lys Val Gln Phe Phe Tyr
1               5                   10

<210> SEQ ID NO 646
<211> LENGTH: 10
<212> TYPE: PRT
<213> ORGANISM: Homo sapiens

<400> SEQUENCE: 646

Asp Ser Lys Leu Tyr Ile Pro Leu Glu Tyr
1               5                   10

<210> SEQ ID NO 647
<211> LENGTH: 10

<212> TYPE: PRT
<213> ORGANISM: Homo sapiens

<400> SEQUENCE: 647

Cys Ser Thr Ala Lys Glu Ser Leu Tyr Tyr
1 5 10

<210> SEQ ID NO 648
<211> LENGTH: 10
<212> TYPE: PRT
<213> ORGANISM: Homo sapiens

<400> SEQUENCE: 648

Gly Val Glu Thr Pro Ser Gln Lys Arg Tyr
1 5 10

<210> SEQ ID NO 649
<211> LENGTH: 10
<212> TYPE: PRT
<213> ORGANISM: Homo sapiens

<400> SEQUENCE: 649

Ile Leu Phe Ile Lys His Phe Ile Ile Tyr
1 5 10

<210> SEQ ID NO 650
<211> LENGTH: 10
<212> TYPE: PRT
<213> ORGANISM: Homo sapiens

<400> SEQUENCE: 650

Thr Ser Phe Ile Glu Asn Asn Arg Leu Tyr
1 5 10

<210> SEQ ID NO 651
<211> LENGTH: 10
<212> TYPE: PRT
<213> ORGANISM: Homo sapiens

<400> SEQUENCE: 651

Pro Thr Asp Leu Ala Gly Val Ile Ile Glu
1 5 10

<210> SEQ ID NO 652
<211> LENGTH: 10
<212> TYPE: PRT
<213> ORGANISM: Homo sapiens

<400> SEQUENCE: 652

Phe Thr Asp Ser Lys Leu Tyr Ile Pro Leu
1 5 10

<210> SEQ ID NO 653
<211> LENGTH: 10
<212> TYPE: PRT
<213> ORGANISM: Homo sapiens

<400> SEQUENCE: 653

Phe Ser Asp Leu Phe Asn Ile Leu Asp Thr
1 5 10

<210> SEQ ID NO 654
<211> LENGTH: 10
<212> TYPE: PRT
<213> ORGANISM: Homo sapiens

<400> SEQUENCE: 654

Arg Asp Gly Phe Asp Leu Asp Leu Thr Tyr
1 5 10

<210> SEQ ID NO 655
<211> LENGTH: 10
<212> TYPE: PRT
<213> ORGANISM: Homo sapiens

<400> SEQUENCE: 655

Pro Thr Tyr Tyr Asp Asn Cys Ser Phe Tyr
1 5 10

<210> SEQ ID NO 656
<211> LENGTH: 10
<212> TYPE: PRT
<213> ORGANISM: Homo sapiens

<400> SEQUENCE: 656

Pro Ser Asp Phe Ala Val Glu Ile Leu Phe
1 5 10

<210> SEQ ID NO 657
<211> LENGTH: 10
<212> TYPE: PRT
<213> ORGANISM: Homo sapiens

<400> SEQUENCE: 657

Ile Lys Glu Val Val Arg Phe Leu Asp Lys
1 5 10

<210> SEQ ID NO 658
<211> LENGTH: 10
<212> TYPE: PRT
<213> ORGANISM: Homo sapiens

<400> SEQUENCE: 658

Asp Leu Ile Phe Thr Asp Ser Lys Leu Tyr
1 5 10

<210> SEQ ID NO 659
<211> LENGTH: 10
<212> TYPE: PRT
<213> ORGANISM: Homo sapiens

<400> SEQUENCE: 659

Ala Tyr Asp Pro Lys His Phe His Asn Arg
1 5 10

<210> SEQ ID NO 660
<211> LENGTH: 10
<212> TYPE: PRT
<213> ORGANISM: Homo sapiens

<400> SEQUENCE: 660

Arg Thr Asp Lys Thr His Ser Glu Lys Phe
1 5 10

<210> SEQ ID NO 661
<211> LENGTH: 10
<212> TYPE: PRT
<213> ORGANISM: Homo sapiens

<400> SEQUENCE: 661

Ala Tyr Phe Ala Gln Val Lys His Leu Tyr
1               5                   10

<210> SEQ ID NO 662
<211> LENGTH: 10
<212> TYPE: PRT
<213> ORGANISM: Homo sapiens

<400> SEQUENCE: 662

Ala Thr Glu Glu Ala Pro Ala Lys Glu Ser
1               5                   10

<210> SEQ ID NO 663
<211> LENGTH: 10
<212> TYPE: PRT
<213> ORGANISM: Homo sapiens

<400> SEQUENCE: 663

Leu Leu Asp Val Thr Leu Ile Leu Ala Asp
1               5                   10

<210> SEQ ID NO 664
<211> LENGTH: 10
<212> TYPE: PRT
<213> ORGANISM: Homo sapiens

<400> SEQUENCE: 664

Val Ile Leu Leu Leu Val Asp Val Val Tyr
1               5                   10

<210> SEQ ID NO 665
<211> LENGTH: 10
<212> TYPE: PRT
<213> ORGANISM: Homo sapiens

<400> SEQUENCE: 665

Val Thr Glu Arg Ile Ile Ala Met Ser Phe
1               5                   10

<210> SEQ ID NO 666
<211> LENGTH: 10
<212> TYPE: PRT
<213> ORGANISM: Homo sapiens

<400> SEQUENCE: 666

Gly Thr Asp Arg Thr Gly Thr Met Val Cys
1               5                   10

<210> SEQ ID NO 667
<211> LENGTH: 10
<212> TYPE: PRT
<213> ORGANISM: Homo sapiens

<400> SEQUENCE: 667

Ala Ser Glu Ile Cys Ser Thr Ala Lys Glu
1               5                   10

<210> SEQ ID NO 668
<211> LENGTH: 10
<212> TYPE: PRT
<213> ORGANISM: Homo sapiens

<400> SEQUENCE: 668

Ile Cys Ser Thr Ala Lys Glu Ser Leu Tyr 1 5 10

<210> SEQ ID NO 669
<211> LENGTH: 10
<212> TYPE: PRT
<213> ORGANISM: Homo sapiens

<400> SEQUENCE: 669

Thr Thr Asp Lys Ile Leu Ile Asp Val Phe
1 5 10

<210> SEQ ID NO 670
<211> LENGTH: 10
<212> TYPE: PRT
<213> ORGANISM: Homo sapiens

<400> SEQUENCE: 670

Ile Asp Val Phe Asp Gly Pro Pro Leu Tyr
1 5 10

<210> SEQ ID NO 671
<211> LENGTH: 10
<212> TYPE: PRT
<213> ORGANISM: Homo sapiens

<400> SEQUENCE: 671

Ser Pro Asp Pro Thr Asp Leu Ala Gly Val
1 5 10

<210> SEQ ID NO 672
<211> LENGTH: 10
<212> TYPE: PRT
<213> ORGANISM: Homo sapiens

<400> SEQUENCE: 672

Ile Ser Glu Ser Val Leu Ala Arg Leu Ser
1 5 10

<210> SEQ ID NO 673
<211> LENGTH: 10
<212> TYPE: PRT
<213> ORGANISM: Homo sapiens

<400> SEQUENCE: 673

Arg Val Phe Val Glu Arg Arg Gln Gln Tyr
1 5 10

<210> SEQ ID NO 674
<211> LENGTH: 10
<212> TYPE: PRT
<213> ORGANISM: Homo sapiens

<400> SEQUENCE: 674

Val Ser Glu Asn Lys Arg Arg Tyr Thr Arg
1 5 10

<210> SEQ ID NO 675
<211> LENGTH: 10
<212> TYPE: PRT
<213> ORGANISM: Homo sapiens

<400> SEQUENCE: 675

Phe Pro Ser Ser Gly Arg Gln Ser Phe Tyr
1 5 10

<210> SEQ ID NO 676
<211> LENGTH: 10
<212> TYPE: PRT
<213> ORGANISM: Homo sapiens

<400> SEQUENCE: 676

Lys Lys His Arg Asn His Tyr Arg Val Tyr
1 5 10

<210> SEQ ID NO 677
<211> LENGTH: 10
<212> TYPE: PRT
<213> ORGANISM: Homo sapiens

<400> SEQUENCE: 677

Val Tyr Asn Leu Cys Ser Glu Arg Ala Tyr
1 5 10

<210> SEQ ID NO 678
<211> LENGTH: 10
<212> TYPE: PRT
<213> ORGANISM: Homo sapiens

<400> SEQUENCE: 678

Cys Ser Glu Arg Ala Tyr Asp Pro Lys His
1 5 10

<210> SEQ ID NO 679
<211> LENGTH: 10
<212> TYPE: PRT
<213> ORGANISM: Homo sapiens

<400> SEQUENCE: 679

Phe Phe Tyr Ser Asn Leu Pro Thr Tyr Tyr
1 5 10

<210> SEQ ID NO 680
<211> LENGTH: 10
<212> TYPE: PRT
<213> ORGANISM: Homo sapiens

<400> SEQUENCE: 680

Leu His Lys Gln Lys Ala Arg Arg Ile Tyr
1 5 10

<210> SEQ ID NO 681
<211> LENGTH: 10
<212> TYPE: PRT
<213> ORGANISM: Homo sapiens

<400> SEQUENCE: 681

Arg Arg Val Ser Glu Asn Lys Arg Arg Tyr
1 5 10

<210> SEQ ID NO 682
<211> LENGTH: 10
<212> TYPE: PRT
<213> ORGANISM: Homo sapiens

<400> SEQUENCE: 682

Asp Leu Glu Asn Ile Val Ala Ile His Cys
1 5 10

<210> SEQ ID NO 683

<211> LENGTH: 10
<212> TYPE: PRT
<213> ORGANISM: Homo sapiens

<400> SEQUENCE: 683

Gly Thr Met Val Cys Ala Phe Leu Ile Ala
1 5 10

<210> SEQ ID NO 684
<211> LENGTH: 10
<212> TYPE: PRT
<213> ORGANISM: Homo sapiens

<400> SEQUENCE: 684

His Ser Glu Lys Phe Gln Gly Val Glu Thr
1 5 10

<210> SEQ ID NO 685
<211> LENGTH: 10
<212> TYPE: PRT
<213> ORGANISM: Homo sapiens

<400> SEQUENCE: 685

Thr Pro Ser Gln Lys Arg Tyr Val Ala Tyr
1 5 10

<210> SEQ ID NO 686
<211> LENGTH: 10
<212> TYPE: PRT
<213> ORGANISM: Homo sapiens

<400> SEQUENCE: 686

His Phe Ile Ile Tyr Ser Ile Pro Arg Tyr
1 5 10

<210> SEQ ID NO 687
<211> LENGTH: 10
<212> TYPE: PRT
<213> ORGANISM: Homo sapiens

<400> SEQUENCE: 687

Val Arg Asp Leu Lys Ile Gln Ile Glu Met
1 5 10

<210> SEQ ID NO 688
<211> LENGTH: 10
<212> TYPE: PRT
<213> ORGANISM: Homo sapiens

<400> SEQUENCE: 688

Gln Phe Phe Tyr Ser Asn Leu Pro Thr Tyr
1 5 10

<210> SEQ ID NO 689
<211> LENGTH: 10
<212> TYPE: PRT
<213> ORGANISM: Homo sapiens

<400> SEQUENCE: 689

Tyr Tyr Asp Asn Cys Ser Phe Tyr Phe Trp
1 5 10

<210> SEQ ID NO 690
<211> LENGTH: 9
<212> TYPE: PRT

<213> ORGANISM: Homo sapiens

<400> SEQUENCE: 690

Ile Leu Leu Leu Val Asp Val Val Tyr
1               5

<210> SEQ ID NO 691
<211> LENGTH: 9
<212> TYPE: PRT
<213> ORGANISM: Homo sapiens

<400> SEQUENCE: 691

Lys Leu Ile Arg Arg Arg Val Ser Glu
1               5

<210> SEQ ID NO 692
<211> LENGTH: 9
<212> TYPE: PRT
<213> ORGANISM: Homo sapiens

<400> SEQUENCE: 692

Tyr Val Ala Tyr Phe Ala Gln Val Lys
1               5

<210> SEQ ID NO 693
<211> LENGTH: 9
<212> TYPE: PRT
<213> ORGANISM: Homo sapiens

<400> SEQUENCE: 693

Arg Val Tyr Asn Leu Cys Ser Glu Arg
1               5

<210> SEQ ID NO 694
<211> LENGTH: 9
<212> TYPE: PRT
<213> ORGANISM: Homo sapiens

<400> SEQUENCE: 694

Val Val Tyr Ile Phe Phe Asp Ile Lys
1               5

<210> SEQ ID NO 695
<211> LENGTH: 9
<212> TYPE: PRT
<213> ORGANISM: Homo sapiens

<400> SEQUENCE: 695

Arg Ile Phe His Leu Phe His Gln Lys
1               5

<210> SEQ ID NO 696
<211> LENGTH: 9
<212> TYPE: PRT
<213> ORGANISM: Homo sapiens

<400> SEQUENCE: 696

Ala Val Glu Ile Leu Phe Gly Glu Lys
1               5

<210> SEQ ID NO 697
<211> LENGTH: 9
<212> TYPE: PRT
<213> ORGANISM: Homo sapiens

<400> SEQUENCE: 697

Ser Val Leu Ala Arg Leu Ser Lys Phe
1 5

<210> SEQ ID NO 698
<211> LENGTH: 9
<212> TYPE: PRT
<213> ORGANISM: Homo sapiens

<400> SEQUENCE: 698

Val Leu Leu Arg Val Phe Val Glu Arg
1 5

<210> SEQ ID NO 699
<211> LENGTH: 9
<212> TYPE: PRT
<213> ORGANISM: Homo sapiens

<400> SEQUENCE: 699

Glu Leu Asp Asn Leu His Lys Gln Lys
1 5

<210> SEQ ID NO 700
<211> LENGTH: 9
<212> TYPE: PRT
<213> ORGANISM: Homo sapiens

<400> SEQUENCE: 700

Glu Val Val Arg Phe Leu Asp Lys Lys
1 5

<210> SEQ ID NO 701
<211> LENGTH: 9
<212> TYPE: PRT
<213> ORGANISM: Homo sapiens

<400> SEQUENCE: 701

Lys Leu Tyr Ile Pro Leu Glu Tyr Arg
1 5

<210> SEQ ID NO 702
<211> LENGTH: 9
<212> TYPE: PRT
<213> ORGANISM: Homo sapiens

<400> SEQUENCE: 702

Arg Leu Ile Ile Leu Leu Arg Ile Phe
1 5

<210> SEQ ID NO 703
<211> LENGTH: 9
<212> TYPE: PRT
<213> ORGANISM: Homo sapiens

<400> SEQUENCE: 703

Ser Leu Tyr Tyr Phe Gly Glu Arg Arg
1 5

<210> SEQ ID NO 704
<211> LENGTH: 9
<212> TYPE: PRT
<213> ORGANISM: Homo sapiens

<400> SEQUENCE: 704

Lys Ile Gln Ile Glu Met Glu Lys Lys
1 5

<210> SEQ ID NO 705
<211> LENGTH: 9
<212> TYPE: PRT
<213> ORGANISM: Homo sapiens

<400> SEQUENCE: 705

Val Leu Asp Asn Ile Thr Thr Asp Lys
1 5

<210> SEQ ID NO 706
<211> LENGTH: 9
<212> TYPE: PRT
<213> ORGANISM: Homo sapiens

<400> SEQUENCE: 706

Ile Val His Ser Ile Val Ser Ser Phe
1 5

<210> SEQ ID NO 707
<211> LENGTH: 9
<212> TYPE: PRT
<213> ORGANISM: Homo sapiens

<400> SEQUENCE: 707

Thr Leu Ile Leu Ala Asp Leu Ile Phe
1 5

<210> SEQ ID NO 708
<211> LENGTH: 9
<212> TYPE: PRT
<213> ORGANISM: Homo sapiens

<400> SEQUENCE: 708

Leu Leu Arg Leu Ile Ile Leu Leu Arg
1 5

<210> SEQ ID NO 709
<211> LENGTH: 9
<212> TYPE: PRT
<213> ORGANISM: Homo sapiens

<400> SEQUENCE: 709

Ile Leu Leu Arg Ile Phe His Leu Phe
1 5

<210> SEQ ID NO 710
<211> LENGTH: 9
<212> TYPE: PRT
<213> ORGANISM: Homo sapiens

<400> SEQUENCE: 710

Leu Leu Arg Ile Phe His Leu Phe His
1 5

<210> SEQ ID NO 711
<211> LENGTH: 9
<212> TYPE: PRT
<213> ORGANISM: Homo sapiens

<400> SEQUENCE: 711

Arg Val Ser Glu Asn Lys Arg Arg Tyr
1 5

<210> SEQ ID NO 712
<211> LENGTH: 9
<212> TYPE: PRT
<213> ORGANISM: Homo sapiens

<400> SEQUENCE: 712

Gly Leu Phe Gly Val Phe Leu Val Leu
1               5

<210> SEQ ID NO 713
<211> LENGTH: 9
<212> TYPE: PRT
<213> ORGANISM: Homo sapiens

<400> SEQUENCE: 713

Ile Val Ile Leu Leu Leu Val Asp Val
1               5

<210> SEQ ID NO 714
<211> LENGTH: 9
<212> TYPE: PRT
<213> ORGANISM: Homo sapiens

<400> SEQUENCE: 714

Ala Ile His Cys Lys Gly Gly Thr Asp
1               5

<210> SEQ ID NO 715
<211> LENGTH: 9
<212> TYPE: PRT
<213> ORGANISM: Homo sapiens

<400> SEQUENCE: 715

Gln Gly Val Glu Thr Pro Ser Gln Lys
1               5

<210> SEQ ID NO 716
<211> LENGTH: 9
<212> TYPE: PRT
<213> ORGANISM: Homo sapiens

<400> SEQUENCE: 716

Asn Leu Pro Pro Arg Arg Ile Leu Phe
1               5

<210> SEQ ID NO 717
<211> LENGTH: 9
<212> TYPE: PRT
<213> ORGANISM: Homo sapiens

<400> SEQUENCE: 717

Asp Val Phe Asp Gly Pro Pro Leu Tyr
1               5

<210> SEQ ID NO 718
<211> LENGTH: 9
<212> TYPE: PRT
<213> ORGANISM: Homo sapiens

<400> SEQUENCE: 718

Arg Ile Tyr Pro Ser Asp Phe Ala Val
1               5

<210> SEQ ID NO 719
<211> LENGTH: 9
<212> TYPE: PRT
<213> ORGANISM: Homo sapiens

<400> SEQUENCE: 719

Arg Val Ser Pro Ile Ser Glu Ser Val
1 5

<210> SEQ ID NO 720
<211> LENGTH: 9
<212> TYPE: PRT
<213> ORGANISM: Homo sapiens

<400> SEQUENCE: 720

Phe Leu Val Leu Leu Asp Val Thr Leu
1 5

<210> SEQ ID NO 721
<211> LENGTH: 9
<212> TYPE: PRT
<213> ORGANISM: Homo sapiens

<400> SEQUENCE: 721

Asp Val Leu Leu Arg Val Phe Val Glu
1 5

<210> SEQ ID NO 722
<211> LENGTH: 9
<212> TYPE: PRT
<213> ORGANISM: Homo sapiens

<400> SEQUENCE: 722

Phe Val Glu Arg Arg Gln Gln Tyr Phe
1 5

<210> SEQ ID NO 723
<211> LENGTH: 9
<212> TYPE: PRT
<213> ORGANISM: Homo sapiens

<400> SEQUENCE: 723

Arg Leu Leu Arg Leu Ile Ile Leu Leu
1 5

<210> SEQ ID NO 724
<211> LENGTH: 9
<212> TYPE: PRT
<213> ORGANISM: Homo sapiens

<400> SEQUENCE: 724

Leu Ile Arg Arg Arg Val Ser Glu Asn
1 5

<210> SEQ ID NO 725
<211> LENGTH: 9
<212> TYPE: PRT
<213> ORGANISM: Homo sapiens

<400> SEQUENCE: 725

Ile Arg Arg Arg Val Ser Glu Asn Lys
1 5

<210> SEQ ID NO 726
<211> LENGTH: 9

<212> TYPE: PRT
<213> ORGANISM: Homo sapiens

<400> SEQUENCE: 726

Asp Leu Asp Leu Thr Tyr Val Thr Glu
1 5

<210> SEQ ID NO 727
<211> LENGTH: 9
<212> TYPE: PRT
<213> ORGANISM: Homo sapiens

<400> SEQUENCE: 727

Ser Val Leu Asp Asn Ile Thr Thr Asp
1 5

<210> SEQ ID NO 728
<211> LENGTH: 9
<212> TYPE: PRT
<213> ORGANISM: Homo sapiens

<400> SEQUENCE: 728

Pro Leu Tyr Asp Asp Val Lys Val Gln
1 5

<210> SEQ ID NO 729
<211> LENGTH: 9
<212> TYPE: PRT
<213> ORGANISM: Homo sapiens

<400> SEQUENCE: 729

Arg Leu Tyr Leu Pro Lys Asn Glu Leu
1 5

<210> SEQ ID NO 730
<211> LENGTH: 9
<212> TYPE: PRT
<213> ORGANISM: Homo sapiens

<400> SEQUENCE: 730

Ile Leu Phe Gly Glu Lys Met Thr Ser
1 5

<210> SEQ ID NO 731
<211> LENGTH: 9
<212> TYPE: PRT
<213> ORGANISM: Homo sapiens

<400> SEQUENCE: 731

Arg Leu Ser Lys Phe Glu Val Glu Asp
1 5

<210> SEQ ID NO 732
<211> LENGTH: 9
<212> TYPE: PRT
<213> ORGANISM: Homo sapiens

<400> SEQUENCE: 732

Ala Ser Tyr Asp Ser Lys Ile Lys Lys
1 5

<210> SEQ ID NO 733
<211> LENGTH: 9
<212> TYPE: PRT
<213> ORGANISM: Homo sapiens

<400> SEQUENCE: 733

Ile Leu Ala Asp Leu Ile Phe Thr Asp
1 5

<210> SEQ ID NO 734
<211> LENGTH: 9
<212> TYPE: PRT
<213> ORGANISM: Homo sapiens

<400> SEQUENCE: 734

Ala Asp Leu Ile Phe Thr Asp Ser Lys
1 5

<210> SEQ ID NO 735
<211> LENGTH: 9
<212> TYPE: PRT
<213> ORGANISM: Homo sapiens

<400> SEQUENCE: 735

Arg Val Phe Val Glu Arg Arg Gln Gln
1 5

<210> SEQ ID NO 736
<211> LENGTH: 9
<212> TYPE: PRT
<213> ORGANISM: Homo sapiens

<400> SEQUENCE: 736

Ile Ile Val Ile Leu Leu Leu Val Asp
1 5

<210> SEQ ID NO 737
<211> LENGTH: 9
<212> TYPE: PRT
<213> ORGANISM: Homo sapiens

<400> SEQUENCE: 737

Lys Leu Leu Arg Asn Ile Pro Arg Trp
1 5

<210> SEQ ID NO 738
<211> LENGTH: 9
<212> TYPE: PRT
<213> ORGANISM: Homo sapiens

<400> SEQUENCE: 738

Leu Leu Arg Leu Leu Arg Leu Ile Ile
1 5

<210> SEQ ID NO 739
<211> LENGTH: 9
<212> TYPE: PRT
<213> ORGANISM: Homo sapiens

<400> SEQUENCE: 739

Arg Asn Pro Ile Lys Glu Val Val Arg
1 5

<210> SEQ ID NO 740
<211> LENGTH: 9
<212> TYPE: PRT
<213> ORGANISM: Homo sapiens

<400> SEQUENCE: 740

Lys Glu Val Val Arg Phe Leu Asp Lys
1 5

<210> SEQ ID NO 741
<211> LENGTH: 9
<212> TYPE: PRT
<213> ORGANISM: Homo sapiens

<400> SEQUENCE: 741

Val Val Arg Ile Met Ile Asp Asp His
1 5

<210> SEQ ID NO 742
<211> LENGTH: 9
<212> TYPE: PRT
<213> ORGANISM: Homo sapiens

<400> SEQUENCE: 742

Asp Leu Glu Asn Ile Val Ala Ile His
1 5

<210> SEQ ID NO 743
<211> LENGTH: 9
<212> TYPE: PRT
<213> ORGANISM: Homo sapiens

<400> SEQUENCE: 743

His Leu Tyr Asn Trp Asn Leu Pro Pro
1 5

<210> SEQ ID NO 744
<211> LENGTH: 10
<212> TYPE: PRT
<213> ORGANISM: Homo sapiens

<400> SEQUENCE: 744

Arg Leu Leu Arg Leu Ile Ile Leu Leu Arg
1 5 10

<210> SEQ ID NO 745
<211> LENGTH: 10
<212> TYPE: PRT
<213> ORGANISM: Homo sapiens

<400> SEQUENCE: 745

Pro Leu Tyr Asp Asp Val Lys Val Gln Phe
1 5 10

<210> SEQ ID NO 746
<211> LENGTH: 10
<212> TYPE: PRT
<213> ORGANISM: Homo sapiens

<400> SEQUENCE: 746

Arg Ile Tyr Pro Ser Asp Phe Ala Val Glu
1 5 10

<210> SEQ ID NO 747
<211> LENGTH: 10
<212> TYPE: PRT
<213> ORGANISM: Homo sapiens

<400> SEQUENCE: 747

Val Ile Leu Leu Leu Val Asp Val Val Tyr

-continued 1 5 10

<210> SEQ ID NO 748
<211> LENGTH: 10
<212> TYPE: PRT
<213> ORGANISM: Homo sapiens

<400> SEQUENCE: 748

Ser Val Leu Asp Asn Ile Thr Thr Asp Lys
1 5 10

<210> SEQ ID NO 749
<211> LENGTH: 10
<212> TYPE: PRT
<213> ORGANISM: Homo sapiens

<400> SEQUENCE: 749

Arg Val Ser Pro Ile Ser Glu Ser Val Leu
1 5 10

<210> SEQ ID NO 750
<211> LENGTH: 10
<212> TYPE: PRT
<213> ORGANISM: Homo sapiens

<400> SEQUENCE: 750

Arg Val Phe Val Glu Arg Arg Gln Gln Tyr
1 5 10

<210> SEQ ID NO 751
<211> LENGTH: 10
<212> TYPE: PRT
<213> ORGANISM: Homo sapiens

<400> SEQUENCE: 751

Ile Leu Leu Arg Ile Phe His Leu Phe His
1 5 10

<210> SEQ ID NO 752
<211> LENGTH: 10
<212> TYPE: PRT
<213> ORGANISM: Homo sapiens

<400> SEQUENCE: 752

Leu Ile Arg Arg Arg Val Ser Glu Asn Lys
1 5 10

<210> SEQ ID NO 753
<211> LENGTH: 10
<212> TYPE: PRT
<213> ORGANISM: Homo sapiens

<400> SEQUENCE: 753

Thr Leu His Gln Met Val Val Phe Thr Lys
1 5 10

<210> SEQ ID NO 754
<211> LENGTH: 10
<212> TYPE: PRT
<213> ORGANISM: Homo sapiens

<400> SEQUENCE: 754

Leu Leu Arg Asn Ile Pro Arg Trp Thr His
1 5 10

<210> SEQ ID NO 755
<211> LENGTH: 10
<212> TYPE: PRT
<213> ORGANISM: Homo sapiens

<400> SEQUENCE: 755

Arg Leu Ile Ile Leu Leu Arg Ile Phe His
1 5 10

<210> SEQ ID NO 756
<211> LENGTH: 10
<212> TYPE: PRT
<213> ORGANISM: Homo sapiens

<400> SEQUENCE: 756

Arg Tyr Val Ala Tyr Phe Ala Gln Val Lys
1 5 10

<210> SEQ ID NO 757
<211> LENGTH: 10
<212> TYPE: PRT
<213> ORGANISM: Homo sapiens

<400> SEQUENCE: 757

Ile Ile Tyr Ser Ile Pro Arg Tyr Val Arg
1 5 10

<210> SEQ ID NO 758
<211> LENGTH: 10
<212> TYPE: PRT
<213> ORGANISM: Homo sapiens

<400> SEQUENCE: 758

Ser Ile Pro Arg Tyr Val Arg Asp Leu Lys
1 5 10

<210> SEQ ID NO 759
<211> LENGTH: 10
<212> TYPE: PRT
<213> ORGANISM: Homo sapiens

<400> SEQUENCE: 759

Asp Leu Lys Ile Gln Ile Glu Met Glu Lys
1 5 10

<210> SEQ ID NO 760
<211> LENGTH: 10
<212> TYPE: PRT
<213> ORGANISM: Homo sapiens

<400> SEQUENCE: 760

Val Val Phe Ser Thr Ile Ser Leu Gly Lys
1 5 10

<210> SEQ ID NO 761
<211> LENGTH: 10
<212> TYPE: PRT
<213> ORGANISM: Homo sapiens

<400> SEQUENCE: 761

Lys Leu Ile Arg Arg Arg Val Ser Glu Asn
1 5 10

<210> SEQ ID NO 762

<211> LENGTH: 10
<212> TYPE: PRT
<213> ORGANISM: Homo sapiens

<400> SEQUENCE: 762

Gln Ile Glu Met Glu Lys Lys Val Val Phe
1 5 10

<210> SEQ ID NO 763
<211> LENGTH: 10
<212> TYPE: PRT
<213> ORGANISM: Homo sapiens

<400> SEQUENCE: 763

Asn Val Ala Ser Tyr Asp Ser Lys Ile Lys
1 5 10

<210> SEQ ID NO 764
<211> LENGTH: 10
<212> TYPE: PRT
<213> ORGANISM: Homo sapiens

<400> SEQUENCE: 764

Asp Val Leu Leu Arg Val Phe Val Glu Arg
1 5 10

<210> SEQ ID NO 765
<211> LENGTH: 10
<212> TYPE: PRT
<213> ORGANISM: Homo sapiens

<400> SEQUENCE: 765

Ala Ile Ile Val Ile Leu Leu Leu Val Asp
1 5 10

<210> SEQ ID NO 766
<211> LENGTH: 10
<212> TYPE: PRT
<213> ORGANISM: Homo sapiens

<400> SEQUENCE: 766

Arg Val Val Arg Ile Met Ile Asp Asp His
1 5 10

<210> SEQ ID NO 767
<211> LENGTH: 10
<212> TYPE: PRT
<213> ORGANISM: Homo sapiens

<400> SEQUENCE: 767

Lys Ile Val His Ser Ile Val Ser Ser Phe
1 5 10

<210> SEQ ID NO 768
<211> LENGTH: 10
<212> TYPE: PRT
<213> ORGANISM: Homo sapiens

<400> SEQUENCE: 768

Ser Ile Ser Leu Ala Ile Ala Leu Phe Phe
1 5 10

<210> SEQ ID NO 769
<211> LENGTH: 10
<212> TYPE: PRT

<213> ORGANISM: Homo sapiens

<400> SEQUENCE: 769

Ile Val Ile Leu Leu Leu Val Asp Val Val
1 5 10

<210> SEQ ID NO 770
<211> LENGTH: 10
<212> TYPE: PRT
<213> ORGANISM: Homo sapiens

<400> SEQUENCE: 770

Asp Val Val Tyr Ile Phe Phe Asp Ile Lys
1 5 10

<210> SEQ ID NO 771
<211> LENGTH: 10
<212> TYPE: PRT
<213> ORGANISM: Homo sapiens

<400> SEQUENCE: 771

Lys Leu Leu Arg Asn Ile Pro Arg Trp Thr
1 5 10

<210> SEQ ID NO 772
<211> LENGTH: 10
<212> TYPE: PRT
<213> ORGANISM: Homo sapiens

<400> SEQUENCE: 772

Asp Leu Ile Phe Thr Asp Ser Lys Leu Tyr
1 5 10

<210> SEQ ID NO 773
<211> LENGTH: 10
<212> TYPE: PRT
<213> ORGANISM: Homo sapiens

<400> SEQUENCE: 773

Phe Leu Met Asp Val Leu Leu Arg Val Phe
1 5 10

<210> SEQ ID NO 774
<211> LENGTH: 10
<212> TYPE: PRT
<213> ORGANISM: Homo sapiens

<400> SEQUENCE: 774

Val Leu Leu Arg Val Phe Val Glu Arg Arg
1 5 10

<210> SEQ ID NO 775
<211> LENGTH: 10
<212> TYPE: PRT
<213> ORGANISM: Homo sapiens

<400> SEQUENCE: 775

Ile Leu Leu Leu Val Asp Val Val Tyr Ile
1 5 10

<210> SEQ ID NO 776
<211> LENGTH: 10
<212> TYPE: PRT
<213> ORGANISM: Homo sapiens

<400> SEQUENCE: 776

His Leu Leu Arg Leu Leu Arg Leu Ile Ile
1 5 10

<210> SEQ ID NO 777
<211> LENGTH: 10
<212> TYPE: PRT
<213> ORGANISM: Homo sapiens

<400> SEQUENCE: 777

Arg Ile Ile Ala Met Ser Phe Pro Ser Ser
1 5 10

<210> SEQ ID NO 778
<211> LENGTH: 10
<212> TYPE: PRT
<213> ORGANISM: Homo sapiens

<400> SEQUENCE: 778

Arg Val Tyr Asn Leu Cys Ser Glu Arg Ala
1 5 10

<210> SEQ ID NO 779
<211> LENGTH: 10
<212> TYPE: PRT
<213> ORGANISM: Homo sapiens

<400> SEQUENCE: 779

Ala Ile His Cys Lys Gly Gly Thr Asp Arg
1 5 10

<210> SEQ ID NO 780
<211> LENGTH: 10
<212> TYPE: PRT
<213> ORGANISM: Homo sapiens

<400> SEQUENCE: 780

Tyr Val Ala Tyr Phe Ala Gln Val Lys His
1 5 10

<210> SEQ ID NO 781
<211> LENGTH: 10
<212> TYPE: PRT
<213> ORGANISM: Homo sapiens

<400> SEQUENCE: 781

His Leu Tyr Asn Trp Asn Leu Pro Pro Arg
1 5 10

<210> SEQ ID NO 782
<211> LENGTH: 10
<212> TYPE: PRT
<213> ORGANISM: Homo sapiens

<400> SEQUENCE: 782

Ile Leu Phe Ile Lys His Phe Ile Ile Tyr
1 5 10

<210> SEQ ID NO 783
<211> LENGTH: 10
<212> TYPE: PRT
<213> ORGANISM: Homo sapiens

<400> SEQUENCE: 783

Arg Leu Tyr Leu Pro Lys Asn Glu Leu Asp
1 5 10

<210> SEQ ID NO 784
<211> LENGTH: 10
<212> TYPE: PRT
<213> ORGANISM: Homo sapiens

<400> SEQUENCE: 784

Lys Gly Ala Thr Glu Glu Ala Pro Ala Lys
1 5 10

<210> SEQ ID NO 785
<211> LENGTH: 10
<212> TYPE: PRT
<213> ORGANISM: Homo sapiens

<400> SEQUENCE: 785

Lys Leu Tyr Ile Pro Leu Glu Tyr Arg Ser
1 5 10

<210> SEQ ID NO 786
<211> LENGTH: 10
<212> TYPE: PRT
<213> ORGANISM: Homo sapiens

<400> SEQUENCE: 786

Asn Ile Pro Arg Trp Thr His Leu Leu Arg
1 5 10

<210> SEQ ID NO 787
<211> LENGTH: 10
<212> TYPE: PRT
<213> ORGANISM: Homo sapiens

<400> SEQUENCE: 787

Arg Arg Thr Asp Lys Thr His Ser Glu Lys
1 5 10

<210> SEQ ID NO 788
<211> LENGTH: 9
<212> TYPE: PRT
<213> ORGANISM: Homo sapiens

<400> SEQUENCE: 788

Ala Pro Ala Lys Glu Ser Pro His Thr
1 5

<210> SEQ ID NO 789
<211> LENGTH: 9
<212> TYPE: PRT
<213> ORGANISM: Homo sapiens

<400> SEQUENCE: 789

Asn Pro Ile Lys Glu Val Val Arg Phe
1 5

<210> SEQ ID NO 790
<211> LENGTH: 9
<212> TYPE: PRT
<213> ORGANISM: Homo sapiens

<400> SEQUENCE: 790

Thr Pro Ser Gln Lys Arg Tyr Val Ala
1 5

<210> SEQ ID NO 791
<211> LENGTH: 9
<212> TYPE: PRT
<213> ORGANISM: Homo sapiens

<400> SEQUENCE: 791

Leu Pro Lys Asn Glu Leu Asp Asn Leu
1 5

<210> SEQ ID NO 792
<211> LENGTH: 9
<212> TYPE: PRT
<213> ORGANISM: Homo sapiens

<400> SEQUENCE: 792

Tyr Pro Ser Asp Phe Ala Val Glu Ile
1 5

<210> SEQ ID NO 793
<211> LENGTH: 9
<212> TYPE: PRT
<213> ORGANISM: Homo sapiens

<400> SEQUENCE: 793

Phe Pro Ser Ser Gly Arg Gln Ser Phe
1 5

<210> SEQ ID NO 794
<211> LENGTH: 9
<212> TYPE: PRT
<213> ORGANISM: Homo sapiens

<400> SEQUENCE: 794

Leu Pro Pro Arg Arg Ile Leu Phe Ile
1 5

<210> SEQ ID NO 795
<211> LENGTH: 9
<212> TYPE: PRT
<213> ORGANISM: Homo sapiens

<400> SEQUENCE: 795

Ser Pro Ile Ser Glu Ser Val Leu Ala
1 5

<210> SEQ ID NO 796
<211> LENGTH: 9
<212> TYPE: PRT
<213> ORGANISM: Homo sapiens

<400> SEQUENCE: 796

Pro Pro Leu Tyr Asp Asp Val Lys Val
1 5

<210> SEQ ID NO 797
<211> LENGTH: 9
<212> TYPE: PRT
<213> ORGANISM: Homo sapiens

<400> SEQUENCE: 797

Asp Pro Thr Asp Leu Ala Gly Val Ile
1 5

<210> SEQ ID NO 798
<211> LENGTH: 9
<212> TYPE: PRT
<213> ORGANISM: Homo sapiens

<400> SEQUENCE: 798

Ala Phe Gly Leu Phe Gly Val Phe Leu
1 5

<210> SEQ ID NO 799
<211> LENGTH: 9
<212> TYPE: PRT
<213> ORGANISM: Homo sapiens

<400> SEQUENCE: 799

Val Pro Thr Leu His Gln Met Val Val
1 5

<210> SEQ ID NO 800
<211> LENGTH: 9
<212> TYPE: PRT
<213> ORGANISM: Homo sapiens

<400> SEQUENCE: 800

Gly Leu Phe Gly Val Phe Leu Val Leu
1 5

<210> SEQ ID NO 801
<211> LENGTH: 9
<212> TYPE: PRT
<213> ORGANISM: Homo sapiens

<400> SEQUENCE: 801

Asp Pro Lys His Phe His Asn Arg Val
1 5

<210> SEQ ID NO 802
<211> LENGTH: 9
<212> TYPE: PRT
<213> ORGANISM: Homo sapiens

<400> SEQUENCE: 802

Ser Pro Asp Pro Thr Asp Leu Ala Gly
1 5

<210> SEQ ID NO 803
<211> LENGTH: 9
<212> TYPE: PRT
<213> ORGANISM: Homo sapiens

<400> SEQUENCE: 803

Ile Pro Arg Trp Thr His Leu Leu Arg
1 5

<210> SEQ ID NO 804
<211> LENGTH: 9
<212> TYPE: PRT
<213> ORGANISM: Homo sapiens

<400> SEQUENCE: 804

Thr Arg Asp Gly Phe Asp Leu Asp Leu
1 5

<210> SEQ ID NO 805
<211> LENGTH: 9

<212> TYPE: PRT
<213> ORGANISM: Homo sapiens

<400> SEQUENCE: 805

Trp Asn Leu Pro Pro Arg Arg Ile Leu
1 5

<210> SEQ ID NO 806
<211> LENGTH: 10
<212> TYPE: PRT
<213> ORGANISM: Homo sapiens

<400> SEQUENCE: 806

Ile Pro Arg Trp Thr His Leu Leu Arg Leu
1 5 10

<210> SEQ ID NO 807
<211> LENGTH: 10
<212> TYPE: PRT
<213> ORGANISM: Homo sapiens

<400> SEQUENCE: 807

Asn Pro Ile Lys Glu Val Val Arg Phe Leu
1 5 10

<210> SEQ ID NO 808
<211> LENGTH: 10
<212> TYPE: PRT
<213> ORGANISM: Homo sapiens

<400> SEQUENCE: 808

Tyr Pro Ser Asp Phe Ala Val Glu Ile Leu
1 5 10

<210> SEQ ID NO 809
<211> LENGTH: 10
<212> TYPE: PRT
<213> ORGANISM: Homo sapiens

<400> SEQUENCE: 809

Ile Pro Leu Glu Tyr Arg Ser Ile Ser Leu
1 5 10

<210> SEQ ID NO 810
<211> LENGTH: 10
<212> TYPE: PRT
<213> ORGANISM: Homo sapiens

<400> SEQUENCE: 810

Ile Pro Arg Tyr Val Arg Asp Leu Lys Ile
1 5 10

<210> SEQ ID NO 811
<211> LENGTH: 10
<212> TYPE: PRT
<213> ORGANISM: Homo sapiens

<400> SEQUENCE: 811

Ser Pro Asp Pro Thr Asp Leu Ala Gly Val
1 5 10

<210> SEQ ID NO 812
<211> LENGTH: 10
<212> TYPE: PRT
<213> ORGANISM: Homo sapiens

<400> SEQUENCE: 812

Val Pro Thr Leu His Gln Met Val Val Phe
1 5 10

<210> SEQ ID NO 813
<211> LENGTH: 10
<212> TYPE: PRT
<213> ORGANISM: Homo sapiens

<400> SEQUENCE: 813

Asp Pro Thr Asp Leu Ala Gly Val Ile Ile
1 5 10

<210> SEQ ID NO 814
<211> LENGTH: 10
<212> TYPE: PRT
<213> ORGANISM: Homo sapiens

<400> SEQUENCE: 814

Gly Pro Pro Leu Tyr Asp Asp Val Lys Val
1 5 10

<210> SEQ ID NO 815
<211> LENGTH: 10
<212> TYPE: PRT
<213> ORGANISM: Homo sapiens

<400> SEQUENCE: 815

Ser Pro Gln Thr Ser Glu Phe Lys Gly Ala
1 5 10

<210> SEQ ID NO 816
<211> LENGTH: 10
<212> TYPE: PRT
<213> ORGANISM: Homo sapiens

<400> SEQUENCE: 816

Ser Pro His Thr Ser Glu Phe Lys Gly Ala
1 5 10

<210> SEQ ID NO 817
<211> LENGTH: 10
<212> TYPE: PRT
<213> ORGANISM: Homo sapiens

<400> SEQUENCE: 817

Asp Pro Lys His Phe His Asn Arg Val Val
1 5 10

<210> SEQ ID NO 818
<211> LENGTH: 10
<212> TYPE: PRT
<213> ORGANISM: Homo sapiens

<400> SEQUENCE: 818

Leu Pro Thr Tyr Tyr Asp Asn Cys Ser Phe
1 5 10

<210> SEQ ID NO 819
<211> LENGTH: 10
<212> TYPE: PRT
<213> ORGANISM: Homo sapiens

<400> SEQUENCE: 819

Arg Val Ser Pro Ile Ser Glu Ser Val Leu
1 5 10

<210> SEQ ID NO 820
<211> LENGTH: 10
<212> TYPE: PRT
<213> ORGANISM: Homo sapiens

<400> SEQUENCE: 820

Phe Ala Phe Gly Leu Phe Gly Val Phe Leu
1 5 10

<210> SEQ ID NO 821
<211> LENGTH: 10
<212> TYPE: PRT
<213> ORGANISM: Homo sapiens

<400> SEQUENCE: 821

Thr Pro Ser Gln Lys Arg Tyr Val Ala Tyr
1 5 10

<210> SEQ ID NO 822
<211> LENGTH: 1320
<212> TYPE: DNA
<213> ORGANISM: Homo sapiens

<400> SEQUENCE: 822
accttgcaga ggagggggcg gcggggacag gacccgggtc tgtgcctgcg cacaccctcg 60
cgggccaacc ccctccccc ccgccccgcc gggtacctgt cacggctact gccgcggcgc 120
gcgcccgcca cgttaagccg gatggcggga ggaggggtgc ggggagggtg gcacggcgcg 180
cgcgtgcgcg ggagtcgccg agcaagaact ggtagtgcgc gcgctcgccg ctcgctcgcg 240
tcccggaggc ggagtctgcg gcggcgggcg gaacgggggc gcgcctatgc tagtcacgtg 300
ggcgctgggg cggggccggg cggccgttca aggcaggggg cggggcgtct ccgagcggcg 360
gggccaaggg agggcacaac agctgctacc tgaacagttt ctgacccaac agttacccag 420
cgccggactc gctgcgcccc ggcggctcta gggacccccg gcgcctacac ttagctccgc 480
gcccgaggtg agcccaggcc ctaagtcctc cgggcggggg taggggtggg ggacgctcct 540
ttttgttggg ggggggtctt ggaggcgcga aggcactagg cgcctcggcg gatggctgaa 600
cccctcgccc gcggctcccc gtgtcttttg gggggccggg tgcgggcgcg gaatccggga 660
ggtgtccgca caaaaggccg agaaaaactc cgcgacgcct ccctccctcc ctccgccctc 720
cccgtcccct cctctccgcg cccgctcctc ctcattcaaa cccggccggc ctgagtggtg 780
ttagctcagt cccggccgcc gccgcgtgag gaaatggcct aggagccgga gccgcaggta 840
aagggggcgc gccccccgcc cgcgccagcc ggggcgcccg cccggtcctg cggaggctcc 900
cgcgccgccc ccgaggcgcc cggctctcgt tgtcttgtcc ccccccagga tgacctgagt 960
tccccgtgtc tgctttctag ccgctcctct agggcgcccc ctccccagct ggctcctgcg 1020
cttccgccca cgggaaggtg cgggcgatcc cgggctgcat ccgctcttgg ccgtcacact 1080
cacgctgcac gatttagaag ggcttggggt gcggggttcc ctgagtctcc gccgggagcg 1140
ggggtccggg ggtctgcggg ggtgggcggt ggggtgctgt tccgaaaagt tgggtcgccc 1200
cgcggggcgg gtctcccaat ttgcccagtc ggcccttggg gcgcgggcgg aggggggacg 1260
tcggcgtagg gtccccagcg atgccccggg aagggctggg acaagttgga aacggtcaaa 1320

<210> SEQ ID NO 823
<211> LENGTH: 21
<212> TYPE: DNA
<213> ORGANISM: Artificial Sequence
<220> FEATURE:
<223> OTHER INFORMATION: Description of the artificial sequence:
oligonucleotide

<400> SEQUENCE: 823
gagtctacaa tctatgcagt g 21

<210> SEQ ID NO 824
<211> LENGTH: 21
<212> TYPE: DNA
<213> ORGANISM: Artificial Sequence
<220> FEATURE:
<223> OTHER INFORMATION: Description of the artificial sequence:
oligonucleotide

<400> SEQUENCE: 824
agaatagaat gtggcctcta g 21

<210> SEQ ID NO 825
<211> LENGTH: 21
<212> TYPE: DNA
<213> ORGANISM: Artificial Sequence
<220> FEATURE:
<223> OTHER INFORMATION: Description of the artificial sequence:
oligonucleotide

<400> SEQUENCE: 825
tgctcttact ccaaaaagat g 21

<210> SEQ ID NO 826
<211> LENGTH: 21
<212> TYPE: DNA
<213> ORGANISM: Artificial Sequence
<220> FEATURE:
<223> OTHER INFORMATION: siRNA sense strand
<220> FEATURE:
<221> NAME/KEY: misc_feature
<222> LOCATION: (1)..(19)
<223> OTHER INFORMATION: ribonucleotide bases

<400> SEQUENCE: 826
cccugccaca uguucauaut t 21

<210> SEQ ID NO 827
<211> LENGTH: 21
<212> TYPE: DNA
<213> ORGANISM: Artificial Sequence
<220> FEATURE:
<223> OTHER INFORMATION: siRNA antisense strand
<220> FEATURE:
<221> NAME/KEY: misc_feature
<222> LOCATION: (1)..(19)
<223> OTHER INFORMATION: ribonucleotide bases

<400> SEQUENCE: 827
auaugaacau guggcagggt t 21

<210> SEQ ID NO 828
<211> LENGTH: 21
<212> TYPE: DNA
<213> ORGANISM: Artificial Sequence
<220> FEATURE:
<223> OTHER INFORMATION: siRNA sense strand
<220> FEATURE:
<221> NAME/KEY: misc_feature -continued

```
<222> LOCATION: (1)..(19)
<223> OTHER INFORMATION: ribonucleotide bases

<400> SEQUENCE: 828

aguuccagua cggcuccaat t                                              21


<210> SEQ ID NO 829
<211> LENGTH: 21
<212> TYPE: DNA
<213> ORGANISM: Artificial Sequence
<220> FEATURE:
<223> OTHER INFORMATION: siRNA antisense strand
<220> FEATURE:
<221> NAME/KEY: misc_feature
<222> LOCATION: (1)..(19)
<223> OTHER INFORMATION: ribonucleotide bases

<400> SEQUENCE: 829

uuggagccgu acuggaacut t                                              21


<210> SEQ ID NO 830
<211> LENGTH: 420
<212> TYPE: DNA
<213> ORGANISM: Homo sapiens

<400> SEQUENCE: 830

gcgcccgcca cgttaagccg gatggcggga ggaggggtgc ggggagggtg gcacggcgcg     60

cgcgtgcgcg ggagtcgccg agcaagaact ggtagtgcgc gcgctcgccg ctcgctcgcg    120

tcccggaggc ggagtctgcg gcggcgggcg gaacgggggc gcgcctatgc tagtcacgtg    180

ggcgctgggg cggggccggg cggccgttca aggcaggggg cggggcgtct ccgagcggcg    240

gggccaaggg agggcacaac agctgctacc tgaacagttt ctgacccaac agttacccag    300

cgccggactc gctgcgcccc ggcggctcta gggacccccg gcgcctacac ttagctccgc    360

gcccgaggtg agcccaggcc ctaagtcctc cgggcggggg taggggtggg ggacgctcct    420
```

GENETIC PRODUCTS WHICH ARE DIFFERENTIALLY EXPRESSED IN TUMORS AND USE THEREOF

Despite interdisciplinary approaches and exhaustive use of classical therapeutic procedures, cancers are still among the leading causes of death. More recent therapeutic concepts aim at incorporating the patient's immune system into the overall therapeutic concept by using recombinant tumor vaccines and other specific measures such as antibody therapy. A prerequisite for the success of such a strategy is the recognition of tumor-specific or tumor-associated antigens or epitopes by the patient's immune system whose effector functions are to be interventionally enhanced. Tumor cells biologically differ substantially from their nonmalignant cells of origin. These differences are due to genetic alterations acquired during tumor development and result, inter alia, also in the formation of qualitatively or quantitatively altered molecular structures in the cancer cells. Tumor-associated structures of this kind which are recognized by the specific immune system of the tumor-harboring host are referred to as tumor-associated antigens. The specific recognition of tumor-associated antigens involves cellular and humoral mechanisms which are two functionally interconnected units: $CD4^+$ and $CD8^+$ T lymphocytes recognize the processed antigens presented on the molecules of the MHC (major histocompatibility complex) classes II and I, respectively, while B lymphocytes produce circulating antibody molecules which bind directly to unprocessed antigens. The potential clinical-therapeutical importance of tumor-associated antigens results from the fact that the recognition of antigens on neoplastic cells by the immune system leads to the initiation of cytotoxic effector mechanisms and, in the presence of T helper cells, can cause elimination of the cancer cells (Pardoll, *Nat. Med.* 4:525-31, 1998). Accordingly, a central aim of tumor immunology is to molecularly define these structures. The molecular nature of these antigens has been enigmatic for a long time. Only after development of appropriate cloning techniques has it been possible to screen cDNA expression libraries of tumors systematically for tumor-associated antigens by analyzing the target structures of cytotoxic T lymphocytes (CTL) (van der Bruggen et al., *Science* 254:1643-7, 1991) or by using circulating autoantibodies (Sahin et al., *Curr. Opin. Immunol.* 9:709-16, 1997) as probes. To this end, cDNA expression libraries were prepared from fresh tumor tissue and recombinantly expressed as proteins in suitable systems. Immunoeffectors isolated from patients, namely CTL clones with tumor-specific lysis patterns, or circulating autoantibodies were utilized for cloning the respective antigens.

In recent years a multiplicity of antigens have been defined in various neoplasias by these approaches. The class of cancer/testis antigens (CTA) is of great interest here. CTA and genes encoding them (cancer/testis genes or CTG) are defined by their characteristic expression pattern [Tureci et al, *Mol Med Today.* 3:342-9, 1997]. They are not found in normal tissues, except testis and germ cells, but are expressed in a number of human malignomas, not tumor type-specifically but with different frequency in tumor entities of very different origins (Chen & Old, *Cancer J. Sci. Am.* 5:16-7, 1999). Serum reactivities against CTA are also not found in healthy controls but only in tumor patients. This class of antigens, in particular owing to its tissue distribution, is particularly valuable for immunotherapeutic projects and is tested in current clinical patient studies (Marchand et al., *Int. J. Cancer* 80:219-30, 1999; Knuth et al., *Cancer Chemother. Pharmacol.* 46:p 46-51, 2000).

However, the probes utilized for antigen identification in the classical methods illustrated above are immunoeffectors (circulating autoantibodies or CTL clones) from patients usually having already advanced cancer. A number of data indicate that tumors can lead, for example, to tolerization and anergization of T cells and that, during the course of the disease, especially those specificities which could cause effective immune recognition are lost from the immunoeffector repertoire. Current patient studies have not yet produced any solid evidence of a real action of the previously found and utilized tumor-associated antigens. Accordingly, it cannot be ruled out that proteins evoking spontaneous immune responses are the wrong target structures.

It was the object of the present invention to provide target structures for a diagnosis and therapy of cancers.

According to the invention, this object is achieved by the subject matter of the claims.

According to the invention, a strategy for identifying and providing antigens expressed in association with a tumor and the nucleic acids coding therefor was pursued. This strategy is based on the fact that actually testis- and thus germ cell-specific genes which are usually silent in adult tissues are reactivated in tumor cells in an ectopic and forbidden manner. First, data mining produces a list as complete as possible of all known testis-specific genes which are then evaluated for their aberrant activation in tumors by expression analyses by means of specific RT-PCR. Data mining is a known method of identifying tumor-associated genes. In the conventional strategies, however, transcriptoms of normal tissue libraries are usually subtracted electronically from tumor tissue libraries, with the assumption that the remaining genes are tumor-specific (Schmitt et al., *Nucleic Acids Res.* 27:4251-60, 1999; Vasmatzis et al., *Proc. Natl. Acad. Sci. USA.* 95:300-4, 1998. Scheurle et al., *Cancer Res.* 60:4037-43, 2000).

The concept of the invention, which has proved much more successful, however, is based on utilizing data mining for electronically extracting all testis-specific genes and then evaluating said genes for ectopic expression in tumors.

The invention thus relates in one aspect to a strategy for identifying genes differentially expressed in tumors. Said strategy combines data mining of public sequence libraries ("in silico") with subsequent evaluating laboratory-experimental ("wet bench") studies.

According to the invention, a combined strategy based on two different bioinformatic scripts enabled new members of the cancer/testis (CT) gene class to be identified. These have previously been classified as being purely testis-, germ cell- or sperm-specific. The finding that these genes are aberrantly activated in tumor cells allows them to be assigned a substantially new quality with functional implications. According to the invention, these tumor-associated genes and the genetic products encoded thereby were identified and provided independently of an immunogenic action.

The tumor-associated antigens identified according to the invention have an amino acid sequence encoded by a nucleic acid which is selected from the group consisting of (a) a nucleic acid which comprises a nucleic acid sequence selected from the group consisting of SEQ ID NOs: 1-5, 19-21, 29, 31-33, 37, 39, 40, 54-57, 62, 63, 70, 74, 85-88, a part or derivative thereof, (b) a nucleic acid which hybridizes with the nucleic acid of (a) under stringent conditions, (c) a nucleic acid which is degenerate with respect to the nucleic acid of (a) or (b), and (d) a nucleic acid which is complementary to the nucleic acid of (a), (b) or (c). In a preferred embodiment, a tumor-associated antigen identified according to the invention has an amino acid sequence encoded by a nucleic acid which is selected from the group consisting of SEQ ID NOs: 1-5, 19-21, 29, 31-33, 37, 39, 40, 54-57, 62, 63, 70, 74, 85-88. In a further preferred embodiment, a tumor-associated antigen identified according to the invention comprises an amino acid sequence selected from the group consisting of SEQ ID NOs: 6-13, 14-18, 22-24, 30, 34-36, 38, 41, 58-61, 64, 65, 71, 75, 80-84, 89-100, 101-117, a part or derivative thereof.

The present invention generally relates to the use of tumor-associated antigens identified according to the invention or of parts thereof, of nucleic acids coding therefor or of nucleic acids directed against said coding nucleic acids or of antibodies directed against the tumor-associated antigens identified according to the invention or parts thereof for therapy and diagnosis. This utilization may relate to individual but also to combinations of two or more of these antigens, functional fragments, nucleic acids, antibodies, etc., in one embodiment also in combination with other tumor-associated genes and antigens for diagnosis, therapy and progress control.

Preferred diseases for a therapy and/or diagnosis are those in which one or more of the tumor-associated antigens identified according to the invention are selectively expressed or abnormally expressed.

The ectopic activation of genes in tumors may also derive from an altered gene methylation pattern of their nucleotide sequence. For example, it has been described that alterations of the methylation of cytosine contribute thereto (De Smet et al., 1996 and 1999).

The invention also relates to nucleic acids and genetic products which are expressed in association with a tumor cell and which are produced by altered splicing (splice variants) of known genes or by altered translation with utilization of alternative open reading frames. Said nucleic acids comprise the sequences according to SEQ ID NO: 2-5, 20, 21, 31-33, 54-57, 85-88 of the sequence listing. Furthermore, the genetic products comprise sequences according to SEQ ID NO: 7-13, 23, 24, 34-36, 58-61, 89-100 of the sequence listing. The splice variants of the invention can be used according to the invention as targets for diagnosis and therapy of tumor diseases.

Very different mechanisms may cause splice variants to be produced, for example

- utilization of variable transcription initiation sites
- utilization of additional exons
- complete or incomplete splicing out of single or two or more exons,
- splice regulator sequences altered via mutation (deletion or generation of new donor/acceptor sequences),
- incomplete elimination of intron sequences.

Altered splicing of a gene results in an altered transcript sequence (splice variant). Translation of a splice variant in the region of its altered sequence results in an altered protein which may be distinctly different in the structure and function from the original protein. Tumor-associated splice variants may produce tumor-associated transcripts and tumor-associated proteins/antigens. These may be utilized as molecular markers both for detecting tumor cells and for therapeutic targeting of tumors. Detection of tumor cells, for example in blood, serum, bone marrow, sputum, bronchial lavage, bodily secretions and tissue biopsies, may be carried out according to the invention, for example, after extraction of nucleic acids by PCR amplification with splice variant-specific oligonucleotides. According to the invention, all sequence-dependent detection systems are suitable for detection. These are, apart from PCR, for example gene chip/microarray systems, Northern blot, RNAse protection assays (RDA) and others. All detection systems have in common that detection is based on a specific hybridization with at least one splice variant-specific nucleic acid sequence. However, tumor-cells may also be detected according to the invention by antibodies which recognize a specific epitope encoded by the splice variant. Said antibodies may be prepared by using for immunization peptides which are specific for said splice variant. Suitable for immunization are particularly the amino acids whose epitopes are distinctly different from the variant(s) of the genetic product, which is (are) preferably produced in healthy cells. Detection of the tumor cells with antibodies may be carried out here on a sample isolated from the patient or as imaging with intravenously administered antibodies. In addition to diagnostic usability, splice variants having new or altered epitopes are attractive targets for immunotherapy. The epitopes of the invention may be utilized for targeting therapeutically active monoclonal antibodies or T lymphocytes. In passive immunotherapy, antibodies or T lymphocytes which recognize splice variant-specific epitopes are adoptively transferred here. As in the case of other antigens, antibodies may be generated also by using standard technologies (immunization of animals, panning strategies for isolation of recombinant antibodies) with utilization of polypeptides which include these epitopes. Alternatively, it is possible to utilize for immunization nucleic acids coding for oligo- or polypeptides which contain said epitopes. Various techniques for in vitro or in vivo generation of epitope-specific T lymphocytes are known and have been described in detail, for example (Kessler J H, et al. 2001, Sahin et al., 1997) and are likewise based on utilizing oligo- or polypeptides which contain the splice variant-specific epitopes or nucleic acids coding for said oligo- or polypeptides. Oligo- or polypeptides which contain the splice variant-specific epitopes or nucleic acids coding for said polypeptides may also be used for utilization as pharmaceutically active substances in active immunotherapy (vaccination, vaccine therapy).

In one aspect, the invention relates to a pharmaceutical composition comprising an agent which recognizes the tumor-associated antigen identified according to the invention and which is preferably selective for cells which have expression or abnormal expression of a tumor-associated antigen identified according to the invention. In particular embodiments, said agent may cause induction of cell death, reduction in cell growth, damage to the cell membrane or secretion of cytokines and preferably have a tumor-inhibiting activity. In one embodiment, the agent is an antisense nucleic acid which hybridizes selectively with the nucleic acid coding for the tumor-associated antigen. In a further embodiment, the agent is an antibody which binds selectively to the tumor-associated antigen, in particular a complement-activated antibody which binds selectively to the tumor-associated antigen. In a further embodiment, the agent comprises two or more agents which each selectively recognize different tumor-associated antigens, at least one of which is a tumor-associated antigen identified according to the invention. Recognition needs not be accompanied directly with inhibition of activity or expression of the antigen. In this aspect of the invention, the antigen selectively limited to tumors preferably serves as a label for recruiting effector mechanisms to this specific location. In a preferred embodiment, the agent is a cytotoxic T lymphocyte which recognizes the antigen on an HLA molecule and lyses the cell labeled in this way. In a further embodiment, the agent is an antibody which binds selectively to the tumor-associated antigen and thus recruits natural or artificial effector mechanisms to said cell. In a further embodiment, the agent is a T helper lymphocyte which enhances effector functions of other cells specifically recognizing said antigen.

In one aspect, the invention relates to a pharmaceutical composition comprising an agent which inhibits expression or activity of a tumor-associated antigen identified according to the invention. In a preferred embodiment, the agent is an antisense nucleic acid which hybridizes selectively with the nucleic acid coding for the tumor-associated antigen. In a further embodiment, the agent is an antibody which binds selectively to the tumor-associated antigen. In a further embodiment, the agent comprises two or more agents which each selectively inhibit expression or activity of different tumor-associated antigens, at least one of which is a tumor-associated antigen identified according to the invention.

The activity of a tumor-associated antigen identified according to the invention may be any activity of a protein or peptide. In one embodiment, the activity is an enzymatic activity such as lactate dehydrogenase activity in the case of sequences relating to LDHC (cf. example 1). In a further embodiment, this activity relates to an involvement in cellular migration and/or metastasis such as in the case of sequences relating to TPTE (cf. example 2). Thus, the methods of therapy and diagnosis of the invention may also aim at the inhibition or reduction of this activity or at testing this activity.

The invention furthermore relates to a pharmaceutical composition which comprises an agent which, when administered, selectively increases the amount of complexes between an HLA molecule and a peptide epitope from the tumor-associated antigen identified according to the invention. In one embodiment, the agent comprises one or more components selected from the group consisting of (i) the tumor-associated antigen or a part thereof, (ii) a nucleic acid which codes for said tumor-associated antigen or a part thereof, (iii) a host cell which expresses said tumor-associated antigen or a part thereof, and (iv) isolated complexes between peptide epitopes from said tumor-associated antigen and an MHC molecule. In one embodiment, the agent comprises two or more agents which each selectively increase the amount of complexes between MHC molecules and peptide epitopes of different tumor-associated antigens, at least one of which is a tumor-associated antigen identified according to the invention.

The invention furthermore relates to a pharmaceutical composition which comprises one or more components selected from the group consisting of (i) a tumor-associated antigen identified according to the invention or a part thereof, (ii) a nucleic acid which codes for a tumor-associated antigen identified according to the invention or for a part thereof, (iii) an antibody which binds to a tumor-associated antigen identified according to the invention or to a part thereof, (iv) an antisense nucleic acid which hybridizes specifically with a nucleic acid coding for a tumor-associated antigen identified according to the invention, (v) a host cell which expresses a tumor-associated antigen identified according to the invention or a part thereof, and (vi) isolated complexes between a tumor-associated antigen identified according to the invention or a part thereof and an HLA molecule.

A nucleic acid coding for a tumor-associated antigen identified according to the invention or for a part thereof may be present in the pharmaceutical composition in an expression vector and functionally linked to a promoter.

A host cell present in a pharmaceutical composition of the invention may secrete the tumor-associated antigen or the part thereof, express it on the surface or may additionally express an HLA molecule which binds to said tumor-associated antigen or said part thereof. In one embodiment, the host cell expresses the HLA molecule endogenously. In a further embodiment, the host cell expresses the HLA molecule and/or the tumor-associated antigen or the part thereof in a recombinant manner. The host cell is preferably nonproliferative. In a preferred embodiment, the host cell is an antigen-presenting cell, in particular a dendritic cell, a monocyte or a macrophage.

An antibody present in a pharmaceutical composition of the invention may be a monoclonal antibody. In further embodiments, the antibody is a chimeric or humanized antibody, a fragment of a natural antibody or a synthetic antibody, all of which may be produced by combinatory techniques. The antibody may be coupled to a therapeutically or diagnostically useful agent.

An antisense nucleic acid present in a pharmaceutical composition of the invention may comprise a sequence of 6-50, in particular 10-30, 15-30 and 20-30, contiguous nucleotides of the nucleic acid coding for the tumor-associated antigen identified according to the invention.

In further embodiments, a tumor-associated antigen, provided by a pharmaceutical composition of the invention either directly or via expression of a nucleic acid, or a part thereof binds to MHC molecules on the surface of cells, said binding preferably causing a cytolytic response and/or inducing cytokine release.

A pharmaceutical composition of the invention may comprise a pharmaceutically compatible carrier and/or an adjuvant. The adjuvant may be selected from saponin, GM-CSF, CpG nucleotides, RNA, a cytokine or a chemokine. A pharmaceutical composition of the invention is preferably used for the treatment of a disease characterized by selective expression or abnormal expression of a tumor-associated antigen. In a preferred embodiment, the disease is cancer.

The invention furthermore relates to methods of treating or diagnosing a disease characterized by expression or abnormal expression of one of more tumor-associated antigens. In one embodiment, the treatment comprises administering a pharmaceutical composition of the invention.

In one aspect, the invention relates to a method of diagnosing a disease characterized by expression or abnormal expression of a tumor-associated antigen identified according to the invention. The method comprises detection of (i) a nucleic acid which codes for the tumor-associated antigen or of a part thereof and/or (ii) detection of the tumor-associated antigen or of a part thereof, and/or (iii) detection of an antibody to the tumor-associated antigen or to a part thereof and/or (iv) detection of cytotoxic or T helper lymphocytes which are specific for the tumor-associated antigen or for a part thereof in a biological sample isolated from a patient. In particular embodiments, detection comprises (i) contacting the biological sample with an agent which binds specifically to the nucleic acid coding for the tumor-associated antigen or to the part thereof, to said tumor-associated antigen or said part thereof, to the antibody or to cytotoxic or T helper lymphocytes specific for the tumor-associated antigen or parts thereof, and (ii) detecting the formation of a complex between the agent and the nucleic acid or the part thereof, the tumor-associated antigen or the part thereof, the antibody or the cytotoxic or T helper lymphocytes. In one embodiment, the disease is characterized by expression or abnormal expression of two or more different tumor-associated antigens and detection comprises detection of two or more nucleic acids coding for said two or more different tumor-associated antigens or of parts thereof, detection of two or more different tumor-associated antigens or of parts thereof, detection of two or more antibodies binding to said two or more different tumor-associated antigens or to parts thereof or detection of two or more cytotoxic or T helper lymphocytes specific for said two or more different tumor-associated antigens. In a further embodiment, the biological sample isolated from the patient is compared to a comparable normal biological sample.

The methods of diagnosing according to the invention may also relate to the use of the tumor-associated antigens identified according to the invention as prognostic markers to predict a metastasis, e.g. by testing the migration behaviour of cells, and thus, a worsened course of the disease, whereby among others planning of a more aggressive therapy becomes possible. In particular, the sequences relating to TPTE (cf. example 2) are useful for this purpose. They are also useful to delimitate still benign alterations, e.g. hyperplasias, from tumor pre-stages which are already to be appraised as unfavourable, and thus, predict a tendency for cancer before an invasive tumor has formed.

In this embodiment, the invention relates to a method for diagnosis of a disease which is characterized by expression or abnormal expression of a tumor-associated antigen identified according to the invention, wherein the method comprises a determination of the migration behaviour of cells from a patient. In particularly preferred embodiments, the method serves for a determination of the extent of or the prediction of metastasis and/or lymph node metastases and/or distant metastases, wherein an increased migration behaviour of cells in particular embodiments is indicative for the fact that the patient tested has the disease which is characterized by expression or abnormal expression of a tumor-associated antigen identified according to the invention, will fall ill with said disease and/or has a potential for such a disease. In particularly preferred embodiments, an increased migration behaviour is indicative for a metastasis and/or the formation of lymph node metastases and/or distant metastases or a potential therefor. In this embodiment, the tumor-associated antigen identified according to the invention preferably has a sequence which is encoded by a nucleic acid selected from the group consisting of: (a) a nucleic acid which comprises a nucleic acid sequence selected from the group consisting of SEQ ID NOs: 19-21 and 54-57, a part or derivative thereof, (b) a nucleic acid which hybridizes with the nucleic acid of (a) under stringent conditions, (c) a nucleic acid which is degenerate with respect to the nucleic acid of (a) or (b), and (d) a nucleic acid which is complementary to the nucleic acid of (a), (b) or (c). The tumor-associated antigen preferably comprises an amino acid sequence selected from the group consisting of SEQ ID NOs: 22-24, 58-61, 81, 82, and 103-105, a part or a derivative thereof.

Methods of treatment according to the invention in this aspect preferably aim at the administration of pharmaceutical compositions which normalize or preferably inhibit the migration behaviour.

In a further embodiment, the invention relates to a method for diagnosis of a disease which is characterized by expression or abnormal expression of a tumor-associated antigen identified according to the invention, wherein the method comprises a determination of the methylation pattern and/or the degree of methylation within a nucleic acid which comprises a nucleic acid sequence which codes for the tumor-associated antigen, in particular within the non-coding regions thereof, more preferably within the promoter region thereof.

Preferably the tumor-associated antigen identified according to the invention has a sequence which is encoded by a nucleic acid selected from the group consisting of: (a) a nucleic acid which comprises a nucleic acid sequence selected from the group consisting of SEQ ID NOs: 19-21 and 54-57, a part or derivative thereof, (b) a nucleic acid which hybridizes with the nucleic acid of (a) under stringent conditions, (c) a nucleic acid which is degenerate with respect to the nucleic acid of (a) or (b), and (d) a nucleic acid which is complementary to the nucleic acid of (a), (b) or (c), and the determination is performed with respect to that nucleic acid, preferably within the promoter region thereof and in particular within the sequence shown in SEQ ID NO:822, in particular within the nucleotides of positions 121 to 540 of the sequence shown in SEQ ID NO:822 (promoter sequence of TPTE on chromosome 21, position −368/+952 with respect to the start of transcription) The tumor-associated antigen preferably comprises an amino acid sequence selected from the group consisting of SEQ ID NOs: 22-24, 58-61, 81, 82 and 103-105, a part or derivative thereof. A degree of methylation which is lower than that of a control or no methylation is preferably indicative for the fact that the patient tested has the disease which is characterized by expression or abnormal expression of a tumor-associated antigen identified according to the invention, will fall ill with said disease and/or has an increased potential for such a disease.

Methods for treatment according to the invention in this aspect preferably aim at the administration of pharmaceutical compositions which normalize, preferably increase the methylation pattern and/or the degree of methylation.

In a further aspect, the invention relates to a method for determining regression, course or onset of a disease characterized by expression or abnormal expression of a tumor-associated antigen identified according to the invention, which method comprises monitoring a sample from a patient who has said disease or is suspected of falling ill with said disease, with respect to one or more parameters selected from the group consisting of (i) the amount of nucleic acid which codes for the tumor-associated antigen or of a part thereof, (ii) the amount of the tumor-associated antigen or a part thereof, (iii) the amount of antibodies which bind to the tumor-associated antigen or to a part thereof, and (iv) the amount of cytolytic T cells or T helper cells which are specific for a complex between the tumor-associated antigen or a part thereof and an MHC molecule. The method preferably comprises determining the parameter(s) in a first sample at a first point in time and in a further sample at a second point in time and in which the course of the disease is determined by comparing the two samples. In particular embodiments, the disease is characterized by expression or abnormal expression of two or more different tumor-associated antigens and monitoring comprises monitoring (i) the amount of two or more nucleic acids which code for said two or more different tumor-associated antigens or of parts thereof, and/or (ii) the amount of said two or more different tumor-associated antigens or of parts thereof, and/or (iii) the amount of two or more antibodies which bind to said two or more different tumor-associated antigens or to parts thereof, and/or (iv) the amount of two or more cytolytic T cells or of T helper cells which are specific for complexes between said two or more different tumor-associated antigens or of parts thereof and MHC molecules.

According to the invention, detection of a nucleic acid or of a part thereof or monitoring the amount of a nucleic acid or of a part thereof may be carried out using a polynucleotide probe which hybridizes specifically to said nucleic acid or said part thereof or may be carried out by selective amplification of said nucleic acid or said part thereof. In one embodiment, the polynucleotide probe comprises a sequence of 6-50, in particular 10-30, 15-30 and 20-30, contiguous nucleotides of said nucleic acid.

In particular embodiments, the tumor-associated antigen to be detected or the part thereof is present intracellularly or on the cell surface. According to the invention, detection of a tumor-associated antigen or of a part thereof or monitoring the amount of a tumor-associated antigen or of a part thereof may be carried out using an antibody binding specifically to said tumor-associated antigen or said part thereof.

In further embodiments, the tumor-associated antigen to be detected or the part thereof is present in a complex with an MHC molecule, in particular an HLA molecule.

According to the invention, detection of an antibody or monitoring the amount of antibodies may be carried out using a protein or peptide binding specifically to said antibody.

According to the invention, detection of cytolytic T cells or of T helper cells or monitoring the amount of cytolytic T cells or of T helper cells which are specific for complexes between an antigen or a part thereof and MHC molecules may be carried out using a cell presenting the complex between said antigen or said part thereof and an MHC molecule.

The polynucleotide probe, the antibody, the protein or peptide or the cell, which is used for detection or monitoring, is preferably labeled in a detectable manner. In particular embodiments, the detectable marker is a radioactive marker or an enzymic marker. T lymphocytes may additionally be detected by detecting their proliferation, their cytokine production, and their cytotoxic activity triggered by specific stimulation with the complex of MHC and tumor-associated antigen or parts thereof. T lymphocytes may also be detected via a recombinant MHC molecule or else a complex of two or more MHC molecules which are loaded with the particular immunogenic fragment of one or more of the tumor-associated antigens and which can identify the specific T lymphocytes by contacting the specific T cell receptor.

In a further aspect, the invention relates to a method of treating, diagnosing or monitoring a disease characterized by expression or abnormal expression of a tumor-associated antigen identified according to the invention, which method comprises administering an antibody which binds to said tumor-associated antigen or to a part thereof and which is coupled to a therapeutic or diagnostic agent. The antibody may be a monoclonal antibody. In further embodiments, the antibody is a chimeric or humanized antibody or a fragment of a natural antibody.

The invention also relates to a method of treating a patient having a disease characterized by expression or abnormal expression of a tumor-associated antigen identified according to the invention, which method comprises (i) removing a sample containing immunoreactive cells from said patient, (ii) contacting said sample with a host cell expressing said tumor-associated antigen or a part thereof, under conditions which favor production of cytolytic T cells against said tumor-associated antigen or a part thereof, and (iii) introducing the cytolytic T cells into the patient in an amount suitable for lysing cells expressing the tumor-associated antigen or a part thereof. The invention likewise relates to cloning the T cell receptor of cytolytic T cells against the tumor-associated antigen. Said receptor may be transferred to other T cells which thus receive the desired specificity and, as under (iii), may be introduced into the patient.

In one embodiment, the host cell endogenously expresses an HLA molecule. In a further embodiment, the host cell recombinantly expresses an HLA molecule and/or the tumor-associated antigen or the part thereof. The host cell is preferably nonproliferative. In a preferred embodiment, the host cell is an antigen-presenting cell, in particular a dendritic cell, a monocyte or a macrophage.

In a further aspect, the invention relates to a method of treating a patient having a disease characterized by expression or abnormal expression of a tumor-associated antigen, which method comprises (i) identifying a nucleic acid which codes for a tumor-associated antigen identified according to the invention and which is expressed by cells associated with said disease, (ii) transfecting a host cell with said nucleic acid or a part thereof, (iii) culturing the transfected host cell for expression of said nucleic acid (this is not obligatory when a high rate of transfection is obtained), and (iv) introducing the host cells or an extract thereof into the patient in an amount suitable for increasing the immune response to the patient's cells associated with the disease. The method may further comprise identifying an MHC molecule presenting the tumor-associated antigen or a part thereof, with the host cell expressing the identified MHC molecule and presenting said tumor-associated antigen or a part thereof. The immune response may comprise a B cell response or a T cell response. Furthermore, a T cell response may comprise production of cytolytic T cells and/or T helper cells which are specific for the host cells presenting the tumor-associated antigen or a part thereof or specific for cells of the patient which express said tumor-associated antigen or a part thereof.

The invention also relates to a method of treating a disease characterized by expression or abnormal expression of a tumor-associated antigen identified according to the invention, which method comprises (i) identifying cells from the patient which express abnormal amounts of the tumor-associated antigen, (ii) isolating a sample of said cells, (iii) culturing said cells, and (iv) introducing said cells into the patient in an amount suitable for triggering an immune response to the cells.

Preferably, the host cells used according to the invention are nonproliferative or are rendered nonproliferative. A disease characterized by expression or abnormal expression of a tumor-associated antigen is in particular cancer.

The present invention furthermore relates to a nucleic acid selected from the group consisting of (a) a nucleic acid which comprises a nucleic acid sequence selected from the group consisting of SEQ ID NOs: 2-5, 20-21, 31-33, 39, 54-57, 62, 63, 85-88, a part or derivative thereof, (b) a nucleic acid which hybridizes with the nucleic acid of (a) under stringent conditions, (c) a nucleic acid which is degenerate with respect to the nucleic acid of (a) or (b), and (d) a nucleic acid which is complementary to the nucleic acid of (a), (b) or (c). The invention furthermore relates to a nucleic acid, which codes for a protein or polypeptide comprising an amino acid sequence selected from the group consisting of SEQ ID NOs: 7-13, 14-18, 23-24, 34-36, 58-61, 64, 65, 89-100, 101-107, a part or derivative thereof.

In a further aspect, the invention relates to promoter sequences of nucleic acids of the invention. These sequences may be functionally linked to another gene, preferably in an expression vector, and thus ensure selective expression of said gene in appropriate cells.

In a further aspect, the invention relates to a recombinant nucleic acid molecule, in particular DNA or RNA molecule, which comprises a nucleic acid of the invention.

The invention also relates to host cells which contain a nucleic acid of the invention or a recombinant nucleic acid molecule comprising a nucleic acid of the invention.

The host cell may also comprise a nucleic acid coding for a HLA molecule. In one embodiment, the host cell endogenously expresses the HLA molecule. In a further embodiment, the host cell recombinantly expresses the HLA molecule and/or the nucleic acid of the invention or a part thereof. Preferably, the host cell is nonproliferative. In a preferred embodiment, the host cell is an antigen-presenting cell, in particular a dendritic cell, a monocyte or a macrophage.

In a further embodiment, the invention relates to oligonucleotides which hybridize with a nucleic acid identified according to the invention and which may be used as genetic probes or as "antisense" molecules. Nucleic acid molecules in the form of oligonucleotide primers or competent samples, which hybridize with a nucleic acid identified according to the invention or parts thereof, may be used for finding nucleic acids which are homologous to said nucleic acid identified according to the invention. PCR amplification, Southern and Northern hybridization may be employed for finding homologous nucleic acids. Hybridization may be carried out under low stringency, more preferably under medium stringency and most preferably under high stringency conditions. The term "stringent conditions" according to the invention refers to conditions which allow specific hybridization between polynucleotides.

In a further aspect, the invention relates to a protein or polypeptide which is encoded by a nucleic acid selected from the group consisting of (a) a nucleic acid which comprises a nucleic acid sequence selected from the group consisting of SEQ ID NOs: 2-5, 20-21, 31-33, 39, 54-57, 62, 63, 85-88, a part or derivative thereof, (b) a nucleic acid which hybridizes with the nucleic acid of (a) under stringent conditions, (c) a nucleic acid which is degenerate with respect to the nucleic acid of (a) or (b), and (d) a nucleic acid which is complementary to the nucleic acid of (a), (b) or (c). In a preferred embodiment, the invention relates to a protein or polypeptide which comprises an amino acid sequence selected from the group consisting of SEQ ID NOs: 7-13, 14-18, 23-24, 34-36, 58-61, 64, 65, 89-100, 101-107, a part or derivative thereof. In a further aspect, the invention relates to an immunogenic fragment of a tumor-associated antigen identified according to the invention. Said fragment preferably binds to a human HLA receptor or to a human antibody. A fragment of the invention preferably comprises a sequence of at least 6, in particular at least 8, at least 10, at least 12, at least 15, at least 20, at least 30 or at least 50, amino acids.

In a further aspect, the invention relates to an agent which binds to a tumor-associated antigen identified according to the invention or to a part thereof. In a preferred embodiment, the agent is an antibody. In further embodiments, the antibody is a chimeric, a humanized antibody or an antibody produced by combinatory techniques or is a fragment of an antibody. Furthermore, the invention relates to an antibody which binds selectively to a complex of (i) a tumor-associated antigen identified according to the invention or a part thereof and (ii) an MHC molecule to which said tumor-associated antigen identified according to the invention or said part thereof binds, with said antibody not binding to (i) or (ii) alone. An antibody of the invention may be a monoclonal antibody. In further embodiments, the antibody is a chimeric or humanized antibody or a fragment of a natural antibody.

The invention furthermore relates to a conjugate between an agent of the invention which binds to a tumor-associated antigen identified according to the invention or to a part thereof or an antibody of the invention and a therapeutic or diagnostic agent. In one embodiment, the therapeutic or diagnostic agent is a toxin.

In a further aspect, the invention relates to a kit for detecting expression or abnormal expression of a tumor-associated antigen identified according to the invention, which kit comprises agents for detection (i) of the nucleic acid which codes for the tumor-associated antigen or of a part thereof, (ii) of the tumor-associated antigen or of a part thereof, (iii) of antibodies which bind to the tumor-associated antigen or to a part thereof, and/or (iv) of T cells which are specific for a complex between the tumor-associated antigen or a part thereof and an MHC molecule. In one embodiment, the agents for detection of the nucleic acid or the part thereof are nucleic acid molecules for selective amplification of said nucleic acid, which comprise, in particular a sequence of 6-50, in particular 10-30, 15-30 and 20-30, contiguous nucleotides of said nucleic acid.

DETAILED DESCRIPTION OF THE INVENTION

According to the invention, genes are described which are expressed in tumor cells selectively or aberrantly and which are tumor-associated antigens.

According to the invention, these genes or their derivatives are preferred target structures for therapeutic approaches. Conceptionally, said therapeutic approaches may aim at inhibiting the activity of the selectively expressed tumor-associated genetic product. This is useful, if said aberrant respective selective expression is functionally important in tumor pathogenecity and if its ligation is accompanied by selective damage of the corresponding cells. Other therapeutic concepts contemplate tumor-associated antigens as labels which recruit effector mechanisms having cell-damaging potential selectively to tumor cells. Here, the function of the target molecule itself and its role in tumor development are totally irrelevant.

"Derivative" of a nucleic acid means according to the invention that single or multiple nucleotide substitutions, deletions and/or additions are present in said nucleic acid. Furthermore, the term "derivative" also comprises chemical derivatization of a nucleic acid on a nucleotide base, on the sugar or on the phosphate. The term "derivative" also comprises nucleic acids which contain nucleotides and nucleotide analogs not occurring naturally.

According to the invention, a nucleic acid is preferably deoxyribonucleic acid (DNA) or ribonucleic acid (RNA). Nucleic acids comprise according to the invention genomic DNA, cDNA, mRNA, recombinantly produced and chemically synthesized molecules. According to the invention, a nucleic acid may be present as a single-stranded or double-stranded and linear or covalently circularly closed molecule.

The nucleic acids described according to the invention have preferably been isolated. The term "isolated nucleic acid" means according to the invention that the nucleic acid was (i) amplified in vitro, for example by polymerase chain reaction (PCR), (ii) recombinantly produced by cloning, (iii) purified, for example by cleavage and gel-electrophoretic fractionation, or (iv) synthesized, for example by chemical synthesis. An isolated nucleic acid is a nucleic acid which is available for manipulation by recombinant DNA techniques.

A nucleic acid is "complementary" to another nucleic acid if the two sequences are capable of hybridizing and forming a stable duplex with one another, with hybridization preferably being carried out under conditions which allow specific hybridization between polynucleotides (stringent conditions). Stringent conditions are described, for example, in Molecular-Cloning: A Laboratory Manual, J. Sambrook et al., Editors, 2nd Edition, Cold Spring Harbor Laboratory press, Cold Spring Harbor, N.Y., 1989 or Current Protocols in Molecular Biology, F. M. Ausubel et al., Editors, John Wiley & Sons, Inc., New York and refer, for example, to hybridization at 65° C. in hybridization buffer (3.5×SSC, 0.02% Ficoll, 0.02% polyvinylpyrrolidone, 0.02% bovine serum albumin, 2.5 mM $NaH_2PO_4$ (pH 7), 0.5% SDS, 2 mM EDTA). SSC is 0.15 M sodium chloride/0.15 M sodium citrate, pH 7. After hybridization, the membrane to which the DNA has been transferred is washed, for example, in 2×SSC at room temperature and then in 0.1-0.5×SSC/0.1×SSC at temperatures of up to 68° C.

According to the invention, complementary nucleic acids have at least 40%, in particular at least 50%, at least 60%, at least 70%, at least 80%, at least 90% and preferably at least 95%, at least 98 or at least 99%, identical nucleotides.

Nucleic acids coding for tumor-associated antigens may, according to the invention, be present alone or in combination with other nucleic acids, in particular heterologous nucleic acids. In preferred embodiments, a nucleic acid is functionally linked to expression control sequences or regulatory sequences which may be homologous or heterologous with respect to said nucleic acid. A coding sequence and a regulatory sequence are "functionally" linked to one another, if they are covalently linked to one another in such a way that expression or transcription of said coding sequence is under the control or under the influence of said regulatory sequence. If the coding sequence is to be translated into a functional protein, then, with a regulatory sequence functionally linked to said coding sequence, induction of said regulatory sequence results in transcription of said coding sequence, without causing a frame shift in the coding sequence or said coding sequence not being capable of being translated into the desired protein or peptide.

The term "expression control sequence" or "regulatory sequence" comprises according to the invention promoters, enhancers and other control elements which regulate expression of a gene. In particular embodiments of the invention, the expression control sequences can be regulated. The exact structure of regulatory sequences may vary as a function of the species or cell type, but generally comprises 5'untranscribed and 5'untranslated sequences which are involved in initiation of transcription and translation, respectively, such as TATA box, capping sequence, CAAT sequence, and the like. More specifically, 5'untranscribed regulatory sequences comprise a promoter region which includes a promoter sequence for transcriptional control of the functionally linked gene. Regulatory sequences may also comprise enhancer sequences or upstream activator sequences.

Thus, on the one hand, the tumor-associated antigens illustrated herein may be combined with any expression control sequences and promoters. On the other hand, however, the promoters of the tumor-associated genetic products illustrated herein may, according to the invention, be combined with any other genes. This allows the selective activity of these promoters to be utilized.

According to the invention, a nucleic acid may furthermore be present in combination with another nucleic acid which codes for a polypeptide controlling secretion of the protein or polypeptide encoded by said nucleic acid from a host cell. According to the invention, a nucleic acid may also be present in combination with another nucleic acid which codes for a polypeptide causing the encoded protein or polypeptide to be anchored on the cell membrane of the host cell or compartmentalized into particular organelles of said cell.

In a preferred embodiment, a recombinant DNA molecule is according to the invention a vector, where appropriate with a promoter, which controls expression of a nucleic acid, for example a nucleic acid coding for a tumor-associated antigen of the invention. The term "vector" is used here in its most general meaning and comprises any intermediary vehicle for a nucleic acid which enables said nucleic acid, for example, to be introduced into prokaryotic and/or eukaryotic cells and, where appropriate, to be integrated into a genome. Vectors of this kind are preferably replicated and/or expressed in the cells. An intermediary vehicle may be adapted, for example, to the use in electroporation, in bombardment with microprojectiles, in liposomal administration, in the transfer with the aid of agrobacteria or in insertion via DNA or RNA viruses. Vectors comprise plasmids, phagemids or viral genomes.

The nucleic acids coding for a tumor-associated antigen identified according to the invention may be used for transfection of host cells. Nucleic acids here mean both recombinant DNA and RNA. Recombinant RNA may be prepared by in-vitro transcription of a DNA template. Furthermore, it may be modified by stabilizing sequences, capping and polyadenylation prior to application. According to the invention, the term "host cell" relates to any cell which can be transformed or transfected with an exogenous nucleic acid. The term "host cells" comprises according to the invention prokaryotic (e.g. *E. coli*) or eukaryotic cells (e.g. dendritic cells, B cells, CHO cells, COS cells, K562 cells, yeast cells and insect cells). Particular preference is given to mammalian cells such as cells from humans, mice, hamsters, pigs, goats, primates. The cells may be derived from a multiplicity of tissue types and comprise primary cells and cell lines. Specific examples comprise keratinocytes, peripheral blood leukocytes, stem cells of the bone marrow and embryonic stem cells. In further embodiments, the host cell is an antigen-presenting cell, in particular a dendritic cell, monocyte or a macrophage. A nucleic acid may be present in the host cell in the form of a single copy or of two or more copies and, in one embodiment, is expressed in the host cell.

According to the invention, the term "expression" is used in its most general meaning and comprises the production of RNA or of RNA and protein. It also comprises partial expression of nucleic acids. Furthermore, expression may be carried out transiently or stably. Preferred expression systems in mammalian cells comprise pcDNA3.1 and pRc/CMV (Invitrogen, Carlsbad, Calif.), which contain a selective marker such as a gene imparting resistance to G418 (and thus enabling stably transfected cell lines to be selected) and the enhancer-promoter sequences of cytomegalovirus (CMV).

In those cases of the invention in which an HLA molecule presents a tumor-associated antigen or a part thereof, an expression vector may also comprise a nucleic acid sequence coding for said HLA molecule. The nucleic acid sequence coding for the HLA molecule may be present on the same expression vector as the nucleic acid coding for the tumor-associated antigen or the part thereof, or both nucleic acids may be present on different expression vectors. In the latter case, the two expression vectors may be cotransfected into a cell. If a host cell expresses neither the tumor-associated antigen or the part thereof nor the HLA molecule, both nucleic acids coding therefor are transfected into the cell either on the same expression vector or on different expression vectors. If the cell already expresses the HLA molecule, only the nucleic acid sequence coding for the tumor-associated antigen or the part thereof can be transfected into the cell.

The invention also comprises kits for amplification of a nucleic acid coding for a tumor-associated antigen. Such kits comprise, for example, a pair of amplification primers which hybridize to the nucleic acid coding for the tumor-associated antigen. The primers preferably comprise a sequence of 6-50, in particular 10-30, 15-30 and 20-30 contiguous nucleotides of the nucleic acid and are nonoverlapping, in order to avoid the formation of primer dimers. One of the primers will hybridize to one strand of the nucleic acid coding for the tumor-associated antigen, and the other primer will hybridize to the complementary strand in an arrangement which allows amplification of the nucleic acid coding for the tumor-associated antigen.

"Antisense" molecules or "antisense" nucleic acids may be used for regulating, in particular reducing, expression of a nucleic acid. The term “antisense molecule” or “antisense nucleic acid” refers according to the invention to an oligonucleotide which is an oligoribonucleotide, oligodeoxyribonucleotide, modified oligoribonucleotide or modified oligodeoxyribonucleotide and which hybridizes under physiological conditions to DNA comprising a particular gene or to mRNA of said gene, thereby inhibiting transcription of said gene and/or translation of said mRNA. According to the invention, the “antisense molecule” also comprises a construct which contains a nucleic acid or a part thereof in reverse orientation with respect to its natural promoter. An antisense transcript of a nucleic acid or of a part thereof may form a duplex with the naturally occurring mRNA specifying the enzyme and thus prevent accumulation of or translation of the mRNA into the active enzyme. Another possibility is the use of ribozymes for inactivating a nucleic acid. Antisense oligonucleotides preferred according to the invention have a sequence of 6-50, in particular 10-30, 15-30 and 20-30, contiguous nucleotides of the target nucleic acid and preferably are fully complementary to the target nucleic acid or to a part thereof.

In preferred embodiments, the antisense oligonucleotide hybridizes with an N-terminal or 5' upstream site such as a translation initiation site, transcription initiation site or promoter site. In further embodiments, the antisense oligonucleotide hybridizes with a 3'untranslated region or mRNA splicing site.

In one embodiment, an oligonucleotide of the invention consists of ribonucleotides, deoxyribonucleotides or a combination thereof, with the 5' end of one nucleotide and the 3' end of another nucleotide being linked to one another by a phosphodiester bond. These oligonucleotides may be synthesized in the conventional manner or produced recombinantly.

In preferred embodiments, an oligonucleotide of the invention is a “modified” oligonucleotide. Here, the oligonucleotide may be modified in very different ways, without impairing its ability to bind its target, in order to increase, for example, its stability or therapeutic efficacy. According to the invention, the term “modified oligonucleotide” means an oligonucleotide in which (i) at least two of its nucleotides are linked to one another by a synthetic internucleoside bond (i.e. an internucleoside bond which is not a phosphodiester bond) and/or (ii) a chemical group which is usually not found in nucleic acids is covalently linked to the oligonucleotide. Preferred synthetic internucleoside bonds are phosphorothioates, alkyl phosphonates, phosphorodithioates, phosphate esters, alkyl phosphonothioates, phosphoramidates, carbamates, carbonates, phosphate triesters, acetamidates, carboxymethyl esters and peptides.

The term “modified oligonucleotide” also comprises oligonucleotides having a covalently modified base and/or sugar. “Modified oligonucleotides” comprise, for example, oligonucleotides with sugar residues which are covalently bound to low molecular weight organic groups other than a hydroxyl group at the 3' position and a phosphate group at the 5' position. Modified oligonucleotides may comprise, for example, a 2' —O-alkylated ribose residue or another sugar instead of ribose, such as arabinose.

Preferably, the proteins and polypeptides described according to the invention have been isolated. The terms “isolated protein” or “isolated polypeptide” mean that the protein or polypeptide has been separated from its natural environment. An isolated protein or polypeptide may be in an essentially purified state. The term “essentially purified” means that the protein or polypeptide is essentially free of other substances with which it is associated in nature or in vivo.

Such proteins and polypeptides may be used, for example, in producing antibodies and in an immunological or diagnostic assay or as therapeutics. Proteins and polypeptides described according to the invention may be isolated from biological samples such as tissue or cell homogenates and may also be expressed recombinantly in a multiplicity of pro- or eukaryotic expression systems.

For the purposes of the present invention, “derivatives” of a protein or polypeptide or of an amino acid sequence comprise amino acid insertion variants, amino acid deletion variants and/or amino acid substitution variants.

Amino acid insertion variants comprise amino- and/or carboxy-terminal fusions and also insertions of single or two or more amino acids in a particular amino acid sequence. In the case of amino acid sequence variants having an insertion, one or more amino acid residues are inserted into a particular site in an amino acid sequence, although random insertion with appropriate screening of the resulting product is also possible. Amino acid deletion variants are characterized by the removal of one or more amino acids from the sequence. Amino acid substitution variants are characterized by at least one residue in the sequence being removed and another residue being inserted in its place. Preference is given to the modifications being in positions in the amino acid sequence which are not conserved between homologous proteins or polypeptides. Preference is given to replacing amino acids with other ones having similar properties such as hydrophobicity, hydrophilicity, electronegativity, volume of the side chain and the like (conservative substitution). Conservative substitutions, for example, relate to the exchange of one amino acid with another amino acid listed below in the same group as the amino acid to be substituted:

1. small aliphatic, nonpolar or slightly polar residues: Ala, Ser, Thr (Pro, Gly)
2. negatively charged residues and their amides: Asn, Asp, Glu, Gln
3. positively charged residues: His, Arg, Lys
4. large aliphatic, nonpolar residues: Met, Leu, Ile, Val (Cys)
5. large aromatic residues: Phe, Tyr, Trp.

Owing to their particular part in protein architecture, three residues are shown in brackets. Gly is the only residue without a side chain and thus imparts flexibility to the chain. Pro has an unusual geometry which greatly restricts the chain. Cys can form a disulfide bridge.

The amino acid variants described above may be readily prepared with the aid of known peptide synthesis techniques such as, for example, by solid phase synthesis (Merrifield, 1964) and similar methods or by recombinant DNA manipulation. Techniques for introducing substitution mutations at predetermined sites into DNA which has a known or partially known sequence are well known and comprise M13 mutagenesis, for example. The manipulation of DNA sequences for preparing proteins having substitutions, insertions or deletions, is described in detail in Sambrook et al. (1989), for example.

According to the invention, “derivatives” of proteins or polypeptides also comprise single or multiple substitutions, deletions and/or additions of any molecules associated with the enzyme, such as carbohydrates, lipids and/or proteins or polypeptides. The term “derivative” also extends to all functional chemical equivalents of said proteins or polypeptides.

According to the invention, a part or fragment of a tumor-associated antigen has a functional property of the polypeptide from which it has been derived. Such functional properties comprise the interaction with antibodies, the interaction with other polypeptides or proteins, the selective binding of nucleic acids and an enzymatic activity. A particular property is the ability to form a complex with HLA and, where appropriate, generate an immune response. This immune response may be based on stimulating cytotoxic or T helper cells. A part or fragment of a tumor-associated antigen of the invention preferably comprises a sequence of at least 6, in particular at least 8, at least 10, at least 12, at least 15, at least 20, at least 30 or at least 50, consecutive amino acids of the tumor-associated antigen.

According to the invention, preferred parts or fragments of a tumor-associated antigen preferably have one of the sequences listed below which are derived from the tumor-associated antigens identified according to the invention, and they are preferably peptide epitopes which according to the invention are in particular useful for stimulating cytotoxic T lymphocytes in vivo and also for preparing expanded and stimulated T lymphocytes for the therapeutic adoptive transfer ex vivo. These sequences are in particular peptide epitopes for the MHC class I alleles listed below:

| Pos | Epitope | Score |
|---|---|---|
| LDHC | | |
| A*0201-Octamers | | |
| 23 | ITIVGTGA | 9 |
| 27 | GTGAVGMA | 9 |
| 29 | GAVGMACA | 9 |
| 38 | SILLKDLA | 9 |
| 42 | KDLADELA | 9 |
| 47 | ELALVDVA | 9 |
| 80 | GKDYSVSA | 9 |
| 89 | SRIVIVTA | 9 |
| 91 | IVIVTAGA | 9 |
| 101 | QEGETRLA | 9 |
| 108 | ALVQRNVA | 9 |
| 116 | IMKSIIPA | 9 |
| 161 | SGCNLDSA | 9 |
| 200 | LWSGVNVA | 9 |
| 203 | GVNVAGVA | 9 |
| 231 | HKQVIQSA | 9 |
| 244 | LKGYTSWA | 9 |
| 307 | NLNSEEEA | 9 |
| 313 | EALFKKSA | 9 |
| A*0201-Nonamers | | |
| 43 | DLADELALV | 28 |
| 172 | YLIGEKLGV | 28 |
| 145 | YIVWKISGL | 26 |
| 262 | SILKNLRRV | 26 |
| 279 | GLYGIKEEL | 26 |

-continued

| Pos | Epitope | Score |
|---|---|---|
| 32 | GMACAISIL | 25 |
| 40 | LLKDLADEL | 25 |
| 210 | ALKTLDPKL | 25 |
| 36 | AISILLKDL | 24 |
| 69 | SLFFSTSKI | 24 |
| 142 | ILTYIVWKI | 24 |
| 251 | AIGLSVMDL | 24 |
| 275 | TMVKGLYGI | 24 |
| 23 | ITIVGTGAV | 23 |
| 86 | SANSRIVIV | 23 |
| 108 | ALVQRNVAI | 23 |
| 116 | IMKSIIPAI | 23 |
| 255 | SVMDLVGSI | 23 |
| 286 | ELFLSIPCV | 23 |
| 47 | ELALVDVAL | 22 |
| 50 | LVDVALDKL | 22 |
| 57 | KLKGEMMDL | 22 |
| 77 | ITSGKDYSV | 22 |
| 106 | RLALVQRNV | 22 |
| 132 | KILVVSNPV | 22 |
| 307 | NLNSEEEAL | 22 |
| 314 | ALFKKSAET | 22 |
| 7 | QLIEKLIED | 21 |
| 39 | ILLKDLADE | 20 |
| 62 | MMDLQHGSL | 20 |
| 119 | SIIPAIVHY | 20 |
| 135 | VVSNPVDIL | 20 |
| 206 | VAGVALKTL | 20 |
| 322 | TLWNIQKDL | 20 |
| 54 | ALDKLKGEM | 19 |
| 115 | AIMKSIIPA | 19 |
| 199 | PLWSGVNVA | 19 |
| 203 | GVNVAGVAL | 19 |
| 213 | TLDPKLGTD | 19 |
| 243 | KLKGYTSWA | 19 |
| 256 | VMDLVGSIL | 19 |
| 259 | LVGSILKNL | 19 |
| 128 | SPDCKILVV | 18 |
| 157 | RVIGSGCNL | 18 |

-continued

| Pos | Epitope | Score |
|---|---|---|
| 258 | DLVGSILKN | 18 |
| 265 | KNLRRVHPV | 18 |
| 295 | LGRNGVSDV | 18 |
| A*0201-Decamers | | |
| 49 | ALVDVALDKL | 29 |
| 39 | ILLKDLADEL | 26 |
| 115 | AIMKSIIPAI | 25 |
| 149 | KISGLPVTRV | 25 |
| 294 | VLGRNGVSDV | 25 |
| 314 | ALFKKSAETL | 25 |
| 44 | LADELALVDV | 24 |
| 189 | IIGEHGDSSV | 24 |
| 258 | DLVGSILKNL | 24 |
| 141 | DILTYIVWKI | 23 |
| 205 | NVAGVALKTL | 23 |
| 108 | ALVQRNVAIM | 22 |
| 133 | ILVVSNPVDI | 22 |
| 250 | WAIGLSVMDL | 22 |
| 3 | TVKEQLIEKL | 21 |
| 32 | GMACAISILL | 21 |
| 76 | KITSGKDYSV | 21 |
| 116 | IMKSIIPAIV | 21 |
| 200 | LWSGVNVAGV | 21 |
| 243 | KLKGYTSWAI | 21 |
| 274 | STMVKGLYGI | 21 |
| 282 | GIKEELFLSI | 21 |
| 134 | LVVSNPVDIL | 20 |
| 164 | NLDSARFRYL | 20 |
| 172 | YLIGEKLGVH | 20 |
| 209 | VALKTLDPKL | 20 |
| 251 | AIGLSVMDLV | 20 |
| 22 | KITIVGTGAV | 19 |
| 35 | CAISILLKDL | 19 |
| 42 | KDLADELALV | 19 |
| 61 | EMMDLQHGSL | 19 |
| 85 | VSANSRIVIV | 19 |
| 107 | LALVQRNVAI | 19 |
| 119 | SIIPAIVHYS | 19 |
| 247 | YTSWAIGLSV | 19 |

-continued

| Pos | Epitope | Score |
|---|---|---|
| 322 | TLWNIQKDLI | 19 |
| 7 | QLIEKLIEDD | 18 |
| 11 | KLIEDDENSQ | 18 |
| 38 | SILLKDLADE | 18 |
| 101 | QEGETRLALV | 18 |
| 127 | YSPDCKILVV | 18 |
| 146 | IVWKISGLPV | 18 |
| 197 | SVPLWSGVNV | 18 |
| 229 | NIHKQVIQSA | 18 |
| 235 | IQSAYEIIKL | 18 |
| 253 | GLSVMDLVGS | 18 |
| 255 | SVMDLVGSIL | 18 |
| 264 | LKNLRRVHPV | 18 |
| 266 | NLRRVHPVST | 18 |
| 286 | ELFLSIPCVL | 18 |
| *** | | |
| A*2402-Nonamers | | |
| 280 | LYGIKEELF | 24 |
| 126 | HYSPDCKIL | 21 |
| 246 | GYTSWAIGL | 20 |
| 287 | LFLSIPCVL | 20 |
| 315 | LFKKSAETL | 17 |
| 4 | VKEQLIEKL | 16 |
| 63 | MDLQHGSLF | 15 |
| 5 | KEQLIEKLI | 14 |
| 125 | VHYSPDCKI | 14 |
| 142 | ILTYIVWKI | 14 |
| A*2402-Decamers | | |
| 144 | TYIVWKISGL | 24 |
| 82 | DYSVSANSRI | 20 |
| 280 | LYGIKEELFL | 20 |
| 169 | RFRYLIGEKL | 18 |
| 209 | VALKTLDPKL | 17 |
| 3 | TVKEQLIEKL | 16 |
| 141 | DILTYIVWKI | 15 |
| 180 | VHPTSCHGWI | 15 |
| 4 | VKEQLIEKLI | 14 |
| 14 | EDDENSQCKI | 14 |
| *** | | |

-continued

| Pos | Epitope | Score |
|---|---|---|
| A*01-Nonamers | | |
| 164 | NLDSARFRY | 27 |
| 273 | VSTMVKGLY | 24 |
| 137 | SNPVDILTY | 23 |
| 119 | SIIPAIYHY | 21 |
| 300 | VSDVVKINL | 21 |
| 309 | NSEEEALFK | 20 |
| 128 | SPDCKILVV | 19 |
| 238 | AYEIIKLKG | 19 |
| 283 | IKEELFLSI | 19 |
| 75 | SKITSGKDY | 18 |
| 44 | LADELALVD | 17 |
| 136 | VSNPVDILT | 17 |
| 239 | YEIIKLKGY | 17 |
| 59 | KGEMMDLQH | 16 |
| 219 | GTDSDKEHW | 16 |
| 221 | DSDKEHWKN | 16 |
| 213 | TLDPKLGTD | 15 |
| 231 | HKQVIQSAY | 15 |
| 274 | STMVKGLYG | 15 |
| 289 | LSIPCVLGR | 15 |
| 311 | EEEALFKKS | 15 |
| A*01-Decamers | | |
| 136 | VSNPVDILTY | 30 |
| 238 | AYEIIKLKGY | 26 |
| 74 | TSKITSGKDY | 20 |
| 118 | KSIIPAIVHY | 19 |
| 100 | QQEGETRLAL | 18 |
| 102 | EGETRLALVQ | 17 |
| 256 | VMDLVGSILK | 17 |
| 272 | PVSTMVKGLY | 17 |
| 300 | VSDVVKINLN | 17 |
| 310 | SEEEALFKKS | 17 |
| 319 | SAETLWNIQK | 17 |
| 41 | LKDLADELAL | 16 |
| 163 | CNLDSARFRY | 16 |
| 193 | HGDSSVPLWS | 16 |
| 213 | TLDPKLGTDS | 16 |
| 219 | GTDSDKEHWK | 16 |

-continued

| Pos | Epitope | Score |
|---|---|---|
| 309 | NSEEEALFKK | 16 |
| 139 | PVDILTYIVW | 15 |
| 223 | DKEHWKNIHK | 15 |
| 230 | IHKQVIQSAY | 15 |
| 247 | YTSWAIGLSV | 15 |
| *** | | |
| A*03-Nonamers | | |
| 49 | ALVDVALDK | 31 |
| 149 | KISGLPVTR | 26 |
| 119 | SIIPAIVHY | 25 |
| 141 | DILTYIVWK | 25 |
| 91 | IVIVTAGAR | 24 |
| 276 | MVKGLYGIK | 24 |
| 124 | IVHYSPDCK | 23 |
| 263 | ILKNLRRVH | 23 |
| 3 | TVKEQLIEK | 22 |
| 93 | IVTAGARQQ | 22 |
| 157 | RVIGSGCNL | 22 |
| 294 | VLGRNGVSD | 22 |
| 297 | RNGVSDVVK | 22 |
| 25 | IVGTGAVGM | 21 |
| 266 | NLRRVHPVS | 21 |
| 293 | CVLGRNGVS | 21 |
| 24 | TIVGTGAVG | 20 |
| 108 | ALVQRNVAI | 20 |
| 205 | NVAGVALKT | 20 |
| 241 | IIKLKGYTS | 20 |
| 243 | KLKGYTSWA | 20 |
| 269 | RVHPVSTMV | 20 |
| 64 | DLQHGSLFF | 19 |
| 110 | VQRNVAIMK | 19 |
| 173 | LIGEKLGVH | 19 |
| 213 | TLDPKLGTD | 19 |
| 34 | ACAISILLK | 18 |
| 47 | ELALVDVAL | 18 |
| 118 | KSIIPAIVH | 18 |
| 169 | RFRYLIGEK | 18 |
| 172 | YLIGEKLGV | 18 |

-continued

| Pos | Epitope | Score |
|---|---|---|
| 203 | GVNVAGVAL | 18 |
| 233 | QVIQSAYEI | 18 |
| A*03-Decamers | | |
| 269 | RVHPVSTMVK | 32 |
| 109 | LVQRNVAIMK | 27 |
| 172 | YLIGEKLGVH | 24 |
| 203 | GVNVAGVALK | 23 |
| 266 | NLRRVHPVST | 23 |
| 293 | CVLGRNGVSD | 23 |
| 43 | DLADELALVD | 22 |
| 90 | RIVIVTAGAR | 22 |
| 123 | AIVHYSPDCK | 22 |
| 208 | GVALKTLDPK | 22 |
| 91 | IVIVTAGARQ | 21 |
| 106 | RLALVQRNVA | 21 |
| 50 | LVDVALDKLK | 20 |
| 177 | KLGVHPTSCH | 20 |
| 262 | SILKNLRRVH | 20 |
| 279 | GLYGIKEELF | 20 |
| 296 | GRNGVSDVVK | 20 |
| 314 | ALFKKSAETL | 20 |
| 11 | KLIEDDENSQ | 19 |
| 140 | VDILTYIVWK | 19 |
| 154 | PVTRVIGSGC | 19 |
| 157 | RVIGSGCNLD | 19 |
| 197 | SVPLWSGVNV | 19 |
| 263 | ILKNLRRVHP | 19 |
| 30 | AVGMACAISI | 18 |
| 48 | LALVDVALDK | 18 |
| 84 | SVSANSRIVI | 18 |
| 93 | IVTAGARQQE | 18 |
| 146 | IVWKISGLPV | 18 |
| 188 | WIIGEHGDSS | 18 |
| 234 | VIQSAYEIIK | 18 |
| 240 | EIIKLKGYTS | 18 |
| 255 | SVMDLVGSIL | 18 |
| 288 | FLSIPCVLGR | 18 |
| *** | | |

-continued

| Pos | Epitope | Score |
|---|---|---|
| B*0702-Nonamers | | |
| 128 | SPDCKILVV | 20 |
| 198 | VPLWSGVNV | 19 |
| 138 | NPVDILTYI | 17 |
| 135 | VVSNPVDIL | 16 |
| 181 | HPTSCHGWI | 16 |
| 42 | KDLADELAL | 15 |
| 47 | ELALVDVAL | 15 |
| 101 | QEGETRLAL | 15 |
| 192 | EHGDSSVPL | 15 |
| 36 | AISILLKDL | 14 |
| B*0702-Decamers | | |
| 271 | HPVSTMVKGL | 21 |
| 198 | VPLWSGVNVA | 18 |
| 291 | IPCVLGRNGV | 18 |
| 138 | NPVDILTYIV | 17 |
| 100 | QQEGETRLAL | 16 |
| 181 | HPTSCHGWII | 16 |
| 191 | GEHGDSSVPL | 15 |
| 41 | LKDLADELAL | 14 |
| 46 | DELALVDVAL | 14 |
| 128 | SPDCKILVVS | 14 |
| TPTE | | |
| A*0201-Octamers | | |
| 4 | SPDPTDLA | 9 |
| 24 | QTSEFKGA | 9 |
| 28 | FKGATEEA | 9 |
| 30 | GATEEAPA | 9 |
| 42 | HTSEFKGA | 9 |
| 43 | TSEFKGAA | 9 |
| 54 | PISESVLA | 9 |
| 64 | SKFEVEDA | 9 |
| 68 | VEDAENVA | 9 |
| 86 | HSIVSSFA | 9 |
| 104 | LDVTLILA | 9 |
| 125 | EYRSISLA | 9 |
| 127 | RSISLAIA | 9 |
| 157 | LFNILDTA | 9 |
| 241 | YVTERIIA | 9 |

-continued

| Pos | Epitope | Score |
|---|---|---|
| 282 | YNLCSERA | 9 |
| 320 | KEVNEWMA | 9 |
| 328 | QDLENIVA | 9 |
| 344 | RTGTMVCA | 9 |
| 348 | MVCAFLIA | 9 |
| 355 | ASEICSTA | 9 |
| 388 | PSQKRYVA | 9 |
| 391 | KRYVAYFA | 9 |
| 516 | DNLHKQKA | 9 |
| 525 | RIYPSDFA | 9 |
| 541 | MTSSDVVA | 9 |
| A*0201-Nonamers | | |
| 9 | DLAGVIIEL | 29 |
| 130 | SLAIALFFL | 28 |
| 137 | FLMDVLLRV | 28 |
| 169 | LLLVDVVYI | 28 |
| 102 | VLLDVTLIL | 27 |
| 164 | AIIVILLLV | 27 |
| 195 | RLLRLIILL | 27 |
| 100 | FLVLLDVTL | 26 |
| 167 | VILLLVDVV | 26 |
| 200 | IILLRIFHL | 26 |
| 95 | GLFGVFLVL | 25 |
| 166 | IVILLLVDV | 25 |
| 192 | HLLRLLRLI | 25 |
| 423 | SIPRYVRDL | 25 |
| 507 | RLYLPKNEL | 25 |
| 160 | ILDTAIIVI | 24 |
| 80 | KIKKIVHSI | 23 |
| 134 | ALFFLMDVL | 23 |
| 176 | YIFFDIKLL | 23 |
| 109 | ILADLIFTD | 22 |
| 112 | DLIFTDSKL | 22 |
| 133 | IALFFLMDV | 22 |
| 193 | LLRLLRLII | 22 |
| 314 | QMVVFTKEV | 22 |
| 325 | WMAQDLENI | 22 |
| 353 | LIASEICST | 22 |
| 413 | ILFIKHFII | 22 |

-continued

| Pos | Epitope | Score |
|---|---|---|
| 445 | TISLGKCSV | 22 |
| 525 | RIYPSDFAV | 22 |
| 98 | GVFLVLLDV | 21 |
| 159 | NILDTAIIV | 21 |
| 163 | TAIIVILLL | 21 |
| 186 | NIPRWTHLL | 21 |
| 207 | HLFHQKRQL | 21 |
| 420 | IIYSIPRYV | 21 |
| 91 | SFAFGLFGV | 20 |
| 101 | LVLLDVTLI | 20 |
| 103 | LLDVTLILA | 20 |
| 108 | LILADLIFT | 20 |
| 121 | YIPLEYRSI | 20 |
| 156 | DLFNILDTA | 20 |
| 263 | PIKEVVRFL | 20 |
| 301 | RIMIDDHNV | 20 |
| 311 | TLHQMVVFT | 20 |
| 96 | LFGVFLVLL | 19 |
| 162 | DTAIIVILL | 19 |
| 304 | IDDHNVPTL | 19 |
| 328 | QDLENIVAI | 19 |
| 502 | FIENNRLYL | 19 |
| 51 | RVSPISESV | 18 |
| 60 | LARLSKFEV | 18 |
| 88 | IVSSFAFGL | 18 |
| 94 | FGLFGVFLV | 18 |
| 105 | DVTLILADL | 18 |
| 170 | LLVDVVYIF | 18 |
| 182 | KLLRNIPRW | 18 |
| 194 | LRLLRLIIL | 18 |
| 412 | RILFIKHFI | 18 |
| 440 | KVVFSTISL | 18 |
| 458 | TTDKILIDV | 18 |
| A*0201-Decamers | | |
| 95 | GLFGVFLVLL | 30 |
| 160 | ILDTAIIVIL | 28 |
| 168 | ILLLVDVVYI | 28 |
| 132 | AIALFFLMDV | 26 |
| 165 | IIVILLLVDV | 26 |

-continued

| Pos | Epitope | Score |
|---|---|---|
| 193 | LLRLLRLIIL | 26 |
| 199 | LIILLRIFHL | 26 |
| 303 | MIDDHNVPTL | 26 |
| 509 | YLPKNELDNL | 26 |
| 59 | VLARLSKFEV | 25 |
| 196 | LLRLIILLRI | 25 |
| 407 | NLPPRRILFI | 25 |
| 134 | ALFFLMDVLL | 24 |
| 54 | PISESVLARL | 23 |
| 100 | FLVLLDVTLI | 23 |
| 159 | NILDTAIIVI | 23 |
| 352 | FLIASEICST | 23 |
| 415 | FIKHFIIYSI | 23 |
| 102 | VLLDVTLILA | 22 |
| 138 | LMDVLLRVFV | 22 |
| 166 | IVILLLVDVV | 22 |
| 4 | SPDPTDLAGV | 21 |
| 87 | SIVSSFAFGL | 21 |
| 163 | TAIIVILLLV | 21 |
| 192 | HLLRLLRLII | 21 |
| 325 | WMAQDLENIV | 21 |
| 453 | VLDNITTDKI | 21 |
| 463 | LIDVFDGPPL | 21 |
| 92 | FAFGLFGVFL | 20 |
| 107 | TLILADLIFT | 20 |
| 113 | LIFTDSKLYI | 20 |
| 162 | DTAIIVILLL | 20 |
| 419 | FIIYSIPRYV | 20 |
| 422 | YSIPRYVRDL | 20 |
| 432 | KIQIEMEKKV | 20 |
| 444 | STISLGKCSV | 20 |
| 457 | ITTDKILIDV | 20 |
| 79 | SKIKKIVHSI | 19 |
| 101 | LVLLDVTLIL | 19 |
| 156 | DLFNILDTAI | 19 |
| 169 | LLLVDVVYIF | 19 |
| 190 | WTHLLRLLRL | 19 |
| 214 | QLEKLIRRRV | 19 |
| 217 | KLIRRRVSEN | 19 |

-continued

| Pos | Epitope | Score |
|---|---|---|
| 302 | IMIDDHNVPT | 19 |
| 8 | TDLAGVIIEL | 18 |
| 62 | RLSKFEVEDA | 18 |
| 80 | KIKKIVHSIV | 18 |
| 90 | SSFAFGLFGV | 18 |
| 103 | LLDVTLILAD | 18 |
| 104 | LDVTLILADL | 18 |
| 108 | LILADLIFTD | 18 |
| 122 | IPLEYRSISL | 18 |
| 129 | ISLAIALFFL | 18 |
| 130 | SLAIALFFLM | 18 |
| 136 | FFLMDVLLRV | 18 |
| 174 | VVYIFFDIKL | 18 |
| 194 | LRLLRLIILL | 18 |
| 230 | YTRDGFDLDL | 18 |
| 258 | SFYRNPIKEV | 18 |
| 353 | LIASEICSTA | 18 |
| 394 | VAYFAQVKHL | 18 |
| 445 | TISLGKCSVL | 18 |
| 517 | NLHKQKARRI | 18 |
| *** | | |
| A*2402-Nonamers | | |
| 175 | VYIFFDIKL | 26 |
| 76 | SYDSKIKKI | 24 |
| 395 | AYFAQVKHL | 22 |
| 472 | LYDDVKVQF | 22 |
| 152 | QYFSDLFNI | 21 |
| 229 | RYTRDGFDL | 21 |
| 488 | YYDNCSFYF | 21 |
| 494 | FYFWLHTSF | 21 |
| 125 | EYRSISLAI | 20 |
| 96 | LFGVFLVLL | 18 |
| 135 | LFFLMDVLL | 18 |
| 153 | YFSDLFNIL | 18 |
| 114 | IFTDSKLYI | 17 |
| 163 | TAIIVILLL | 17 |
| 294 | HFHNRVVRI | 17 |
| 495 | YFWLHTSFI | 17 |
| 508 | LYLPKNELD | 17 |

-continued

| Pos | Epitope | Score |
|---|---|---|
| 93 | AFGLFGVFL | 16 |
| 102 | VLLDVTLIL | 16 |
| 106 | VTLILADLI | 16 |
| 157 | LFNILDTAI | 16 |
| 200 | IILLRIFHL | 16 |
| 201 | ILLRIFHLF | 16 |
| 407 | NLPPRRILF | 16 |
| 58 | SVLARLSKF | 15 |
| 89 | VSSFAFGLF | 15 |
| 101 | LVLLDVTLI | 15 |
| 185 | RNIPRWTHL | 15 |
| 195 | RLLRLIILL | 15 |
| 289 | AYDPKHFHN | 15 |
| 328 | QDLENIVAI | 15 |
| A*2402-Decamers | | |
| 175 | VYIFFDIKLL | 27 |
| 120 | LYIPLEYRSI | 23 |
| 487 | TYYDNCSFYF | 23 |
| 472 | LYDDVKVQFF | 22 |
| 526 | IYPSDFAVEI | 22 |
| 152 | QYFSDLFNIL | 21 |
| 99 | VFLVLLDVTL | 20 |
| 145 | VFVERRQQYF | 20 |
| 426 | RYVRDLKIQI | 20 |
| 494 | FYFWLHTSFI | 20 |
| 501 | SFIENNRLYL | 20 |
| 250 | SFPSSGRQSF | 18 |
| 91 | SFAFGLFGVF | 17 |
| 493 | SFYFWLHTSF | 17 |
| 157 | LFNILDTAII | 16 |
| 178 | FFDIKLLRNI | 16 |
| 127 | RSISLAIALF | 15 |
| 185 | RNIPRWTHLL | 15 |
| 191 | THLLRLLRLI | 15 |
| 194 | LRLLRLIILL | 15 |
| 199 | LIILLRIFHL | 15 |
| 200 | IILLRIFHLF | 15 |
| 406 | WNLPPRRILF | 15 |
| *** | | |

-continued

| Pos | Epitope | Score |
|---|---|---|
| A*01-Nonamers | | |
| 360 | STAKESLYY | 29 |
| 118 | SKLYIPLEY | 23 |
| 4 | SPDPTDLAG | 22 |
| 154 | FSDLFNILD | 22 |
| 414 | LFIKHFIIY | 22 |
| 233 | DGFDLDLTY | 21 |
| 359 | CSTAKESLY | 21 |
| 396 | YFAQVKHLY | 21 |
| 252 | PSSGRQSFY | 20 |
| 385 | VETPSQKRY | 20 |
| 458 | TTDKILIDV | 20 |
| 501 | SFIENNRLY | 20 |
| 31 | ATEEAPAKE | 19 |
| 168 | ILLLVDVVY | 19 |
| 388 | PSQKRYVAY | 19 |
| 465 | DVFDGPPLY | 19 |
| 466 | VFDGPPLYD | 19 |
| 242 | VTERIIAMS | 18 |
| 341 | GTDRTGTMV | 18 |
| 502 | FIENNRLYL | 18 |
| 543 | SSDVVAGSD | 18 |
| 7 | PTDLAGVII | 17 |
| 103 | LLDVTLILA | 17 |
| 113 | LIFTDSKLY | 17 |
| 115 | FTDSKLYIP | 17 |
| 145 | VFVERRQQY | 17 |
| 178 | FFDIKLLRN | 17 |
| 231 | TRDGFDLDL | 17 |
| 282 | YNLCSERAY | 17 |
| 327 | AQDLENIVA | 17 |
| 474 | DDVKVQFFY | 17 |
| 512 | KNELDNLHK | 17 |
| 55 | ISESVLARL | 16 |
| 69 | EDAENVASY | 16 |
| 160 | ILDTAIIVI | 16 |
| 171 | LVDVVYIFF | 16 |
| 223 | VSENKRRYT | 16 |
| 271 | LDKKHRNHY | 16 |

| Pos | Epitope | Score |
|---|---|---|
| 274 | KHRNHYRVY | 16 |
| 373 | RTDKTHSEK | 16 |
| 419 | FIIYSIPRY | 16 |
| 480 | FFYSNLPTY | 16 |
| 481 | FYSNLPTYY | 16 |
| 519 | HKQKARRIY | 16 |
| 25 | TSEFKGATE | 15 |
| 43 | TSEFKGAAR | 15 |
| 123 | PLEYRSISL | 15 |
| 190 | WTHLLRLLR | 15 |
| 222 | RVSENKRRY | 15 |
| 230 | YTRDGFDLD | 15 |
| 264 | IKEVVRFLD | 15 |
| 289 | AYDPKHFHN | 15 |
| 355 | ASEICSTAK | 15 |
| 378 | HSEKFQGVE | 15 |
| 487 | TYYDNCSFY | 15 |
| 528 | PSDFAVEIL | 15 |
| A*01-Decamers | | |
| 270 | FLDKKHRNHY | 28 |
| 68 | VEDAENVASY | 27 |
| 473 | YDDVKVQFFY | 27 |
| 117 | DSKLYIPLEY | 25 |
| 359 | CSTAKESLYY | 25 |
| 384 | GVETPSQKRY | 25 |
| 413 | ILFIKHFIIY | 23 |
| 500 | TSFIENNRLY | 22 |
| 7 | PTDLAGVIIE | 21 |
| 115 | FTDSKLYIPL | 21 |
| 154 | FSDLFNILDT | 21 |
| 232 | RDGFDLDLTY | 21 |
| 486 | PTYYDNCSFY | 21 |
| 528 | PSDFAVEILF | 20 |
| 264 | IKEVVRFLDK | 19 |
| 112 | DLIFTDSKLY | 18 |
| 289 | AYDPKHFHNR | 18 |
| 373 | RTDKTHSEKF | 18 |
| 395 | AYFAQVKHLY | 18 |
| 31 | ATEEAPAKES | 17 |

| Pos | Epitope | Score |
|---|---|---|
| 103 | LLDVTLILAD | 17 |
| 167 | VILLLVDVVY | 17 |
| 242 | VTERIIAMSF | 17 |
| 341 | GTDRTGTMVC | 17 |
| 355 | ASEICSTAKE | 17 |
| 358 | ICSTAKESLY | 17 |
| 458 | TTDKILIDVF | 17 |
| 464 | IDVFDGPPLY | 17 |
| 4 | SPDPTDLAGV | 16 |
| 55 | ISESVLARLS | 16 |
| 144 | RVFVERRQQY | 16 |
| 223 | VSENKRRYTR | 16 |
| 251 | FPSSGRQSFY | 16 |
| 273 | KKHRNHYRVY | 16 |
| 281 | VYNLCSERAY | 16 |
| 285 | CSERAYDPKH | 16 |
| 480 | FFYSNLPTYY | 16 |
| 518 | LHKQKARRIY | 16 |
| 221 | RRVSENKRRY | 15 |
| 329 | DLENIVAIHC | 15 |
| 346 | GTMVCAFLIA | 15 |
| 378 | HSEKFQGVET | 15 |
| 387 | TPSQKRYVAY | 15 |
| 418 | HFIIYSIPRY | 15 |
| 428 | VRDLKIQIEM | 15 |
| 479 | QEFYSNLPTY | 15 |
| 488 | YYDNCSFYFW | 15 |
| *** | | |
| A*03-Nonamers | | |
| 168 | ILLLVDVVY | 30 |
| 217 | KLIRRRVSE | 28 |
| 393 | YVAYFAQVK | 28 |
| 280 | RVYNLCSER | 26 |
| 174 | VVYIFFDIK | 25 |
| 204 | RIFHLFHQK | 25 |
| 532 | AVEILFGEK | 25 |
| 58 | SVLARLSKF | 24 |
| 141 | VLLRVFVER | 24 |
| 514 | ELDNLHKQK | 24 |

-continued

| Pos | Epitope | Score |
|---|---|---|
| 266 | EVVRFLDKK | 23 |
| 119 | KLYIPLEYR | 22 |
| 198 | RLIILLRIF | 22 |
| 365 | SLYYFGERR | 22 |
| 432 | KIQIEMEKK | 22 |
| 453 | VLDNITTDK | 22 |
| 84 | IVHSIVSSF | 21 |
| 107 | TLILADLIF | 21 |
| 196 | LLRLIILLR | 21 |
| 201 | ILLRIFHLF | 21 |
| 202 | LLRIFHLFH | 21 |
| 222 | RVSENKRRY | 21 |
| 95 | GLFGVFLVL | 20 |
| 166 | IVILLLVDV | 20 |
| 335 | AIHCKGGTD | 20 |
| 383 | QGVETPSQK | 20 |
| 407 | NLPPRRILF | 20 |
| 465 | DVFDGPPLY | 20 |
| 525 | RIYPSDFAV | 20 |
| 51 | RVSPISESV | 19 |
| 100 | FLVLLDVTL | 19 |
| 140 | DVLLRVFVE | 19 |
| 146 | FVERRQQYF | 19 |
| 195 | RLLRLIILL | 19 |
| 218 | LIRRRVSEN | 19 |
| 219 | IRRRVSENK | 19 |
| 236 | DLDLTYVTE | 19 |
| 452 | SVLDNITTD | 19 |
| 471 | PLYDDVKVQ | 19 |
| 507 | RLYLPKNEL | 19 |
| 535 | ILFGEKMTS | 19 |
| 62 | RLSKFEVED | 18 |
| 75 | ASYDSKIKK | 18 |
| 109 | ILADLIFTD | 18 |
| 111 | ADLIFTDSK | 18 |
| 144 | RVFVERRQQ | 18 |
| 165 | IIVILLLVD | 18 |
| 182 | KLLRNIPRW | 18 |
| 193 | LLRLLRLII | 18 |

-continued

| Pos | Epitope | Score |
|---|---|---|
| 261 | RNPIKEVVR | 18 |
| 265 | KEVVRFLDK | 18 |
| 299 | VVRIMIDDH | 18 |
| 329 | DLENIVAIH | 18 |
| 402 | HLYNWNLPP | 18 |
| A*03-Decamers | | |
| 195 | RLLRLIILLR | 26 |
| 471 | PLYDDVKVQF | 26 |
| 525 | RIYPSDFAVE | 26 |
| 167 | VILLLVDVVY | 25 |
| 452 | SVLDNITTDK | 25 |
| 51 | RVSPISESVL | 24 |
| 144 | RVFVERRQQY | 24 |
| 201 | ILLRIFHLFH | 24 |
| 218 | LIRRRVSENK | 24 |
| 311 | TLHQMVVFTK | 24 |
| 183 | LLRNIPRWTH | 23 |
| 198 | RLIILLRIFH | 23 |
| 392 | RYVAYFAQVK | 23 |
| 420 | IIYSIPRYVR | 23 |
| 423 | SIPRYVRDLK | 23 |
| 430 | DLKIQIEMEK | 23 |
| 441 | VVFSTISLGK | 23 |
| 217 | KLIRRRVSEN | 22 |
| 434 | QIEMEKKVVF | 22 |
| 73 | NVASYDSKIK | 21 |
| 140 | DVLLRVFVER | 21 |
| 164 | AIIVILLLVD | 21 |
| 298 | RVVRIMIDDH | 21 |
| 83 | KIVHSIVSSF | 20 |
| 128 | SISLAIALFF | 20 |
| 166 | IVILLLVDVV | 20 |
| 173 | DVVYIFFDIK | 20 |
| 182 | KLLRNIPRWT | 20 |
| 112 | DLIFTDSKLY | 19 |
| 137 | FLMDVLLRVF | 19 |
| 141 | VLLRVFVERR | 19 |
| 168 | ILLLVDVVYI | 19 |
| 192 | HLLRLLRLII | 19 |

-continued

| Pos | Epitope | Score |
|---|---|---|
| 245 | RIIAMSFPSS | 19 |
| 280 | RVYNLCSERA | 19 |
| 335 | AIHCKGGTDR | 19 |
| 393 | YVAYFAQVKH | 19 |
| 402 | HLYNWNLPPR | 19 |
| 413 | ILFIKHFIIY | 19 |
| 507 | RLYLPKNELD | 19 |
| 29 | KGATEEAPAK | 18 |
| 119 | KLYIPLEYRS | 18 |
| 186 | NIPRWTHLLR | 18 |
| 372 | RRTDKTHSEK | 18 |
| *** | | |
| B*0702-Nonamers | | |
| 35 | APAKESPHT | 21 |
| 262 | NPIKEVVRF | 20 |
| 387 | TPSQKRYVA | 20 |
| 510 | LPKNELDNL | 20 |
| 527 | YPSDFAVEI | 20 |
| 251 | FPSSGRQSF | 19 |
| 408 | LPPRRILFI | 19 |
| 53 | SPISESVLA | 18 |
| 470 | PPLYDDVKV | 18 |
| 6 | DPTDLAGVI | 17 |
| 93 | AFGLFGVFL | 17 |
| 309 | VPTLHQMVV | 17 |
| 95 | GLFGVFLVL | 16 |
| 291 | DPKHFHNRV | 16 |
| 4 | SPDPTDLAG | 15 |
| 187 | IPRWTHLLR | 15 |
| 231 | TRDGFDLDL | 15 |
| 406 | WNLPPRRIL | 15 |
| B*0702-Decamers | | |
| 187 | IPRWTHLLRL | 25 |
| 262 | NPIKEVVRFL | 23 |
| 527 | YPSDFAVEIL | 23 |
| 122 | IPLEYRSISL | 21 |
| 424 | IPRYVRDLKI | 21 |
| 4 | SPDPTDLAGV | 19 |
| 309 | VPTLHQMVVF | 19 |

-continued

| Pos | Epitope | Score |
|---|---|---|
| 6 | DPTDLAGVII | 18 |
| 469 | GPPLYDDVKV | 18 |
| 22 | SPQTSEFKGA | 17 |
| 40 | SPHTSEFKGA | 17 |
| 291 | DPKHFHNRVV | 17 |
| 485 | LPTYYDNCSF | 16 |
| 51 | RVSPISESVL | 15 |
| 92 | FAFGLFGVFL | 15 |
| 387 | TPSQKRYVAY | 15 |
| *** | | |

A part or a fragment of a nucleic acid coding for a tumor-associated antigen relates according to the invention to the part of the nucleic acid, which codes at least for the tumor-associated antigen and/or for a part or a fragment of said tumor-associated antigen, as defined above.

The isolation and identification of genes coding for tumor-associated antigens also make possible the diagnosis of a disease characterized by expression of one or more tumor-associated antigens. These methods comprise determining one or more nucleic acids which code for a tumor-associated antigen and/or determining the encoded tumor-associated antigens and/or peptides derived therefrom. The nucleic acids may be determined in the conventional manner, including by polymerase chain reaction or hybridization with a labeled probe.

Tumor-associated antigens or peptides derived therefrom may be determined by screening patient antisera with respect to recognizing the antigen and/or the peptides. They may also be determined by screening T cells of the patient for specificities for the corresponding tumor-associated antigen.

The present invention also enables proteins binding to tumor-associated antigens described herein to be isolated, including antibodies and cellular binding partners of said tumor-associated antigens.

According to the invention, particular embodiments ought to involve providing "dominant negative" polypeptides derived from tumor-associated antigens. A dominant negative polypeptide is an inactive protein variant which, by way of interacting with the cellular machinery, displaces an active protein from its interaction with the cellular machinery or which competes with the active protein, thereby reducing the effect of said active protein. For example, a dominant negative receptor which binds to a ligand but does not generate any signal as response to binding to the ligand can reduce the biological effect of said ligand. Similarly, a dominant negative catalytically inactive kinase which usually interacts with target proteins but does not phosphorylate said target proteins may reduce phosphorylation of said target proteins as response to a cellular signal. Similarly, a dominant negative transcription factor which binds to a promoter site in the control region of a gene but does not increase transcription of said gene may reduce the effect of a normal transcription factor by occupying promoter binding sites, without increasing transcription.

The result of expression of a dominant negative polypeptide in a cell is a reduction in the function of active proteins.

The skilled worker may prepare dominant negative variants of a protein, for example, by conventional mutagenesis methods and by evaluating the dominant negative effect of the variant polypeptide.

The invention also comprises substances such as polypeptides which bind to tumor-associated antigens. Such binding substances may be used, for example, in screening assays for detecting tumor-associated antigens and complexes of tumor-associated antigens with their binding partners and in a purification of said tumor-associated antigens and of complexes thereof with their binding partners. Such substances may also be used for inhibiting the activity of tumor-associated antigens, for example by binding to such antigens.

The invention therefore comprises binding substances such as, for example, antibodies or antibody fragments, which are capable of selectively binding to tumor-associated antigens. Antibodies comprise polyclonal and monoclonal antibodies which are produced in the conventional manner.

It is known that only a small part of an antibody molecule, the paratope, is involved in binding of the antibody to its epitope (cf. Clark, W. R. (1986), *The Experimental Foundations of Modern Immunology*, Wiley & Sons, Inc., New York; Roitt, I. (1991), *Essential Immunology,* 7th Edition, Blackwell Scientific Publications, Oxford). The pFc' and Fc regions are, for example, effectors of the complement cascade but are not involved in antigen binding. An antibody from which the pFc' region has been enzymatically removed or which has been produced without the pFc' region, referred to as $F(ab')_2$ fragment, carries both antigen binding sites of a complete antibody. Similarly, an antibody from which the Fc region has been enzymatically removed or which has been produced without said Fc region, referred to Fab fragment, carries one antigen binding site of an intact antibody molecule. Furthermore, Fab fragments consist of a covalently bound light chain of an antibody and part of the heavy chain of said antibody, referred to as Fd. The Fd fragments are the main determinants of antibody specificity (a single Fd fragment can be associated with up to ten different light chains, without altering the specificity of the antibody) and Fd fragments, when isolated, retain the ability to bind to an epitope.

Located within the antigen-binding part of an antibody are complementary-determining regions (CDRs) which interact directly with the antigen epitope and framework regions (FRs) which maintain the tertiary structure of the paratope. Both the Fd fragment of the heavy chain and the light chain of IgG immunoglobulins contain four framework regions (FR1 to FR4) which are separated in each case by three complementary-determining regions (CDR1 to CDR3). The CDRs and, in particular, the CDR3 regions and, still more particularly, the CDR3 region of the heavy chain are responsible to a large extent for antibody specificity.

Non-CDR regions of a mammalian antibody are known to be able to be replaced by similar regions of antibodies with the same or a different specificity, with the specificity for the epitope of the original antibody being retained. This made possible the development of "humanized" antibodies in which nonhuman CDRs are covalently linked to human FR and/or Fc/pFc' regions to produce a functional antibody.

WO 92/04381 for example, describes production and use of humanized murine RSV antibodies in which at least part of the murine FR regions have been replaced with FR regions of a human origin. Antibodies of this kind, including fragments of intact antibodies with antigen-binding capability, are often referred to as "chimeric" antibodies.

The invention also provides $F(ab')_2$, Fab, Fv, and Fd fragments of antibodies, chimeric antibodies, in which the Fc and/or FR and/or CDR1 and/or CDR2 and/or light chain-CDR3 regions have been replaced with homologous human or nonhuman sequences, chimeric $F(ab')_2$-fragment antibodies in which the FR and/or CDR1 and/or CDR2 and/or light chain-CDR3 regions have been replaced with homologous human or nonhuman sequences, chimeric Fab-fragment antibodies in which the FR and/or CDR1 and/or CDR2 and/or light chain-CDR3 regions have been replaced with homologous human or nonhuman sequences, and chimeric Fd-fragment antibodies in which the FR and/or CDR1 and/or CDR2 regions have been replaced with homologous human or nonhuman sequences. The invention also comprises "single-chain" antibodies.

Preferably, an antibody used according to the invention is directed against one of the sequences shown in SEQ ID NO:14-18, 80-84, or 101-116 of the sequence listing and/or can be obtained by immunization with these peptides.

The invention also comprises polypeptides which bind specifically to tumor-associated antigens. Polypeptide binding substances of this kind may be provided, for example, by degenerate peptide libraries which may be prepared simply in solution in an immobilized form or as phage-display libraries. It is likewise possible to prepare combinatorial libraries of peptides with one or more amino acids. Libraries of peptoids and nonpeptidic synthetic residues may also be prepared.

Phage display may be particularly effective in identifying binding peptides of the invention. In this connection, for example, a phage library is prepared (using, for example, the M13, fd or lambda phages) which presents inserts of from 4 to about 80 amino acid residues in length. Phages are then selected which carry inserts which bind to the tumor-associated antigen. This process may be repeated via two or more cycles of a reselection of phages binding to the tumor-associated antigen. Repeated rounds result in a concentration of phages carrying particular sequences. An analysis of DNA sequences may be carried out in order to identify the sequences of the expressed polypeptides. The smallest linear portion of the sequence binding to the tumor-associated antigen may be determined. The "two-hybrid system" of yeast may also be used for identifying polypeptides which bind to a tumor-associated antigen. Tumor-associated antigens described according to the invention or fragments thereof may be used for screening peptide libraries, including phage-display libraries, in order to identify and select peptide binding partners of the tumor-associated antigens. Such molecules may be used, for example, for screening assays, purification protocols, for interference with the function of the tumor-associated antigen and for other purposes known to the skilled worker.

The antibodies described above and other binding molecules may be used, for example, for identifying tissue which expresses a tumor-associated antigen. Antibodies may also be coupled to specific diagnostic substances for displaying cells and tissues expressing tumor-associated antigens. They may also be coupled to therapeutically useful substances. Diagnostic substances comprise, in a nonlimiting manner, barium sulfate, iocetamic acid, iopanoic acid, calcium ipodate, sodium diatrizoate, meglumine diatrizoate, metrizamide, sodium tyropanoate and radio diagnostics, including positron emitters such as fluorine-18 and carbon-11, gamma emitters such as iodine-123, technetium-99m, iodine-131 and indium-111, nuclides for nuclear magnetic resonance, such as fluorine and gadolinium. According to the invention, the term "therapeutically useful substance" means any therapeutic molecule which, as desired, is selectively guided to a cell which expresses one or more tumor-associated antigens, including anticancer agents, radioactive iodine-labeled compounds, toxins, cytostatic or cytolytic drugs, etc. Anticancer agents comprise, for example, aminoglutethimide, azathioprine, bleomycin sulfate, busulfan, carmustine, chlorambucil, cisplatin, cyclophosphamide, cyclosporine, cytarabidine, dacarbazine, dactinomycin, daunorubin, doxorubicin, taxol, etoposide, fluorouracil, interferon-α, lomustine, mercaptopurine, methotrexate, mitotane, -procarbazine HCl, thioguanine, vinblastine sulfate and vincristine sulfate. Other anticancer agents are described, for example, in Goodman and Gilman, "The Pharmacological Basis of Therapeutics", 8th Edition, 1990, McGraw-Hill, Inc., in particular Chapter 52 (Antineoplastic Agents (Paul Calabresi and Bruce A. Chabner). Toxins may be proteins such as pokeweed antiviral protein, cholera toxin, pertussis toxin, ricin, gelonin, abrin, diphtheria exotoxin or *Pseudomonas* exotoxin. Toxin residues may also be high energy-emitting radionuclides such as cobalt-60.

For TPTE it could be shown according to the invention that it is not only a protein which is localized at the membrane but is also able to internalize (cf. example 2). Thus, the tumor-associated antigens identified according to the invention which relate to TPTE can serve themselves for a transport of substances binding thereto, in particular the therapeutic antibodies described above, from the membrane into the cytoplasm and thus, for an internalization, where these substances preferably exert their effect such as a cell destruction effect.

The term "patient" means according to the invention a human being, a nonhuman primate or another animal, in particular a mammal such as a cow, horse, pig, sheep, goat, dog, cat or a rodent such as a mouse and rat. In a particularly preferred embodiment, the patient is a human being.

According to the invention, the term "disease" refers to any pathological state in which tumor-associated antigens are expressed or abnormally expressed. "Abnormal expression" means according to the invention that expression is altered, preferably increased, compared to the state in a healthy individual. An increase in expression refers to an increase by at least 10%, in particular at least 20%, at least 50% or at least 100%. In one embodiment, the tumor-associated antigen is expressed only in tissue of a diseased individual, while expression in a healthy individual is repressed. One example of such a disease is cancer, in particular seminomas, melanomas, teratomas, gliomas, colorectal cancer, breast cancer, prostate cancer, cancer of the uterus, ovarian cancer and lung cancer.

According to the invention, a biological sample may be a tissue sample and/or a cellular sample and may be obtained in the conventional manner such as by tissue biopsy, including punch biopsy, and by taking blood, bronchial aspirate, urine, feces or other body fluids, for use in the various methods described herein.

According to the invention, the term "immunoreactive cell" means a cell which can mature into an immune cell (such as B cell, T helper cell, or cytolytic T cell) with suitable stimulation. Immunoreactive cells comprise $CD34^+$ hematopoietic stem cells, immature and mature T cells and immature and mature B cells. If production of cytolytic or T helper cells recognizing a tumor-associated antigen is desired, the immunoreactive cell is contacted with a cell expressing a tumor-associated antigen under conditions which favor production, differentiation and/or selection of cytolytic T cells and of T helper cells. The differentiation of T cell precursors into a cytolytic T cell, when exposed to an antigen, is similar to clonal selection of the immune system.

Some therapeutic methods are based on a reaction of the immune system of a patient, which results in a lysis of antigen-presenting cells such as cancer cells which present one or more tumor-associated antigens. In this connection, for example autologous cytotoxic T lymphocytes specific for a complex of a tumor-associated antigen and an MHC molecule are administered to a patient having a cellular abnormality. The production of such cytotoxic T lymphocytes in vitro is known. An example of a method of differentiating T cells can be found in WO-A-9633265. Generally, a sample containing cells such as blood cells is taken from the patient and the cells are contacted with a cell which presents the complex and which can cause propagation of cytotoxic T lymphocytes (e.g. dendritic cells). The target cell may be a transfected cell such as a COS cell. These transfected cells present the desired complex on their surface and, when contacted with cytotoxic T lymphocytes, stimulate propagation of the latter. The clonally expanded autologous cytotoxic T lymphocytes are then administered to the patient.

In another method of selecting antigen-specific cytotoxic T lymphocytes, fluorogenic tetramers of MHC class I molecule/peptide complexes are used for detecting specific clones of cytotoxic T lymphocytes (Altman et al., *Science* 274:94-96, 1996; Dunbar et al., *Curr. Biol.* 8:413-416, 1998). Soluble MHC class I molecules are folded in vitro in the presence of β2 microglobulin and a peptide antigen binding to said class I molecule. The MHC/peptide complexes are purified and then labeled with biotin. Tetramers are formed by mixing the biotinylated peptide-MHC complexes with labeled avidin (e.g. phycoerythrin) in a molar ratio of 4:1. Tetramers are then contacted with cytotoxic T lymphocytes such as peripheral blood or lymph nodes. The tetramers bind to cytotoxic T lymphocytes which recognize the peptide antigen/MHC class I complex. Cells which are bound to the tetramers may be sorted by fluorescence-controlled cell sorting to isolate reactive cytotoxic T lymphocytes. The isolated cytotoxic T lymphocytes may then be propagated in vitro.

In a therapeutic method referred to as adoptive transfer (Greenberg, *J. Immunol.* 136(5):1917, 1986; Riddel et al., *Science* 257:238, 1992; Lynch et al., *Eur. J. Immunol.* 21:1403-1410, 1991; Kast et al., *Cell* 59:603-614, 1989), cells presenting the desired complex (e.g. dendritic cells) are combined with cytotoxic T lymphocytes of the patient to be treated, resulting in a propagation of specific cytotoxic T lymphocytes. The propagated cytotoxic T lymphocytes are then administered to a patient having a cellular anomaly characterized by particular abnormal cells presenting the specific complex. The cytotoxic T lymphocytes then lyse the abnormal cells, thereby achieving a desired therapeutic effect.

Often, of the T cell repertoire of a patient, only T cells with low affinity for a specific complex of this kind can be propagated, since those with high affinity have been extinguished due to development of tolerance. An alternative here may be a transfer of the T cell receptor itself. For this too, cells presenting the desired complex (e.g. dendritic cells) are combined with cytotoxic T lymphocytes of healthy individuals. This results in propagation of specific cytotoxic T lymphocytes with high affinity if the donor had no previous contact with the specific complex. The high affinity T cell receptor of these propagated specific T lymphocytes is cloned and can be transduced via gene transfer, for example using retroviral vectors, into T cells of other patients, as desired. Adoptive transfer is then carried out using these genetically altered T lymphocytes (Stanislawski et al., Nat Immunol. 2:962-70, 2001; Kessels et al., Nat Immunol. 2:957-61, 2001).

The therapeutic aspects above start out from the fact that at least some of the abnormal cells of the patient present a complex of a tumor-associated antigen and an HLA molecule. Such cells may be identified in a manner known per se. As soon as cells presenting the complex have been identified, they may be combined with a sample from the patient, which contains cytotoxic T lymphocytes. If the cytotoxic T lymphocytes lyse the cells presenting the complex, it can be assumed that a tumor-associated antigen is presented.

Adoptive transfer is not the only form of therapy which can be applied according to the invention. Cytotoxic T lymphocytes may also be generated in vivo in a manner known per se. One method uses nonproliferative cells expressing the complex. The cells used here will be those which usually express the complex, such as irradiated tumor cells or cells transfected with one or both genes necessary for presentation of the complex (i.e. the antigenic peptide and the presenting HLA molecule). Various cell types may be used. Furthermore, it is possible to use vectors which carry one or both of the genes of interest. Particular preference is given to viral or bacterial vectors. For example, nucleic acids coding for a tumor-associated antigen or for a part thereof may be functionally linked to promoter and enhancer sequences which control expression of said tumor-associated antigen or a fragment thereof in particular tissues or cell types. The nucleic acid may be incorporated into an expression vector. Expression vectors may be nonmodified extrachromosomal nucleic acids, plasmids or viral genomes into which exogenous nucleic acids may be inserted. Nucleic acids coding for a tumor-associated antigen may also be inserted into a retroviral genome, thereby enabling the nucleic acid to be integrated into the genome of the target tissue or target cell. In these systems, a microorganism such as vaccinia virus, pox virus, Herpes simplex virus, retrovirus or adenovirus carries the gene of interest and de facto "infects" host cells. Another preferred form is the introduction of the tumor-associated antigen in the form of recombinant RNA which may be introduced into cells by liposomal transfer or by electroporation, for example. The resulting cells present the complex of interest and are recognized by autologous cytotoxic T lymphocytes which then propagate.

A similar effect can be achieved by combining the tumor-associated antigen or a fragment thereof with an adjuvant in order to make incorporation into antigen-presenting cells in vivo possible. The tumor-associated antigen or a fragment thereof may be represented as protein, as DNA (e.g. within a vector) or as RNA. The tumor-associated antigen is processed to produce a peptide partner for the HLA molecule, while a fragment thereof may be presented without the need for further processing. The latter is the case in particular, if these can bind to HLA molecules. Preference is given to administration forms in which the complete antigen is processed in vivo by a dendritic cell, since this may also produce T helper cell responses which are needed for an effective immune response (Ossendorp et al., *Immunol Lett.* 74:75-9, 2000; Ossendorp et al., *J. Exp. Med.* 187:693-702, 1998). In general, it is possible to administer an effective amount of the tumor-associated antigen to a patient by intradermal injection, for example. However, injection may also be carried out intranodally into a lymph node (Maloy et al., *Proc Natl Acad Sci USA* 98:3299-303, 2001). It may also be carried out in combination with reagents which facilitate uptake into dendritic cells. In vivo preferred tumor-associated antigens comprise those which react with allogenic cancer antisera or with T cells of many cancer patients. Of particular interest, however, are those against which no spontaneous immune responses pre-exist. Evidently, it is possible to induce against these immune responses which can lyse tumors (Keogh et al., *J. Immunol.* 167:787-96, 2001; Appella et al., *Biomed Pept Proteins Nucleic Acids* 1:177-84, 1995; Wentworth et al., *Mol Immunol.* 32:603-12, 1995).

The pharmaceutical compositions described according to the invention may also be used as vaccines for immunization. According to the invention, the terms "immunization" or "vaccination" mean an increase in or activation of an immune response to an antigen. It is possible to use animal models for testing an immunizing effect on cancer by using a tumor-associated antigen or a nucleic acid coding therefor. For example, human cancer cells may be introduced into a mouse to generate a tumor, and one or more nucleic acids coding for tumor-associated antigens may be administered. The effect on the cancer cells (for example reduction in tumor size) may be measured as a measure for the effectiveness of an immunization by the nucleic acid.

As part of the composition for an immunization, one or more tumor-associated antigens or stimulating fragments thereof are administered together with one or more adjuvants for inducing an immune response or for increasing an immune response. An adjuvant is a substance which is incorporated into the antigen or administered together with the latter and which enhances the immune response. Adjuvants may enhance the immune response by providing an antigen reservoir (extracellularly or in macrophages), activating macrophages and stimulating particular lymphocytes. Adjuvants are known and comprise in a nonlimiting way monophosphoryl lipid A (MPL, SmithKline Beecham), saponins such as QS21 (SmithKline Beecham), DQS21 (SmithKline Beecham; WO 96/33739), QS7, QS17, QS18 and QS-L1 (So et al., Mol. Cells 7:178-186, 1997), incomplete Freund's adjuvant, complete Freund's adjuvant, vitamin E, montanide, alum, CpG oligonucleotides (cf. Kreig et al., Nature 374:546-9, 1995) and various water-in-oil emulsions prepared from biologically degradable oils such as squalene and/or tocopherol. Preferably, the peptides are administered in a mixture with DQS21/MPL. The ratio of DQS21 to MPL is typically about 1:10 to 10:1, preferably about 1:5 to 5:1 and in particular about 1:1. For administration to humans, a vaccine formulation typically contains DQS21 and MPL in a range from about 1 μg to about 100 μg.

Other substances which stimulate an immune response of the patient may also be administered. It is possible, for example, to use cytokines in a vaccination, owing to their regulatory properties on lymphocytes. Such cytokines comprise, for example, interleukin-12 (IL-12) which was shown to increase the protective actions of vaccines (cf. *Science* 268:1432-1434, 1995), GM-CSF and IL-18.

There are a number of compounds which enhance an immune response and which therefore may be used in a vaccination. Said compounds comprise costimulating molecules provided in the form of proteins or nucleic acids. Examples of such costimulating molecules are B7-1 and B7-2 (CD80 and CD86, respectively) which are expressed on dendritic cells (DC) and interact with the CD28 molecule expressed on the T cells. This interaction provides a costimulation (signal 2) for an antigen/MHC/TCR-stimulated (signal 1) T cell, thereby enhancing propagation of said T cell and the effector function. B7 also interacts with CTLA4 (CD152) on T cells, and studies involving CTLA4 and B7 ligands demonstrate that B7-CTLA4 interaction can enhance antitumor immunity and CTL propagation (Zheng, P. et al., *Proc. Natl. Acad. Sci. USA* 95(11):6284-6289 (1998)).

B7 is typically not expressed on tumor cells so that these are no effective antigen-presenting cells (APCs) for T cells. Induction of B7 expression would enable tumor cells to stimulate more effectively propagation of cytotoxic T lymphocytes and an effector function. Costimulation by a combination of B7/IL-6/IL-12 revealed induction of IFN-gamma and Th1-cytokine profile in a T cell population, resulting in further enhanced T cell activity (Gajewski et al., *J. Immunol.* 154:5637-5648 (1995)).

A complete activation of cytotoxic T lymphocytes and a complete effector function require an involvement of T helper cells via interaction between the CD40 ligand on-said T helper cells and the CD40 molecule expressed by dendritic cells (Ridge et al., *Nature* 393:474 (1998), Bennett et al., *Nature* 393:478 (1998), Schönberger et al., *Nature* 393:480 (1998)). The mechanism of this costimulating signal probably relates to the increase in B7 production and associated IL-6/IL-12 production by said dendritic cells (antigen-presenting cells). CD40-CD40L interaction thus complements the interaction of signal 1 (antigen/MHC-TCR) and signal 2 (B7-CD28).

The use of anti-CD40 antibodies for stimulating dendritic cells would be expected to directly enhance a response to tumor antigens which are usually outside the range of an inflammatory response or which are presented by nonprofessional antigen-presenting cells (tumor cells). In these situations, T helper and B7-costimulating signals are not provided. This mechanism could be used in connection with therapies based on antigen-pulsed dendritic cells or in situations in which T helper epitopes have not been defined in known TRA precursors.

The invention also provides for administration of nucleic acids, polypeptides or peptides. Polypeptides and peptides may be administered in a manner known per se. In one embodiment, nucleic acids are administered by ex vivo methods, i.e. by removing cells from a patient, genetic modification of said cells in order to incorporate a tumor-associated antigen and reintroduction of the altered cells into the patient. This generally comprises introducing a functional copy of a gene into the cells of a patient in vitro and reintroducing the genetically altered cells into the patient. The functional copy of the gene is under the functional control of regulatory elements which allow the gene to be expressed in the genetically altered cells. Transfection and transduction methods are known to the skilled worker. The invention also provides for administering nucleic acids in vivo by using vectors such as viruses and target-controlled liposomes.

In a preferred embodiment, a viral vector for administering a nucleic acid coding for a tumor-associated antigen is selected from the group consisting of adenoviruses, adeno-associated viruses, pox viruses, including vaccinia virus and attenuated pox viruses, Semliki Forest virus, retroviruses, Sindbis virus and Ty virus-like particles. Particular preference is given to adenoviruses and retroviruses. The retroviruses are typically replication-deficient (i.e. they are incapable of generating infectious particles).

Various methods may be used in order to introduce according to the invention nucleic acids into cells in vitro or in vivo. Methods of this kind comprise transfection of nucleic acid $CaPO_4$ precipitates, transfection of nucleic acids associated with DEAE, transfection or infection with the above viruses carrying the nucleic acids of interest, liposome-mediated transfection, and the like. In particular embodiments, preference is given to directing the nucleic acid to particular cells. In such embodiments, a carrier used for administering a nucleic acid to a cell (e.g. a retrovirus or a liposome) may have a bound target control molecule. For example, a molecule such as an antibody specific for a surface membrane protein on the target cell or a ligand for a receptor on the target cell may be incorporated into or attached to the nucleic acid carrier. Preferred antibodies comprise antibodies which bind selectively a tumor-associated antigen. If administration of a nucleic acid via liposomes is desired, proteins binding to a surface membrane protein associated with endocytosis may be incorporated into the liposome formulation in order to make target control and/or uptake possible. Such proteins comprise capsid proteins or fragments thereof which are specific for a particular cell type, antibodies to proteins which are internalized, proteins addressing an intracellular site, and the like.

The therapeutic compositions of the invention may be administered in pharmaceutically compatible preparations. Such preparations may usually contain pharmaceutically compatible concentrations of salts, buffer substances, preservatives, carriers, supplementing immunity-enhancing substances such as adjuvants, CpG and cytokines and, where appropriate, other therapeutically active compounds.

The therapeutically active compounds of the invention may be administered via any conventional route, including by injection or infusion. The administration may be carried out, for example, orally, intravenously, intraperitonealy, intramuscularly, subcutaneously or transdermally. Preferably, antibodies are therapeutically administered by way of a lung aerosol. Antisense nucleic acids are preferably administered by slow intravenous administration.

The compositions of the invention are administered in effective amounts. An "effective amount" refers to the amount which achieves a desired reaction or a desired effect alone or together with further doses. In the case of treatment of a particular disease or of a particular condition characterized by expression of one or more tumor-associated antigens, the desired reaction relates to inhibition of the course of the disease. This comprises slowing down the progress of the disease and, in particular, interrupting the progress of the disease. The desired reaction in a treatment of a disease or of a condition may also be delay of the onset or a prevention of the onset of said disease or said condition.

An effective amount of a composition of the invention will depend on the condition to be treated, the severeness of the disease, the individual parameters of the patient, including age, physiological condition, size and weight, the duration of treatment, the type of an accompanying therapy (if present), the specific route of administration and similar factors.

The pharmaceutical compositions of the invention are preferably sterile and contain an effective amount of the therapeutically active substance to generate the desired reaction or the desired effect.

The doses administered of the compositions of the invention may depend on various parameters such as the type of administration, the condition of the patient, the desired period of administration, etc. In the case that a reaction in a patient is insufficient with an initial dose, higher doses (or effectively higher doses achieved by a different, more localized route of administration) may be used.

Generally, doses of the tumor-associated antigen of from 1 ng to 1 mg, preferably from 10 ng to 100 μg, are formulated and administered for a treatment or for generating or increasing an immune response. If the administration of nucleic acids (DNA and RNA) coding for tumor-associated antigens is desired, doses of from 1 ng to 0.1 mg are formulated and administered.

The pharmaceutical compositions of the invention are generally administered in pharmaceutically compatible amounts and in pharmaceutically compatible compositions. The term "pharmaceutically compatible" refers to a nontoxic material which does not interact with the action of the active component of the pharmaceutical composition. Preparations of this kind may usually contain salts, buffer substances, preservatives, carriers and, where appropriate, other therapeutically active compounds. When used in medicine, the salts should be pharmaceutically compatible. However, salts which are not pharmaceutically compatible may used for preparing pharmaceutically compatible salts and are included in the invention. Pharmacologically and pharmaceutically compatible salts of this kind comprise in a nonlimiting way those prepared from the following acids: hydrochloric, hydrobromic, sulfuric, nitric, phosphoric, maleic, acetic, salicylic, citric, formic, malonic, succinic acids, and the like. Pharmaceutically compatible salts may also be prepared as alkali metal salts or alkaline earth metal salts, such as sodium salts, potassium salts or calcium salts.

A pharmaceutical composition of the invention may comprise a pharmaceutically compatible carrier. According to the invention, the term "pharmaceutically compatible carrier" refers to one or more compatible solid or liquid fillers, diluents or encapsulating substances, which are suitable for administration to humans. The term "carrier" refers to an organic or inorganic component, of a natural or synthetic nature, in which the active component is combined in order to facilitate application. The components of the pharmaceutical composition of the invention are usually such that no interaction occurs which substantially impairs the desired pharmaceutical efficacy.

The pharmaceutical compositions of the invention may contain suitable buffer substances such as acetic acid in a salt, citric acid in a salt, boric acid in a salt and phosphoric acid in a salt.

The pharmaceutical compositions may, where appropriate, also contain suitable preservatives such as benzalkonium chloride, chlorobutanol, paraben and thimerosal.

The pharmaceutical compositions are usually provided in a uniform dosage form and may be prepared in a manner known per se. Pharmaceutical compositions of the invention may be in the form of capsules, tablets, lozenges, suspensions, syrups, elixir or in the form of an emulsion, for example.

Compositions suitable for parenteral administration usually comprise a sterile aqueous or nonaqueous preparation of the active compound, which is preferably isotonic to the blood of the recipient. Examples of compatible carriers and solvents are Ringer solution and isotonic sodium chloride solution. In addition, usually sterile, fixed oils are used as solution or suspension medium.

The present invention is described in detail by the figures and examples below, which are used only for illustration purposes and are not meant to be limiting. Owing to the description and the examples, further embodiments which are likewise included in the invention are accessible to the skilled worker.

FIGURES

FIG. 1: Diagrammatic representation of the cloning of eCT. The strategy comprises identifying candidate genes (GOI="Genes of interest") in databases and testing said genes by means of RT-PCR.

Figure 2:
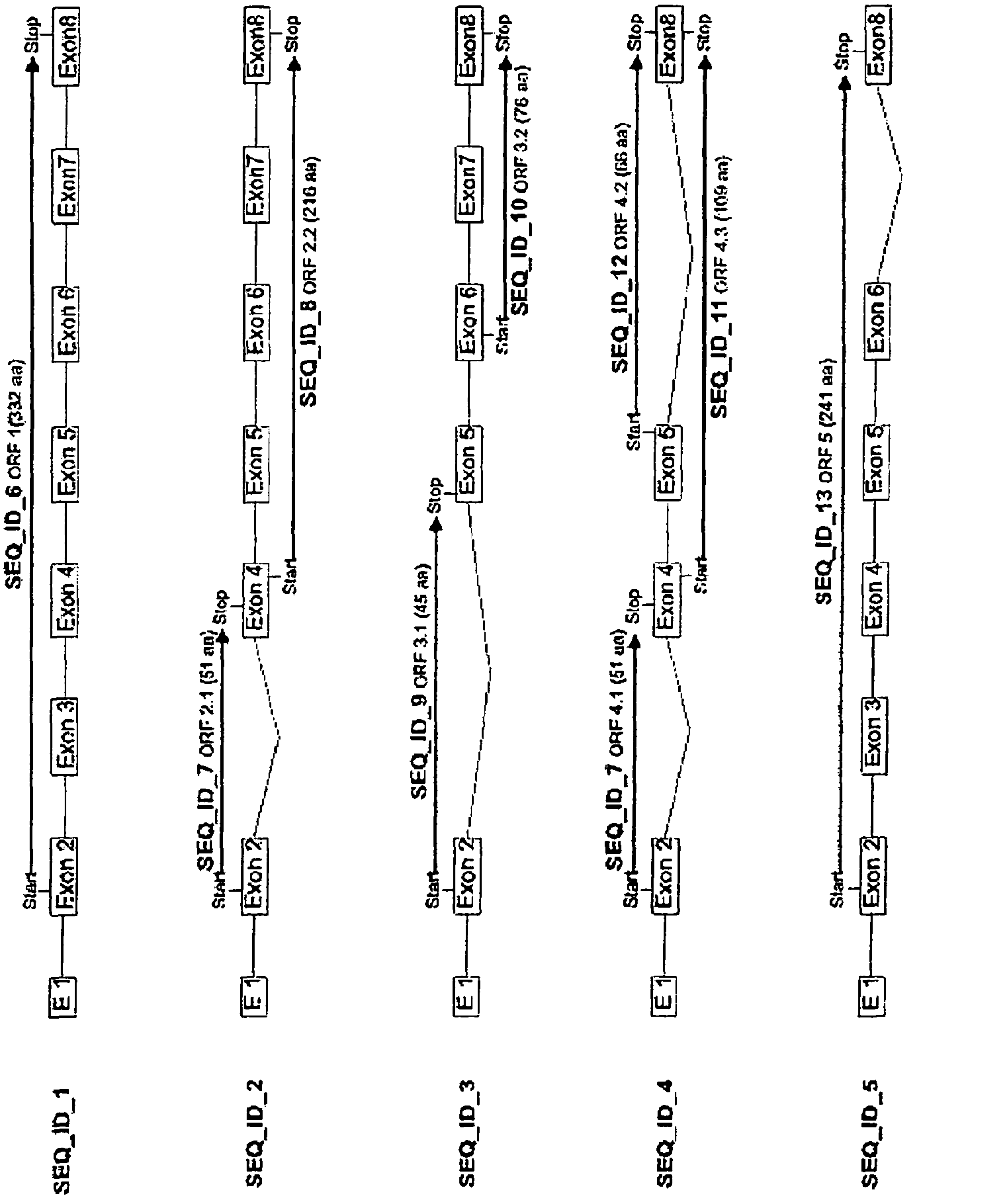

FIG. 2: Splicing of LDH C. Alternative splicing events result in the absence of exon 3 (SEQ ID NO:2), of the two exons 3 and 4 (SEQ ID NO:3), of the exons 3, 6 and 7 (SEQ ID NO:4) and of exon 7 (SEQ ID NO:5). ORF=open reading frame, aa=amino acid.

FIG. 3: Alignment of possible LDH-C proteins. SEQ ID NO:8 and SEQ ID NO:10 are truncated portions of the prototype protein (SEQ ID NO:6). The protein sequences of SEQ ID NO:7, SEQ ID NO:9, SEQ ID NO:11, SEQ ID NO:12 and SEQ ID NO:13 are additionally altered and contain only tumor-specific epitopes (printed in bold type). The catalytic centre is framed.

Figure 4:
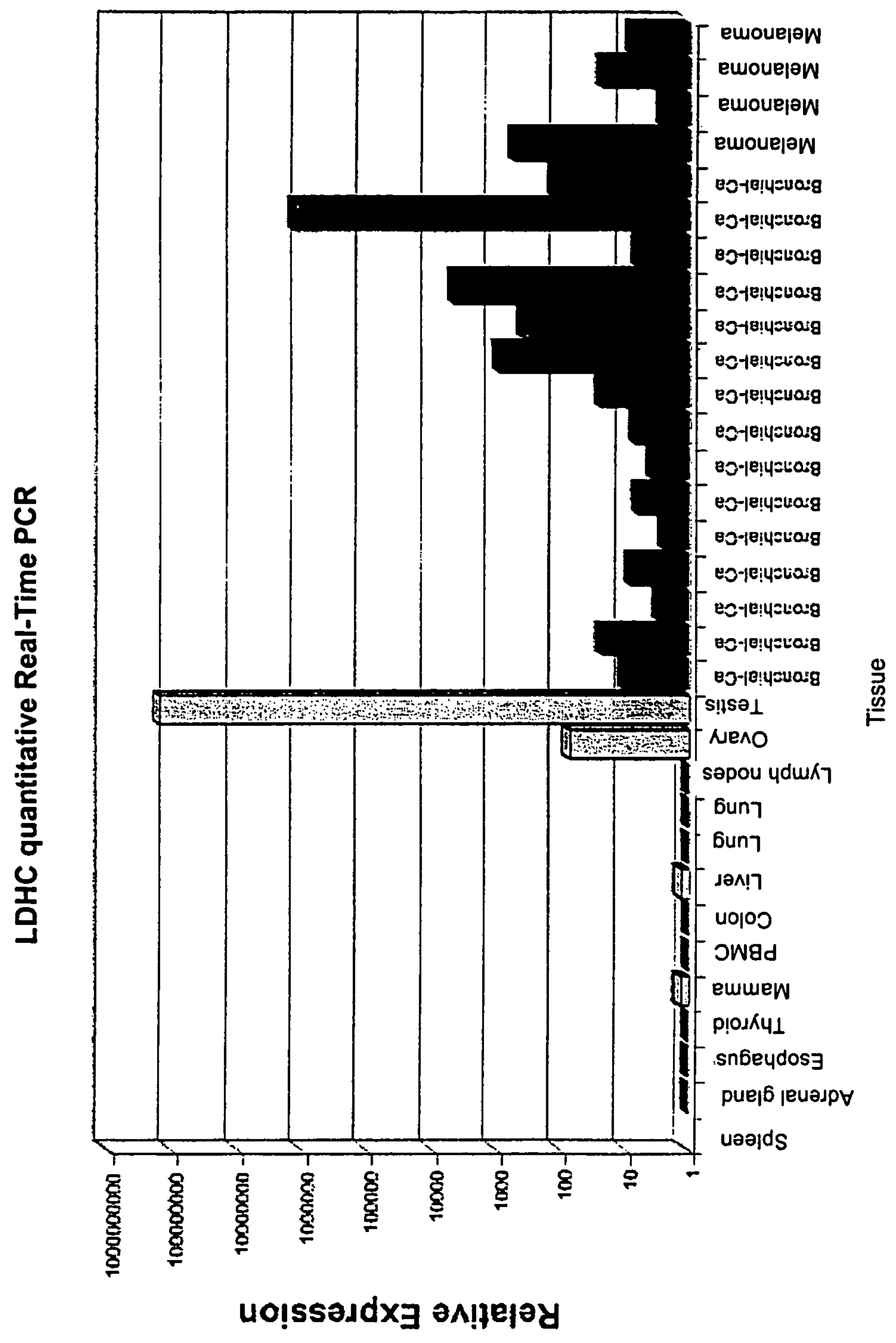

FIG. 4: Quantification of LDH C in various tissues by means of real time PCR. No transcripts were detected in normal tissues other than testis, but significant levels of expression were detected in tumors.

Figure 5:
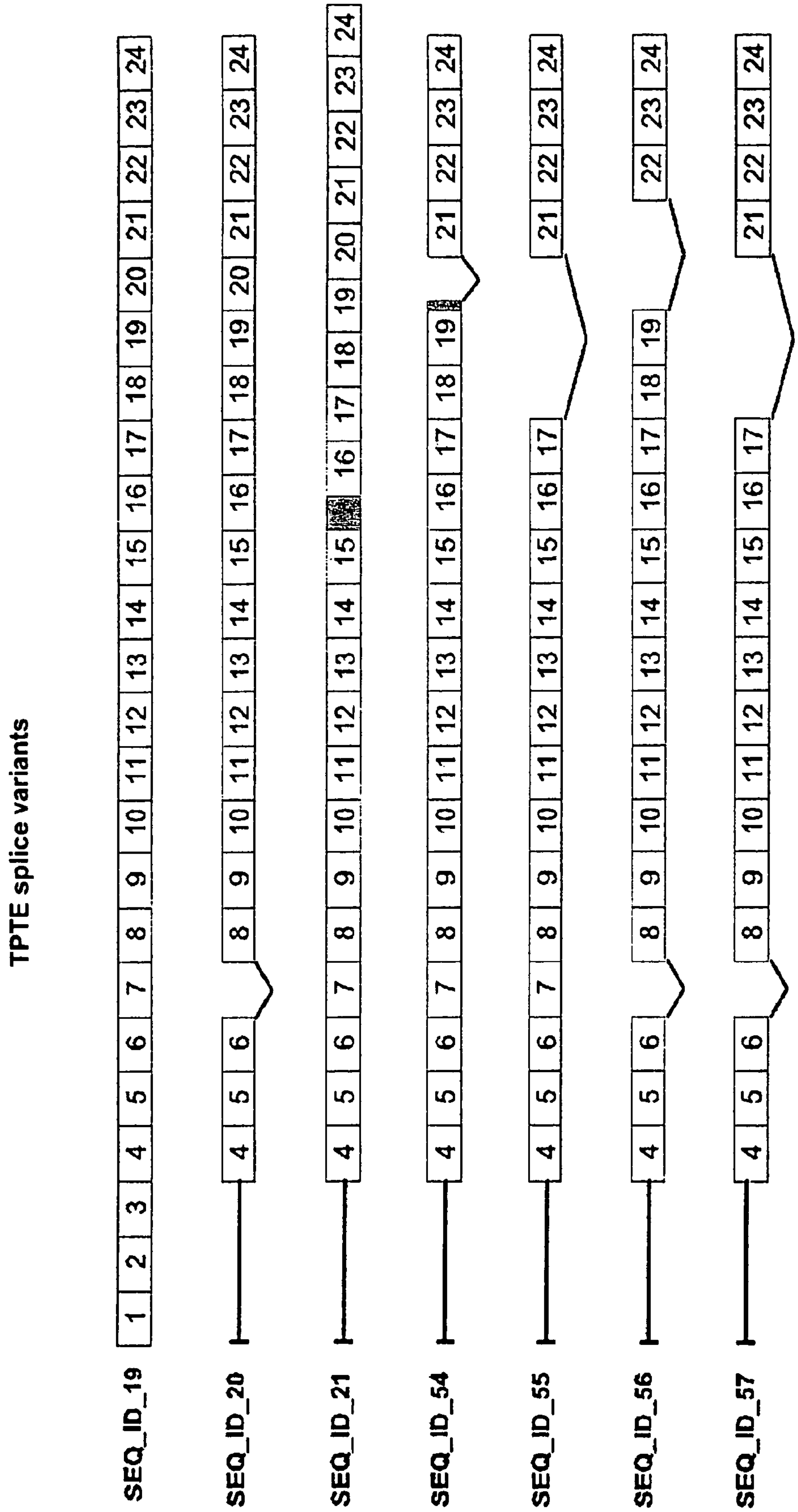

FIG. 5: Exon composition of TPTE variants. According to the invention, splice variants were identified (SEQ ID NO:20, SEQ ID NO:21, SEQ ID NO:54, SEQ ID NO:55, SEQ ID NO:56, SEQ ID NO:57) which are expressed in testicular tissues and in tumors and which have frame shifts and thus altered sequence regions.

FIG. 6: Alignment of the possible TPTE proteins. Alternative splicing events result in alterations of the encoded proteins, with the reading frame being retained in principle. The putative transmembrane domains are printed in bold type, the catalytic domain is framed.

FIG. 7: Alignment of TSBP variants at the nucleotide level. The differences in the nucleotide sequences of the TSBP variants found according to the invention (SEQ ID NO:31, SEQ ID NO:32, SEQ ID NO:33) to the known sequence (NM_006781, SEQ ID NO: 29) are printed in bold type.

FIG. 8: Alignment of TSBP variants at the protein level. In the proteins encoded by the TSBP variants found according to the invention (SEQ ID NO:34, SEQ ID NO:35, SEQ ID NO:36), frame shifts cause substantial differences to the previously described protein (SEQ ID NO:30, NM_006781) and are indicated by bold type.

Figure 9:
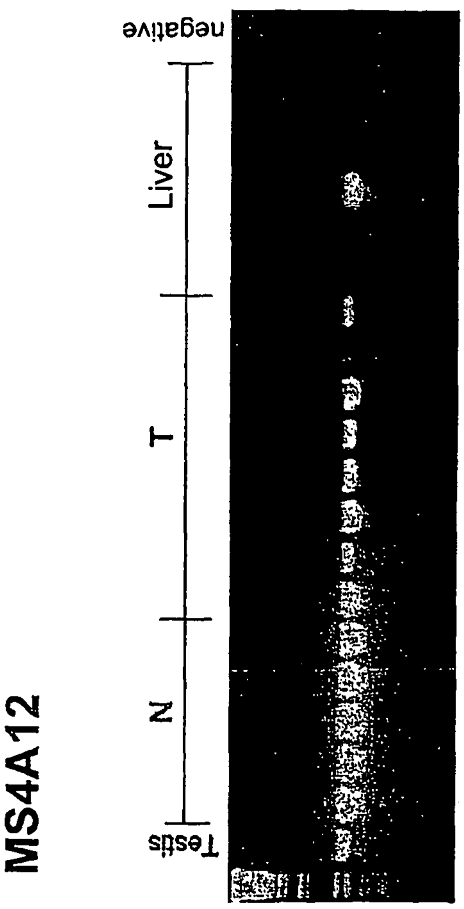

FIG. 9: RT-PCR for MS4A12. Expression was detected in the tissues tested only in testis, colon and colorectal carcinomas (colon ca's). In one of the 6 liver tissue samples shown, a positive detection was carried out for MS4A12, since this sample has been infiltrated by a colon carcinoma metastasis. Later studies also demonstrated distinct expression in colon carcinoma metastases.

Figure 10:
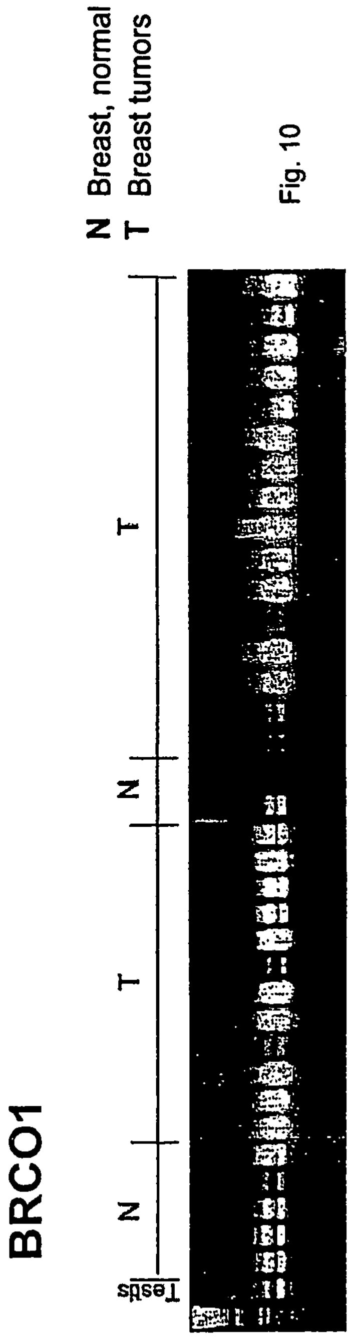

FIG. 10: RT-PCR for BRCO1. BRCO1 is distinctly overexpressed in breast tumors in comparison with expression in normal mammary gland tissue.

Figure 11:
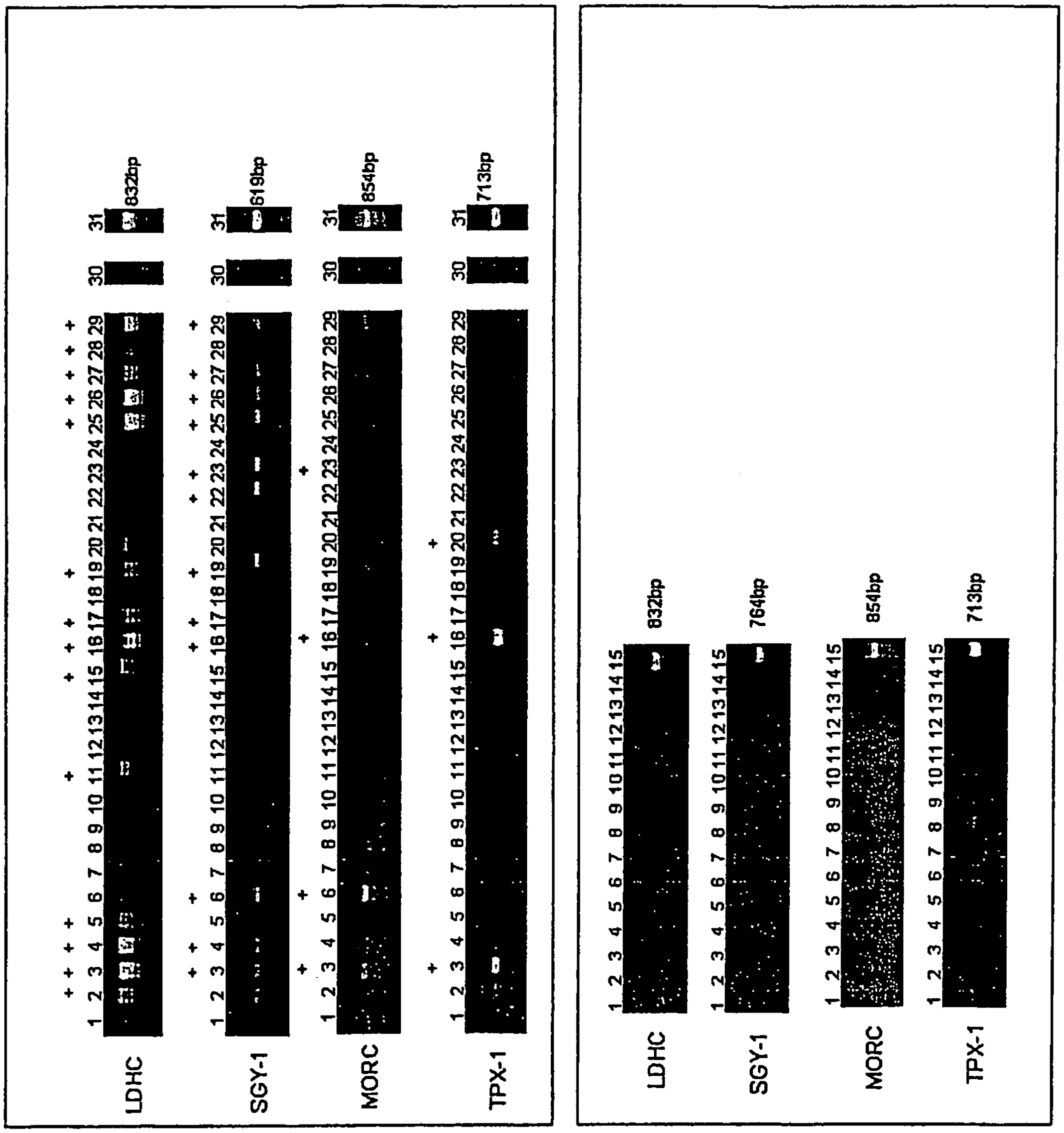

FIG. 11: RT-PCR for MORC, TPX1, LDHC, SGY-1. A study of various normal tissues reveals expression only in testis (1 skin, 2 small intestine, 3 colon, 4 liver, 5 lung, 6 stomach, 7 breast, 8 kidney, 9 ovary, 10 prostate, 11 thyroid, 12 leukocytes, 13 thymus, 14 negative control, 15 testis). The examination of tumors (1-17 lung tumors, 18-29 melanomas, 30 negative control, 31 testis) reveals ectopic expression in said tumors with different frequencies for the individual eCT.

Figure 12:
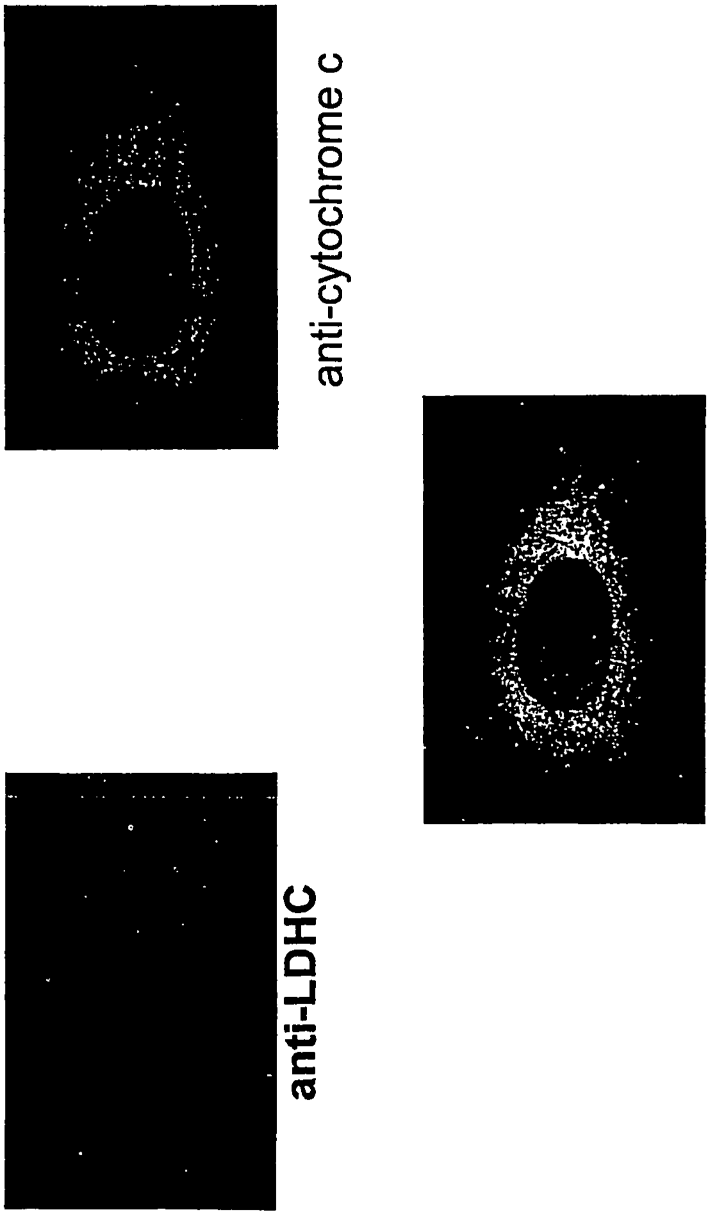

FIG. 12: Mitochondrial localization of LDHC in the MCF-7 breast cancer cell line. MCF-7 cells were transiently transfected with an LDHC expression plasmid. The antigen was detected with LDHC-specific antibodies and showed distinct colocalization with the mitochondrial respiratory chain enzyme cytochrome C-oxidase.

Figure 13:
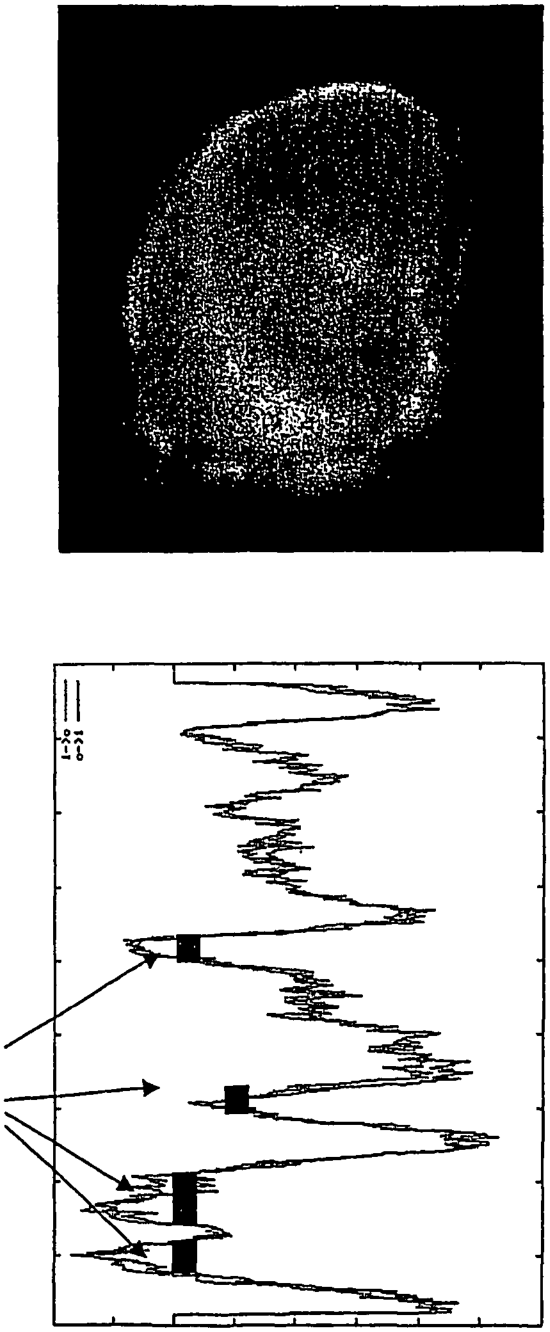

FIG. 13: Predicted topology of TPTE and subcellular localization on the cell surface of MCF-7 cells The diagram on the left-hand side depicts the 4 putative TPTE transmembrane domains (arrows). MCF-7 cells were transiently transfected with a TPTE expression plasmid. The antigen was detected using TPTE-specific antibodies and showed distinct colocalization with MHC I molecules located on the cell surface.

Figure 14:

FIG. 14: MS4A12 localization on the cell membrane.

Tumor cells were transiently transfected with a GFP-tagged MS4A12 construct and showed complete colocalization with plasma membrane markers in confocal immunofluorescence microscopy.

Figure 15:
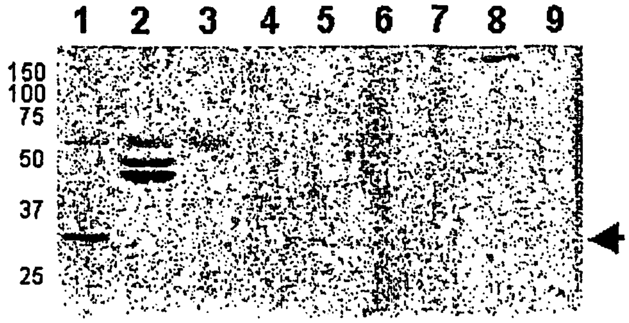

FIG. 15: Western blot detection of LDHC in normal tissues.

Expression of LDHC is only detectable in testis while all other normal tissues tested are negative. 1-testis, normal tissue, 2-skin, normal tissue, 3-breast, normal tissue, 4-liver, normal tissue, 5-spleen, normal tissue, 6-colon, normal tissue, 7-lung, normal tissue, 8-kidney, normal tissue, 9-lymph node, normal tissue.

FIG. 16: Expression of LDHC in the cell line HCT116 DKO.

HCT116 P and HCT116 DKO were stained using a LDHC-specific antibody. Endogenous LDHC is only detectable in HCT116 DKO cells.

Figure 17:
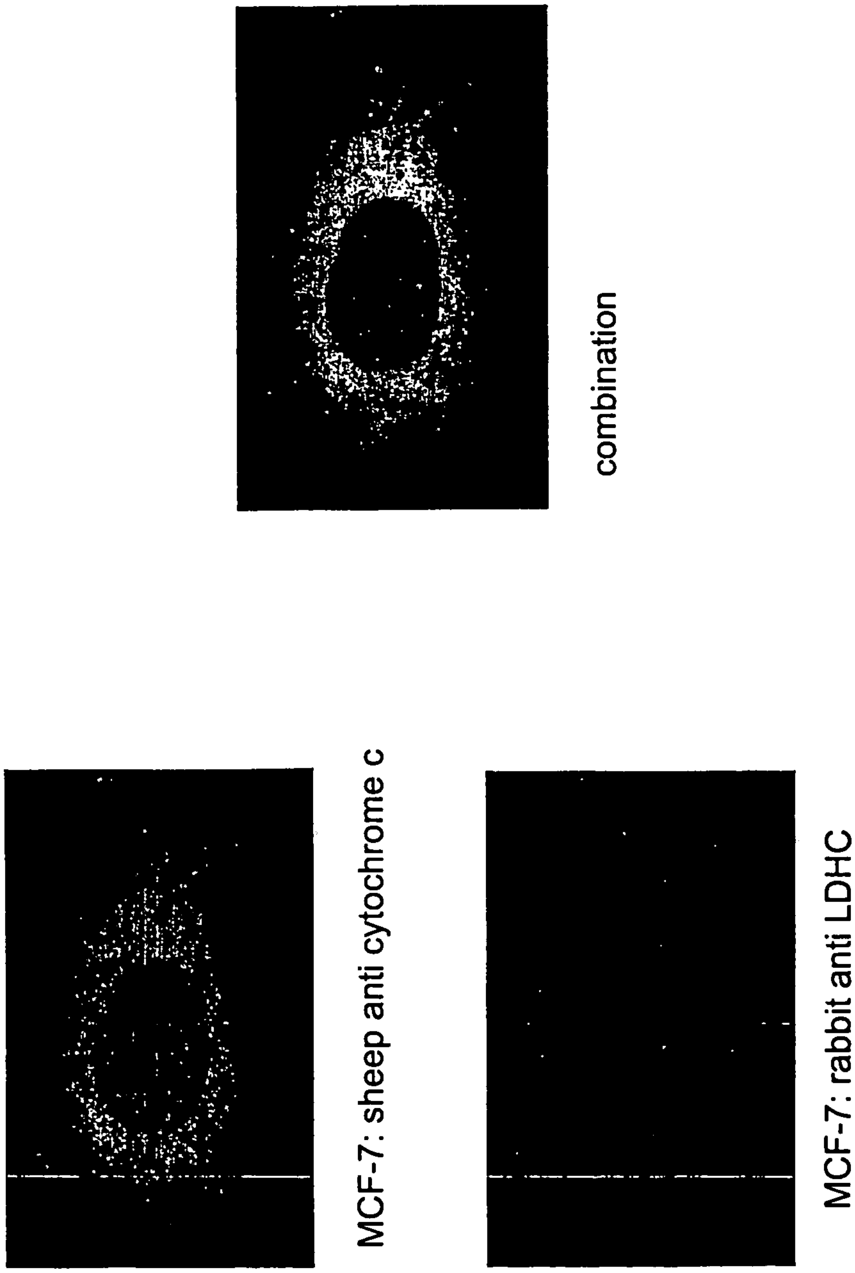

FIG. 17: Mitochondrial localization of LDHC in the MCF-7 breast cancer cell line.

MCF-7 cells were transiently transfected with an LDHC expression plasmid. The antigen was detected with LDHC-specific antibodies and showed distinct co-localization with the mitochondrial respiratory chain enzyme cytochrome C-oxidase.

FIG. 18: Localization on the cell membrane of heterologously and endogenously expressed TPTE in cell lines.

(Left) NIH3T3 cells were transfected transiently with a TPTE expression plasmid. TPTE was detected using specific antibodies and showed a distinct co-localization with MHC I molecules located on the cell surface. (Right) Endogenous TPTE in SK-Mel 37 cells was detected using a specific antibody and showed distinct membrane localization.

Figure 19:
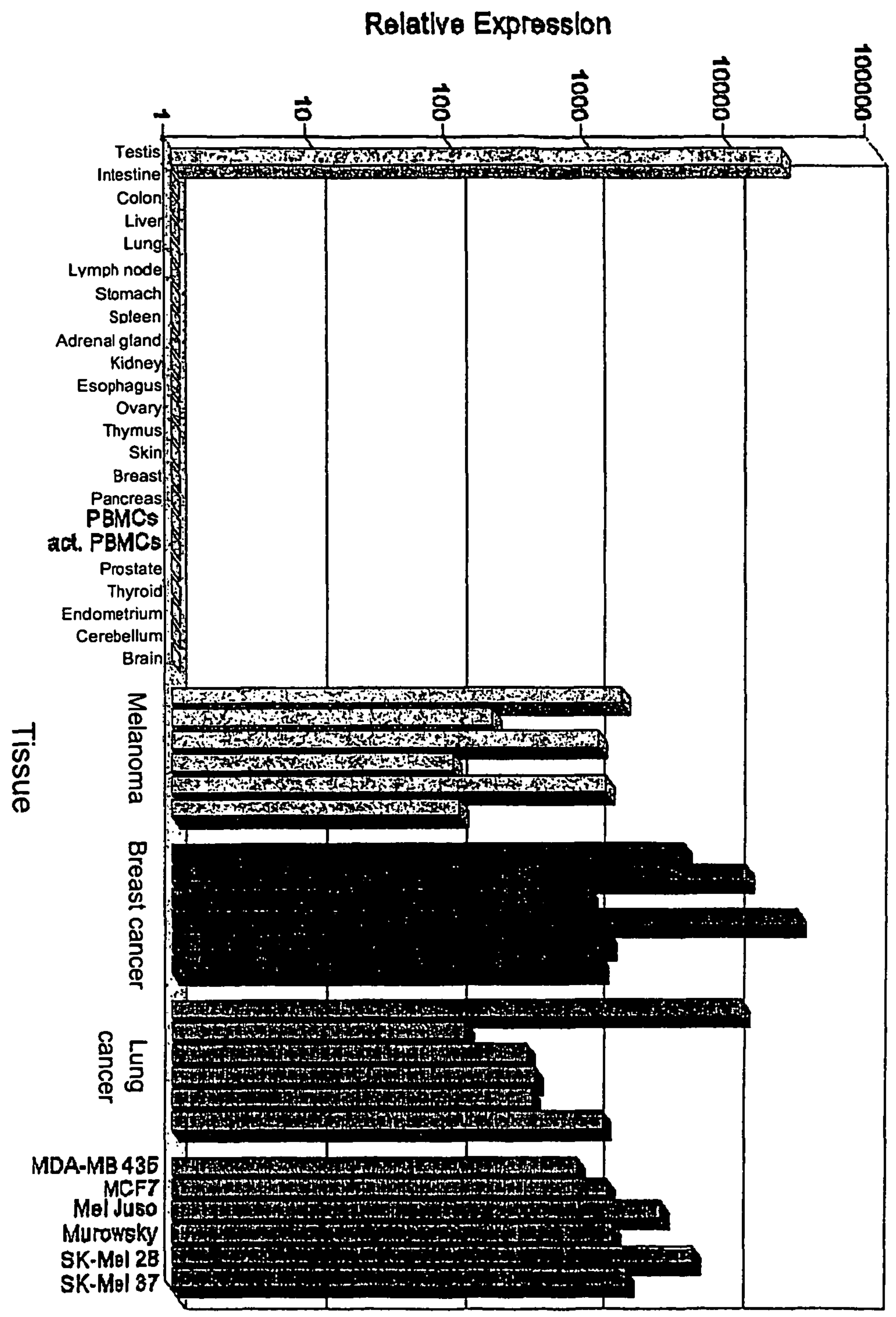

FIG. 19: Quantification of the expression of TPTE mRNA in different tissues by real-time PCR.

Expression in normal tissues is only detectable in testis. Significant expression levels are found also in tumors and tumor cell lines.

Figure 20:
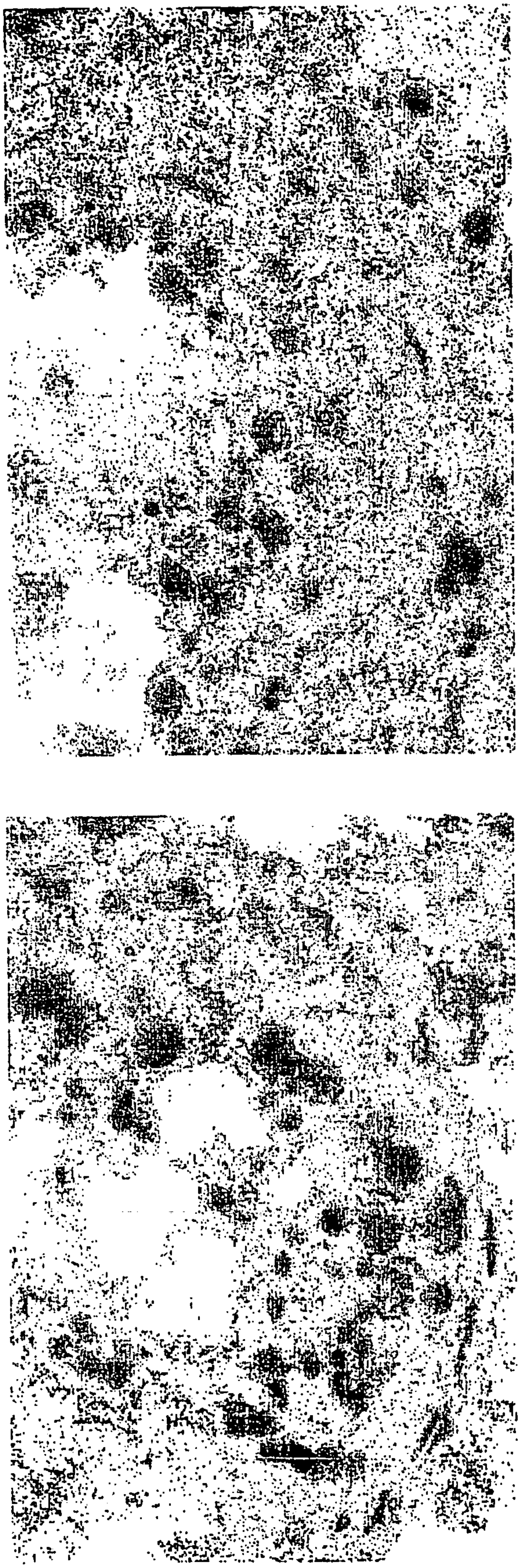

FIG. 20: Detection of the antibody specificity.

Sections of testis tissue were stained with a TPTE specific antibody. The specific detection of TPTE is inhibited by blocking (right) of the antibody with the peptide used for immunization.

Figure 21:
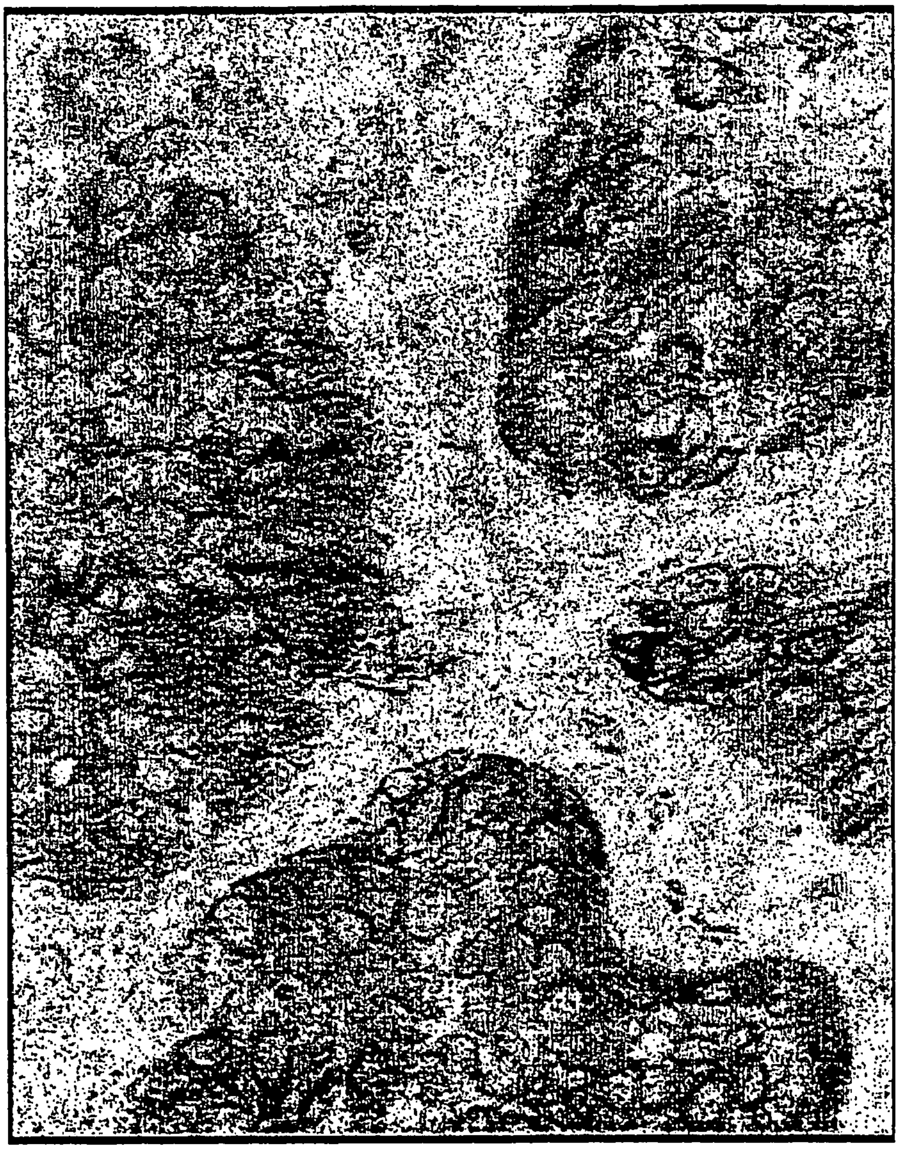

FIG. 21: Immunohistochemical detection of TPTE in bronchial carcinomas.

Sections of bronchial carcinomas were stained with a TPTE specific antibody. TPTE is expressed homogeneously in the entire tumor and is localized at the cell membrane.

Figure 22:
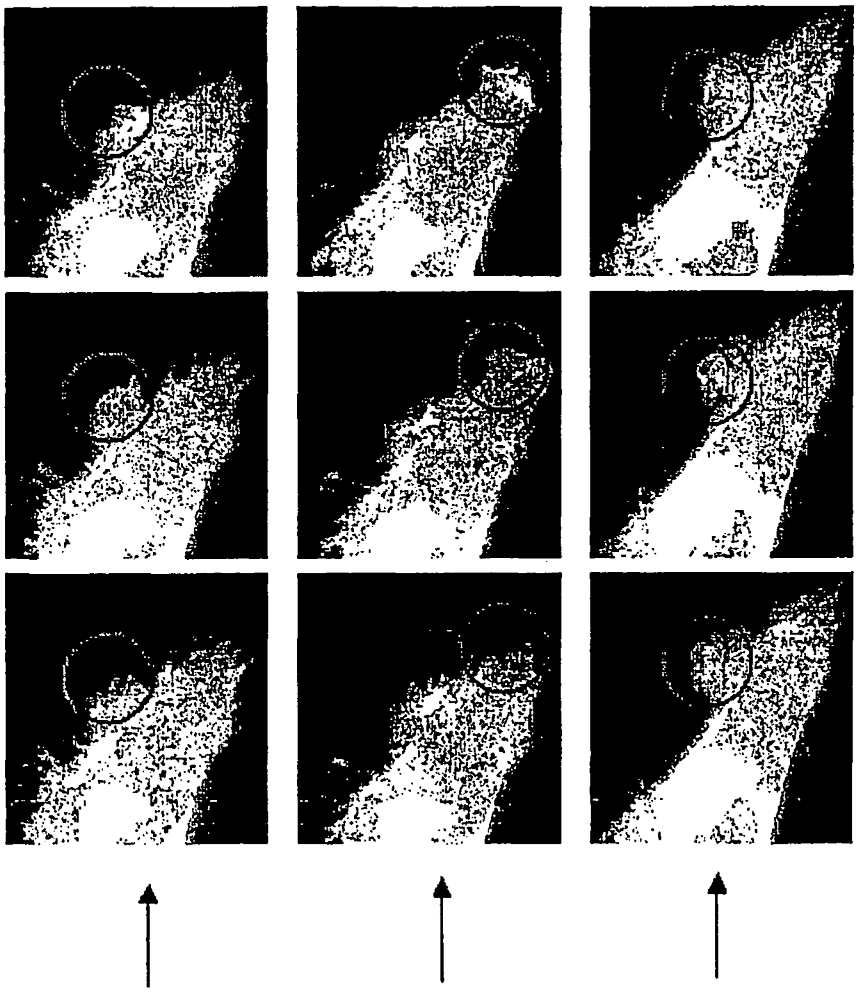

FIG. 22: Detection of the localization of TPTE in vital cells.

NIH3T3 cells were transiently transfected with a TPTE expression plasmid and analyzed by time-lapse microscopy. The localization of TPTE on the membrane of cell protrusions and pseudopodias results in immediate retraction of the respective membrane regions.

Figure 23:
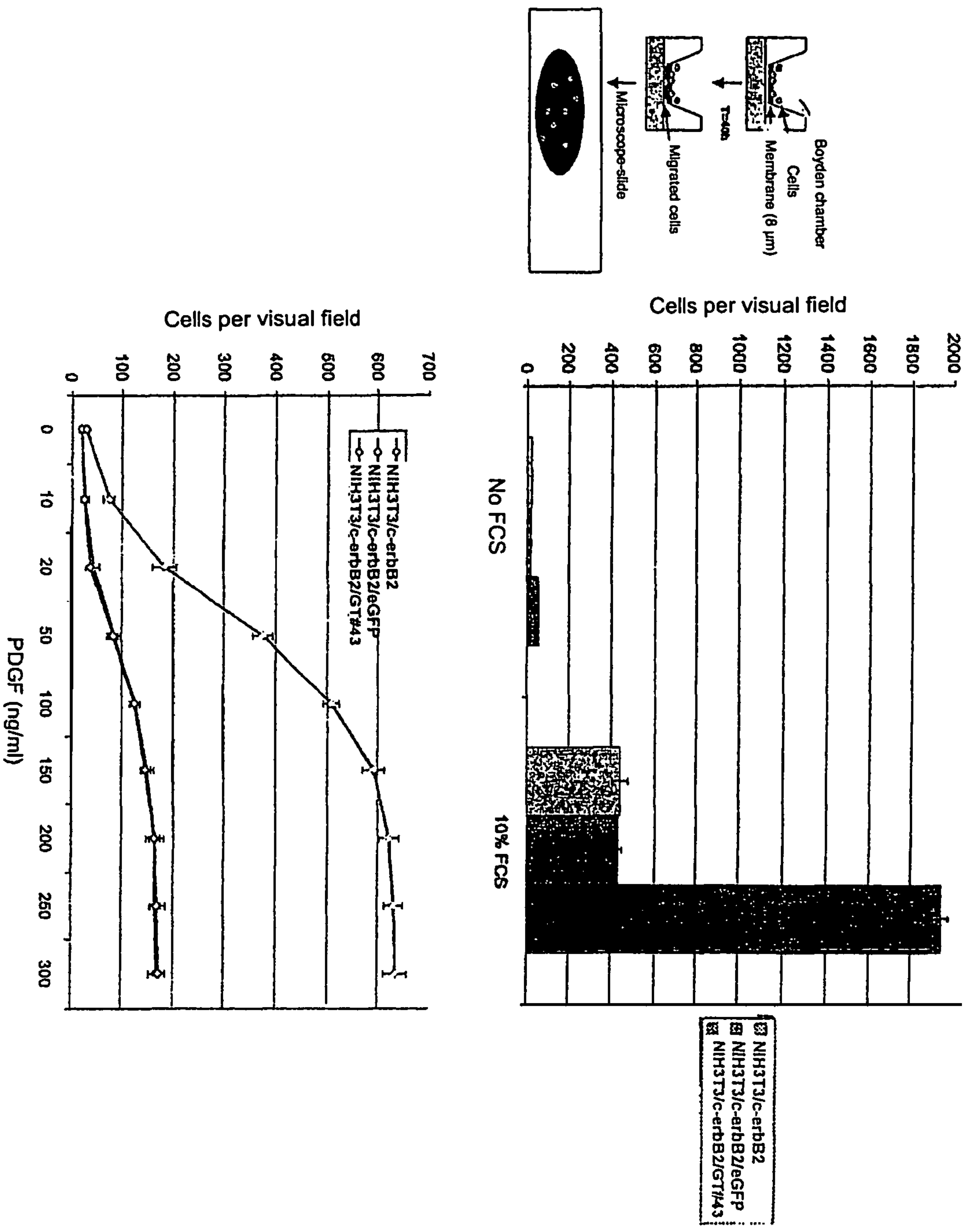

FIG. 23: TPTE enhances cell migration in chemotactic gradients.

(Left) Diagrammatic representation of the Boyden chamber assay. NIH3T3/c-erbB-2 cells were transfected with TPTE-eGFP and the migration of the cells was determined compared to cells which have not been transfected or which have been transfected with the empty pEGFP vector. (Upper right) The expression of TPTE results in a migration of the cells which is increased by a factor of 4-5 if 10% FCS is used as a chemotactic agent. (Lower right) The expression of TPTE results in a significant enhancement of migration even at very low concentrations of PDGF.

FIG. 24: Expression of TPTE in tumors is associated with metastasis.

Statistic evaluation of the TNM stages of 58 tumor samples in correlation with the expression of TPTE shows that TPTE positive tumors metastasize in a lymphogenic and hematogenic manner at a significant higher frequency.

FIG. 25: Expression of TSBP in the HCT116 DKO cell line.

HCT116 P and HCT116 DKO were stained with a TSBP specific antibody. Endogenous TSBP is only detectable in HCT116 DKO cells and is associated with the nuclear membrane.

FIG. 26: Detection of the expression of MS4A12 mRNA in tissues by RT-PCR and real-time PCR.

The expression of MS4A12 in normal tissues is restricted to colon, rectum, terminal ileum and testis. 80% of the colon carcinomas and 80% of the colon carcinoma metastases show significant expression levels of MS4A12.

Figure 27:
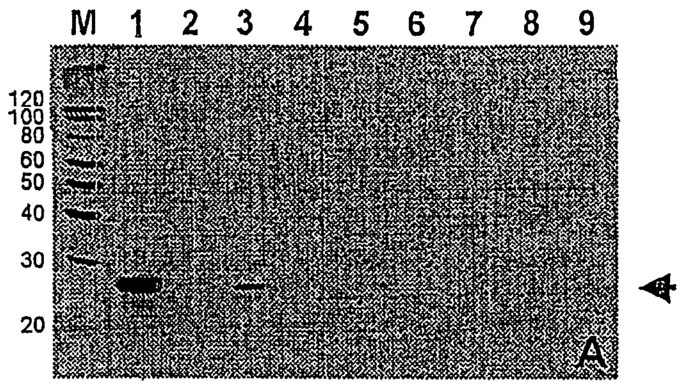

FIG. 27: Western blot detection of MS4A12 in colon and colon carcinomas.

The specific band is detectable in normal colon tissue and in several colon carcinomas. M-MagicMark (Invitrogen), 1-colon tissue, normal, 2-6-colon tissue, tumor.

Figure 28:
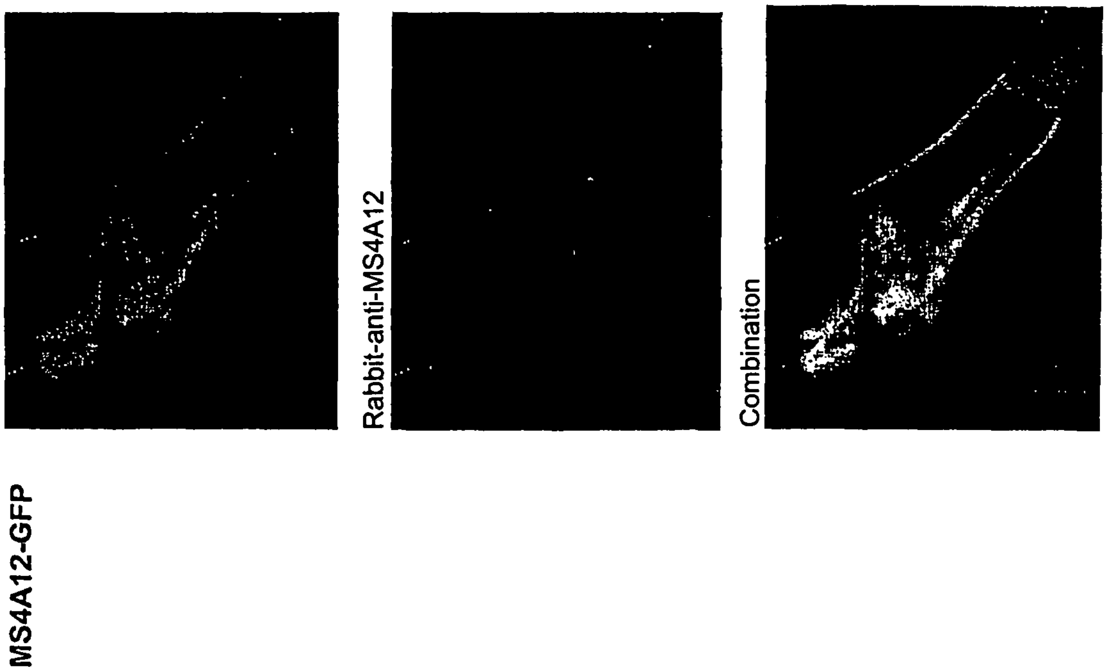

FIG. 28: MS4A12 localization at the cell membrane.

Tumor cells were transiently transfected with MS4A12-eGFP and showed localization at the plasma membrane in confocal immune fluorescence microscopy using a MS4A12-specific antibody.

FIG. 29: Immunohistochemical detection of MS4A12 in colon and colon carcinomas.

Tissue sections were stained with a MS4A12-specific antibody. In normal colon MS4A12 is only expressed in apical enterocytes. In colon carcinomas expression of MS4A12 is detectable in all tumor cells.

Figure 30:
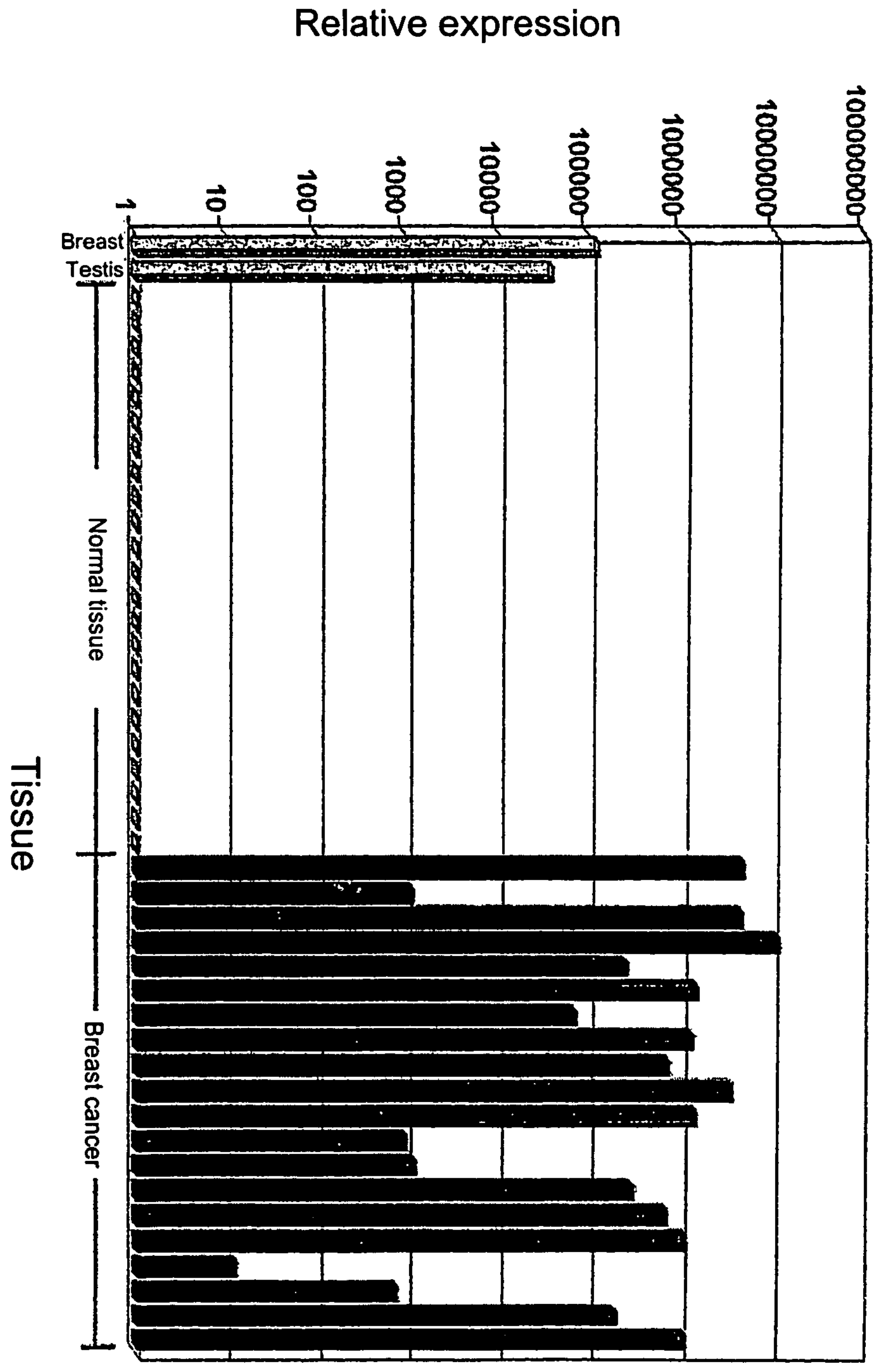

FIG. 30: Quantification of the expression of BRCO1 mRNA in different tissues by real-time PCR.

Expression of BRCO1 in normal tissues is restricted to breast and testis. Significant expression levels of BRCO1 are detectable in all mamma carcinomas tested. 50% of the tumors show overexpression of BRCO1 when compared to expressing normal tissues.

Figure 31:
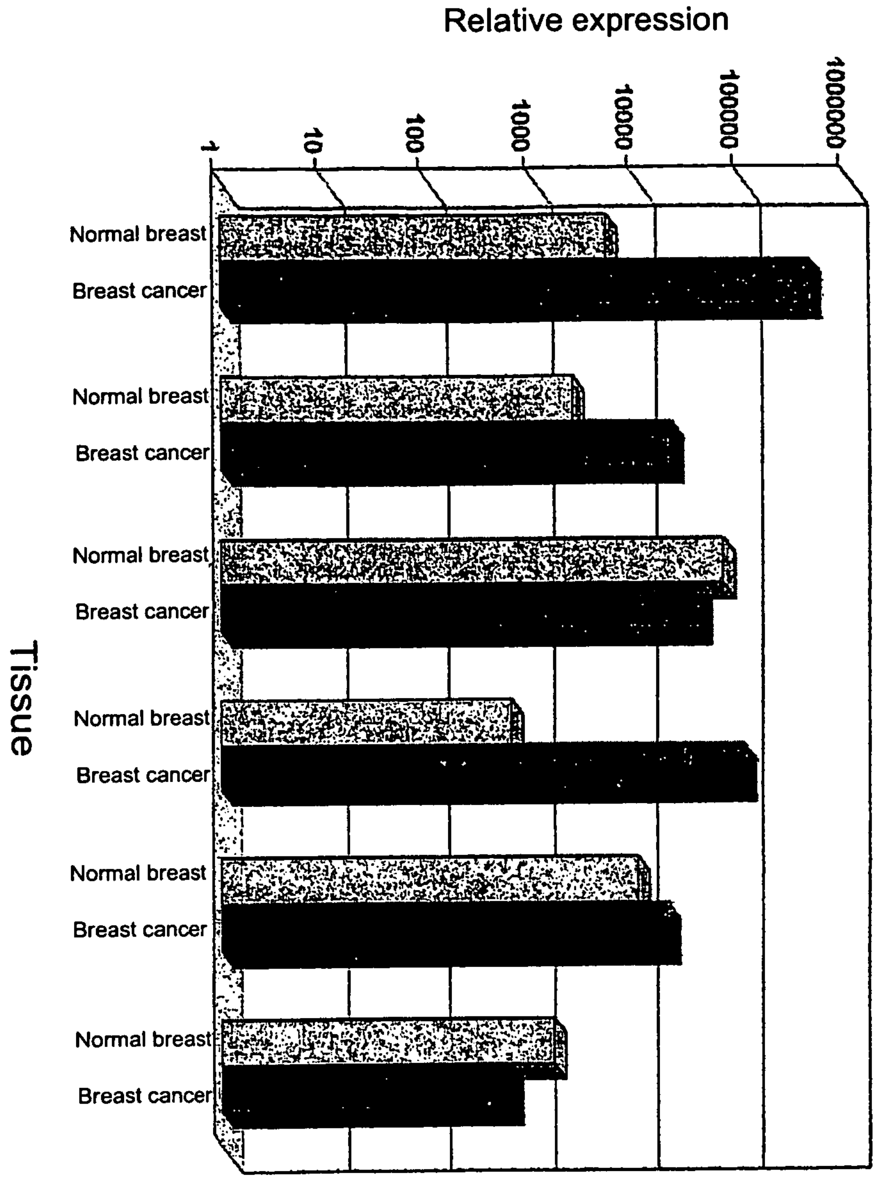

FIG. 31: Overexpression of BRCO1 in mamma carcinomas. Real-time PCR assays for BRCO1 in mamma carcinomas and adjacent normal tissues showed overexpression of BRCO1 in 50% of the mamma carcinomas.

Figure 32:
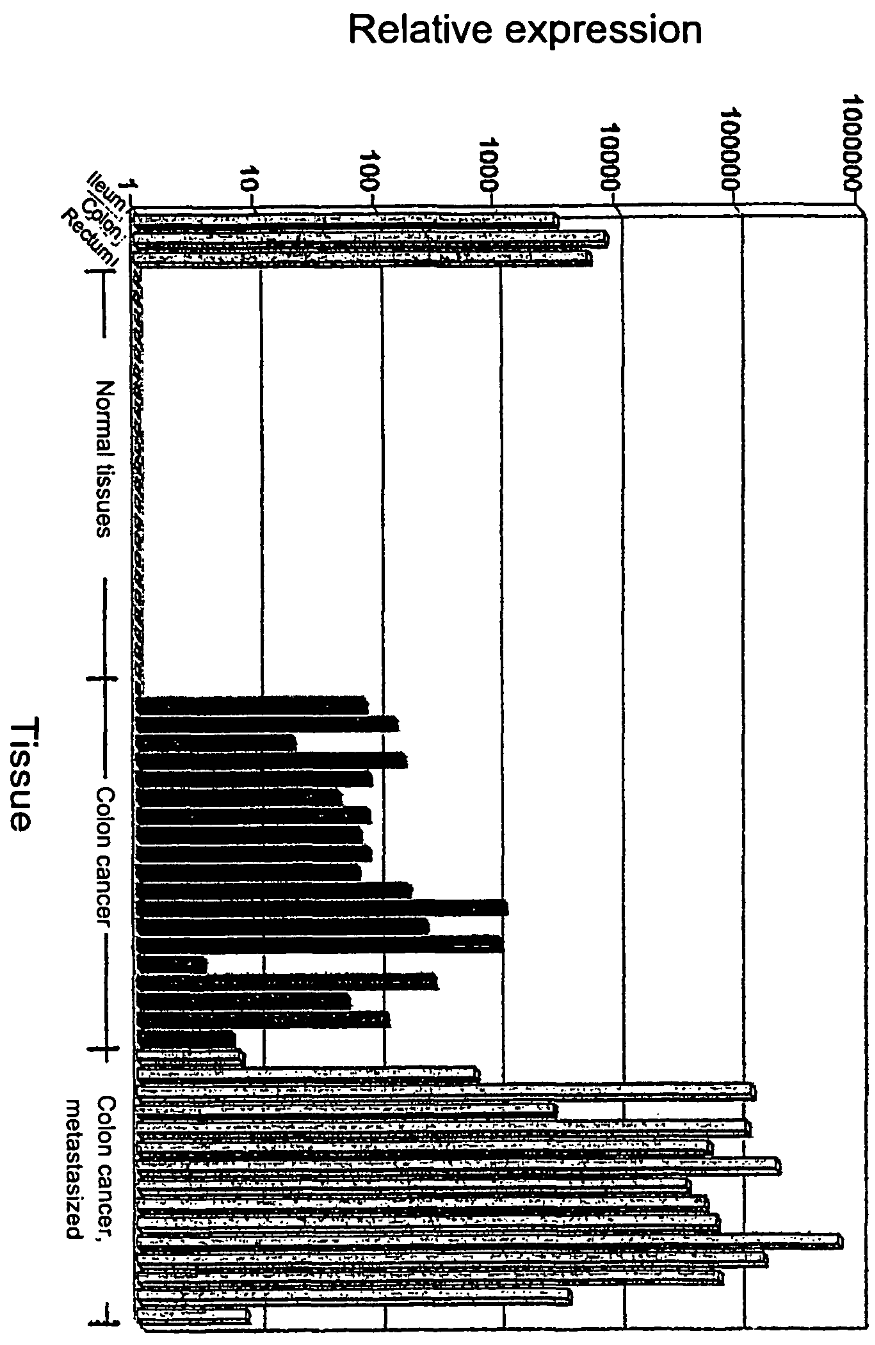

FIG. 32: Quantification of the expression of PCSC mRNA in different tissues by real-time PCR.

Expression of PCSC in normal tissues is restricted to colon, rectum, and terminal ileum. Expression of PCSC is detectable in all colon carcinomas. 85% of the colon carcinoma metastasis showed significant overexpression of PCSC when compared to the primary tumors.

Figure 33:
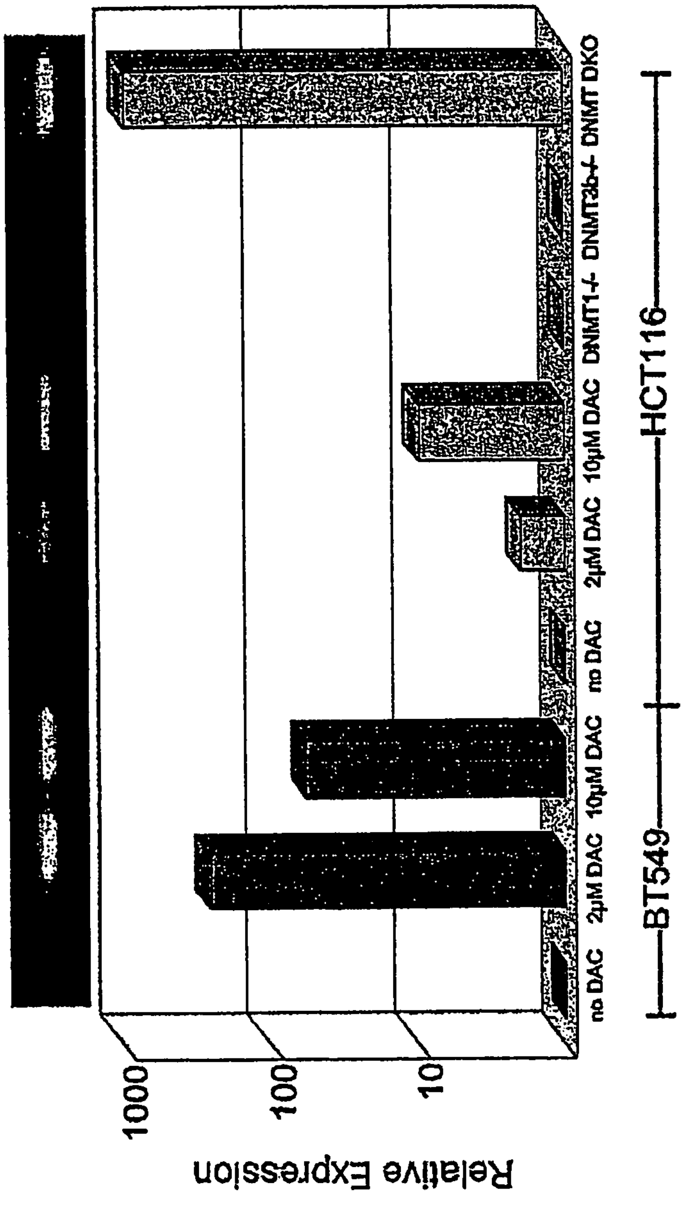

FIG. 33: Detection of the induceability of TPTE by genomic demethylation.

Real-time RT-PCR analysis of the TPTE expression in the non-expressing cell lines BT549 and HCT116 following treatment of the cells with 2 μM and 10 μM 5-aza-2'-desoxycytidine, respectively, and in HCT116 cells which are deficient for DNA methyltransferase.

Figure 34:
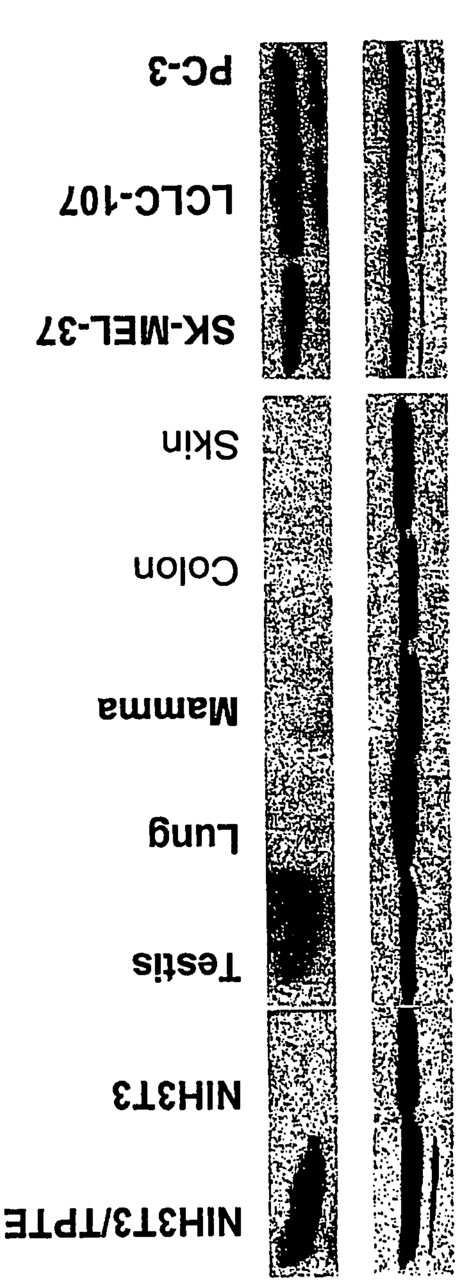

FIG. 34: Western blot analysis of TPTE in normal tissues and tumor cell lines.

Expression of LDHC is only detectable in testis and tumor cell lines (SK-Mel-37, LCLC-107, PC-3), while all other normal tissues tested are negative. The specificity of the antibody is confirmed by the detection of TPTE in transfected NIH3T3 cells (TPTE-pcDNA3.1).

Figure 35:
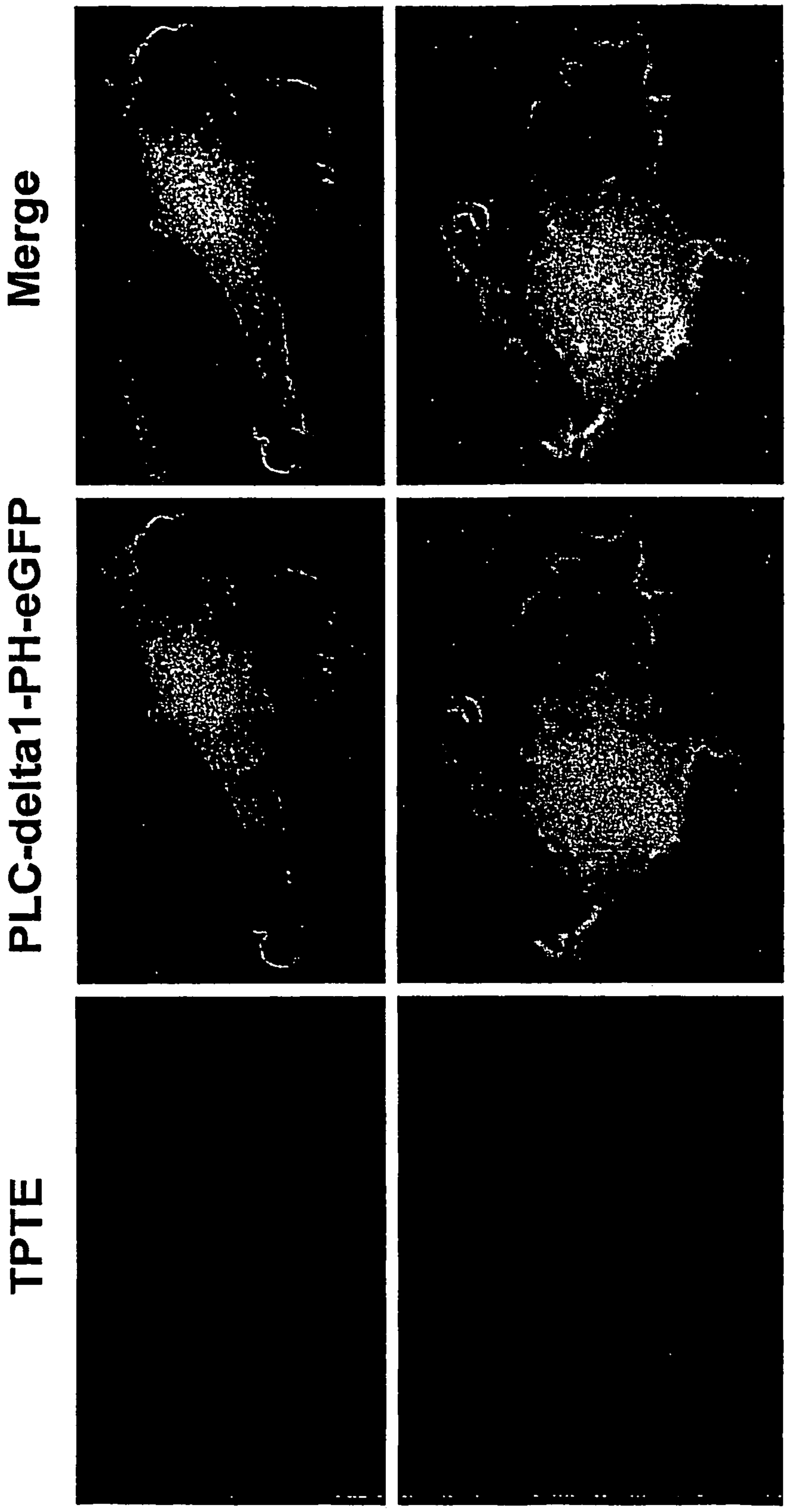

FIG. 35: TPTE co-localizes with $PIP_{4,5}$.

NIH3T3/c-erb-2 cells transfected with TPTE were cotransfected with PH-eGFP of PLC-deltal and stained with a TPTE-specific antibody. The superimposition shows distinct co-localization of TPTE with PLC-deltal-PH-eGFP as a marker for $PIP_{4,5}$.

Figure 36:
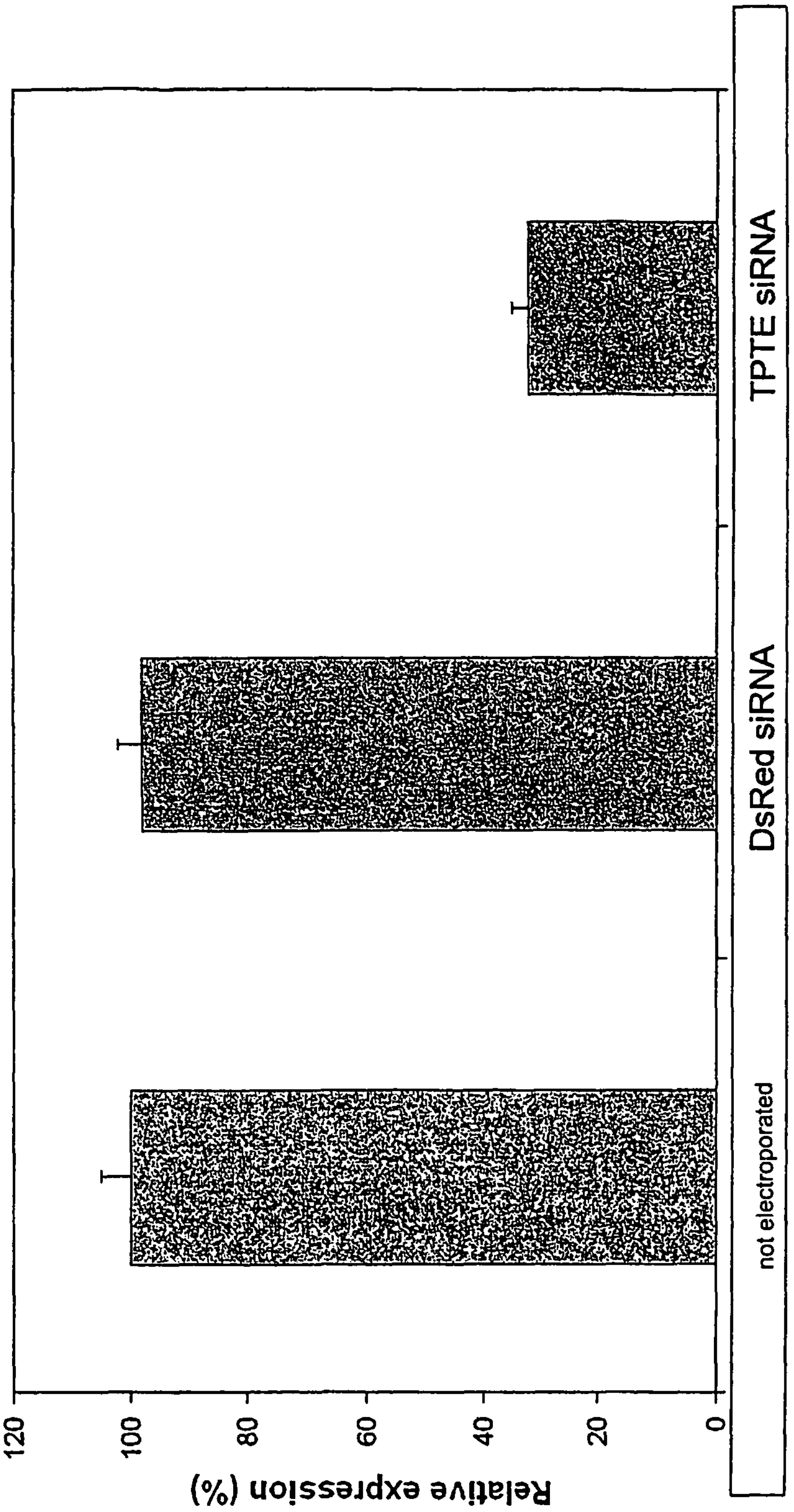

FIG. 36: Knock-down of TPTE expression in PC-3 cells using RNAi.

PC-3 cells were electroporated using 1 μM siRNA specific for TPTE. After 24 h mRNA expression was quantified by real-time RT-PCR. Non-electroporated cells and cells electroporated with DsRed siRNA served as controls.

Figure 37:
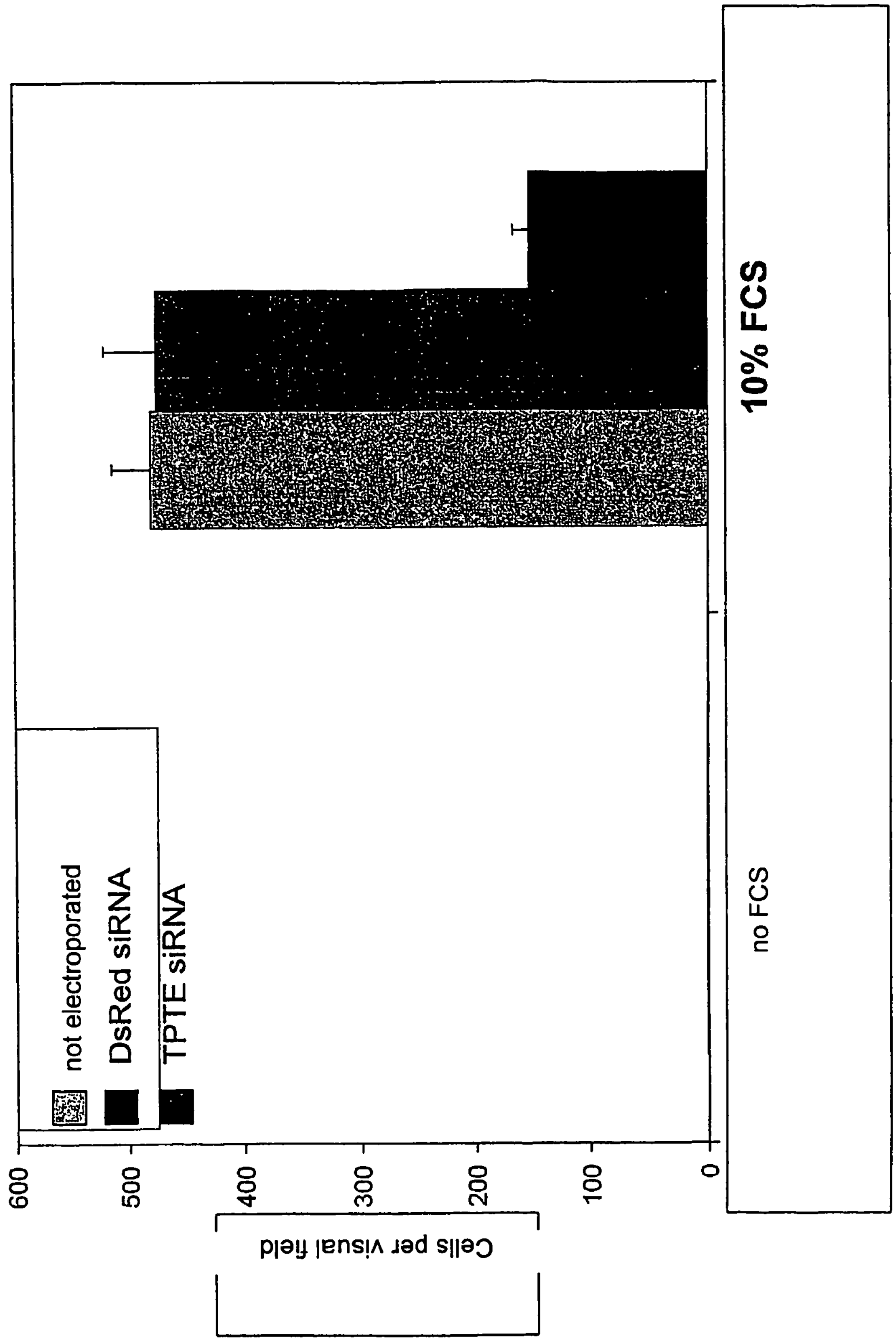

FIG. 37: Reduction of cell migration of PC-3 cells following electroporation with TPTE-siRNA.

Relevant decrease of cell migration in the Boyden chamber assay was detected 48 h after electroporation with 1 μM TPTE-siRNA.

Figure 38:
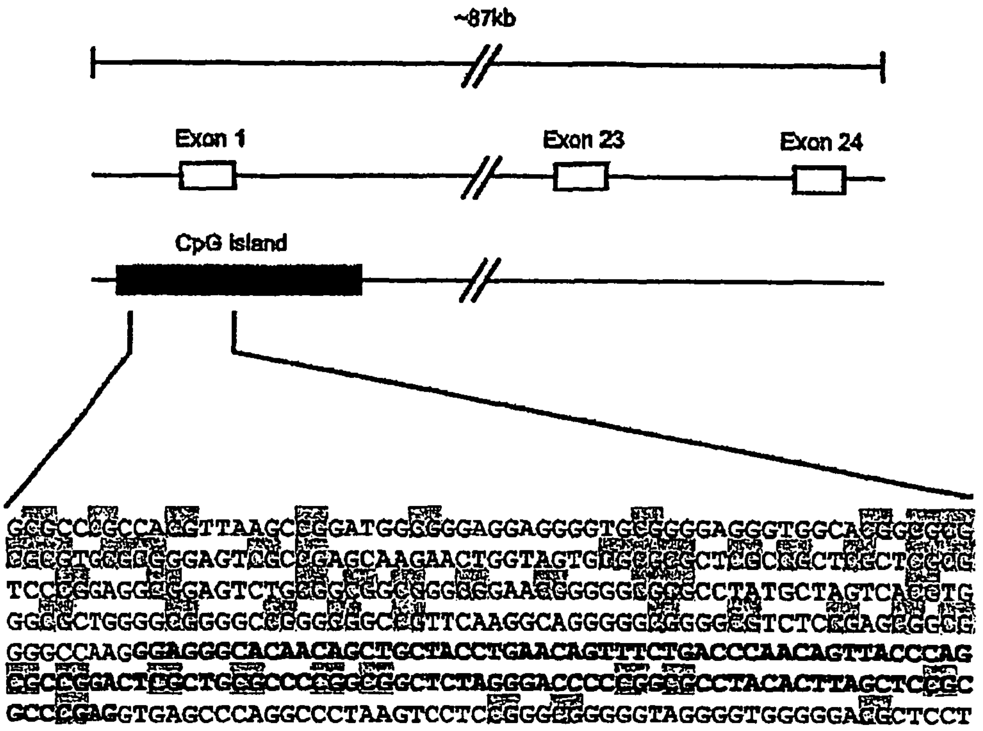

FIG. 38: Region of positions 121 to 540 (SEQ ID NO: 830) in the sequence shown in SEQ ID NO:822 of the sequence listing.

EXAMPLES

Material and Methods

The terms "in silico", "electronic" and "virtual cloning" refer solely to the utilization of methods based on databases, which may also be used to simulate laboratory experimental processes.

Unless expressly defined otherwise, all other terms and expressions are used so as to be understood by the skilled worker. The techniques and methods mentioned are carried out in a manner known per se and are described, for example, in Sambrook et al., Molecular Cloning: A Laboratory Manual, 2nd Edition (1989) Cold Spring Harbor Laboratory Press, Cold Spring Harbor, N.Y. All methods including the use of kits and reagents are carried out according to the manufacturers' information.

Datamining-Based Strategy for Determining eCT (Electronically Cloned Cancer/Testis Genes)

Two in silico strategies, namely GenBank keyword search and the cDNAxProfiler, were combined (FIG. 1). Utilizing the NCBI ENTREZ Search and Retrieval System (http://www.ncbi.nlm.nih.gov/Entrez), a GenBank search was carried out for candidate genes annotated as being specifically expressed in testicular tissue (Wheeler et al., *Nucleic Acids Research* 28:10-14, 2000).

Carrying out queries with the keywords "testis-specific gene", "sperm-specific gene", "spermatogonia-specific gene", candidate genes (GOI, genes of interest) were extracted from the databases. The search was restricted to part of the total information of these databases by using the limits "homo sapiens", for the organism, and "mRNA", for the type of molecule.

The list of the GOI found was curated by determining different names for the same sequence and eliminating such redundancies.

All candidate genes obtained by the keyword search were in turn studied with respect to their tissue distribution by the "electronic Northern" (eNorthen) method. The eNorthern is based on aligning the sequence of a GOI with an EST (expressed sequence tag) database (Adams et al., *Science* 252: 1651, 1991) (http://www.ncbi.nlm.nih.gov/BLAST). The tissue origin of each EST which is found to be homologous to the GOI can be determined and in this way the sum of all ESTs produces a preliminary assessment of the tissue distribution of the GOI. Further studies were carried out only with those GOI which had no homologies to EST from nontesticular normal tissues with the exception of placenta and fetal tissue. This evaluation also took into account that the public domain contains wrongly annotated cDNA libraries (Scheurle et al., *Cancer Res.* 60:4037-4043, 2000) (www.fau.edu/cmbb/publications/cancergenes6.htm).

The second datamining method utilized was the CDNA xprofiler of the NCBI Cancer Genome Anatomy Project (http://cgap.nci.nih.gov/Tissues/xProfiler) (Hillier et al., *Genome Research* 6:807-828, 1996; Pennisi, *Science* 276: 1023-1024, 1997). This allows pools of transcriptomes deposited in databases to be related to one another by logical operators. We have defined a pool A to which all expression libraries prepared from testis were assigned, excluding mixed libraries. All cDNA libraries prepared from normal tissues other than testis, ovary or fetal tissue were assigned to pool B. Generally, all cDNA libraries were utilized independently of underlying preparation methods, but only those with a size >1000 were admitted. Pool B was digitally subtracted from pool A by means of the BUT NOT operator. The set of GOI found in this manner was also subjected to eNorthern studies and validated by a literature research.

This combined datamining includes all of the about 13 000 full-length genes in the public domain and predicts out of these genes a total of 140 genes having potential testis-specific expression. Among the latter were 25 previously known genes of the CT gene class, underlining the efficiency of our strategy.

All other genes were first evaluated in normal tissues by means of specific RT-PCR. All GOI which had proved to be expressed in nontesticular normal tissues had to be regarded as false-positives and were excluded from further studies. The remaining ones were studied in a large panel of a wide variety of tumor tissues. The antigens depicted below proved here to be ectopically activated in tumor cells.

RNA Extraction, Preparation of Poly-d(T) Primed cDNA and RT-PCR Analysis

Total RNA was extracted from native tissue material by using guanidium isothiocyanate as chaotropic agent (Chomczynski & Sacchi, *Anal. Biochem.* 162:156-9, 1987). After extraction with acidic phenol and precipitation with isopropanol, said RNA was dissolved in DEPC-treated water.

First strand cDNA synthesis from 2-4 μg of total RNA was carried out in a 20 μl reaction mixture by means of Superscript II (Invitrogen), according to the manufacturer's information. The primer used was a dT(18) oligonucleotide. Integrity and quality of the cDNA were checked by amplification of p53 in a 30 cycle PCR (sense CGTGAGCGCTTCGAGATGTTCCG (SEQ ID NO: 52), antisense CCTAACCAGCTGCCCAACTGTAG (SEQ ID NO: 53), hybridization temperature 67° C.).

An archive of first strand cDNA was prepared from a number of normal tissues and tumor entities. For expression studies, 0.5 μl of these cDNAs was amplified in a 30 μl reaction mixture, using GOI-specific primers (see below) and 1 U of HotStarTaq DNA polymerase (Qiagen). Each reaction mixture contained 0.3 mM dNTPs, 0.3 μM of each primer and 3 μl of 10× reaction buffer. The primers were selected so as to be located in two different exons, and elimination of the interference by contaminating genomic DNA as the reason for false-positive results was confirmed by testing nonreverse-transcribed DNA as template. After 15 minutes at 95° C. to activate the HotStarTaq DNA polymerase, 35 cycles of PCR were carried out (1 min at 94° C., 1 min at the particular hybridization temperature, 2 min at 72° C. and final elongation at 72° C. for 6 min). 20 μl of this reaction were fractionated and analyzed on an ethidium bromide-stained agarose gel.

The following primers were used for expression analysis of the corresponding antigens at the hybridization temperature indicated.

```
LDH-C (67° C.)
sense           TGCCGTAGGCATGGCTTGTGC,

antisense       CAACATCTGAGACACCATTCC

TPTE (64° C.)
sense           TGGATGTCACTCTCATCCTTG,
```

-continued

| | |
|---|---|
| antisense | CCATAGTTCCTGTTCTATCTG |
| TSBP (63° C.) | |
| sense | TCTAGCACTGTCTCGATCAAG, |
| antisense | TGTCCTCTTGGTACATCTGAC |
| MS4A12 (66°) | |
| sense | CTGTGTCAGCATCCAAGGAGC, |
| antisense | TTCACCTTTGCCAGCATGTAG |
| BRCO1 (60° C.) | |
| sense | CTTGCTCTGAGTCATCAGATG, |
| antisense | CACAGAATATGAGCCATACAG |
| TPX1 (65° C.) | |
| sense | TTTTGTCTATGGTGTAGGACC, |
| antisense | GGAATGGCAATGATGTTACAG |

Preparation of Random Hexamer-Primed cDNA and Quantitative Real Time PCR

LDHC expression was quantified by means of real time PCR.

The principle of quantitative real time PCR using the ABI PRISM Sequence Detection System (PE Biosystems, USA) utilizes the 5'-3' exonuclease activity of Taq DNA polymerase for direct and specific detection of PCR products via release of fluorescence reporter dyes. In addition to sense and antisense primers, the PCR employs a doubly fluorescently labeled probe (TaqMan probe) which hybridizes to a sequence of the PCR product. The probe is labeled 5' with a reporter dye (e.g. FAM) and 3' with a quencher dye (e.g. TAMRA). If the probe is intact, the spatial proximity of reporter to quencher suppresses the emission of reporter fluorescence. If the probe hybridizes to the PCR product during the PCR, said probe is cleaved by the 5'-3' exonuclease activity of Taq DNA polymerase and suppression of the reporter fluorescence is removed. The increase in reporter fluorescence as a consequence of the amplification of the target, is measured after each PCR cycle and utilized for quantification. Expression of the target gene is quantified absolutely or relative to expression of a control gene with constant expression in the tissues to be studied. LDHC expression was calculated by means of the ΔΔ-$C_t$ method (PE Biosystems, USA), after normalizing the samples to 18s RNA as “housekeeping” gene. The reactions were carried out in duplex mixtures and determined in duplicate. cDNA was synthesized using the High Capacity cDNA Archive Kit (PE Biosystems, USA) and hexamer primers according to the manufacturer’s information. In each case 5 μl of the diluted cDNA were used for the PCR in a total volume of 25 sense primer (GGTGTCACTTCTGTGCCTTCCT (SEQ ID NO: 48)) 300 nM; antisense primer (CGGCACCAGTTCCAACAATAG (SEQ ID NO: 49)) 300 nM; TaqMan probe (CAAAGGTTCTCCAAATGT (SEQ ID NO: 50)) 250 nM; sense primer 18s RNA 50 nM; antisense primer 18s RNA 50 nM; 18s RNA sample 250 nM; 12.5 μl TaqMan Universal PCR Master Mix; initial denaturation 95° C. (10 min); 95° C. (15 sec); 60° C. (1 min); 40 cycles. Due to amplification of a 128 bp product beyond the border of exon 1 and exon 2, all LDHC splice variants described were included in the quantification.

Expression of TPTE, MS4A12, PCSC and BRCO1 was also quantified using real-time PCR, however, the PCR products were detected using SYBR-Green as reporter dye. The reporter fluorescence of SYBR-Green is suppressed in solution and the dye is only active following binding to double-stranded DNA fragments. The increase of SYBR-Green fluorescence due to the specific amplification by means of GOI-specific primers following each PCR cycle is used for quantification. Quantification of expression of the target gene is performed absolute or relative to the expression of a control gene with constant expression in the tissues to be studied. LDHC expression was calculated by means of the ΔΔ-CT method (PE Biosystems, USA), after normalizing the samples to 18s RNA as “house-keeping” gene. The reactions were carried out in duplex mixtures and determined in triplicate. The QuantiTect SYBR-Green PCR kit (Qiagen, Hilden) was used according to the manufacturer’s instructions. cDNA was synthesized using the High Capacity cDNA Archive Kit (PE Biosystems, USA) and hexamer primers according to the manufacturer’s information. In each case, 5 μl of the deluted cDNA were used for the PCR in a total volume of 25 μl: sense primer 300 nM, antisense primer 300 nM, initial denaturation 95° C. 15 min; 95° C. 30 sec; annealing 30 sec; 72° C. 30 sec; 40 cycles.

| | |
|---|---|
| TPTE (62°) | |
| sense | GAGTCTACAATCTATGCAGTG, |
| antisense | CCATAGTTCCTGTTCTATCTG |
| MS4A12 (65°) | |
| sense | CTGTGTCAGCATCCAAGGAGC, |
| antisense | TTCACCTTTGCCAGCATGTAG |
| PCSC (59°) | |
| sense | AGAATAGAATGTGGCCTCTAG, |
| antisense | TGCTCTTACTCCAAAAAGATG |
| BRCO1 (60°) | |
| sense | CTTGCTCTGAGTCATCAGATG, |
| antisense | CACAGAATATGAGCCATACAG |

Cloning and Sequence Analysis

Full length genes and gene fragments were cloned by common methods. The sequence was determined by amplifying corresponding antigens by means of the pfu proofreading polymerase (Stratagene). After completion of the PCR, adenosine was ligated by means of HotStarTaq DNA polymerase to the ends of the amplicon in order to clone the fragments into the TOPO-TA vector according to the manufacturer’s information. A commercial service carried out the sequencing. The sequences were analyzed by means of common prediction programs and algorithms.

Western Blot

Cells from cell culture (endogenous expression of the target gene or synthesis of the target protein following transfection of an expression vector coding for the target protein) or tissue samples which may contain the target protein are lysed in 1% SDS solution. The SDS denatures the proteins contained in the lysate. The lysates of an experimental setup are separated electrophoretically by size on 8-15% denaturing polyacrylamide gels depending on the expected size of the proteins (containing 1% SDS) (SDS polyacrylamide gel electrophoresis, SDS-PAGE). Subsequently, proteins are transferred to nitrocellulose membrane (Schleicher & Schull) using the semi-dry electroblot procedure (Biorad), on which the desired protein can be detected. The membrane is first blocked (e.g. using milk powder) and then incubated with the specific antibody in a 1:20-1:200 dilution (depending on the specificity of the antibody) for 60 minutes. The membrane is washed and incubated with a second antibody coupled with a marker (e.g. an enzyme such as peroxidase or alkaline phosphatase), whereby the second antibody recognizes the first antibody. Following a further washing step, the target protein is visualized on the membrane by means of an enzymatic reaction in a colour or chemiluminescence reaction (e.g. ECL, Amersham Bioscience). The result is documented by taking pictures with a suitable camera.

Immunofluorescence

Cells of established cell lines are used which either synthesize the target protein endogenously (the RNA is detected in a RT-PCR or the protein is detected in a Western blot) or which have been transfected with plasmid DNA prior to the IF. Various methods are well-established for transfecting cell lines with DNA (e.g. electroporation, transfection based on liposomes, calcium phosphate precipitation) (see, for example, Lemoine et al. Methods Mol. Biol. 1997; 75: 441-7). In immunofluorescence, the transfected plasmid may encode the unmodified protein or may couple diverse amino acid markers to the target protein. The most important markers are, for example, the fluorescing "green fluorescent protein" (GFP) in its various distinctly fluorescing forms and short peptide sequences of 6-12 amino acids for which highly affine and specific antibodies are available. Cells which synthesize the target protein are fixed using paraformaldehyde, saponine or methanol. Then, cells may be permeabilized by incubation with detergents (e.g. 0.2% Triton X-100), if necessary. Following fixation/permeabilization, cells are incubated with a primary antibody which is directed to the target protein or one of the coupled markers. Following a washing step, the mixture is incubated with a second antibody coupled to a fluorescent marker (e.g. fluoresceine, Texas Red, dako), whereby the second antibody binds to the first antibody. Then, the cells labelled in this way are covered with glycerine and are analyzed by means of a fluorescence microscope according to the manufacturer's instructions. Specific fluorescence emissions thereby are achieved by means of specific excitation depending on the substance used. The analysis generally allows the exact localization of the target protein, wherein in double stainings in addition to the target protein also the coupled amino acid markers or other marker proteins whose localization has already been described in the literature are stained to verify the antibody quality and the target protein. GFP which may be excited directly and fluoresces autonomously and its derivatives represent a special case such that no antibodies are required for detection.

Immunohistochemistry

The IHC serves to (1) be able to estimate the amount of target protein in tumor and normal tissues, (2) analyze how many cells in tumor and healthy tissue synthesize the target gene, (3) define the cell type in a tissue (tumor, healthy cells), in which the target protein is detectable.

Depending on the respective antibody different protocols are to be used (see, for example, "Diagnostic Immunohistochemistry by David J., M D Dabbs ISBN: 0443065667" or in "Microscopy, Immunohistochemistry, and Antigen Retrieval Methods: For Light and Electron Microscopy ISBN: 0306467704").

Tissue sections which are fixed in formalin (different fixation: e.g. methanol) and are embedded in paraffin having a thickness of about 4 μm are mounted on a glass slide and are deparaffinated using for example xylol. The samples are washed with TBS-T and blocked with serum. Then, they are incubated with the first antibody (dilution 1:2 to 1:2000) for 1-18 hours, whereby generally affinity purified antibodies are used. Following a washing step, they are incubated for about 30-60 minutes with a second antibody coupled to alkaline phosphatase (alternatively: e.g. peroxidase) which is directed against the first antibody. Subsequently, it is stained using the alkaline phosphatase (references: Shi et al., J. Histochem. Cytochem. 1991, 39: 741-748; Shin et al., Lab Invest. 1991, 64: 693-702). For detecting antibody specificity, the reaction can be blocked by previously adding the immunogen.

Immunization (See also Monoclonal Antibodies: A Practical Approach by Philip Shepherd, Christopher Dean ISBN 0-19-963722-9; Antibodies: A Laboratory Manual by Ed Harlow, David Lane ISBN: 0879693142; Using Antibodies: A Laboratory Manual: Portable Protocol NO by Edward Harlow, David Lane, Ed Harlow ISBN: 0879695447).

In the following, the process for manufacturing antibodies is briefly described, whereby details may be taken from the cited publications. First, animals (e.g. rabbits) are immunized by means of a first injection of the desired target protein. By means of a second or third immunization within a defined period of time (about 2-4 weeks following the first immunization), the immune response of the animal to the immunogen may be enhanced. After different defined periods of time (first bleeding after 4 weeks, then about every 2 weeks with a total of up to 5 collections), blood is taken from the animals and an immune serum is obtained therefrom.

Immunization of the animals generally is performed by means of one of four well-established procedures whereby other procedures also exist. Immunization can be achieved using peptides which are specific for the target protein, the entire protein, extracellular partial sequences of a protein which may be identified experimentally or by means of prediction programs.

(1) In the first case, peptides conjugated to KLH (keyhole limpet hemocyanin) (length: 8-12 amino acids) are synthesized by means of a standardized in vitro procedure and these peptides are used for immunization. Generally, three immunizations are performed using a concentration of 5-1000 μg/immunization. Immunization may also be performed by service providers.

(2) Alternatively, immunization can be performed by means of recombinant proteins. To this end, the cloned DNA of the target gene is cloned into an expression vector and the target protein in accordance with the conditions of the respective manufacturer (for example Roche Diagnostics, Invitrogen, Clontech, Qiagen) synthesized, e.g. in vitro free of cells, in bacteria (e.g. *E. coli*), in yeast (e.g. *S. pombe*), in insect cells or in mammalian cells. Following synthesis in one of these systems, the target protein is purified, whereby purification is performed generally by means of standardized chromatographic procedures. To this end, also proteins may be used for immunization which have a molecular anchor to aid purification (e.g. His-tag, Qiagen; FLAG-tag, Roche Diagnostics; Gst fusion proteins). A plurality of protocols can be found, for example, in the "Current Protocols in Molecular Biology" (John Wiley & Sons Ltd., Wiley InterScience).

(3) If a cell line is available which synthesizes the desired protein endogenously said cell line may be used for preparing the specific antiserum. Immunization is performed by means of 1-3 injections each containing about 1-5×$10^7$ cells.

(4) Immunization may also be achieved by injecting DNA (DNA immunization). To this end, the target gene is first cloned into an expression vector such that the target sequence is under the control of a strong eukaryotic promoter (e.g. CMV promotor). Then, 5-100 μg DNA are transferred as immunogen into capillary regions of an organism which are well-supplied with blood (e.g. mouse, rabbit) using a "gene gun". The transferred DNA is taken up by cells of the animal, the target gene is expressed and the animal then develops an immune response against the target gene (Jung et al., Mol Cells 12: 41-49, 2001; Kasinrerk et al., Hybrid Hybridomics 21: 287-293, 2002).

Affinity Purification

Purification of polyclonal serums was done in the case of the peptide antibodies entirely or in the case of the antibodies against recombinant proteins partially as a service by the instructed companies. To this end, in both cases the respective peptide or recombinant protein was bound covalently to a matrix which following coupling was equilibrated using a native buffer (PBS: phosphate buffered saline) and then incubated using the crude serum. Following a further wash using PBS, the antibody was eluted using 100 mM glycine pH 2.7 and the eluate was neutralized using 2 M TRIS pH 8. The antibodies purified in this way could then be used for specific detection of the target proteins by Western blotting as well as immunofluorescence.

Boyden Chamber Migration Assay

The Boyden chamber is for quantifying cell migration in reaction to chemotactic stimuli. The chamber consists of two compartments separated by a micropore membrane. Cells in minimal medium are added to the upper compartment, while the lower compartment is filled with medium containing the respective chemotactic agent. Cells migrate according to the gradient through the membrane and adhere to the bottom side of the membrane. Following fixation transmigrated cells can be counted using a microscope.

The migration assay was used for determining the promigratory potential of TPTE. NIH3T3 fibroblasts transfected with TPTE-eGFP and transformed with c-erbB2 were used. Non-transfected cells and cells transfected with the empty eGFP-N3 vector were used as controls. Transwell chambers (Becton Dickinson) with 8.0 μm pore membranes were used for the assay. $4\times10^4$ cells in 400 μl serum-free DMEM medium were each added to the upper compartment. The lower compartment was filled with 800 μl DMEM medium supplemented with 10% FCS or PDGF-BB in increasing concentrations (10-300 ng/μl). Chambers were incubated for 40 h at 37° C. Then, transmigrated cells were fixed in ice-cold methanol, membranes were excised, placed on microscope slides and mounted with Hoechst nuclear stain (DAKO) for fluorescence microscopy. Cells in five visual fields (20× magnification) were counted for each membrane. All experiments were done in triplicates.

RNA Intereference (RNAi)

siRNA oligos were designed according to the Tuschl rules (Elbashir et al., *Nature* 411(6836):428-9, 2001). TPTE siRNA oligos (sense 5'CCCUGCCACAUGUUCAUAU-dIdT-3[1] (SEQ ID NO: 826P; antisense 5'-AUAUGAACAU-GUGGCAGGGdTdT-3'(SEQ ID NO: 827)) targeted nucleotides 2043-2061 of the TPTE mRNA sequence (NM_013315). siRNA oligos which are specific for the irrelevant DsRed fluorescence protein (AF506025) were used as controls (sense 5'-AGUUCCAGUACGGCUCCAAdTdT-5' (SEQ ID NO: 828); antisense 5'-UUGGAGCCGUACUG-GAACUdTdT-3' (SEQ ID NO: 829)). For generating siRNA duplexes 200 μM of each the respective sense and antisense oligos were incubated one hour at 37° C. in hybridization buffer (30 mM HEPES (pH 7.4), 100 mM sodium acetate, 2 mM magnesium acetate) following an initial denaturation (1 min at 90° C.)

Electroporation of siRNA $5\times10^6$ cells were taken up in 250 μl serum-free X-VIVO 15 medium and electroporated using 1 μM of the respective siRNA duplexes (200 V, 250 μF). Expression of TPTE mRNA was quantified 24 h later by means of real-time RT-PCR.

Methylation Studies

For investigating the induceability of TPTE expression by genomic demethylation, TPTE negative cell lines BT549 (Mamma-Ca) and HCT116 (Colon-Ca) were cultivated for 72 h with 2 μM or 10 μM 5-aza-2'-desoxycytidine. Then, the TPTE expression was quantified by means of real-time RT-PCR. Furthermore, TPTE expression was quantified in DNA methyl transferase (DNMT) deficient HCT116 cells. While DNMT1 ($HCT116^{DNMT1-/-}$) or DNMT3b ($HCT116^{ENMT3b-/-}$) deficient cells show an almost unchanged methylation pattern when compared to the parental cell line ($HCT116^{Par}$), cells in which both DNMTs have been simultaneously deleted ($HCT116^{DKO}$) are characterized by an almost complete demethylation of genomic DNA.

Time-Lapse Microscopy

Membrane localization of TPTE and the involvement in regulation of membrane dynamics in vital cells was studied using time-lapse microscopy. To this end TPTE-eGFP transfected cells were incubated for 12 h in serum free DMEM medium. For induction of spontaneous cell membrane dynamics in the form of membrane protrusions, pseudopodias and filopodias, cells were stimulated by adding FCS prior to analysis. Pictures of the vital cells were taken every 30 seconds using an Invert Olympus microscope (IX70) and a TILL IMAGO-VGA CCD camera.

Preparation of EGFP Transfectants

For immunofluorescence microscopy of heterologously expressed TPTE, the complete ORF of TPTE was cloned into pEGFP-C1 and pEGFP-N3 vectors (Clontech). CHO and NIH3T3 cells which were cultivated on glass slides were transfected with the respective plasmid constructs using Fugene transfection reagent (Roche) according to the manufacturer's instructions and analyzed by immunofluorescence microscopy 12-24 h later.

Prediction of Peptide Epitopes for MHC Class I

Peptide epitopes of each of the protein sequences binding to the polymorphic HLA alleles A*0201, A*2402, A*0101, A*0301, B*0702 were identified using the prediction algorithm available from http://syfpeithi.bmi-heidelberg.com/. 8-, 9- and 10-mers were allowed as peptide length and a cutoff set at a score of 15. If the search resulted in less than 10 peptides for the respective length, alternatively the 10 best peptides were chosen.

Example 1

Identification of LDH C as a New Tumor Antigen

LDH C (SEQ ID NO:1) and its translation product (SEQ ID NO:6) have been described as testis-specific isoenzyme of the lactate dehydrogenase family. The sequence has been published in GenBank under accession number NM_017448. The enzyme forms a homotetramer having a molecular weight of 140 kDa (Goldberg, E. et al., *Contraception* 64(2): 93-8, 2001; Cooker et al., *Biol. Reprod.* 48(6):1309-19, 1993; Gupta, G. S., *Crit. Rev. Biochem. Mol. Biol.* 34(6):361-85, 1999).

RT-PCR studies for expression analysis using a primer pair (5'-TGCCGTAGGCATGGCTTGTGC-3' (SEQ ID NO: 25), 5'-CAACATCTGAGACACCATTCC-3' (SEQ ID NO: 26)) which does not cross-amplify the related and ubiquitously expressed isoenzymes LDH A and LDH B and which is based on the LDH C prototype sequence NM_017448 which has previously been described as being testis-specific, confirmed according to the invention the lack of expression in all normal tissues tested, but demonstrated that the stringent transcriptional repression of this antigen in somatic cells has been removed in the case of tumors; cf. Table 1. As has been described classically for CT genes, LDH C is expressed in a number of tumor entities.

TABLE 1

Expression of LDHC in tumors

| Tissue | Tested in total | Positive | % |
|---|---|---|---|
| Melanoma | 16 | 7 | 44 |
| Mammary carcinomas | 20 | 7 | 35 |
| Colorectal tumors | 20 | 3 | 15 |
| Prostate carcinomas | 8 | 3 | 38 |
| Bronchial carcinomas | 17 | 8 | 47 |
| Kidney cell carcinomas | 7 | 4 | 57 |
| Ovarian carcinomas | 7 | 3 | 43 |
| Thyroid carcinomas | 4 | 1 | 25 |
| Cervical carcinomas | 6 | 5 | 83 |
| Melanoma cell lines | 8 | 5 | 63 |
| Bronchial carcinoma cell lines | 6 | 2 | 33 |

The expected size of the amplification product is 824 bp, using the PCR primers mentioned above. According to the invention, however, amplification of multiple additional bands was observed in tumors, but not in testis. Since this is indicative for the presence of alternative splice variants, the complete open reading frame was amplified using LDH-C-specific primers (5'-TAGCGCCTCAACTGTCGTTGG-3' (SEQ ID NO: 51), 5'-CAACATCTGAGACACCATTCC-3' (SEQ ID NO: 26)) and independent full-length clones were sequenced. Alignments with the prototype ORF of the LDH C sequence described (SEQ ID NO:1) and the genomic sequence on chromosome 11 confirm additional splice variants (SEQ ID NO:2-5). The alternative splicing events result in the absence of exon 3 (SEQ ID NO:2), of the two exons 3 and 4 (SEQ ID NO:3), of the exons 3, 6 and 7 (SEQ ID NO:4) or of exon 7 (SEQ ID NO:5) (cf. FIG. 2).

These new splice variants are generated exclusively in tumors, but not in testis. Alternative splicing causes alterations in the reading frame and results in new possible ORFs encoding the amino acid sequences depicted in SEQ ID NO:7-13 (ORF for SEQ ID NO:7: nucleotide position 59-214 of SEQ ID NO:2 and, respectively, SEQ ID NO:4; ORF for SEQ ID NO:8: nucleotide position 289-939 of SEQ ID NO:2; ORF for SEQ ID NO:9: nucleotide position 59-196 of SEQ ID NO:3; ORF for SEQ ID NO:10: nucleotide position 535-765 of SEQ ID NO:3; ORF for SEQ ID NO:11: nucleotide position 289-618 of SEQ ID NO:4; ORF for SEQ ID NO:12: nucleotide position 497-697 of SEQ ID NO:4; ORF for SEQ ID NO:13: nucleotide position 59-784 of SEQ ID NO:5) (FIG. 2, 3). Apart from premature termination, utilization of alternative start codons is also possible so that the encoded proteins may be truncated both N-terminally and C-terminally.

While SEQ ID NO:8 and SEQ ID NO:10 represent truncated portions of the prototype protein, the protein sequence of SEQ ID NO:7, SEQ ID NO:9, SEQ ID NO:11, SEQ ID NO:12 and SEQ ID NO:13 are additionally altered and contain only tumor-specific epitopes (printed in bold type in FIG. 3). Peptide regions which could result in tumor-specific epitopes are as follows (the strictly tumor-specific portion produced by frame shifts is underlined):

SEQ ID NO:14:
GAVGMACAISILLKITVYLQTPE
(of SEQ ID NO:7)

-continued

SEQ ID NO:15:
GAVGMACAISILLKWIF
(of SEQ ID NO:9)

SEQ ID NO:16:
GWIIGEHGDSSGIIWNKRRTLSQYPLCLGAEWCLRCCEN
(of SEQ ID NO:11)

SEQ ID NO:17:
MVGLLENMVILVGLYGIKEELFL
(of SEQ ID NO:12)

SEQ ID NO:18:
EHWKNIHKQVIQRDYME
(of SEQ ID NO:13)

These regions may potentially contain epitopes which can be recognized on MHC I or MHC II molecules by T lymphocytes and which result in a strictly tumor-specific response.

Not all of the predicted proteins have the catalytic lactate dehydrogenase domain for NADH-dependent metabolization of pyruvate to lactate, which represents the last step of anaerobic glycolysis. This domain would be required for the enzymatic function as lactate dehydrogenase (framed in FIG. 3). Further analyses, for example using algorithms such as TMpred and pSORT (Nakai & Kanehisa, 1992), predict different subcellular localizations for the putative proteins.

According to the invention, the level of expression was quantified by real time PCR using a specific primer-sample set. The amplicon is present in the junction between exon 1 and exon 2 and thus detects all variants (SEQ ID NO:1-5). These studies too, do not detect any transcripts in normal tissues except testis. They confirm significant levels of expression in tumors (FIG. 4).

Antibodies were produced by immunizing rabbits with peptides each resembling different variants as described above:

SEQ ID NO:80:
MSTVKEQLIEKLIEDDENSQ (aa 1-19)

SEQ ID NO:101:
RNGVSDVVKINLNSE (C terminus)

SEQ ID NO:102:
GIIWNKRRTLSQYPL (specific for variant 5.3)

The data for antibodies which are directed against SEQ ID NO:80 are given as an example. These antibodies in Western blots recognize LDHC protein in testis tissue but not in other normal tissues (FIG. 15) and thus, confirm the RT-PCR data on the transcript level. The specific antibody may be used also under different fixation conditions for immunofluorescence assays. In this respect, RT-PCR assays showed that the colon carcinoma cell line HCT 116 P does not express LDHC. However, a variant thereof being deleted with respect to DNA methyl transferase, HCT 116 DKO, is positive for LDHC. Comparative stainings of both cell lines with the above described antibody were able to detect the respective protein in an amount which could be easily detected in a specific manner in the cell lines which were typed positive (FIG. 16). Correspondingly, this antibody qualifies itself also for immunohistochemical stainings of normal and tumor tissue sections by the person skilled in the art. The staining of testis tissue, for example, shows that germ cells are distinctly positive (FIG. 16).

Lactate dehydrogenases catalyze the interconversion of pyruvate and lactate within the glycolysis. Under aerobe conditions, pyruvate as end product of the glycolysis is transported into mitochondrias where it serves as substrate for the citrate cycle. The Krebs cycle provides reduction equivalents in the form of NADH which are consumed for producing ATP within the respiratory chain (oxidative phosphorylation). Under anaerobic conditions, it is not possible to produce ATP via the respiratory chain. The cell regulates its energy metabolism under these conditions almost exclusively via the glycolysis. Pyruvate which under these condition cannot be metabolized is reduced to lactate by lactate dehydrogenases.

The different lactate dehydrogenase isoforms differ from each other primarily in their tissue distribution and substrate specificities and affinities. The germ cell specific LDHC preferably catalyzes the oxidation of lactate to pyruvate and is also not inhibited in its activity by high concentrations of lactate (Goldberg *E. Exp. Clin. Immunogenet.* 2:120-4, 1985). These properties are reasonable from a physiological point of view since the spermatides develop in a milieu which is characterized by high lactate concentrations. Spermatides prefer lactate as energy source over glucose, fructose or pyruvate (Mita M. *Biol. Reprod.* 26:445-55, 1982). The oxidation of lactate by LDHC provides pyruvate as starting substrate for the citrate cycle. Accordingly, spermatides preferably use the citrate cycle as major source for generating energy (Storey B. T. *Biol. Reprod.* 16:549-556, 1977).

It is known for a long time that tumor cells frequently cover their energy demand through anaerobic glycolysis, i.e. they produce lactate in increased amounts, and do not use the citrate cycle and the respiratory chain even under aerobic conditions. The molecular bases of this phenomenon which is described as Warburg effect are not elucidated until now and enzyme defects in the mitochondrias and overexpression of key enzymes of the glycolysis are discussed as the cause. In this context, expression of LBHC which is not inhibited in its function by high concentrations of lactate could be of advantage for the energy metabolism of the tumor cell if lactate is used for producing ATP. Defects of mitochondrias, in particular enzyme defects of the citrate cycle are known alterations in tumor cells. If the citrate cycle fails, no reduction equivalents can be produced for the respiratory chain. A mitochondrial lactate dehydrogenase having high affinity for lactate such as LDHC could circumvent a defective citrate cycle. Lactate which is transported into mitochondrias by monocarboxylate transporters (MCT) could be oxidized to pyruvate intramitochondrially and thus serve for the production of reduction equivalents which are consumed in the respiratory chain to produce ATP. To analyze the subcellular localization of LDHC, the LDHC negative breast tumor cell line MCF-7 was transfected with a fusion construct consisting of LDHC and green fluorescent protein and this transfectant was stained with an antibody against the mitochondrial marker cytochrome C. The co-localization of both signals in convocal laser microscopy (FIG. 17) evidences the presence of LDHC in mitochondrias. Thus, it could be possible that the expression of LDHC in tumor cells indeed has a benefit effect for the energy metabolism of the cell and that a specific inhibition of LDHC activity in tumors may be used in the therapy of tumor diseases.

Example 2

Identification of TPTE as a New Tumor Antigen

The sequences of the TPTE transcript (SEQ ID NO:19) and of its translation product (SEQ ID NO:22) have been published in GenBank under accession number NM_013315 (Walker, S. M. et al., *Biochem. J.* 360(Pt 2):277-83, 2001; Guipponi M. et al., *Hum. Genet.* 107(2):127-31, 2000; Chen H. et al., *Hum. Genet.* 105(5):399-409, 1999). TPTE has been described as a gene coding for a possible transmembrane tyrosinephosphatase, with testis-specific expression located in the pericentromeric region of chromosomes 21, 13, 15, 22 and Y (Chen, H. et al., *Hum. Genet.* 105:399-409, 1999). Alignment studies in accordance with the invention additionally reveal homologous genomic sequences on chromosomes 3 and 7.

The membrane localization which, for example, is a prerequisite for the accessibility of therapeutic antibodies could be detected without any doubt by transfection of TPTE negative cells with a fusion construct consisting of TPTE and green fluorescent protein (FIG. 18, right hand). This accumulates at the membrane surface and can be detected at this location in co-localization with other known membrane markers such as HLA molecules.

According to the invention, PCR primers (5'-TGGATGTCACTCTCATCCTTG-3' (SEQ ID NO: 27) and 5'-CCATAGTTCCTGTTCTATCTG-3' (SEQ ID NO: 28)) were generated based on the sequence of TPTE (SEQ ID NO:19) and used for RT-PCR analyses (95° 15 min; 94° 1 min; 63° 1 min; 72° 1 min; 35 cycles) in a number of human tissues. Expression in normal tissues was shown to be limited to testis. As described for the other eCT, TPTE variants were shown according to the invention to be ectopically activated in a number of tumor tissues; cf. Table 2.

TABLE 2

Expression of TPTE in tumors

| Tissue | Tested in total | Positive | % |
|---|---|---|---|
| Melanoma | 18 | 9 | 50 |
| Mammary carcinomas | 36 | 17 | 47 |
| Colorectal tumors | 20 | 0 | 0 |
| Prostate carcinomas | 8 | 3 | 38 |
| Bronchial carcinomas | 45 | 25 | 55 |
| Kidney cell carcinomas | 7 | 2 | 29 |
| Ovarian carcinomas | 7 | 2 | 29 |
| Thyroid carcinomas | 4 | 0 | 0 |
| Cervical carcinomas | 6 | 1 | 17 |
| Melanoma cell lines | 8 | 5 | 62 |
| Bronchial carcinoma cell lines | 6 | 2 | 33 |
| Mammary carcinoma cell lines | 5 | 4 | 80 |

A quantitative real-time PCR (40 cycles, initial denaturation 15 min 95° C., 30 sec 94° C., 30 sec 62° C. and 30 sec 72° C.) was performed using specific primers (sense GAGTCTACAATCTATGCAGTG (SEQ ID NO: 823); antisense CCATAGTTCCTGTTCTATCTG (SEQ ID NO: 28)) (FIG. 19). This not also confirmed the lack of TPTE in non-testicular normal tissue and the ectopic expression in tumors but also showed high transcript levels in the tumors which were comparable to the physiologic expression in testis tissue. The ectopic expression of many known CT genes in tumors is induced by promoter demethylation. To test whether this mechanism is also effective for the ectopic activation of TPTE, the non-expressing cell lines BT549 (Mamma-Ca) and HCT116 (Colon-Ca) were cultivated in the presence of 5-aza-2'-desoxycytidine which is a pharmacologic inhibitor of DNA methylation. In both cases demethylation of DNA resulted in a strong induction of TPTE expression (FIG. 33). The same effect is also present in HCT116 cells which are deficient for DNA methyltransferases DNMTI and DNMT3b and are characterized by an almost complete loss of DNA methylation. These results demonstrate that the promoter demethylation of the gene locus is also effective for the ectopic induction of TPTE expression. For detecting TPTE protein, antibodies were produced by immunizing rabbits. The following peptides or a purified protein which was recombinantly expressed in *E. coli* were used for propagating these antibodies:

| | |
|---|---|
| SEQ ID NO: 103: | FTDSKLYIPLEYRSC (aa 116-128) |
| SEQ ID NO: 104: | CFDIKLLRNIPRWT (aa 179-191) |
| SEQ ID NO: 105: | MNESPDPTDLAGVIIELGPNDSPQTSEFKGATEE APAKESPHTSEFKGAARVSP (rec. prot. aa 1-54) |

Data of antibodies which are directed against SEQ ID NO:105 are given as an example. The specific antibody may be used for immunofluorescence assays under different fixation conditions. In comparative stainings of RT-PCR positive as well as negative cell lines, the respective protein can be specifically detected in amounts which are easily detectable in the cell lines which have been typed as positive (FIG. 18, right hand). The endogenous protein is located at the membrane. This antibody was further used for the immunohistochemical staining of tissue sections. As expected, the antibody stains testis tissue in a specific manner. In particular, the germ cells are stained (FIG. 20). Tissue sections of lung carcinomas are also stained. TPTE protein is detected in large amounts in all cells of a tumor in a homogeneous manner. The location of the protein at the membrane of the cells is here confirmed as well (FIG. 21). The specificity of the staining was confirmed by competition experiments. The specific antibody was first pre-incubated with recombinant TPTE protein and then added to the tissue sections (using e.g. testis as positive control, FIG. 20). Hereby, the reactivity may be blocked successfully. Using this antibody many different primary tumor types (also breast tumors, melanomas, etc.) but not the respective normal tissue may be stained successfully. The staining of prostate tissue is also given as an example. Normal prostate tissue is negative while invasive prostate tumors as well as prostate tumors which have not yet invaded are positive for this molecule. A simple hypertrophy of prostate epithelium is also not stained but premalign regions which are already present within these benign alterations which will transform are positive for TPTE. Accordingly, such a specific antibody against TPTE may be used for the early detection of an existing disposition of prostate carcinomas in a diagnostic manner. Furthermore, the antibody was used for detecting expression of TPTE in Western blots. Expression of protein could be detected in lysates of testis tissue as well as spontaneously expressing cell lines, while normal tissues did not show expression as expected (FIG. 34).

According to the invention, further splice variants were identified for TPTE (SEQ ID NO:20, SEQ ID NO:21, SEQ ID NO:54, SEQ ID NO:55, SEQ ID NO:56, SEQ ID NO:57) which are expressed in testicular tissue and tumors and have frame shifts and thus, altered sequence regions (FIG. 5).

The TPTE genomic sequence consists of 24 exons (accession number NT_029430). The transcript depicted in SEQ ID NO:19 contains all of these exons. The splice variant depicted in SEQ ID NO:20 is produced by splicing out exon 7. The splice variant depicted in SEQ ID NO:21 shows partial incorporation of an intron downstream of exon 15. As the variants SEQ ID NO:54, SEQ ID NO:55, SEQ ID NO:56, SEQ ID NO:57 indicate, it is alternatively also possible to splice out exons 18, 19, 20 and 21.

These alternative splicing events result in alterations of the encoded protein, with the reading frame being retained in principle (FIG. 6). For example, the translation product encoded by the sequence depicted in SEQ ID NO:20 (SEQ ID NO:23) has a deletion of 13 amino acids in comparison to the sequence depicted in SEQ ID NO:22. The translation product encoded by the sequence depicted in SEQ ID NO:21 (SEQ ID NO:24) carries an additional insertion in the central region of the molecule and thereby differs from the other variants by 14 amino acids.

The translation products of the variants SEQ ID NO:54, SEQ ID NO:55, SEQ ID NO:56, SEQ ID NO:57, namely the proteins SEQ ID NO:58, SEQ ID NO:59, SEQ ID NO:60, SEQ ID NO:61, are likewise altered.

Analyses for predicting the functional domains reveal the presence of a tyrosinephosphatase domain for SEQ ID NO:22, SEQ ID NO:23, SEQ ID NO:24, SEQ ID NO:58, SED ID NO:60 but not for SEQ ID NO:59, SEQ ID NO:61. For all variants, 3-4 transmembrane domains are predicted (FIG. 6).

Analysis of TPTE antigen expression, using specific antibodies, confirmed selective expression in testis and in a number of different tumors. Colocalization studies moreover revealed that according to the invention TPTE is located together with class I immunoglobulins on the cell surface of tumor cells. Previously, TPTE had been described only as a Golgi-associated protein. Owing to TPTE expression on the cell surface of tumor cells, this tumor antigen is suitable according to the invention as an outstanding target for developing diagnostic and therapeutic monoclonal antibodies. Owing to the predicted membrane topology of TPTE, the extracellulary exposed regions are particularly suitable for this purpose according to the invention. According to the invention, this comprises the peptides FTDSKLYIPLEYRS (SEQ ID NO:81) and FDIKLLRNIPRWT (SEQ ID NO: 82). In addition, TPTE was shown to promote the migration of tumor cells.

Cells which have been cultivated for several hours in minimal medium without FCS tend to spontaneously develop pseudopodia and membrane protrusions. Distinct accumulation of the protein at the membrane of this structure could be detected in heterologously expressing cells (TPTE-eGFP) as well as in spontaneously expressing cell lines (AK-staining). Furthermore, co-staining using rhodamine-phalloidine showed a distinct co-localization of TPTE and F-actin in these regions. Actin polymerization which is mediated by second messengers such as phosphoinositides and calcium is a critical factor for initiating cell migration in response to extracellular gradients of chemotactic agents. Signal transduction via these second messengers is mainly initiated by receptor tyrosine kinases (RTK). One of the most important factors in the regulation of second messenger signaling via phosphoinositides and the modulation of the actin cytoskeleton resulting therefrom is the RTK c-erbB-2 (HER2) which is frequently overexpressed in several tumor types. These results gave rise to considering that TPTE as a lipid phosphatase which is located at the cell membrane and has substrate specificity for $PIP_{3,4,5}$ has a regulatory function on the signal transduction mediated by RTK and thus, a modulating effect on the membrane dynamics in tumor cells. For a detailed analysis TPTE-eGFP was expressed in NIH3T3 fibroblasts which due to transformation with c-erbB-2 have a constitutively activated PI-3 kinase signaling and thus, an overproduction of the second messenger $PIP_{3,4,5}$. Time-lapse microscopy of these cells after cultivation for several hours in minimal medium demonstrated that the location of TPTE at the membrane of pseudopodia and protrusions resulted immediately in the retraction of the respective membrane region. An explanation for this observation is the PI-3 kinase antagonistic effect of TPTE which by the termination of the RTK mediated signal transduction terminates actin polymerization below the membrane region concerned. These PI-3K antagonistic effects of TPTE are mediated by dephosphorylation of the second messenger $PIP_{3,4,5}$ to $PIP_{4,5}$. $PIP_{4,5}$ regulates the cortical actin polymerization and mediates adhesion of the cytoskeleton to the plasma membrane. To detect co-localization of TPTE and $PIP_{4,5}$, TPTE transfected NIH3T3/c-erbB2 cells were co-transfected with the eGFP coupled PH domain of phospholipase C-δ1 (PLC-δ1). The PH domain mediates specific binding of PLC-δ1 to its physiological substrate $PIP_{4,5}$ and thus, it is well suited for displaying the distribution of $PIP_{4,5}$ at the plasma membrane. As expected, a distinct co-localization of TPTE and $PIP_{4,5}$ was demonstrated at the plasma membrane in the cotransfected cells (FIG. 35). This could be again confirmed in further assays by co-staining using an antibody specific for $PIP_{4,5}$. It was shown recently that PTEN which is homologous to TPTE regulates the migratory potential of cells in a positive manner. Cell migration is a directional process for which the perception of extracellular gradients of chemotactic agents is essential. Directed cell migration results in polarization of the cell in direction to the gradient following detection of the chemotactic agent. PTEN mediates the polarization of the cell by forming an intracellular gradient of the second messenger $PIP_{3,4,5}$ in direction to the extracellular gradient and thus, mediates a directed actin polymerization and migration. To test whether TPTE has similar promigratory properties, a Transwell migration assay was performed. TPTE transfected NIH3T3/c-erbB-2 cells and respective control cells (non-transfected NIH3T3/c-erbB-2 cells and NIH3T3/c-erbB-2 cells transfected with empty peGFP vector) were tested using different amounts of chemical attractants. Cells expressing TPTE showed a significantly increased migration rate which was more than 4-fold compared to the control cells in reaction to 10% FCS (FIG. 23). Using RNA interference (RNAi), it could be demonstrated that also the spontaneous expression of TPTE in tumor cell lines enhances the chemotaxis of these cells. To this end, TPTE positive PC-3 prostate carcinoma cells were electroporated with TPTE specific double-stranded RNA oligos (sense 5'-CCCUGCCACAUGUU-CAUAUdTdT-3' (SEQ ID NO: 826) and antisense 5'-AUAUGAACAUGUGGCAGGGdTdT-3' (SEQ ID NO: 827)). 24 hours later, a decrease in TPTE expression by 70% could be detected by means of quantitative real-time RT-PCR (FIG. 36). The Transwell migration assay showed a distinct reduction of the migration rate (70%) compared to the respective controls (untreated PC-3 cells and PC-3 cells electroporated with irrelevant siRNA) (FIG. 37). While PTEN is a cytoplasmatic protein which can be directed to the plasma membrane by PH-domain recruiting second messengers such as $PIP_{3,4,5}$, TPTE could modulate perception of chemotactic gradients directly at the membrane by blocking signal transduction of activated RTKs which are frequently overexpressed in cancer cells and thus mediate perception of a spatial gradient.

Phosphatases are frequently involved in cell motility and migration. To examine the significance of TPTE in cell migration, TPTE was introduced as fusion protein with green fluorescence protein into a TPTE negative cell line and the distribution of this protein observed in vivo by real-time microscopy. Cells form membrane extensions (protrusions) as pre-stage to migration. Following formation of such a protrusion, TPTE accumulates in this membrane region (FIG. 22). When flattening of the protrusion starts, TPTE is removed from the membrane and internalized and obviously is involved in the process of motility events of the cell. Similarly, the comparison of migration properties of cells transfected with TPTE versus cells transfected with control plasmid in the migration chamber (BOYDEN chamber) demonstrates that TPTE results in a significant enhancement of migration along chemotactic gradients of growth factors (e.g. PDGF=platelet-derived growth factor, or FCS=fetal calf serum) (FIG. 23).

Since TPTE of a cell obviously mediates promigratory properties, breast and lung tumors of a total of 58 patients were examined with respect to expression of TPTE and statistically compared with the course of the disease of these patients. Those tumors which express TPTE tend to form lymph node as well as distant metastases at a significant higher frequency than TPTE negative tumors (FIG. 24).

These functional data indicate that TPTE may play a major role in the formation of metastases in tumors. Accordingly TPTE may be considered as a marker for a prognostically worsened course and tendency to form metastases. Furthermore, methods which inhibit the endogenous activity of TPTE in tumor cells according to the invention, e.g. by using antisense RNA, different methods of RNA interference (RNAi) by means of expression vectors or retroviruses, as well as by using small molecules, can result in a reduced formation of metastases and thus, could be very important from a therapeutic point of view.

Example 3

Identification of TSBP as a New Tumor Antigen

The electronic cloning method employed according to the invention produced TSBP (SEQ ID NO:29) and the protein derived therefrom (SEQ ID NO:30). The gene has been described previously as being testis-specifically regulated (accession number NM_006781). The gene was predicted to encode a basic protein and to be located on chromosome 6 close to a sequence coding for an MHC complex (C6orf10) (Stammers M. et al., *Immunogenetics* 51(4-5):373-82, 2000). According to the invention, the previously described sequence was shown to be incorrect. The sequence of the invention is substantially different from the known sequence. According to the invention, 3 different splicing variants were cloned. The differences in the nucleotide sequences of the TSBP variants found according to the invention (SEQ ID NO:31, SEQ ID NO: 32, SEQ ID NO:33) to the known sequence (NM_006781, SEQ ID NO:29) are depicted in FIG. 7 (differences depicted in bold type). They result in frame shifts so that the proteins encoded by the TSBP variants found according to the invention (SEQ ID NO:34, SEQ ID NO:35, SEQ ID NO:36) differ substantially from the previously described protein (SEQ ID NO:30) (FIG. 8).

It was confirmed according to the invention that this antigen is strictly transcriptionally repressed in normal tissues (PCR primers 5'-TCTAGCACTGTCTCGATCAAG-3' (SEQ ID NO: 42) and 5'-TGTCCTCTTGGTACATCTGAC-3' (SEQ ID NO: 43)). However, in 25 normal tissues studied, TSBP was expressed, apart from in testis, also in normal lymph node tissue. According to the invention, ectopic activation of TSBP in tumors was also detected, and it therefore qualifies as a tumor marker or tumor-associated antigen (Table 3).

Although TSBP expression is found in primary tumor tissue, it is not found in permanent cell lines of corresponding tumor entities. Moreover, the gene is in the direct neighborhood of Notch 4 which is specifically expressed in arteries and involved in vascular morphogenesis. These are significant indications of this being a marker for specific endothelial cells. TSBP may therefore serve as a potential marker for tumor endothelia and for neovascular targeting.

Consequently, the TSBP promoter may be cloned to another genetic product whose selective expression in lymph nodes is desired.

Analysis of TSBP antigen expression, using specific antibodies, confirmed the selective localization of the protein in testis and lymph nodes and also in melanomas and bronchial carcinomas. In addition, immunohistological studies using GFP-tagged TSBP revealed a distinct perinucleic accumulation.

TABLE 3

Expression of TSBP in tumors

| Tissue | Tested in total | Positive | % |
|---|---|---|---|
| Melanoma | 12 | 2 | 16 |
| Mammary carcinomas | 15 | 0 | — |
| Colorectal tumors | 15 | 0 | — |
| Prostate carcinomas | 8 | 0 | — |
| Bronchial carcinomas | 7 | 17 | 41 |
| Kidney cell carcinomas | 7 | 0 | — |
| Ovarian carcinomas | 7 | 0 | — |
| Thyroid carcinomas | 4 | 0 | — |
| Cervical carcinomas | 6 | 0 | — |
| Melanoma cell lines | 8 | 0 | — |
| Bronchial carcinoma cell lines | 6 | 0 | — |

For detecting TSBP protein antibodies were produced by immunizing rabbits. The following peptides or purified protein which was recombinantly expressed in *E. coli* were used for propagating these antibodies:

```
SEQ ID NO:106:
CYQHKVTLHMITERDP (aa 60-74)

SEQ ID NO:107:
CRIPQVHTMDSSGKI (aa 191-204)

SEQ ID NO:108:
RRKQSEMHISRYSSEQSARLLDYEDGRGSRHAYSTQSDTSCDNRERSKRD

YTPSTNSLALSRSSIALPQGSMSSIKCLQTTEELPSRTAGAMMQFTAPIP

GATGPIKLSQKTIVQTPGPIVQYPGPNVRSHPHTITGPPSAPRGPPMAPI

IISQRTASQLAAPIIISQRTARIPQVHTMDSSGKTTLTPVVILTGYMDEE

LAKKSCSKIQILKCGGTARSQNSREENKEALKNDIIFTNSVESLKSAHIK

EPEREGKGTDLEKDKIGMEVKVDSDAGIPKRQETQLKISEMSIPQGQGAQ

IKKSVSDVPRGQESQVKKSESGVPKGQEAQVTKSGLVVLKGQEAQVEKSE

MGVPRRQESQVKKSQSGVSKGQEAQVKKRESVVLKGQEAQVEKSELKVPK

GQEGQVEKTEADVPKEQEVQEKKSEAGVLKGPESQVKNTEVSVPETLESQ

VKKSESGVLKGQEAQEKKESFEDKGNNDKEKERDAEKDPNKKEKGDKNTK

GDKGKDKVKGKRESEINGEKSKGSKRAKANTGRKYNKKVEE

(rec. prot. 29-569)
```

Data for antibodies which are directed against SEQ ID NO:108 are given as an example. The specific antibody may be used for immunofluorescence assays under different fixation conditions. RT-PCR assays demonstrated that the colon carcinoma cell line HCT 116 P does not express TSBP. The variant HCT 116 DKO which is deleted for DNA methyltransferase, however, is positive for TSBP. Comparative stainings of both cell lines with the above described antibody detected the respective protein specifically in the cell lines which were typed as positive in amounts which were easily detectable (FIG. 25). The endogenous protein is primarily located at the nuclear and ER membrane, whereby the plasma membrane is slightly stained.

This antibody was further used for the immunohistochemical staining of tissue sections. As expected, the antibody stains testis tissue in a specific manner. In particular, the germ cells are stained (FIG. 25).

The bioinformatic analysis demonstrated that TSBP is a strongly basic protein having a nuclear localization signal. Accordingly, it is predicted that the subcellular location of the protein is to the nucleus, while the endogenously expressed protein is located at the nuclear membrane as described above. The N terminus contains a transmembrane domain followed by a proteolytic cleavage site which is indicative for the fact that the transmembrane domain is cleaved by proteases during the processing of the protein. This combination of nuclear localization signals, location of the protein at the nuclear, ER or plasma membranes and transmembrane domains followed by proteolytic cleavage sites is found with a distinct class of transcription factors of which members of the NOTCH family and SREBP are best characterized (Weinmaster G. *Curr. Opin. Genet. Dev.* 10(4):363-9, 2000; Hoppe T. et al. *Curr. Opin. Cell. Biol.* 13(3):344-8, 2001)). The biological activity of these factors is regulated by the mechanism of the regulated intramembrane proteolysis (RIP). Following translation, the proteins are integrated via the transmembrane domain into the nuclear, ER or plasma membrane. In the case of NOTCH, the binding of a specific ligand induces the proteolytic cleavage below the membrane domain such that the protein reaches the site where it exerts its effect. Transcriptional processes can be regulated in this manner, for example, during the course of organ development in a milieu dependent manner. Due to its structural properties and the location at the membrane, TSBP could be integrated into this class. It is true that the TSBP sequence does not contain specific DNA binding structural elements but the strong basicity of the protein makes binding to DNA likely such that TSBP may be a transcription factor or a transcription modulating factor.

Example 4

Identification of MS4A12 as a New Tumor Antigen

MS4A12 (SEQ ID NO:37, accession number NM_017716) and its translation product (SEQ ID NO:38) have been described previously as members of a multigene family related to the B cell-specific antigen CD20, the hematopoietic cell-specific protein HTm4 and the 13 chain of the high affinity IgE receptor. All family members are characterized by at least four potential transmembrane domains and both the C and the N-terminus are cytoplasmic (Liang Y. et al., Immunogenetics 53(5):357-68, 2001; Liang Y. & Tedder, *Genomics* 72(2):119-27, 2001). According to the invention, RT-PCR studies on MS4A12 were carried out. The primers were selected based on the published MS4A12 sequence (NM_017716) (sense: CTGTGTCAGCATCCAAGGAGC (SEQ ID NO: 44), antisense: TTCACCTTTGCCAGCATG-TAG (SEQ ID NO 45)). In the tissues tested, expression was detected only in testis, colon (6/8) and colorectal carcinomas (colon-Ca's) (16/20) and in colonic metastases (12/15) (FIG. 9).

The high incidence in colonic metastases makes TSBP an attractive diagnostic and therapeutic target. According to the invention, the predicted extracellular region comprising the protein sequence GVAGQDYWAVLSGKG (SEQ ID NO:83) is particularly suitable for producing monoclonal antibodies and small chemical inhibitors. According to the invention, the intracellular localization of the MS4A12 protein on the cell membrane was also confirmed by fluorescence superposition using plasma membrane markers in confocal immunofluorescence.

TABLE 4

Expression of MS4A12 in normal tissues and colorectal carcinomas and metastasis

| | |
|---|---|
| Ileum | + |
| Colon | + |
| Liver | – |
| Lung | – |
| Lymph nodes | – |
| Stomach | – |
| Spleen | – |
| Adrenal gland | – |
| Kidney | – |
| Esophagus | – |
| Ovary | – |
| Rectum | + |
| Testis | + |
| Thymus | – |
| Skin | – |
| Mamma | – |
| Pancreas | – |
| PBMC | – |
| PBMC act. | – |
| Prostate | – |
| Thyroid | – |
| Tube | – |
| Uterus | – |
| Cerebrum | – |
| Cerebellum | – |
| Colorectal tumors | 16/20 |
| Colorectal tumors metastases | 12/15 |

Thus, MS4A12 is a cell membrane-located differentiation antigen for normal colon epithelia, which is also expressed in colorectal tumors and metastases.

A quantitative real-time PCR (40 cycles, initial denaturation 15 min 95° C., 30 sec 94° C., 30 sec 62° C. and 30 sec 72° C.) using specific primers (CTGTGTCAGCATCCAAGGAGC (SEQ ID NO: 44) and TTCACCTTTGCCAGCATGTAG (SEQ ID NO: 45)) was performed (FIG. 26). This not only confirmed that MS4A12 was absent in the majority of the normal tissues except testis and colorectal normal tissues but also detected high transcript levels, for example, in primary intestinal tumors and their metastases. For detecting MS4A12 protein, antibodies were prepared by immunizing rabbits. The following peptides or purified protein which was expressed recombinantly in *E. coli* were used for propagating these antibodies:

```
SEQ ID NO:109:
MMSSKPTSHAEVNETC (aa 1-15)

SEQ ID NO:110:
CGVAGQDYWAVLSGKG (aa 64-73)

SEQ ID NO:111:
MMSSKPTSHAEVNETIPNPYPPGSFMAPGFQQPLGSINLENQAQGAQRAQ

PYGITSPGIFASS (rec. prot. aa 1-63)
```

Data for antibodies which are directed against SEQ ID NO:111 are given as an example. A specific band having the expected size is detectable in Western blots for normal intestine, colon carcinomas but not normal tissues (FIG. 27). The specific antibody may be used for immunofluorescence assays under different fixation conditions. If RT-PCR positive as well as negative cell lines are stained, the respective protein can be specifically detected in the cell lines typed as positive in an amount which is easily detectable and MS4A12 which is recombinantly expressed in eukaryotes is specifically detected as well (FIG. 28). These experiments also confirm the membrane localization. This antibody was further used for the immunohistochemical staining of tissue sections. As expected, the antibody stains healthy intestinal tissue, however, only the apical epithelial cells of the colon mucosa (FIG. 29, left hand). Tumor cells of intestinal tumors are also stained at the membrane in a homogeneous manner (FIG. 29, right hand).

Example 5

Identification of BRCO1 as a New Tumor Antigen

BRCO1 and its translation product have not been described previously. The datamining method of the invention produced the EST (expressed sequence tag) AI668620. RT-PCR studies using specific primers (sense: CTTGCTCTGAGTCATCAGATG (SEQ ID NO: 46), antisense: CACAGAATATGAGCCATACAG (SEQ ID NO: 47)) were carried for expression analysis. According to the invention, specific expression was found in testicular tissue and additionally in normal mammary gland (Table 5). In all other tissues, this antigen is transcriptionally repressed. It is likewise detected in mammary gland tumors (20 out of 20). BRCO1 is distinctly overexpressed in breast tumors in comparison with expression in normal mammary gland tissue (FIG. 10)

Utilizing EST contigs (the following ESTs were incorporated: AW137203, BF327792, BF327797, BE069044, BF330665), more than 1500 bp of this transcript were cloned according to the invention by electronic full-length cloning (SEQ ID NO:39). The sequence maps to chromosome 10p11-12. In the same region, in immediate proximity, the gene for a mammary differentiation antigen, NY-BR-1, has been described previously (NM_052997; Jager, D. et al., *Cancer Res.* 61(5):2055-61, 2001).

TABLE 5

Expression of BRCO1 in normal tissues and breast tumors

| | |
|---|---|
| Ileum | – |
| Colon | – |
| Liver | – |
| Lung | – |
| Lymph nodes | – |
| Stomach | – |
| Spleen | – |
| Adrenal gland | – |
| Kidney | – |
| Esophagus | – |
| Ovary | – |
| Rectum | – |
| Testis | + |
| Thymus | – |
| Skin | – |
| Mamma | + |
| Pancreas | – |
| PBMC | – |
| PBMC act. | – |
| Prostate | – |
| Thyroid | – |
| Tube | – |
| Uterus | – |

TABLE 5-continued

| Expression of BRCO1 in normal tissues and breast tumors | |
|---|---|
| Cerebrum | – |
| Cerebellum | – |
| Mammary carcinomas | ++ (20/20) |

Matched pair (mammary carcinoma and adjacent normal tissue) studies revealed BRCO1 overexpression in 70% of the mammary carcinomas in comparison with the normal tissue.

Thus, BRCO1 is a new differentiation antigen for normal mammary gland epithelia, which is overexpressed in breast tumors.

This also confirms the quantitative real-time PCR (40 cycles, initial denaturation 15 min 95° C., 30 sec 94° C., 30 sec 60° C. and 30 sec 72° C.) using specific primers (5'-CTTGCTCTGAGTCATCAGATG-3' (SEQ ID NO: 46); 5'-CACAGAATATGAGCCATACAG-3' (SEQ ID NO: 47)) (FIGS. 30 and 31). This not only confirmed that BRCO1 is absent in the majority of normal tissues except testis and breast normal tissues but also revealed overexpression in breast tumors.

For detecting BRCO1 protein, antibodies were prepared by immunizing rabbits. The following peptides were used for propagating these antibodies:

```
SEQ ID NO:115:
IAPNTRGQQTIVL

SEQ ID NO:116:
VWKSNGKSILKMPF
```

Example 6

Identification of TPX1 as a New Tumor Antigen

The sequence of TPX1 (Acc. No. NM_003296; SEQ ID NO: 40) and of its translation product (SEQ ID NO:41) are known. The antigen has been described previously only as being testis-specific, that is as an element of the outer fibers and of the acrosome of sperms. Previously, an involvement as adhesion molecule in the attachment of sperms to Sertoli cells has been attributed to said antigen (O'Bryan, M. K. et al., *Mol. Reprod. Dev.* 58(1):116-25, 2001; Maeda, T. et al., *Dev. Growth Differ.* 41(6):715-22, 1999). The invention reveals, for the first time, aberrant expression of TPX1 in solid tumors (Table 6). Owing to the marked amino acid homology between TPX1 and the neutrophile-specific matrix glycoprotein SGP 28 (Kjeldsen et al., FEBS Lett 380:246-259, 1996), TPX1-specific protein sequences comprising the peptide SREVTTNAQR (SEQ ID NO:84) are suitable according to the invention for preparing diagnostic and therapeutic molecules.

TABLE 6

Expression of TPX1 in tumors

| Tissue | Tested in total | Positive | % |
|---|---|---|---|
| Melanoma | 16 | 1 | 6 |
| Mammary carcinomas | 20 | 3 | 15 |
| Colorectal tumors | 20 | 0 | 0 |
| Prostate carcinomas | 8 | 3 | 37 |
| Bronchial carcinomas | 17 | 2 | 11 |
| Kidney cell carcinomas | 7 | 1 | 14 |
| Ovarian carcinomas | 7 | 1 | 14 |
| Thyroid carcinomas | 4 | 0 | 0 |
| Cervical carcinomas | 6 | 1 | 16 |
| Melanoma cell lines | 8 | 2 | 25 |
| Bronchial carcinoma cell lines | 6 | 1 | 16 |

Example 7

Identification of BRCO2 as a New Tumor Genetic Product

BROC2 and its translation product have not been described previously. The method of the invention produced the ESTs (expressed sequence tag) BE069341, BF330573 and AA601511. RT-PCR studies using specific primers (sense: AGACATGGCTCAGATGTGCAG (SEQ ID NO: 66), anti-sense: GGAAATTAGCAAGGCTCTCGC (SEQ ID NO: 67)) were carried out for expression analysis. According to the invention, specific expression was found in testicular tissue and additionally in normal mammary gland (Table 7). In all other tissues, this genetic product is transciptionally repressed. It is likewise detected in mammary gland tumors. Utilizing EST contigs (the following ESTs were incorporated: BF330573, AL044891 and AA601511), 1300 bp of this transcript were cloned according to the invention by electronic full-length cloning (SEQ ID 62). The sequence maps to chromosome 10p11-12. In the same region, in immediate proximity, the gene for a mammary differentiation genetic product, NY-BR-1, has been described previously (NM_052997; Jager, D. et al., *Cancer Res.* 61(5):2055-61, 2001), and here the BRCO1 described above under Example 6 is located. Further genetic analyses revealed according to the invention that the sequence listed under SEQ ID NO:62 represents the 3' untranslated region of the NY-BR-1 gene, which has not been described previously.

TABLE 7

Expression of BRCO2 in normal tissues and breast tumors

| Tissue | Expression |
|---|---|
| Testis | + |
| Mamma | + |
| Skin | – |
| Liver | – |
| Prostate | – |
| Thymus | – |
| Brain | – |
| Lung | – |
| Lymph nodes | – |
| Spleen | – |
| Adrenal gland | – |
| Ovary | – |
| Leukocytes | – |
| Colon | – |
| Esophagus | – |
| Uterus | – |
| Skeleton muscle | – |
| Epididymis | – |
| Bladder | – |

TABLE 7-continued

| Expression of BRCO2 in normal tissues and breast tumors | |
|---|---|
| Tissue | Expression |
| Kidney | − |
| Mammary carcinoma | + |

BRCO2 is a new differentiation genetic product for normal mammary gland epithelia, which is also expressed in breast tumors.

Example 8

Identification of PCSC as a New Tumor Genetic Product

PCSC (SEQ ID NO:63) and its translation product have not been described previously. The datamining method of the invention produced the EST (expressed sequence tag) BF064073. RT-PCR studies using specific primers (sense: TCAGGTATTCCCTGCTCTTAC (SEQ ID NO: 68), antisense: TGGGCAATTCTCTCAGGCTTG (SEQ ID NO: 69)) were carried out for expression analysis. According to the invention, specific expression was found in normal colon, and additionally in colon carcinomas (Table 5). In all other tissues, this genetic product is transcriptionally repressed. PCSC codes for three putative ORFs (SEQ ID 64, SEQ ID 65 and SEQ ID 117). Sequence analysis of SEQ ID 64 revealed a structural homology to CXC cytokines. In addition, 4 alternative PCSC cDNA fragments were cloned (SEQ ID NO:85-88). In each case, according to the invention, each cDNA contains 3 putative ORFs which code for the polypeptides depicted in SEQ ID NO:89-100.

TABLE 8

| Expression of PCSC in normal tissues and colorectal carcinomas | |
|---|---|
| Ileum | + |
| Colon | + |
| Liver | − |
| Lung | − |
| Lymph nodes | − |
| Stomach | − |
| Spleen | − |
| Adrenal gland | − |
| Kidney | − |
| Esophagus | − |
| Ovary | − |
| Rectum | + |
| Testis | − |
| Thymus | − |
| Skin | − |
| Mamma | − |
| Pancreas | − |
| PBMC | − |
| PBMC act. | − |
| Prostate | − |
| Thyroid | − |
| Tube | − |
| Uterus | − |
| Cerebrum | − |
| Cerebellum | − |
| Colorectal tumors | 19/20 |
| Colorectal tumors metastases | 15/15 |

Thus, PCSC is a differentiation antigen for normal colon epithelia which is also expressed in colorectal tumors and in all colon metastases studied. PCSC expression detected in all colorectal metastases according to the invention renders this tumor antigen a very interesting target for prophylaxis and treatment of metastasizing colon tumors.

A quantitative real-time PCR (40 cycles, initial denaturation 15 min 95° C., 30 sec 94° C., 30 sec 59° C. and 30 sec 72° C.) was performed using specific primers (5'-AGAATAGAATGTGGCCTCTAG-3 (SEQ ID NO: 824); 5'-TGCTCTTACTCCAAAAAGATG-3' (SEQ ID NO: 825)) (FIG. 32). This not only confirmed that PCSC is absent in the majority of the normal tissues except testis and colorectal normal tissues but also revealed high transcript levels, for example, in intestinal tumors. Metastases of intestinal tumors show a significant higher expression than primary tumors. This and the fact that PCSC has homologies to the chemokine family corroborate a role in increased cell motility and the formation of metastases.

For detecting PCSC protein antibodies were prepared by immunizing rabbits. The following peptides were used for propagating these antibodies:

```
SEQ ID NO:112:
GHGPGHPPPGPHH

SEQ ID NO:113:
KPERIAQLTWNEA

SEQ ID NO:114:
PRSPTPWSTSLRK
```

Example 9

Identification of SGY-1 as a New Tumor Antigen

The sequences of the SGY-1 transcript (SEQ ID NO:70) and of its translation product (SEQ ID NO:71) have been published in GenBank under accession number AF177398 (Krupnik et al., *Gene* 238, 301-313, 1999). Soggy-1 has previously been described as a member of the Dickkopf protein family which act as inhibitors and antagonists of the Wnt family of proteins. The Wnt proteins in turn have important functions in embryonic development. Based on the sequence of SGY-1 (SEQ ID NO:70), PCR primers (5'-CTCCTATCCATGATGCTGACG-3' (SEQ ID NO: 72) and 5'-CCTGAGGATGTACAGTAAGTG-3' (SEQ ID NO: 73)) were generated according to the invention and used for RT-PCR analyses (95° 15 min; 94° 1 min; 63° 1 min; 72° 1 min; 35 cycles) in a number of human tissues. Expression in normal tissues was shown to be limited to testis. As described for the other eCT, SGY-1 was shown according to the invention to be ectopically activated in a number of tumor tissues; cf. Table 9.

TABLE 9

| Expression of SGY-1 in tumors | | | |
|---|---|---|---|
| Tissue | Tested in total | Positive | % |
| Melanoma | 16 | 4 | 25 |
| Mammary carcinomas | 20 | 4 | 20 |
| Colorectal tumors | 20 | 0 | 0 |
| Prostate carcinomas | 8 | 1 | 13 |
| Bronchial carcinomas | 32 | 3 | 18 |
| Kidney cell carcinomas | 7 | 0 | 0 |
| Ovarian carcinomas | 7 | 4 | 57 |
| Thyroid carcinomas | 4 | 0 | 0 |
| Cervical carcinomas | 6 | 2 | 33 |
| Melanoma cell lines | 8 | 2 | 25 |

TABLE 9-continued

| Expression of SGY-1 in tumors | | | |
|---|---|---|---|
| Tissue | Tested in total | Positive | % |
| Bronchial carcinoma cell lines | 6 | 2 | 33 |
| Mammalian carcinoma cell lines | | | |

Example 10

Identification of MORC as a New Tumor Antigen

The sequences of the MORC transcript (SEQ ID NO:74) and of its translation product (SEQ ID NO:75) have been published in GenBank under the accession number XM_037008 (Inoue et al., *Hum Mol Genet. July:*8(7):1201-7, 1999).

MORC has originally been described as being involved in spermatogenesis. Mutation of this protein in the mouse system results in underdevelopment of the gonads.

Based on the sequence of MORC (SEQ ID NO:74), PCR primers (5'-CTGAGTATCAGCTACCATCAG-3' (SEQ ID NO: 76) and 5'-TCTGTAGTCCTTCACATATCG-3' (SEQ ID NO: 77)) were generated according to the invention and used for RT-PCR analyses (95° 15 min; 94° 1 min; 63° 1 min; 72° 1 min; 35 cycles) in a number of human tissues. Expression in normal tissues was shown to be limited to testis. As described for the other eCT, MORC was shown according to the invention to be ectopically activated in a number of tumor tissues: cf. Table 10.

TABLE 10

| Expression of MORC in tumors | | | |
|---|---|---|---|
| Tissue | Tested in total | Positive | % |
| Melanoma | 16 | 3 | 18 |
| Mammary carcinomas | 20 | 0 | 0 |
| Colorectal tumors | 20 | 0 | 0 |
| Prostate carcinomas | 8 | 0 | 0 |
| Bronchial carcinomas | 17 | 3 | 18 |
| Kidney cell carcinomas | 7 | 0 | 0 |
| Ovarian carcinomas | 7 | 1 | 14 |
| Thyroid carcinomas | 4 | 0 | 0 |
| Cervical carcinomas | 6 | 0 | 0 |
| Melanoma cell lines | 8 | 1 | 12 |
| Bronchial carcinoma cell lines | 6 | 1 | 17 |

The invention claimed is:

1. A method of determining the tendency of a tumor to form metastases which method comprises:

(i) detection of a nucleic acid that encodes for a tumor-associated antigen, or (ii) detection of a tumor-associated antigen, in a biological sample comprising tumor cells isolated from a patient having a tumor, wherein the tumor-associated antigen is encoded by the nucleic acid of SEQ ID NO: 19, wherein the tumor is a melanoma, breast carcinoma, bronchial carcinoma, kidney carcinoma, ovarian carcinoma, or cervical carcinoma, and wherein the method further comprises the step of determining the tendency of the tumor to form metastases, wherein the presence of the nucleic acid that encodes for the tumor-associated antigen or presence of the tumor-associated antigen in the sample is indicative of the tendency of cells of the tumor to metastasize.

2. The method of claim 1, wherein the detecting comprises (i) contacting the biological sample with an agent that binds specifically to the nucleic acid or the tumor-associated antigen; and (ii) detecting the formation of a complex between the agent and the nucleic acid or the tumor-associated antigen, wherein the agent is a polynucleotide probe that hybridizes specifically to the nucleic acid or an antibody that specifically binds to the tumor-associated antigen.

3. The method of claim 1, wherein the level of the nucleic acid or the tumor-associated antigen is quantified by comparison to the level of the same nucleic acid or the tumor-associated antigen present in a comparable normal biological sample.

4. The method of claim 1, wherein the nucleic acid is detected using a polynucleotide probe that hybridizes specifically to the nucleic acid.

5. The method of claim 4, wherein the polynucleotide probe comprises a nucleotide sequence that is complementary to 6-50 contiguous nucleotides of the nucleic acid that encodes for the tumor-associated antigen.

6. The method of claim 1, wherein the nucleic acid is detected by selectively amplifying the nucleic acid.

7. The method of claim 1, wherein the tumor-associated antigen or a portion thereof is detected using an antibody that specifically binds thereto.

8. The method of claim 1, wherein the nucleic acid or the tumor-associated antigen is detected and quantified in a first biological sample at a first point in time, and subsequently is detected and quantified in at least one additional biological sample taken at a later point in time, and in which the course of the disease is monitored by comparing the level of the nucleic acid or the tumor-associated antigen found in the first biological sample to the level of the nucleic acid or the tumor-associated antigen found in the at least one additional biological sample.

9. The method of claim 1, wherein the biological sample comprises a body fluid, a tissue, or a combination thereof.

10. The method according to claim 1, wherein the tumor-associated antigen comprises the amino acid sequence of SEQ ID NO: 22.

11. A method of determining the presence of tumor pre-stages which method comprises:

detecting co-localization of a tumor-associated antigen and F-actin or $PIP_{4,5}$ at the plasma membrane of a cell in a biological sample isolated from a patient, wherein the tumor-associated antigen is encoded by the nucleic acid of SEQ ID NO: 19 and wherein the method further comprises the step of determining the presence of tumor pre-stages, wherein co-localization of the tumor-associated antigen and F-actin or $PIP_{4,5}$ at the plasma membrane of the cell is indicative of the presence of tumor pre-stages.

12. The method of claim 11, wherein the detecting comprises (i) contacting the biological sample with an agent that binds specifically to the tumor-associated antigen; and (ii) detecting the formation of a complex between the agent and the tumor-associated antigen, wherein the agent is an antibody that specifically binds to the tumor-associated antigen.

13. The method of claim 2, wherein the agent is a polynucleotide probe that hybridizes specifically to the nucleic acid.

14. The method of claim 2, wherein the agent is an antibody that specifically binds to the tumor-associated antigen.

15. A method of determining the tendency of a tumor to form metastases which method comprises:

detecting a tumor-associated antigen in a biological sample comprising tumor cells isolated from a patient having a tumor, wherein the tumor-associated antigen is encoded by the nucleic acid of SEQ ID NO: 19, wherein the method further comprises the step of determining the tendency of the tumor to form metastases, wherein the presence of the tumor-associated antigen in the sample is indicative of the tendency of cells of the tumor to metastasize; and wherein the detecting comprises:

contacting the biological sample with a monoclonal antibody that binds specifically to the tumor-associated antigen, wherein the monoclonal antibody binds to an epitope within the amino acid sequence according to SEQ ID NOs: 81, 82, 103, 104, or 105; and detecting the formation of a complex between the antibody and the tumor-associated antigen.

16. The method according to claim 15, wherein the tumor-associated antigen comprises the amino acid sequence of SEQ ID NO: 22.

17. The method of claim 15, wherein the tumor-associated antigen is detected and quantified in a first biological sample at a first point in time, and subsequently is detected and quantified in at least one additional biological sample taken at a later point in time, and in which the course of the disease is monitored by comparing the level of the tumor-associated antigen found in the first biological sample to the level of the tumor-associated antigen found in the at least one additional biological sample.

18. The method of claim 16, wherein the biological sample comprises a body fluid, a tissue, or a combination thereof.

19. The method of claim 16, wherein the monoclonal antibody binds to an epitope within the amino acid sequence according to SEQ ID NO: 81.

20. The method of claim 16, wherein the monoclonal antibody binds to an epitope within the amino acid sequence according to SEQ ID NO: 82.

21. The method of claim 16, wherein the monoclonal antibody binds to an epitope within the amino acid sequence according to SEQ ID NO: 103.

22. The method of claim 16, wherein the monoclonal antibody binds to an epitope within the amino acid sequence according to SEQ ID NO: 104.

23. The method of claim 16, wherein the monoclonal antibody binds to an epitope within the amino acid sequence according to SEQ ID NO: 105.

24. The method of claim 16, wherein the monoclonal antibody is coupled to a diagnostic agent.

* * * * *